US005770696A

United States Patent [19]
Warren et al.

[11] Patent Number: 5,770,696
[45] Date of Patent: Jun. 23, 1998

[54] AUXILIARY PROTEINS FOR ENHANCING THE INSECTICIDAL ACTIVITY OF PESTICIDAL PROTEINS

[75] Inventors: Gregory W. Warren; Michael G. Koziel, both of Cary; Martha A. Mullins, Raleigh; Gordon J. Nye, Apex; Brian Carr; Nalini M. Desai, both of Cary; Kristy Kostichka, Durham; Nicholas B. Duck, Cary; Juan J. Estruch, Durham, all of N.C.

[73] Assignee: Novartis Corporation

[21] Appl. No.: 471,033

[22] Filed: Jun. 6, 1995

Related U.S. Application Data

[60] Division of Ser. No. 463,483, Jun. 5, 1995, which is a continuation-in-part of Ser. No. 314,594, Sep. 28, 1994, which is a continuation-in-part of Ser. No. 218,018, Mar. 23, 1994, abandoned, which is a continuation-in-part of Ser. No. 37,057, Mar. 25, 1993, abandoned.

[51] Int. Cl.$^6$ .................................................. C07K 14/32
[52] U.S. Cl. ....................... 530/350; 536/23.1; 536/23.7; 536/23.71; 530/825
[58] Field of Search ........................... 530/350; 536/23.1, 536/23.7, 23.71, 825

[56] References Cited

U.S. PATENT DOCUMENTS

| | | | |
|---|---|---|---|
| 3,632,747 | 1/1972 | Satohiro et al. | 424/93 |
| 3,651,215 | 3/1972 | Satohiro et al. | 424/93 |
| 4,996,155 | 2/1991 | Sick et al. | 435/252.3 |
| 5,262,323 | 11/1993 | Baird et al. | 435/252.5 |

FOREIGN PATENT DOCUMENTS

| | | |
|---|---|---|
| 0498537A2 | 1/1992 | European Pat. Off. . |
| 0501650A2 | 2/1992 | European Pat. Off. . |
| WO88/08880 | 11/1988 | WIPO . |
| WO90/13651 | 11/1990 | WIPO . |
| WO91/16432 | 10/1991 | WIPO . |
| WO91/16434 | 10/1991 | WIPO . |
| US94/03131 | 7/1994 | WIPO . |
| WO 94/21795 | 9/1994 | WIPO . |

OTHER PUBLICATIONS

Hofte, H., et al., "Insecticidal Crystal Proteins of *Bacillus thuringiensis*", *Microbiological Reviews*, 53(2):242–255 (1989).

Koziel, M.G., et al., "Field Performance of Elite Tansgenic Maize Plants Expressing an Insecticidal Protein Derived from *Bacillus thuringiensis*", *Bio/Technology*, 11:194–200 (1993).

Krieg, A., "Concerning Alpha–exotoxin Produced by Vegetative Cells of *Bacillus thuringiensis* and *Bacillus cereus*", *J. Invert. Path.*, 17:134–135 (1971).

Myers, P.S., et al., "Localization of a Mosquito–Larval Toxin of *Bacillus sphaericus* 1593", *Appl. Environ. Microbiol.*, 39(1):1205–1211 (1980).

Porter, A.G., et al., "Mosquitocidal Toxins of Bacilli and Their Genetic Manipulation for Effective Biological Control of Mosquitoes", *Microbiological Reviews*, 57(4):838–861 (1993).

Sekar, V., "The Insecticidal Crystal Protein Gene is Expressed in Vegetative Cells of *Bacillus thuringiensis* var. *temebropmos*", *Current Microbiology*, 17:347–349.

Shivakumar, A.G., et al., Abstract,:Cloned Crystal Protein Genes Express Vegetatively in *Bacillus subtilis*, *Plasmid*, 16(3):230 (1986).

Thanabalu, T., et al., "Proteolytic Processing of the Mosquitocidal Toxin from *Bacillus sphaericus* SSII–1", *J. Bacteriol.*, 174(15):5051–5056 (1992).

Yoshisue, H., et al., "Effects of *Bacillus thuringiensis* var. *israelensis* 20 kDa Protein on Production of the Bti 130–kDa Crystal Protein in *Escherichia coli*", *Bioscience, Biotechnology, and Biochemistry*, 56(9):1429–1433 (1992).

Arellano, A., et al., "Evidence of a New *Bacillus thuringiensis* Toxin Active Against the Australian Sheep Blowfly *Lucilla cuprina*", *Proceedings and Abstracts of the 5th International Colloquium on Invertebrate Pathology and Microbial Control, Adelaide, Austrailia*, 20–24 Aug., 1990, p. 291.

Beecher, Douglas J., et al., "A Novel Bicomponent Hemolysin from *Bacillus cereus*", *Inspection and Immunity*, 58(7):2220–2227 (1990).

Faust, R.M., "Bacterial Diseases", In: *Insect Diseases*, G. Cantwell, ed., Marcel Dekker, NY 1974, pp. 84–89 and 108–120.

Gilmore, Michael S., et al., "A *Bacillus cereus* Cytolytic Determinant, Cereolysin AB, Which Comprises the Phospholipase C and Sphingomyelinase Genes: Nucleotide Sequence and Genetic Linkage", *Journal of Bacteriology*, 171(2):744–753 (1989).

Heimpel, A.M., "The pH in the Gut and Blood of the Larch Sawfly, *Pristiphora erichsonii* (HTG), and Other Insects with Reference to the Pathogenicity of *Bacillus cereus* FR. and FR.", *Can. J. Zool.*, 33:99–106 (1955).

Heimpel, A.M., "Investigations of the Mode of Action of Strains of *Bacillus cereus* FR. and FR. Pathogenic for the Larch Sawfly, *Pristiphora erichsonii* (HTG.)", *Can. J. Zool.*, 33:311–326 (1995).

Krieg, A., "Thuricin, a Bacteriocin Produced by *Bacillus thuringiensis*", *J. Invert. Path.*, 15:291 (1970).

(List continued on next page.)

*Primary Examiner*—Robert A. Wax
*Assistant Examiner*—Nashaat T. Nashed
*Attorney, Agent, or Firm*—Gary M. Pace

[57] ABSTRACT

The present invention is drawn to pesticidal strains and proteins. Bacillus strains which are capable of producing pesticidal proteins and auxiliary proteins during vegetative growth are provided. "The auxiliary proteins enhance the insecticidal activity of pesticidal proteins." Also provided are the purified proteins, nucleotide sequences encoding the proteins and methods for using the strains, proteins and genes for controlling pests.

6 Claims, 1 Drawing Sheet

OTHER PUBLICATIONS

Kushner, D.J., et al., "Lecithinase Production by Strains of *Bacillus cereus* FR. and FR. Pathogenic for the Larch Sawfly, *Pristiphora erichsonii* (HTG.)", *Can. J. Microbiol.*, 3:547–551 (1957).

Luthy, P., et al., "*Bacillus thuringiensis* as a Bacterial Insecticide: Basic Consideration and Application", In: *Microbial and Viral Pesticides*, E. Kurstak, Ed., Marcel Dekker, NY 1982, pp. 37–39, 54–56.

European International Search Report dated May 3, 1996.

Bernier et al., "*Bacillus thuringiensis* Strains A20 and A29 and Insecticidal Compounds therefrom, and Compositions Containing These Compounds", Abstract No. 227249, *New Zealand Patent Office Journal*, 80(6):798, (1988).

Jellis et al., "*Bacillus Thuringiensis* δ–Endotoxin Variants and Insecticidal Compositions", Abstract No. 228108, *New Zealand Patent Office Journal*, 81(3):359, (1992).

Schurter et al., "Genetic Manifpulation of *B. thuringiensis B. cereus* Vectors and Insecticidal Composition", Abstract No. 229191, *New Zealand Patent Office Journal*, 81(3):363, (1992).

Tayabali et al., "Semiautomated Quantification of Cytotoxic Damage Induced in Cultured Insect Cells Exposed to Commercial *Bacillus thuringiensis* Biopesticides", *Journal of Applied Toxicology*, 15(5):365–373 (1995).

Thanabalu et al., "Cytotoxicity and ADP–Ribosylating Activity of the Mosquitocidal Toxin from *Bacillus sphaericus* SSII–1: Possible Roles of the 27–and 70–Kilodaron Peptides", *Journal of Bacteriology*, 175(8):2314–2320 (1993).

Vaithlingam et al., "Anti–Coleopteran Toxin and Gene", Abstract No. 226442, *New Zealand Patent Office Journal*, 80(7):931, (1991).

Wahisaka et al., "*Bacillus Thuringiensis* Mutant and Bacterial Insecticide", Abstract No. 199725, *New Zealand Patent Office Journal*, (1982).

Walther et al., "Analysis of Mosquito Larvicidal Potential Exhibited by Vegetative Cells of *Bacillus thuringiensis* subsp. *israelensis*", *Applied and Environmental Microbiology*, 52(4):650–653 (1986).

Ward et al., "*Bacillus thuringiensis* var. *israelensis* δ–Endotoxin Cloning and Expression of the Toxin in Sporogenic and Asporogenic Strains of *Bacillus subtilis*", *Journal of Molecular Biology*, 191(1): 13–22 (1986).

Figure 1

Characterization of pCIB6022

| | Activity vs. WCRW |
|---|---|
| pCIB6022 | +++ |
| pCIB6203 | — |
| pCIB6023 | — |
| pCIB6206 | — |
| pCIB6024 | — |

VIP2A(a)    VIP1A(a)

Functional Complementation of VIP Clones

| | Activity vs. WCRW |
|---|---|
| pCIB6203 / pCIB6023 | +++ |
| pCIB6203 / pCIB6206 | +++ |
| pCIB6023 / pCIB6024 | +++ |

AUXILIARY PROTEINS FOR ENHANCING THE INSECTICIDAL ACTIVITY OF PESTICIDAL PROTEINS

This is a divisional application of Ser. No. 08/463,483, filed Jun. 5, 1995 which is a continuation-in-part of Ser. No. 08/314,594 filed Sep. 28, 1994, now pending, which is a continuation-in-part of Ser. No. 08/218,018, filed Mar. 23, 1994, now abandoned, which is a continuation-in-part of Ser. No. 08/037,057, filed Mar. 25, 1993, now abandoned.

FIELD OF THE INVENTION

The present invention is drawn to methods and compositions for controlling plant and non-plant pests.

BACKGROUND OF THE INVENTION

Insect pests are a major factor in the loss of the world's commercially important agricultural crops. Broad spectrum chemical pesticides have been used extensively to control or eradicate pests of agricultural importance. There is, however, substantial interest in developing effective alternative pesticides.

Microbial pesticides have played an important role as alternatives to chemical pest control. The most extensively used microbial product is based on the bacterium *Bacillus thuringiensis* (*Bt*). *Bt* is a gram-positive spore forming Bacillus which produces an insecticidal crystal protein (ICP) during sporulation.

Numerous varieties of *Bt* are known that produce more than 25 different but related ICP's. The majority of ICP's made by *Bt* are toxic to larvae of certain insects in the orders Lepidoptera, Diptera and Coleoptera. In general, when an ICP is ingested by a susceptible insect the crystal is solubilized and transformed into a toxic moiety by the insect gut proteases. None of the ICP's active against coleopteran larvae such as Colorado potato beetle (*Leptinotarsa decemlineata*) or Yellow mealworm (*Tenebrio molitor*) have demonstrated significant effects on members of the genus Diabrotica particularly *Diabrotica virgifera virgifera*, the western corn rootworm (WCRW) or *Diabrotica longicornis barberi*, the northern corn rootworm.

*Bacillus cereus* (*Bc*) is closely related to *Bt*. A major distinguishing characteristic is the absence of a parasporal crystal in *Bc*. *Bc* is a widely distributed bacterium that is commonly found in soil and has been isolated from a variety of foods and drugs. The organism has been implicated in the spoilage of food.

Although *Bt* has been very useful in controlling insect pests, there is a need to expand the number of potential biological control agents.

SUMMARY OF THE INVENTION

The present invention is drawn to compositions and methods for controlling plant and non-plant pests. Particularly, new pesticidal proteins are disclosed which are isolatable from the vegetative growth stage of Bacillus. Bacillus strains, proteins, and genes encoding the proteins are provided.

The methods and compositions of the invention may be used in a variety of systems for controlling plant and non-plant pests.

BRIEF DESCRIPTION OF THE FIGURE

FIG. 1: Characterization of pCIB6022. Boxed regions represent the extent of VIP1A(a) and VIP2A(a). White box represents the portion of VIP1 encoding the 80 kDa peptide observed in Bacillus. Dark box represents the N-terminal 'propeptide' of VIP1A(a) predicted by DNA sequence analysis. Stippled box represents the VIP2A(a) coding region. Large 'X' represents the location of the frameshift mutation introduced into VIP1A(a). Arrows represent constructs transcribed by the beta-galactosidase promoter. Restriction Sites: C-Cla I; X-Xba I; S-Sca I; RI-Eco RI; B-Bgl II; RV-Eco RV.

DETAILED DESCRIPTION OF THE INVENTION

Compositions and methods for controlling plant pests are provided. In particular, novel pesticidal proteins are provided which are produced during vegetative growth of Bacillus strains. The proteins are useful as pesticidal agents.

The present invention recognizes that pesticidal proteins are produced during vegetative growth of Bacillus strains. To date, all of the identified pesticidal proteins of the invention are secreted from the cell. Prior to the present invention, there was no recognition in the art that a class or classes of pesticidal proteins are produced during vegetative growth of Bacillus. The only report was of a single mosquitocidal toxin from *Bacillus sphaericus* SSII-1 by Myers and Yousten in *Infect. Immun.*, 19:1047–1053 (1978). Having recognized that such a class exists, the present invention embraces all vegetative insecticidal proteins, hereinafter referred to as VIPs, except for the mosquitocidal toxin from *B. sphaericus*.

The present VIPs are not abundant after sporulation and are particularly expressed during log phase growth before stationary phase. For the purpose of the present invention vegetative growth is defined as that period of time before the onset of sporulation. Genes encoding such VIPs can be isolated, cloned and transformed into various delivery vehicles for use in pest management programs.

For purposes of the present invention, pests include but are not limited to insects, fungi, bacteria, nematodes, mites, ticks, protozoan pathogens, animal-parasitic liver flukes, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera.

Tables 1–10 gives a list of pests associated with major crop plants and pests of human and veterinary importance. Such pests are included within the scope of the present invention.

TABLE 1

Lepidoptera (Butterflies and Moths)

| Maize | Sunflower |
|---|---|
| *Ostrinia nubilalis*, European corn borer | *Suleima helianthana*, sunflower bud moth |

TABLE 1-continued

Lepidoptera (Butterflies and Moths)

| | |
|---|---|
| *Agrotis ipsilon*, black cutworm | *Homoeosoma electellum*, sunflower moth |
| *Helicoverpa zea*, corn earworm | Cotton |
| *Spodoptera frugiperda*, fall armyworm | *Heliothis virescens*, cotton boll worm |
| *Diatraea grandiosella*, southwestern corn borer | *Helicoverpa zea*, cotton bollworm |
| | *Spodoptera exigua*, beet armyworm |
| *Elasmopalpus lignosellus*, lesser cornstalk borer | *Pectinophora gossypiella*, pink bollworm |
| | Rice |
| *Diatraea saccharalis*, sugarcane borer | *Diatraea saccharalis*, sugarcane borer |
| Sorghum | *Spodopterafrugiperda*, fall armyworm |
| *Chilo partellus*, sorghum borer | *Helicoverpa zea*, corn earworm |
| *Spodoptera frugiperda*, fall armyworm | Soybean |
| *Helicoverpa zea*, corn earworm | *Pseudoplusia includens*, soybean looper |
| *Elasmopalpus lignosellus*, lesser cornstalk borer | *Anticarsia gemmatalis*, velvetbean caterpillar |
| *Feltia subterranea*, granulate cutworm | *Plathypena scabra*, green cloverworm |
| Wheat | *Ostrinia nubilalis*, European corn borer |
| *Pseudaletia unipunctata*, army worm | *Agrotis ipsilon*, black cutworm |
| *Spodoptera frugiperda*, fall armyworm | *Spodoptera exigua*, beet armyworm |
| *Elasmopalpus lignosellus*, lesser cornstalk borer | *Heliothis virescens*, cotton boll worm |
| | *Helicoverpa zea*, cotton bollworm |
| *Agrotis orthogonia*, pale western cutworm | Barley |
| *Elasmopalpus lignosellus*, lesser cornstalk borer | *Ostrinia nubilalis*, European corn borer |
| | *Agrotis ipsilon*, black cutworm |

TABLE 2

Coleoptera (Beetles)

Maize
*Diabrotica virgifera virgifera*, western corn rootworm
*Diabrotica longicornis barberi*, northern corn rootworm
*Diabrotica undecimpunctata howardi*, southern corn rootworm
Melanotus spp., wireworms
*Cyclocephala borealis*, northern masked chafer (white grub)
*Cyclocephala immaculata*, southern masked chafer (white grub)
*Popillia japonica*, Japanese beetle
*Chaetocnema pulicaria*, corn flea beetle
*Sphenophorus maidis*, maize billbug
Sorghum
*Phyllophaga crinita*, white grub
Eleodes, Conoderus, and Aeolus spp., wireworms
*Oulema melanopus*, cereal leaf beetle
*Chaetocnema pulicaria*, corn flea beetle
*Sphenophorus maidis*, maize billbug
Wheat
*Oulema melanopus*, cereal leaf beetle
*Hypera punctata*, clover leaf weevil
*Diabrotica undecimpunctata howardi*, southern corn rootworm
Sunflower
*Zygogramma exclamationis*, sunflower beetle
*Bothyrus gibbosus*, carrot beetle
Cotton
*Anthonomus grandis*, boll weevil
Rice
*Colaspis brunnea*, grape colaspis
*Lissorhoptrus oryzophilus*, rice water weevil
*Sitophilus oryzae*, rice weevil
Soybean
*Epilachna varivestis*, Mexican bean beetle

TABLE 3

Homoptera (Whiteflies, Aphids etc..)

Maize
*Rhopalosiphum maidis*, corn leaf aphid
*Anuraphis maidiradicis*, corn root aphid
Sorghum
*Rhopalosiphum maidis*, corn leaf aphid
*Sipha flava*, yellow sugarcane aphid
Wheat

TABLE 3-continued

Homoptera (Whiteflies, Aphids etc..)

Russian wheat aphid
*Schizaphis graminum*, greenbug
*Macrosiphum avenae*, English grain aphid
Cotton
*Aphis gossypii*, cotton aphid
*Pseudatomoscelis seriatus*, cotton fleahopper
*Trialeurodes abutilonea*, bandedwinged whitefly
Rice
*Nephotettix nigropictus*, rice leafhopper
Soybean
*Myzus persicae*, green peach aphid
*Empoasca fabae*, potato leafhopper
Barley
*Schizaphis graminum*, greenbug
Oil Seed Rape
*Brevicoryne brassicae*, cabbage aphid

TABLE 4

Hemiptera (Bugs)

Maize
*Blissus leucopterus leucopterus*, chinch bug
Sorghum
*Blissus leucopterus leucopterus*, chinch bug
Cotton
*Lygus lineolaris*, tarnished plant bug
Rice
*Blissus leucopterus leucopterus*, chinch bug
*Acrosternum hilare*, green stink bug
Soybean
*Acrosternum hilare*, green stink bug
Barley
*Blissus leucopterus leucopterus*, chinch bug
*Acrosternum hilare*, green stink bug
*Euschistus servus*, brown stink bug

TABLE 5

Orthoptera (Grasshoppers, Crickets, and Cockroaches)

Maize
*Melanoplus femurrubrum*, redlegged grasshopper
*Melanoplus sanguinipes*, migratory grasshopper
Wheat
*Melanoplus femurrubrum*, redlegged grasshopper
*Melanoplus differentialis*, differential grasshopper
*Melanoplus sanguinipes*, migratory grasshopper
Cotton
*Melanoplus femurrubrum*, redlegged grasshopper
*Melanoplus differentialis*, differential grasshopper
Soybean
*Melanoplus femurrubrum*, redlegged grasshopper
*Melanoplus differentialis*, differential grasshopper
Structural/Household
*Periplaneta americana*, American cockroach
*Blattella germanica*, German cockroach
*Blatta orientalis*, oriental cockroach

TABLE 6

Diptera (Flies and Mosquitoes)

Maize
*Hylemya platura*, seedcorn maggot
*Agromyza parvicornis*, corn blotch leafminer
Sorghum
*Contarinia sorghicola*, sorghum midge
Wheat
*Mayetiola destructor*, Hessian fly
*Sitodiplosis mosellana*, wheat midge
*Meromyza americana*, wheat stem maggot
*Hylemya coarctata*, wheat bulb fly
Sunflower
*Neolasioptera murtfeldtiana*, sunflower seed midge
Soybean
*Hylemya platura*, seedcorn maggot
Barley
*Hylemya platura*, seedcorn maggot
*Mayetiola destructor*, Hessian fly
Insects attacking humans and animals and disease carriers
*Aedes aegypti*, yellowfever mosquito
*Aedes albopictus*, forest day mosquito
*Phlebotomus papatasii*, sand fly
*Musca domestica*, house fly
*Tabanus atratus*, black horse fly
*Cochliomyia hominivorax*, screwworm fly

TABLE 7

Thysanoptera (Thrips)

Maize
*Anaphothrips obscurus*, grass thrips
Wheat
*Frankliniella fusca*, tobacco thrips
Cotton
*Thrips tabaci*, onion thrips
*Frankliniella fusca*, tobacco thrips
Soybean
*Sericothrips variabilis*, soybean thrips
*Thrips tabaci*, onion thrips

TABLE 8

Hymenoptera (Sawflies, Ants, Wasps, etc.)

Maize
*Solenopsis milesta*, thief ant
Wheat
*Cephus cinctus*, wheat stem sawfly

TABLE 9

Other Orders and Representative Species

Dermaptera (Earwigs)
*Forficula auricularia*, European earwig
Isoptera (Termites)
*Reticulitermes flavipes*, eastern subterranean termite
Mallophaga (Chewing Lice)
*Cuclotogaster heterographa*, chicken head louse
*Bovicola bovis*, cattle biting louse
Anoplura (Sucking Lice)
*Pediculus humanus*, head and body louse
Siphonaptera (Fleas)
*Ctenocephalides felis*, cat flea

TABLE 10

Acari (Mites and Ticks)

Maize
*Tetranychus urticae*, twospotted spider mite
Sorghum
*Tetranychus cinnabarinus*, carmine spider mite
*Tetranychus urticae*, twospotted spider mite
Wheat
*Aceria tulipae*, wheat curl mite
Cotton
*Tetranychus cinnabarinus*, carmine spider mite
*Tetranychus urticae*, twospotted spider mite
Soybean
*Tetranychus turkestani*, strawberry spider mite
*Tetranychus urticae*, twospotted spider mite
Barley
*Petrobia latens*, brown wheat mite
Important human and animal Acari
*Demacentor variabilis*, American dog tick
*Argas persicus*, fowl tick
*Dermatophagoides farinae*, American house dust mite
*Dermatophagoides pteronyssinus*, European house dust mite Now that it has been recognized that pesticidal proteins can be isolated from the vegetative growth phase of Bacillus, other strains can be isolated by standard techniques and tested for activity against particular plant and non-plant pests. Generally Bacillus strains can be isolated from any environmental sample, including soil, plant, insect, grain elevator dust, and other sample material, etc., by methods known in the art. See, for example, Travers et al. (1987) Appl. Environ. Microbiol. 53:1263–1266; Saleh et al. (1969) Can J. Microbiol. 15:1101–1104; DeLucca et al. (1981) Can. J. Microbiol. 27:865–870; and Norris, et al. (1981) "The genera Bacillus and Sporolactobacillus," In Starr et al. (eds.), The Prokaryotes: A Handbook on Habitats, Isolation, and Identification of Bacteria, Vol. II, Springer-Verlog Berlin Heidelberg. After isolation, strains can be tested for pesticidal activity during vegetative growth. In this manner, new pesticidal proteins and strains can be identified.

Such Bacillus microorganisms which find use in the invention include *Bacillus cereus* and *Bacillus thuringiensis*, as well as those Bacillus species listed in Table 11.

TABLE 11

List of Bacillus species

| Morphological Group 1 | Unassigned Strains |
|---|---|
| *B. megaterium* | Subgroup A |
| *B. cereus** | *B. apiarus** |
| *B. cereus* var. *mycoides* | *B. filicolonicus* |

TABLE 11-continued

List of Bacillus species

| | |
|---|---|
| B. thuringiensis* | B. thiaminolyticus |
| B. licheniformis | B. alcalophilus |
| B. subtilis* | Subgroup B |
| B. pumilus | B. cirroflagellosus |
| B. firmus* | B. chitinosporus |
| B. coagulans | B. lentus |
| Morphological Group 2 | Subgroup C |
| B. polymyxa | B. badius |
| B. macerans | B. aneurinolyticus |
| B. circulans | B. macroides |
| B. stearothermophilus | B. freundenreichii |
| B. alvei* | Subgroup D |
| B. laterosporus* | B. pantothenticus |
| B. brevis | B. epiphytus |
| B. pulvifaciens | Subgroup E1 |
| B. popilliae* | B. aminovorans |
| B. lentimorbus* | B. globisporus |
| B. larvae* | B. insolitus |
| Morphological Group 3 | B. psychrophilus |
| B. sphaericus* | Subgroup E2 |
| B. pasteurii | B. psychrosaccharolyticus |
| | B. macquariensis |

* = Those Bacillus strains that have been previously found associated with insects Grouping according to Parry, J. M. et al. (1983) Color Atlas of Bacillus species, Wolfe Medical Publications, London.

In accordance with the present invention, the pesticidal proteins produced during vegetative growth can be isolated from Bacillus. In one embodiment, insecticidal proteins produced during vegetative growth, can be isolated. Methods for protein isolation are known in the art. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example *Current Protocols in Molecular Biology*, Vols. 1 and 2, Ausubel et al. (eds.), John Wiley & Sons, N.Y. (1988). Additionally, antibodies can be prepared against substantially pure preparations of the protein. See, for example, Radka et al. (1983) *J. Immunol.* 128:2804; and Radka et al. (1984) *Immunogenetics* 19:63. Any combination of methods may be utilized to purify protein having pesticidal properties. As the protocol is being formulated, pesticidal activity is determined after each purification step.

Such purification steps will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) *J. Biol. Chem.* 257:9751–9758; Liu et al. (1983) *Int. J. Pept. Protein Res.* 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

It is recognized that the pesticidal proteins may be oligomeric and will vary in molecular weight, number of protomers, component peptides, activity against particular pests, and in other characteristics. However, by the methods set forth herein, proteins active against a variety of pests may be isolated and characterized.

Once the purified protein has been isolated and characterized it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component protomers, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the pesticidal protein. However, when it is difficult to predict the exact effect of the substitution, deletion, or insertion in advance of doing so, one skilled in the art will appreciate that the effect will be evaluated by routine screening assays.

The proteins or other component polypeptides described herein may be used alone or in combination. That is, several proteins may be used to control different insect pests.

Some proteins are single polypeptide chains while many proteins consist of more than one polypeptide chain, i.e., they are oligomeric. Additionally, some VIPs are pesticidally active as oligomers. In these instances, additional protomers are utilized to enhance the pesticidal activity or to activate pesticidal proteins. Those protomers which enhance or activate are referred to as auxiliary proteins. Auxiliary proteins activate or enhance a pesticidal protein by interacting with the pesticidal protein to form an oligomeric protein having increased pesticidal activity compared to that observed in the absence of the auxiliary protein.

Auxiliary proteins activate or increase the activity of pesticidal proteins such as the VIP1 protein from AB78. Such auxiliary proteins are exemplified by, but not limited to, the VIP2 protein from AB78. As demonstrated in the Experimental section of the application, auxiliary proteins can activate a number of pesticidal proteins. Thus, in one embodiment of the invention, a plant, Parent 1, can be transformed with an auxiliary protein. This Parent 1 can be crossed with a number of Parent 2 plants transformed with one or more pesticidal proteins whose pesticidal activities are activated by the auxiliary protein.

The pesticidal proteins of the invention can be used in combination with Bt endotoxins or other insecticidal proteins to increase insect target range. Furthermore, the use of the VIPs of the present invention in combination with Bt δ-endotoxins or other insecticidal principles of a distinct nature has particular utility for the prevention and/or management of insect resistance. Other insecticidal principles include protease inhibitors (both serine and cysteine types), lectins, α-amylase and peroxidase. In one preferred embodiment, expression of VIPs in a transgenic plant is accompanied by the expression of one or more Bt δ-endotoxins. This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of Bt δ-endotoxin. By crossing Parent 1 with Parent 2, progeny plants are obtained which express all the genes introduced into Parents 1 and 2. Particularly preferred Bt δ-endotoxins are those disclosed in U.S. Pat. No. 5,625,136, herein incorporated by reference.

A substantial number of cytotoxic proteins, though not all, are binary in action. Binary toxins typically consist of two protein domains, one called the A domain and the other called the B domain (see *Sourcebook of Bacterial Protein Toxins*, J. E. Alouf and J. H. Freer eds.(1991) Academic Press). The A domain possesses a potent cytotoxic activity. The B domain binds an external cell surface receptor before being internalized. Typically, the cytotoxic A domain must be escorted to the cytoplasm by a translocation domain. Often the A and B domains are separate polypeptides or protomers, which are associated by a protein-protein interaction or a di-sulfide bond. However, the toxin can be a single polypeptide which is proteolytically processed within the cell into two domains as in the case for Pseudomonas exotoxin A. In summary binary toxins typically have three important domains, a cytotoxic A domain, a receptor binding B domain and a translocation domain. The A and B domain are often associated by protein-protein interacting domains.

The receptor binding domains of the present invention are useful for delivering any protein, toxin, enzyme, transcription factor, nucleic acid, chemical or any other factor into target insects having a receptor recognized by the receptor binding domain of the binary toxins described in this patent. Similarly, since binary toxins have translocation domains which penetrate phosopholipid bilayer membranes and escort cytotoxins across those membranes, such translocation domains may be useful in escorting any protein, toxin, enzyme, transcription factor, nucleic acid, chemical or any other factor across a phospholipid bilayer such as the plasma membrane or a vesicle membrane. The translocation domain may itself perforate membranes, thus having toxic or insecticidal properties. Further, all binary toxins have cytotoxic domains; such a cytotoxic domain may be useful as a lethal protein, either alone or when delivered into any target cell(s) by any means.

Finally, since binary toxins comprised of two polypeptides often form a complex, it is likely that there are protein-protein interacting regions within the components of the binary toxins of the invention. These protein-protein interacting domains may be useful in forming associations between any combination of toxins, enzymes, transcription factors, nucleic acids, antibodies, cell binding moieties, or any other chemicals, factors, proteins or protein domains.

Toxins, enzymes, transcription factors, antibodies, cell binding moieties or other protein domains can be fused to pesticidal or auxiliary proteins by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

One strategy of altering pesticidal or auxiliary proteins is to fuse a 15-amino-acid "S-tag" to the protein without destroying the insect cell binding domain(s), translocation domains or protein-protein interacting domains of the proteins. The S-tag has a high affinity ($K_d=10^{-9}M$) for a ribonuclease S-protein, which, when bound to the S-tag, forms an active ribonuclease (See F. M. Richards and H. W. Wyckoff (1971) in "The Enzymes", Vol. IV (Boyer, P. D. ed.). pp. 647–806. Academic Press, New York). The fusion can be made in such a way as to destroy or remove the cytotoxic activity of the pesticidal or auxiliary protein, thereby replacing the VIP cytotoxic activity with a new cytotoxic ribonuclease activity. The final toxin would be comprised of the S-protein, a pesticidal protein and an auxiliary protein, where either the pesticidal protein or the auxiliary protein is produced as translational fusions with the S-tag. Similar strategies can be used to fuse other potential cytotoxins to pesticidal or auxiliary proteins including (but not limited to) ribosome inactivating proteins, insect hormones, hormone receptors, transcription factors, proteases, phosphatases, Pseudomonas exotoxin A, or any other protein or chemical factor that is lethal when delivered into cells. Similarly, proteins can be delivered into cells which are not lethal, but might alter cellular biochemistry or physiology.

The spectrum of toxicity toward different species can be altered by fusing domains to pesticidal or auxiliary proteins which recognize cell surface receptors from other species. Such domains might include (but are not limited to) antibodies, transferrin, hormones, or peptide sequences isolated from phage displayed affinity selectable libraries. Also, peptide sequences which are bound to nutrients, vitamins, hormones, or other chemicals that are transported into cells could be used to alter the spectrum of toxicity. Similarly, any other protein or chemical which binds a cell surface receptor or the membrane and could be internalized might be used to alter the spectrum of activity of VIP1 and VIP2.

The pesticidal proteins of the present invention are those proteins which confer a specific pesticidal property. Such proteins may vary in molecular weight, having component polypeptides at least a molecular weight of 30 kDa or greater, preferably about 50 kDa or greater.

The auxiliary proteins of the invention may vary in molecular weight, having at least a molecular weight of about 15 kDa or greater, preferably about 20 kDa or greater; more preferably, about 30 kDa or greater. The auxiliary proteins themselves may have component polypeptides.

It is possible that the pesticidal protein and the auxiliary protein may be components of a multimeric, pesticidal protein. Such a pesticidal protein which includes the auxiliary proteins as one or more of its component polypeptides may vary in molecular weight, having at least a molecular weight of 50 kDa up to at least 200 kDa, preferably about 100 kDa to 150 kDa.

An auxiliary protein may be used in combination with the pesticidal proteins of the invention to enhance activity or to activate the pesticidal protein. To determine whether the auxiliary protein will affect activity, the pesticidal protein can be expressed alone and in combination with the auxiliary protein and the respective activities compared in feeding assays for pesticidal activity.

It may be beneficial to screen strains for potential pesticidal activity by testing activity of the strain alone and in combination with the auxiliary protein. In some instances an auxiliary protein in combination with the native proteins of the strains yields pesticidal activity where none is seen in the absence of an auxiliary protein.

The auxiliary protein can be modified, as described above, by various methods known in the art. Therefore, for purposes of the invention, the term "Vegetative Insecticidal Protein" (VIP) encompasses those proteins produced during vegetative growth which alone or in combination can be used for pesticidal activity. This includes pesticidal proteins, auxiliary proteins and those proteins which demonstrate activity only in the presence of the auxiliary protein or the polypeptide components of these proteins.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones which express an active pesticidal protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

The present invention also encompasses nucleotide sequences from organisms other than Bacillus, where the nucleotide sequences are isolatable by hybridization with the Bacillus nucleotide sequences of the invention. Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or others well-known in the art.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example U.S. Pat. No. 5,625,136; EPA 0359472; EPA 0385962; WO 91/16432; Perlak et al. (1991) Proc. Natl. Acad. Sci. USA 88:3324–3328; and Murray et al. (1989) Nucleic Acids Research 17:477–498. In this manner, the genes can be synthesized utilizing plant preferred codons. That is the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray et al. (1989), Nucleic Acids Research 17:477–498, the disclosure of which is incorporated herein by reference. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, synthetic or partially optimized sequences may also be used.

In like manner, the nucleotide sequences can be optimized for expression in any microorganism. For Bacillus preferred codon usage, see, for example U.S. Pat. No. 5,024,837 and Johansen et al. (1988) Gene 65:293–304.

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP genes can be used in expression cassettes.

Generally, for the introduction of foreign DNA into plants Ti plasmid vectors have been utilized for the delivery of foreign DNA as well as direct DNA uptake, liposomes, electroporation, micro-injection, and the use of microprojectiles. Such methods had been published in the art. See, for example, Guerche et al., (1987) Plant Science 52:111–116; Neuhause et al., (1987) Theor. App. Genet. 75:30–36; Klein et al., (1987) Nature 327: 70–73; Howell et al., (1980) Science 208:1265; Horsch et al., (1985) Science 227: 1229–1231; DeBlock et al., (1989) Plant Physiology 91:694–701; Methods for Plant Molecular Biology (Weissbach and Weissbach, eds.) Academic Press, Inc. (1988); and Methods in Plant Molecular Biology (Schuler and Zielinski, eds.) Academic Press, Inc. (1989). See also U.S. patent application Ser. No. 08/008,374 herein incorporated by reference. See also, EPA 0193259 and EPA 0451878A1. It is understood that the method of transformation will depend upon the plant cell to be transformed.

It is further recognized that the components of the expression cassette may be modified to increase expression. For example, truncated sequences, nucleotide substitutions or other modifications may be employed. See, for example Perlak et al. (1991) Proc. Natl. Acad. Sci. USA 88:3324–3328; Murray et al., (1989) Nucleic Acids Research 17:477–498; and WO 91/16432.

The construct may also include any other necessary regulators such as terminators, (Guerineau et al., (1991), Mol. Gen. Genet., 226:141–144; Proudfoot, (1991), Cell, 64:671–674; Sanfacon et al., (1991), Genes Dev., 5:141–149; Mogen et al., (1990), *Plant Cell*, 2:1261–1272; Munroe et al., (1990), *Gene*, 91:151–158; Ballas et al et al., (1989), *Nucleic Acids Res.*, 17:7891–7903; Joshi et al., (1987), *Nucleic Acid Res.*, 15:9627–9639); plant translational consensus sequences (Joshi, C. P., (1987), *Nucleic Acids Research*, 15:6643–6653), introns (Luehrsen and Walbot, (1991), *Mol. Gen. Genet.*, 225:81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (encephalomyocarditis 5' noncoding region) (Elroy-Stein, O., Fuerst, T. R., and Moss, B. (1989) *PNAS USA* 86:6126–6130);

Potyvirus leaders, for example, TEV leader (Tobacco Etch Virus) (Allison et al., (1986); MDMV leader (Maize Dwarf Mosaic Virus); *Virology*, 154:9–20), and Human inmunoglobulin heavy-chain binding protein (BiP), (Macejak, D. G., and Sarnow, P., (1991), *Nature*, 353:90–94;

Untranslated leader from the coat protein MRNA of alfalfa mosaic virus (AMV RNA 4), (Jobling, S. A., and Gehrke, L., (1987), *Nature*, 325:622–625;

Tobacco mosaic virus leader (TMV), (Gallie, D. R. et al., (1989), *Molecular Biology of RNA* pages 237–256; and Maize Chlorotic Mottle Virus leader (MCMV) (Lommel, S. A. et al., (1991), *Virology*, 81:382–385. See also, Della-Cioppa et al., (1987), *Plant Physiology*, 84:965–968.

A plant terminator may be utilized in the expression cassette. See, Rosenberg et al., (1987), *Gene*, 56:125; Guerineau et al., (1991), *Mol. Gen. Genet.*, 226:141–144; Proudfoot, (1991), *Cell*, 64:671–674; Sanfacon et al., (1991), *Genes Dev.*, 5:141–149: Mogen et al., (1990), *Plant Cell*, 2:1261–1272; Munroe et al., (1990), *Gene*, 91:151–158: Ballas et al., (1989), *Nucleic Acids Res.*, 17:7891–7903; Joshi et al., (1987), *Nucleic Acid Res.*, 15:9627–9639.

For tissue specific expression, the nucleotide sequences of the invention can be operably linked to tissue specific promoters. See, for example, U.S. Pat. No. 5,625,136 herein incorporated by reference.

It is recognized that the genes encoding the pesticidal proteins can be used to transform insect pathogenic organisms. Such organisms include Baculoviruses, fingi, protozoa, bacteria and nematodes.

The Bacillus strains of the invention may be used for protecting agricultural crops and products from pests. Alternatively, a gene encoding the pesticide may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfullly competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonasfluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pollulans*. Of particular interest are the pigmented microorganisms.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is finctional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such a Saccharomyces and Schizosaccharromyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula sp., Aureobasidium sp., Saccharomyces sp.,* and *Sporobolomyces sp.*; phylloplane organisms such as *Pseudomonas sp., Erwinia sp.* and *Flavobacterium sp.*; or such other organisms as Escherichia, *LactoBacillus sp., Bacillus sp.,* and the like. Specific organisms include *Pseudomonas aeurginosa, Pseudomonasfluorescens, Saccharomyces cerevisiae, Bacillus thuringiensis, Escherichia coli, Bacillus subtilis,* and the like.

VIP genes can be introduced into micro-organisms that multiply on plants (epiphytes) to deliver VIP proteins to potential target pests. Epiphytes can be gram-positive or gram-negative bacteria for example.

Root colonizing bacteria, for example, can be isolated from the plant of interest by methods known in the art. Specifically, a *Bacillus cereus* strain which colonizes roots could be isolated from roots of a plant (for example see J. Handelsman, S. Raffel, E. Mester, L. Wunderlich and C. Grau, *Appl. Environ. Microbiol.* 56:713–718, (1990)). VIP1 and/or VIP2 could be introduced into a root colonizing *Bacillus cereus* by standard methods known in the art.

Specifically, VIP1 and/or VIP2 derived from *Bacillus cereus* strain AB78 can be introduced into a root colonizing *Bacillus cereus* by means of conjugation using standard methods (J. Gonzalez, B. Brown and B. Carlton, *Proc. Natl. Acad. Sci.* 79:6951–6955, (1982)).

Also, VIP1 and/or VIP2 or other VIPs of the invention can be introduced into the root colonizing Bacillus by means of electro-transformation. Specifically, VIPs can be cloned into a shuttle vector, for example, pHT3101 (D. Lereclus et al., *FEMS Microbiol. Letts.*, 60:211–218 (1989)) as described in Example 10. The shuttle vector pHT3101 containing the coding sequence for the particular VIP can then be transformed into the root colonizing Bacillus by means of electroporation (D. Lereclus et al. 1989,*FEMS Microbiol. Letts.* 60:211–218).

Expression systems can be designed so that VIP proteins are secreted outside the cytoplasm of gram negative bacteria, *E. coli*, for example. Advantages of having VIP proteins secreted are (1) it avoids potential toxic effects of VIP proteins expressed within the cytoplasm and (2) it can increase the level of VIP protein expressed and (3) can aid in efficient purification of VIP protein.

VIP proteins can be made to be secreted in *E. coli*, for example, by fusing an appropriate *E. coli* signal peptide to the amino-terminal end of the VIP signal peptide or replacing the VIP signal peptide with the *E. coli* signal peptide. Signal peptides recognized by *E. coli* can be found in proteins already known to be secreted in *E. coli*, for example the OmpA protein (J. Ghrayeb, H. Kimura, M. Takahara, Y. Masui and M. Inouye, *EMBO J.*, 3:2437–2442 (1984)). OmpA is a major protein of the *E. coli* outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, *Methods in Enzymology.* 153:492 (1987)).

Specifically, unique BamHI restriction sites can be introduced at the amino-terminal and carboxy-terminal ends of the VIP coding sequences using standard methods known in the art. These BamHI fragments can be cloned, in frame, into the vector pIN-III-ompA1, A2 or A3 (J. Ghrayeb, H. Kimura, M. Takahara, H. Hsiung, Y. Masui and M. Inouye, *EMBO J.*, 3:2437–2442 (1984)) thereby creating ompA:VIP fusion gene which is secreted into the periplasmic space. The other restriction sites in the polylinker of pIN-III-ompA can be eliminated by standard methods known in the art so that the VIP amino-terminal amino acid coding sequence is directly after the ompA signal peptide cleavage site. Thus, the secreted VIP sequence in *E. coli* would then be identical to the native VIP sequence.

When the VIP native signal peptide is not needed for proper folding of the mature protein, such signal sequences can be removed and replaced with the ompA signal sequence. Unique BamHI restriction sites can be introduced at the amino-termini of the proprotein coding sequences directly after the signal peptide coding sequences of VIP and at the carboxy-termini of VIP coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIPs can be fermented in a bacterial host and the resulting bacteria processed and used as a microbial spray in the same manner that *Bacillus thuringiensis* strains have been used as insecticidal sprays. In the case of a VIP(s) which is secreted from Bacillus, the secretion signal is removed or mutated using procedures known in the art. Such mutations and/or deletions prevent secretion of the VIP protein(s) into the growth medium during the fermentation process. The VIPs are retained within the cell and the cells are then processed to yield the encapsulated VIPs. Any suitable microorganism can be used for this purpose. Psuedomonas has been used to express *Bacillus thuringiensis* endotoxins as encapsulated proteins and the resulting cells processed and sprayed as an insecticide. (H. Gaertner et al. 1993, In Advanced Engineered Pesticides, L. Kim ed.)

Various strains of *Bacillus thuringiensis* are used in this manner. Such *Bt* strains produce endotoxin protein(s) as well as VIPs. Alternatively, such strains can produce only VIPs. A sporulation deficient strain of *Bacillus subtilis* has been shown to produce high levels of the CryIIIA endotoxin from *Bacillus thuringiensis* (Agaisse, H. and Lereclus, D., "Expression in *Bacillus subtilis* of the *Bacillus thuringiensis* CryIIIA toxin gene is not dependent on a sporulation-specific sigma factor and is increased in a spoOA mutant", *J. Bacteriol.*, 176:4734–4741 (1994)). A similar spoOA mutant can be prepared in *Bacillus thuringiensis* and used to produce encapsulated VIPs which are not secreted into the medium but are retained within the cell.

To have VIPs maintained within the Bacillus cell the signal peptide can be disarmed so that it no longer functions as a secretion signal. Specifically, the putative signal peptide for VIP1 encompasses the first 31 amino acids of the protein with the putative consensus cleavage site, Ala-X-Ala, at the C-terminal portion of this sequence (G. von Heijne ,*J. Mol. Biol.* 184:99–105 (1989)) and the putative signal peptide for VIP2 encompasses the first 40 amino acids of the protein with the putative cleavage site after Ala40. The cleavage sites in either VIP1 or VIP2 can be mutated with methods known in the art to replace the cleavage site consensus sequence with alternative amino acids that are not recognized by the signal peptidases.

Alternatively, the signal peptides of VIP1, VIP2 and/or other VIPs of the invention can be eliminated from the sequence thereby making them unrecognizable as secretion proteins in Bacillus. Specifically, a methionine start site can be engineered in front of the proprotein sequence in VIP1, starting at Asp32, or the proprotein sequence in VIP2, starting at Glu41 using methods known in the art.

VIP genes can be introduced into micro-organisms that mutiply on plants (epiphytes) to deliver VIP proteins to potential target pests. Epiphytes can be gram-positive or gram-negative bacteria for example.

The Bacillus strains of the invention or the microorganisms which have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

In one embodiment of the invention a *Bacillus cereus* microorganism has been isolated which is capable of killing *Diabrotica virgifera virgifera*, and *Diabrotica longicornis barberi*. The novel *B. cereus* strain AB78 has been deposited in the Agricultural Research Service, Patent Culture Collection (NRRL), Northern Regional Research Center, 1815 North University Street, Peoria, Ill. 61604, USA and given Accession No. NRRL B-21058.

A fraction protein has been substantially purified from the *B. cereus* strain. This purification of the protein has been verified by SDS-PAGE and biological activity. The protein has a molecular weight of about 60 to about 100 kDa, particularly about 70 to about 90 kDa, more particularly about 80 kDa, hereinafter VIP.

Amino-terminal sequencing has revealed the N-terminal amino-acid sequence to be:

NH$_2$-Lys-Arg-Glu-Ile-Asp-Glu-Asp-Thr-Asp-Thr-Asx-Gly-Asp-Ser-Ile-Pro-  (SEQ ID NO:8)

where Asx represents either Asp or Asn. The entire amino acid sequence is given in SEQ ID NO:7. The DNA sequence which encodes the amino acid sequence of SEQ ID NO:7 is disclosed in SEQ ID NO:6.

An oligonucleotide probe for the region of the gene encoding amino acids 3–9 of the NH$_2$-terminus has been generated. The probe was synthesized based on the codon usage of a *Bacillus thuringiensis* (*Bt*) δ-endotoxin gene. The nucleotide sequence of the oligonucleotide probe used for Southern hybridizations was as follows:

5'-GAA ATT GAT CAA GAT ACN GAT-3'   (SEQ ID NO:9)

where N represents any base.

In addition, the DNA probe for the Bc AB78 VIP1 gene described herein, permits the screening of any Bacillus strain or other organisms to determine whether the VIP1 gene (or related gene) is naturally present or whether a particular transformed organism includes the VIP1 gene.

The invention now being generally described, the same will be better understood by reference to the following detailed examples that are provided for the purpose of illustration and are not to be considered limiting of the invention unless so specified.

A standard nomenclature has been developed based on the sequence identity of the proteins encompassed by the present invention. The gene and protein names for the detailed examples which follow and their relationship to the names used in the parent application are shown below.

| Gene/Protein Name under Standard Nomenclature | Gene/Protein Name in Parent | Description of Protein |
| --- | --- | --- |
| VIP1A(a) | VIP1 | VIP1 from strain AB78 as disclosed in SEQ ID NO: 5. |
| VIP2A(a) | VIP2 | VIP2 from strain AB78 as disclosed in SEQ ID NO: 2. |
| VIP1A(b) | VIP1 homolog | VIP1 from *Bacillus thuringiensis* var. *tenebrionis* as disclosed in SEQ ID NO: 21. |
| VIP2A(b) | VIP2 homolog | VIP2 from *Bacillus thuringiensis* var. *tenebrionis* as disclosed in SEQ ID NO: 20. |
| VIP3A(a) | — | VIP from strain AB88 as disclosed in SEQ ID NO: 28 of the present application |
| VIP3A(b) | — | VIP from strain AB424 as disclosed in SEQ ID NO: 31 of the present application |

EXPERIMENTAL

Example 1

AB78 Isolation and Characterization

*Bacillus cereus* strain AB78 was isolated as a plate contaminant in the laboratory on T3 media (per liter: 3 g tryptone, 2 g tryptose, 1.5 g yeast extract, 0.05M sodium phosphate (pH 6.8), and 0.005 g $MnCl_2$; Travers, R. S. 1983). During log phase growth, AB78 gave significant activity against western corn rootworm. Antibiotic activity against gram-positive *Bacillus spp.* was also demonstrated (Table 12).

TABLE 12

Antibiotic activity of AB78 culture supernatant

| Bacteria tested | Zone of inhibition (cm) | |
|---|---|---|
| | AB78 | Streptomycin |
| E. coli | 0.0 | 3.0 |
| B. megaterium | 1.1 | 2.2 |
| B. mycoides | 1.3 | 2.1 |
| B. cereus CB | 1.0 | 2.0 |
| B. cereus 11950 | 1.3 | 2.1 |
| B. cereus 14579 | 1.0 | 2.4 |
| B. cereus AB78 | 0.0 | 2.2 |
| Bt var. israelensis | 1.1 | 2.2 |
| Bt var. tenebrionis | 0.9 | 2.3 |

Morphological characteristics of AB78 are as follows:

Vegetative rods straight, 3.1–5.0 mm long and 0.5–2.0 mm wide. Cells with rounded ends, single in short chains. Single subterminal, cylindrical-oval, endospore formed per cell. No parasporal crystal formed. Colonies opaque, erose, lobate and flat. No pigments produced. Cells motile. Flagella present.

Growth characteristics of AB78 are as follows:

Facultative anaerobe with optimum growth temperature of 21°–30° C. Will grow at 15°, 20°, 25°, 30° and 37° C. Will not grow above 40° C. Grows in 5–7% NaCl. Table 13 provides the biochemical profile of AB78.

TABLE 13

Biochemical characteristics of *B. cereus* strain AB78.

| | | | |
|---|---|---|---|
| Acid from L-arabinose | − | Methylene blue reoxidized | + |
| Gas from L-arabinose | − | Nitrate reduced | + |
| Acid from D-xylose | − | $NO_3$ reduced to $NO_2$ | + |
| Gas from D-xylose | − | VP | + |
| Acid from D-glucose | + | $H_2O_2$ decomposed | + |
| Gas from D-glucose | − | Indole | − |
| Acid from lactose | − | Tyrosine decomposed | + |
| Gas from lactose | − | Dihydroxiacetone | − |
| Acid from sucrose | − | Litmus milk acid | − |
| Gas from sucrose | − | Litmus milk coagulated | − |
| Acid from D-mannitol | − | Litmus milk alkaline | − |
| Gas from D-mannitol | − | Litmus milk peptonized | − |
| Proprionate utilization | + | Litmus milk reduced | − |
| Citrate utilization | + | Casein hydrolyzed | + |
| Hippurate hydrolysis | w | Starch hydrolyzed | + |
| Methylene blue reduced | + | Gelatin liquidified | + |
| | | Lecithinase produced | w | w = weak reaction

Example 2

Bacterial Culture

A subculture of *Bc* strain AB78 was used to inoculate the following medium, known as TB broth:

| | |
|---|---|
| Tryptone | 12 g/l |
| Yeast Extract | 24 g/l |
| Glycerol | 4 ml/l |

-continued

| | |
|---|---|
| $KH_2PO_4$ | 2.1 g/l |
| $K_2HPO_4$ | 14.7 g/l |
| pH 7.4 | |

The potassium phosphate was added to the autoclaved broth after cooling. Flasks were incubated at 30° C. on a rotary shaker at 250 rpm for 24 h.–36 h, which represents an early to mid-log growth phase.

The above procedure can be readily scaled up to large fermentors by procedures well known in the art.

During vegetative growth, usually 24–36 h. after starting the culture, which represents an early to mid-log growth phase, AB78 bacteria were centrifuged from the culture supernatant. The culture supernatant containing the active protein was used in bioassays.

Example 3

Insect Bioassays

*B. cereus* strain AB78 was tested against various insects as described below.

Western, Northern and Southern corn rootworm, *Diabrotica virgifera virgifera, D. longcornis barberi* and *D. undecempunctata howardi*, respectively: dilutions were made of AB78 culture supernatant grown 24–36 h., mixed with molten artificial diet (Marrone et al. (1985) *J. of Economic Entomology* 78:290–293) and allowed to solidify. Solidified diet was cut and placed in dishes. Neonate larvae were placed on the diet and held at 30° C. Mortality was recorded after 6 days.

*E. coli clone bioassay: E. coli* cells were grown overnight in broth containing 100 μg/ml ampicillin at 37° C. Ten ml culture was sonicated 3× for 20 sec each. 500 μl of sonicated culture was added to molten western corn rootworm diet.

Colorado potato beetle, *Leptinotarsa decemlineata*: dilutions in Triton X-100 (to give final concentration of 0.1% TX-100) were made of AB78 culture supernatant grown 24–36 h. Five $cm^2$ potato leaf pieces were dipped into these dilutions, air dried, and placed on moistened filter paper in plastic dishes. Neonate larvae were placed on the leaf pieces and held at 30° C. Mortality was recorded after 3–5 days.

Yellow mealworm, *Tenebrio molitor*: dilutions were made of AB78 culture supernatant grown 24–36 h., mixed with molten artificial diet (Bioserv #F9240) and allowed to solidify. Solidified diet was cut and placed in plastic dishes. Neonate larvae were placed on the diet and held at 30° C. Mortality was recorded after 6–8 days.

European corn borer, black cutworm, tobacco budworm, tobacco hornworm and beet armyworm; *Ostrinia nubilalis, Agrotis ipsilon, Heliothis virescens, Manduca sexta* and *Spodoptera exigua*, respectively: dilutions, in TX-100 (to give final concentration of 0.1% TX-100), were made of AB78 culture supernatant grown 24–36 hrs. 100 μl was pipetted onto the surface of 18 $cm^2$ of solidified artificial diet (Bioserv #F9240) and allowed to air dry. Neonate larvae were then placed onto the surface of the diet and held at 30° C. Mortality was recorded after 3–6 days.

Northern house mosquito, *Culex pipiens*:-dilutions were made of AB78 culture supernatant grown 24–36 h. 100 μl was pipetted into 10 ml water in a 30 ml plastic cup. Third instar larvae were added to the water and held at room temperature. Mortality was recorded after 24–48 hours. The spectrum of entomocidal activity of AB78 is given in Table 14.

TABLE 14

Activity of AB78 culture supernatant against various insect species

| Insect species tested to date | Order | Activity |
|---|---|---|
| Western corn rootworm (*Diabrotica virgifera virgifera*) | Col | +++ |
| Northern corn rootworm (*Diabrotica longicornis barberi*) | Col | +++ |
| Southern corn rootworm (*Diabrotica undecimpunctata howardi*) | Col | – |
| Colorado potato beetle (*Leptinotarsa decemlineata*) | Col | – |
| Yellow mealworm (*Tenebrio molitor*) | Col | – |
| European corn borer (*Ostrinia nubilalis*) | Lep | – |
| Tobacco budworm (*Heliothis virescens*) | Lep | – |
| Tobacco hornworm (*Manduca sexta*) | Lep | – |
| Beet armyworm (*Spodoptera exigua*) | Lep | – |
| Black cutworm (*Agrotis ipsilon*) | Lep | – |
| Northern house mosquito (*Culex pipiens*) | Dip | – |

The newly discovered *B. cereus* strain AB78 showed a significantly different spectrum of insecticidal activity as compared to known coleopteran active δ-endotoxins from *Bt*. In particular, AB78 showed more selective activity against beetles than known coleopteran-active *Bt* strains in that it was specifically active against *Diabrotica spp*. More specifically, it was most active against *D. virgifera virgifera* and *D. longicornis barberi* but not *D. undecimpunctata howardi*.

A number of Bacillus strains were bioassayed for activity during vegetative growth (Table 15) against western corn rootworm. The results demonstrate that AB78 is unique in that activity against western corn rootworm is not a general phenomenon.

TABLE 15

Activity of culture supernatants from various Bacillus spp. against western corn rootworm

| Bacillus strain | Percent WCRW mortality |
|---|---|
| *B. cereus* AB78 (Bat. 1) | 100 |
| *B. cereus* AB78 (Bat. 2) | 100 |
| *B. cereus* (Carolina Bio.) | 12 |
| *B. cereus* ATCC 11950 | 12 |
| *B. cereus* ATCC 14579 | 8 |
| *B. mycoides* (Carolina Bio.) | 30 |
| *B. popilliae* | 28 |
| *B. thuringiensis* HD135 | 41 |
| *B. thuringiensis* HD191 | 9 |
| *B. thuringiensis* GC91 | 4 |
| *B. thuringiensis* isrealensis | 24 |
| Water Control | 4 |

Specific activity of AB78 against western corn rootworm is provided in Table 16.

TABLE 16

Activity of AB78 culture supernatant against neonate western corn rootworm

| Culture supernatant concentration (µl/ml) | Percent WCRW mortality |
|---|---|
| 100 | 100 |
| 25 | 87 |
| 10 | 80 |
| 5 | 40 |
| 2.5 | 20 |
| 1 | 6 |
| 0 | 0 |

The $LC_{50}$ was calculated to be 6.2 µl of culture supernatant per ml of western corn rootworm diet.

The cell pellet was also bioassayed and had no activity against WCRW. Thus, the presence of activity only in the supernatant indicates that this VIP is an exotoxin.

Example 4

Isolation and Purification of Corn Rootworm Active Proteins from AB78.

Culture media free of cells and debris was made to 70% saturation by the addition of solid ammonium sulfate (472 g/L). Dissolution was at room temperature followed by cooling in an ice bath and centrifugation at 10,000×g for thirty minutes to pellet the precipitated proteins. The supernatant was discarded and the pellet was dissolved in 1/10 the original volume of 20 mM TRIS-HCl at pH 7.5. The dissolved pellet was desalted either by dialysis in 20 mM TRIS-HCl pH 7.5, or passing through a desalting column.

The desalted material was titrated to pH 3.5 using 20 mM sodium citrate pH 2.5. Following a thirty minute room temperature incubation the solution was centrifuged at 3000×g for ten minutes. The supernatant at this stage contained the greatest amount of active protein.

Following neutralization of the pH to 7.0 the supernatant was applied to a Mono-Q, anion exchange, column equilibrated with 20 mM TRIS pH 7.5 at a flow rate of 300 mL/min. The column was developed with a stepwise and linear gradient employing 400 mM NaCl in 20 mM TRIS pH 7.5.

Bioassay of the column fractions and SDS-PAGE analysis were used to confirm the active fractions. SDS-PAGE analysis identified the biologically active protein as having components of a molecular weight in the range of about 80 kDa and 50 kDa.

Example 5

Sequence Analysis of the Corn Rootworm Active Protein

The 80 kDa component isolated by SDS-PAGE was transferred to PVDF membrane and was subjected to amino-terminal sequencing as performed by repetitive Edman cycles on an ABI 470 pulsed-liquid sequencer. Transfer was carried out in 10 mM CAPS buffer with 10% methanol pH 11.0 as follows:

Incubation of the gel following electrophoresis was done in transfer buffer for five minutes. ProBlott PVDF membrane was wetted with 100% MeOH briefly then equilibrated in transfer buffer. The sandwich was arranged between foam sponges and filter paper squares with the configuration of cathode-gel-membrane-anode.

Transfer was performed at 70 V constant voltage for 1 hour.

Following transfer, the membrane was rinsed with water and stained for two minutes with 0.25% Coomassie Blue R-250 in 50% MeOH.

Destaining was done with several rinses with 50% MeOH 40% water 10% acetic acid.

Following destaining the membrane was air dried prior to excision of the bands for sequence analysis. A BlottCartridge and appropriate cycles were utilized to achieve maximum efficiency and yield. Data analysis was performed using model 610 Sequence Analysis software for identifying and quantifying the PTH-amino acid derivatives for each sequential cycle.

The N-terminal sequence was determined to be: NH2-Lys-Arg-Glu-Ile-Asp-Glu-Asp-Thr-Asp-Thr-Asx-Gly-Asp-Ser-Ile-Pro-(SEQ ID NO:8) where Asx represents Asp or Asn. The complete amino acid sequence for the 80 kDa component is disclosed in SEQ ID NO:7. The DNA sequence which encodes SEQ ID NO:7 is disclosed in SEQ ID NO:6.

Example 6

Construction of DNA Probe

An oligonucleotide probe for the region of the gene encoding amino acids 3–9 of the N-terminal sequence (Example 5) was generated. The probe was synthesized based on the codon usage of a *Bacillus thuringiensis* (*Bt*) δ-endotoxin gene. The nucleotide sequence

5'-GAA ATT GAT CAA GAT ACN GAT-3'     (SEQ ID NO:9)

was used as a probe in Southern hybridizations. The oligonucleotide was synthesized using standard procedures and equipment.

Example 7

Isoelectric Point Determination of the Corn Rootworm Active Protein

Purified protein from step 5 of the purification process was analyzed on a 3–9 pI isoelectric focusing gel using the Phastgel electrophoresis system (Pharmacia). Standard operating procedures for the unit were followed for both the separation and silver staining development procedures. The pI was approximated at about 4.9.

Example 8

PCR Data on AB78

PCR analysis (See, for example U.S. patent application Ser. No. 08/008,006; and, Carozzi et al. (1991) *Appl. Environ. Microbiol.* 57(11):3057–3061, herein incorporated by reference.) was used to verify that the *B. cereus* strain AB78 did not contain any insecticidal crystal protein genes of *B. thuringiensis* or *B. sphaericus* (Table 17).

TABLE 17

Bacillus insecticidal crystal protein gene primers tested by PCR against AB78 DNA.

| Primers Tested | Product Produced |
| --- | --- |
| 2 sets specific for CryIIIA | Negative |
| CryIIIB | Negative |
| 2 sets specific for CryIA | Negative |
| CryIA(a) | Negative |
| CryIA(b) specific | Negative |
| CryIB | Negative |
| CryIC specific | Negative |
| CryIE specific | Negative |
| 2 sets specific for *B. sphaericus* | Negative |
| 2 sets specific for CryIV | Negative |
| Bacillus control (PI-PLC) | Positive |

Example 9

Cosmid Cloning of Total DNA from *B. cereus* Strain AB78

The VIP1A(a) gene was cloned from total DNA prepared from strain AB78 as follows:

Isolation of AB78 DNA was as follows:
1. Grow bacteria in 10 ml L-broth overnight. (Use 50 ml sterile centrifuge tube)
2. Add 25 ml of fresh L-broth and ampicillin (30 μg/ml).
3. Grow cells 2–6 h. at 30° C. with shaking.
4. Spin cells in a 50 ml polypropylene orange cap tube in IEC benchtop clinical centrifuge at ¾ speed.
5. Resuspend cell pellet in 10 ml TES (TES=50 mM TRIS pH 8.0, 100 mM EDTA, 15 mM NaCl).
6. Add 30 mg lysozyme and incubate 2 hrs at 37° C.
7. Add 200 μl 20% SDS and 400 μl Proteinase K stock (20 mg/ml). Incubate at 37° C.
8. Add 200 μl fresh Proteinase K. Incubate 1 hr. at 55° C. Add 5 ml TES to make 15 ml final volume.
9. Phenol extract twice (10 ml phenol, spin at room temperature at ¾ speed in an IEC benchtop clinical centrifuge). Transfer supernatant (upper phase) to a clean tube using a wide bore pipette.
10. Extract once with 1:1 vol. phenol:chloroform/isoamyl alcohol (24:1 ratio).
11. Precipitate DNA with an equal volume of cold isopropanol; Centrifuge to pellet DNA.
12. Resuspend pellet in 5 ml TE.
13. Precipitate DNA with 0.5 ml 3M NaOAc pH 5.2 and 11 ml 95% ethanol. Place at −20° C. for 2 h.
14. "Hook" DNA from tube with a plastic loop, transfer to a microfuge tube, spin, pipette off excess ethanol, dry in vacuo.
15. Resuspend in 0.5 ml TE. Incubate 90 min. at 65° C. to help get DNA back into solution.
16. Determine concentration using standard procedures.

Cosmid Cloning of AB78

All procedures, unless indicated otherwise, were performed according to Stratagene Protocol, Supercos 1 Instruction Manual, Cat. No. 251301.

Generally, the steps were as follows:
A. Sau 3A partial digestion of the AB78 DNA.
B. Preparation of vector DNA
C. Ligation and packaging of DNA
D. Tittering the cosmid library
   1. Start a culture of HB101 cells by placing 50 ml of an overnight culture in 5 mls of TB with 0.2% maltose. Incubate 3.5 hrs. at 37° C.

2. Spin out cells and resuspend in 0.5 ml 10 mM MgSO$_4$.
3. Add together:
   100 μl cells
   100 μl diluted packaging mixture
   100 μl 10 mM MgSO$_4$
   30 μl TB
4. Adsorb at room temperature for 30 minutes with no shaking.
5. Add 1 ml TB and mix gently. Incubate 30 minutes at 37° C.
6. Plate 200 μl onto L-amp plates. Incubate at 37° C. overnight.

At least 400 cosmid clones were selected at random and screened for activity against western corn rootworm as described in Example 3. DNA from 5 active clones and 5 non-active clones were used in Southern hybridizations. Results demonstrated that hybridization using the above described oligonucleotide probe correlated with western corn rootworm activity (Table 18).

Cosmid clones P3-12 and P5-4 have been deposited with the Agricultural Research Service Patent Culture Collection (NRRL) and given Accession Nos. NRRL B-21061 and NRRL B-21059 respectively.

TABLE 18

Activity of AB78 cosmid clones against western corn rootworm.

| Clone | Mean percent mortality (N = 4) |
|---|---|
| Clones which hybridize with probe | |
| P1-73 | 47 |
| P1-83 | 64 |
| P2-2 | 69 |
| P3-12 | 85 |
| P5-4 | 97 |
| Clones which do not hybridize with probe | |
| P1-2 | 5 |
| P3-8 | 4 |
| P3-9 | 12 |
| P3-18 | 0 |
| P4-6 | 9 |

Example 10

Identification of a 6 KB Region Active Against Western Corn Rootworm.

DNA from P3-12 was partially digested with restriction enzyme Sau 3A, and ligated into the E. coli vector pUC19 and transformed into E. coli. A DNA probe specific for the 80 kDa VIP1A(a) protein was synthesized by PCR amplification of a portion of P3-12 DNA. Oligonucleotides MK113 and MK117, which hybridize to portions of VIP1A(a), were synthesized using the partial amino acid sequence of the 80 kDa protein. Plasmid subclones were identified by colony hybridization to the PCR-generated probe, and tested for activity against western corn rootworm. One such clone, PL2, hybridized to the PCR-generated fragment, and was active against western corn rootworm in the assay previously described.

A 6 kb Cla I restriction fragment from pL2 was cloned into the Sma I site of the E. coli-Bacillus shuttle vector pHT 3101 (Lereclus, D. et al., FEMS Microbiology Letters 60:211–218 (1989)) to yield pCIB6201. This construct confers anti-western corn rootworm activity upon both Bacillus and E.coli strains, in either orientation. pCIB6022 contains this same 6 kb Cla I fragment in pBluescript SK(+) (Stratagene), produces equivalent VIP1A(a) protein (by western blot), and is also active against western corn rootworm.

The nucleotide sequence of pCIB6022 was determined by the dideoxy termination method of Sanger et al., Proc. Natl. Acad. Sci. USA, 74:5463–5467 (1977), using PRISM Ready Reaction Dye Deoxy Terminator Cycle Sequencing Kits and PRISM Sequenase® Terminator Double-Stranded DNA Sequencing Kit and analyzed on an ABI 373 automatic sequencer. The sequence is given in SEQ ID NO: 1. The 6 kb fragment encodes both VIP1A(a) and VIP2A(a), as indicated by the open reading frames described in SEQ ID NO:1. The sequence encoding VIP1A(a) is further disclosed in SEQ ID NO:4. The relationship between VIP1A(a) and VIP2A(a) within the 6 kb fragment found in pCIB6022 is depicted in FIG. 1 pCIB6022 was deposited with the Agricultural Research Service, Patent Culture Collection, (NRRL), Northern Regional Research Center, 1815 North University Street, Peoria, Ill. 61604,USA, and given the Accession No. NRRL B-21222.

Example 11

Functional Dissection of the VIP1A(a) DNA Region.

To confirm that the VIP1A(a) open reading frame (ORF) is necessary for insecticidal activity a translational frameshift mutation was created in the gene. The restriction enzyme Bgl II recognizes a unique site located 857 bp into the coding region of VIP1A(a). pCIB6201 was digested with Bgl II, and the single-stranded ends filled-in with DNA polymerase (Klenow fragment) and dNTPS. The plasmid was re-ligated and transformed into E. coli. The resulting plasmid, pCIB6203, contains a four nucleotide insertion in the coding region of VIP1A(a). ppCIB6203 does not confer WCRW insecticidal activity, confirming that VIP1A(a) is an essential component of western corn rootworm activity.

To further define the region necessary to encode VIP1A (a), subclones of the VIP1A(a) and VIP2A(a) (auxiliary protein) region were constructed and tested for their ability to complement the mutation in pCIB6203. pCIB6023 contains the 3.7 kb Xba I-EcoRV fragment in pBluescript SK(+) (Stratagene). Western blot analysis indicates that pCIB6023 produces VIP1A(a) protein of equal size and quantity as clones PL2 and pCIB6022. pCIB6023 contains the entire gene encoding the 80 kD protein. pCIB6023 was deposited with the Agricultural Research Service, Patent Culture Collection, (NRRL), Northern Regional Research Center, 1815 North University Street, Peoria, Ill. 61604, USA, and given the Accession No. NRRL B-21223N. pCIB6206 contains the 4.3 kb Xba I-Cla I fragment from pCIB6022 in pBluescript SK(+) (Stratagene). pCIB6206 was also deposited with the Agricultural Research Service, Patent Culture Collection, (NRRL), Northern Regional Research Center, 1815 North University Street, Peoria, Ill. 61604, USA, and given the Accession No. NRRL B-21321.

pCIB6023, pCIB6206, and pCIB6203 do not produce detectable western corn rootworm activity when tested individually. However, a mixture of cells containing pCIB6203 (VIP1A(a)-mutated, plus VIP2A(a)) and cells containing pCIB6023 (only VIP1A(a)) shows high activity against western corn rootworm. Similarly, a mixture of cells containing pCIB6206 and cells containing pCIB6203 shows high activity against western corn rootworm.

To further define the limits of VIP2A(a), we constructed pCIB6024, which contains the entirety of VIP2A(a), but lacks most of the VIP1A(a) coding region. pCIB6024 was constructed by gel purifying the 2.2 kb Cla I-Sca I restriction fragment from pCIB6022, filling in the single-stranded ends with DNA polymerase (Klenow fragment) and dNTPs, and ligating this fragment into pBluescript SK(+) vector (Stratagene) digested with the enzyme Eco RV. Cells containing pCIB6024 exhibit no activity against western corn rootworm. However, a mixture of cells containing pCIB6024 and cells containing pCIB6023 shows high activity against western corn rootworm.(See FIG. 1).

Thus, pCIB6023 and pCIB6206 must produce a functional VIP1A(a) gene product, while pCIB6203 and pCIB6024 must produce a functional VIP2A(a) gene product. These results suggest a requirement for a gene product (s) from the VIP2A(a) region, in combination with VIP1A (a), to confer maximal western corn rootworm activity. (See FIG. 1.)

Example 12

AB78 Antibody Production

Antibody production was initiated in 2 Lewis rats to allow for both the possibility of moving to production of hybridoma cell lines and also to produce enough serum for limited screening of genomic DNA library. Another factor was the very limited amount of antigen available and the fact that it could only be produced to purity by PAGE and subsequent electrotransfer to nitrocellulose.

Due to the limited availability of antigen on nitrocellulose, the nitrocellulose was emulsified in DMSO and injected into the hind footpads of the animals to elicit B-cell production in the popliteal lymph nodes just upstream. A strong reacting serum was produced as judged by western blot analysis with the first production bleed. Several subsequent injections and bleeds produced enough serum to accomplish all of the screening required.

Hybridoma production with one of the rats was then initiated. The popliteal lymph node was excised, macerated, and the resulting cells fused with mouse myeloma P3x63Ag8.653. Subsequent cell screening was accomplished as described below. Four initial wells were selected which gave the highest emulsified antigen reaction to be moved to limited dilution cloning. An additional 10 wells were chosen for expansion and cryoperservation.

Procedure to Emulsify AB78 on Nitrocellulose in DMSO for ELISA Screening

After electrotransfer of AB78 samples run on PAGE to nitrocellulose, the reversible strain Ponceau S is used to visualize all protein transferred. The band corresponding to AB78 toxin, previously identified and N-terminal sequenced, was identified and excised from nitrocellulose. Each band is approximately 1 mm×5 mm in size to minimize the amount of nitrocellulose emulsified. A single band is placed in a microfuge tube with 250 μl of DMSO and macerated using a plastic pestle (Kontes, Vineland, N.J.). To aid in emulsification, the DMSO mixture is heated for 2–3 minutes at 37° C.–45° C. Some further maceration might be necessary following heating; however, all of the nitrocellulose should be emulsified. Once the AB78 sample is emulsified, it is placed on ice. In preparation for microtiter plate coating with the emulsified antigen, the sample must be diluted in borate buffered saline as follows: 1:5, 1:10, 1:15, 1:20, 1:30, 1:50, 1:100, and 0. The coating antigen must be prepared fresh immediately prior to use.

ELISA protocol:
1. Coat with AB78/DMSO in BBS. Incubate overnight at 4° C.
2. Wash plate 3× with 1× ELISA wash buffer.
3. Block (1% BSA & 0.05% Tween 20 in PBS) for 30 minutes at Room Temperature.
4. Wash plate 3× with 1× ELISA wash buffer.
5. Add rat serum. Incubate 1.5 hours at 37° C.
6. Wash plate 3× with 1× ELISA wash buffer.
7. Add goat anti-rat at a concentration of 2 μg/ml in ELISA diluent. Incubate 1 hr.at 37° C.
8. Wash plate 3× with 1× ELISA wash buffer.
9. Add rabbit anti-goat alkaline phosphatase at 2 μg/ml in ELISA diluent. Incubate1 hr.at37° C.
10. Wash 3× with 1× ELISA wash buffer.
11. Add Substrate. Incubate 30 minutes at room temperature.
12. Stop with 3N NaOH after 30 minutes.

Preparation of VIP2A(a) Antisera

A partially purified AB78 culture supernatant was separated by discontinuous SDS PAGE (Novex) following manufacturer's instructions. Separated proteins were electrophoresed to nitrocellulose (S&S #21640) as described by Towbin et al., (1979). The nitrocellulose was stained with Ponceau S and the VIP2A(a) band identified. The VIP2A(a) band was excised and emulsified in DMSO immediately prior to injection. A rabbit was initially immunized with emulsified VIP2A(a) mixed approximately 1:1 with Freund's Complete adjuvant by intramuscular injection at four different sites. Subsequent immunizations occurred at four week intervals and were identical to the first, except for the use of Freund' Incomplete adjuvant. The first serum harvested following immunization reacted with VIP2A(a) protein. Western blot analysis of AB78 culture supernatant using this antisera identifies predominately full length VIP2A(a) protein.

Example 13

Activation of Insecticidal Activity of Non-Active BT Strains with AB78 VIP Clones.

Adding pCIB6203 together with a 24 h culture (early to mid-log phase) supernatant from *Bt* strain GC91 produces 100% mortality in *Diabrotica virgifera virgifera*. Neither pCIB6203 nor GC91 is active on *Diabrotica virgifera virgifera* by itself. Data are shown below:

| Test material | Percent Diabrotica mortality |
| --- | --- |
| pCIB6203 | 0 |
| GC91 | 16 |
| pCIB6203 + GC91 | 100 |
| Control | 0 |

Example 14

Isolation and Biological Activity of *B. cereus* AB81.

A second *B. cereus* strain, designated AB81, was isolated from grain bin dust samples by standard methodologies. A subculture of AB81 was grown and prepared for bioassay as described in Example 2. Biological activity was evaluated as described in Example 3. The results are as follows:

| Insect species tested | Percent Mortality |
| --- | --- |
| Ostrinia nubilalis | 0 |
| Agrotis ipsilon | 0 |
| Diabrotica virgifera virgifera | 55 |

Example 15

Isolation and Biological Activity of B. thuringiensis AB6.

A B. thuringiensis strain, designated AB6, was isolated from grain bin dust samples by standard methods known in the art. A subculture of AB6 was grown and prepared for bioassay as described in Example 2. Half of the sample was autoclaved 15 minutes to test for the presence of β-exotoxin.

Biological activity was evaluated as described in Example 3. The results are as follows:

| Insect species tested | Percent Mortality |
| --- | --- |
| Ostrinia nubilalis | 0 |
| Agrotis ipsilon | 100 |
| Agrotis ipsilon (autoclaved sample) | 0 |
| Diabrotica virgifera virgifera | 0 |

The reduction of insecticidal acitivity of the culture supernatant to insignificant levels by autoclaving indicates that the active principle is not β-exotoxin.

Strain AB6 has been deposited in the Agricultural Research Service, Patent Culture Collection (NRRL), Northern Regional Research Center, 1815 North University Street, Peoria, Ill. 61604, USA, and given Accession No. NRRL B-21060.

Example 16

Isolation and Biological Characterization of B. thuringiensis AB88.

A Bt strain, designated AB88, was isolated from grain bin dust samples by standard methodologies. A subculture of AB88 was grown and prepared for bioassay as described in Example 2. Half of the sample was autoclaved 15 minutes to test for the presence of β-exotoxin. Biological activity was evaluated against a number of insect species as described in Example 3. The results are as follows:

| Insect species tested | Order | Percent mortality of culture supernatant | |
| --- | --- | --- | --- |
| | | Non-autoclaved | Autoclaved |
| Agrotis ipsilon | Lepidoptera | 100 | 5 |
| Ostrinia nubilalis | Lepidoptera | 100 | 0 |
| Spodoptera frugiperda | Lepidoptera | 100 | 4 |
| Helicoverpa zea | Lepidoptera | 100 | 12 |
| Heliothis virescens | Lepidoptera | 100 | 12 |
| Leptinotarsa decemlineata | Coleoptera | 0 | 0 |
| Diabrotica virgifera virgifera | Coleoptera | 0 | 5 |

The reduction of insecticidal acitivity of the culture supernatant to insignificant levels by autoclaving indicates that the active principle is not β-exotoxin.

Delta-endotoxin crystals were purified from strain AB88 by standard methodologies. No activity from pure crystals was observed when bioassayed against Agrotis ipsilon.

Example 17

Purification of VIPs from Strain AB88

Bacterial liquid culture was grown overnight at 30° C. in TB media. Cells were spun out and the supernatant retained. Proteins were precipitated with ammonium sulfate (70% saturation), centrifuiged and the pellet retained. The pellet was resuspended in the original volume of 20 mM Tris pH 7.5 and dialyzed against the same buffer. AB88 dialysate was more turbid than comparable material from AB78. AB88 proteins have been separated by several different methods following clarification including isoelectric focusing (Rotofor, BioRad, Hercules, Calif.), precipitation at pH 4.5, ion-exchange chromotography, size exclusion chromatography and ultrafiltration.

European corn borer (ECB)-active protein remained in the pellet obtained by pH 4.5 precipitation of dialysate. When preparative IEF was done on the dialysate using pH 3–10 ampholytes, ECB insecticidal activity was found in all fractions with pH of 7 or greater. SDS-PAGE analysis of these fractions showed protein bands of MW ~60 kDa and ~80 kDa. The 60 kDa and 80 kDa bands were separated by anion exchange HPLC on a Poros-Q column (PerSeptive Biosystems, Cambridge, Mass.). N-terminal sequence was obtained from two fractions containing proteins of slightly differing MW, but both of approximately 60 kDa in size. The sequences obtained were similar to each other and to some δ-endotoxins. anion exchange fraction 23 (smaller): xEPFVSAxxxQxxx (SEQ ID NO:10) anion exchange fraction 28 (larger): xEYENVEPFVSAx (SEQ ID NO:11)

When the ECB-active pH 4.5 pellet was further separated by anion exchange on a Poros-Q column, activity was found only in fractions containing a major band of ~60 kDa.

Black cutworm-active protein also remained in the pellet when AB88 dialysate was brought down to pH 4.5. In preparative IEF using pH 3–10 ampholytes, activity was not found in the ECB-active IEF fractions; instead, it was highest in a fraction of pH 4.5–5.0. Its major components have molecular weights of ~35 and ~80 kDa.

The pH 4.5 pellet was separated by anion exchange HPLC to yield fractions containing only the 35 kDa material and fractions containing both 35 kDa and 80 kDa bands.

Example 18

Characterization of AB88 VIP.

Fractions containing the various lepidopteran active vegetative proteins were generated as described in Example 17. Biological analysis of fractions demonstrated that different VIPs were responsible for the different lepidopteran species activity.

The Agrotis ipsilon activity is due to an 80 kDa and/or a 35 kDa protein, either delivered singly or in combination. These proteins are not related to any δ-endotoxins from Bt as evidenced by the lack of sequence homology of known Bt δ-endotoxin sequences. Also, these proteins are not found in the AB88 δ-endotoxin crystal. N-terminal sequences of the major δ-endotoxin proteins were compared with the N-terminal sequences of the 80 kDa and 35 kDa VIP and revealed no sequence homology. A summary of the results follows:

| Agrotis VIP N-terminal sequences | N-terminal sequence of major δ-endotoxin proteins |
|---|---|
| | 130 kDa<br>MDNNPNINE (SEQ ID NO: 14) |
| 80 kDa<br>MNKNNTKLPTRALP<br>(SEQ ID NO: 12) | 80 kDa<br>MDNNPNINE (SEQ ID NO: 15) |
| | 60 kDa<br>MNVLNSGRTTI (SEQ ID NO: 16) |
| 35 kDa<br>ALSENTGKDGGYIVP<br>(SEQ ID NO: 13) | |

The *Ostrinia nubilalis* activity is due to a 60 kDa VIP and the *Spodoptera frugiperda* activity is due to a VIP of unknown size.

*Bacillus thuringiensis* strain AB88 has been deposited in the Agricultural Research Service, Patent Culture Collection (NRRL), Northern Regional Research Center, 1815 North University Street, Peoria, Ill. 61604, USA and given the Accession No. NRRL B-21225.

Example 18

Isolation and Biological Activity of *B. Thuringiensis* AB424

A *B. thuringiensis* strain, designated AB424, was isolated from a moss covered pine cone sample by standard methods known in the art. A subculture of AB424 was grown and prepared for bioassay as described in Example 2.

Biological activity was evaluated as described in Example 3. The results are as follows:

| Insect species tested | Percent mortality |
|---|---|
| *Ostrinia nubilalis* | 100 |
| *Agrotis ipsilon* | 100 |
| *Diabrotica virgifera virgifera* | 0 |

Strain AB424 has been deposited in the Agricultural Research Service, Patent Culture Collection (NRRL), Northern Regional Research Center, 1815 North University Street, Peoria, Ill. 61604, USA, and given Accession No. NRRL B-21439.

Example 18B

Cloning of the VIP3A(a) and VIP3A(b) Genes which Encode Proteins Active Against Black Cutworm.

DNA from isolates AB88 and AB424 was digested with the restriction enzymes XbaI and EcoRI respectively, ligated into pBluescript vector previously linearized with the same enzymes and dephosphorylated, and transformed into *E. coli* DHα strain. Recombinant clones were blotted onto nitrocellulose filters which were subsequently probed with a 33-bases long oligonucleotide corresponding to the 11-N terminal amino acids of the 80 kDa protein active against *Agrotis ipsilon* (black cutworm). Four out of 400 recombinant clones were positive. Insect bioassays of the positive recombinants exhibited toxicity to black cutworm larvae comparable to that of AB88 or AB424 supernantants.

The nucleotide sequence of pCIB7104, a positive recombinant clone from AB88, and of pCIB7107, a positive recombinant clone from AB424, was determined by the dideoxy termination method of Sanger et al., *Proc. Natl. Acad. Sci. USA*, 74: 5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

The clone pCIB7104 contains the VIP3A(a) gene whose coding region is disclosed in SEQ ID NO:28 and the encoded protein sequence is disclosed in SEQ ID NO:29. A synthetic version of the coding region designed to be highly expressed in maize is given in SEQ ID NO:30. Any number of synthetic genes can be designed based on the amino acid sequence given in SEQ ID NO:29.

The clone pCIB7107 contains the VIP3A(b) gene whose coding region is disclosed in SEQ ID NO:31 and the encoded protein is disclosed in SEQ ID NO:32. Both pCIB7104 and pCIB7107 have been deposited with the Agricultural Research Service Patent Culture Collection (NRRL) and given Accession Nos. NRRL B-21422 and B-21423, respectively.

Example 18C

Identification of Novel VIP3-like Genes by Hybridization

To identify Bacillus containing genes related to the VIP3A(a) from isolate AB88, a collection of Bacillus isolates was screened by hybridization. Cultures of 463 Bacillus strains were grown in microtiter wells until sporulation. A 96-pin colony stampel was used to transfer the cultures to 150 mm plates containing L-agar. Inoculated plates were kept at 30° C. for 10 hours, then at 4° C. overnight. Colonies were blotted onto nylon filters and probed with a 1.2 Kb HindIII VIP3A(a) derived fragment. Hybridization was performed overnight at 62° C. using hybridization conditions of Maniatis et al. *Molecular Cloning: A Laboratory Manual* (1982). Filters were washed with 2×SSC/0.1% SDS at 62° C. and exposed to X-ray film.

Of the 463 Bacillus strains screened, 60 contain VIP3-like genes that could detected by hybridization.

Example 18D

Characterization of a *B. thuringiensis* Strain M2194 Containing a Cryptic VIP3-Like Gene A *B. thuringiensis* strain, designated M2194, was shown to contain VIP3-like gene(s) by colony hybridization as described in Example 18C. The M2194 VIP3 like gene is considered cryptic since no expression can be detected throughout the bacterial growth phases either by immunoblot analysis using polyclonal antibodies raised against the VIP3A(a) protein isolated from AB88 or by bioassay as described in Example 3.

The M2194 VIP3-like gene was cloned into pKS by following the protocol described in Example 9, which created pCIB7108. *E. coli* containing pCIB7108 which comprises the M2194 VIP3 gene were active against black cutworm demonstrating that the gene encodes a functional protein with insecticidal activity. The plasmid pCIB7108 has been deposited with the Agricultural Research Service Patent Culture Collection (NRRL) and given Accession No. NRRL B-21438.

Example 19

Isolation and Biological Activity of Other Bacillus sp.

Other Bacillus species have been isolated which produce proteins with insecticidal activity during vegetative growth.

These strains were isolated from environmental samples by standard methodologies. Isolates were prepared for bioassay and assayed as described in Examples 2 and 3 respectively. Isolates which produced insecticidal proteins during vegetative growth with activity against *Agrotis ipsilon* in the bioassay are tabulated below. No correlation was observed between the presence of a δ-endotoxin crystal and vegetative insecticidal protein production.

| Bacillus isolate | Presence of δ-endotoxin crystal | Percent mortality |
| --- | --- | --- |
| AB6 | + | 100 |
| AB53 | – | 80 |
| AB88 | + | 100 |
| AB195 | – | 60 |
| AB211 | – | 70 |
| AB217 | – | 83 |
| AB272 | – | 80 |
| AB279 | – | 70 |
| AB289 | + | 100 |
| AB292 | + | 80 |
| AB294 | – | 100 |
| AB300 | – | 80 |
| AB359 | – | 100 |

Isolates AB289, AB294 and AB359 have been deposited in the Agricultural Research Service, Patent Culture Collection (NRRL), Northern Regional Research Center, 1815 North University Street, Peoria Ill. 61604, USA and given the Accession Numbers NRRL B-21227, NRRL B-21229, and NRRL B-21226 respectively.

Bacillus isolates which produce insecticidal proteins during vegetative growth with activity against *Diabrotica virgifera virgifera* are tabulated below.

| Bacillus isolate | Presence of δ-endotoxin crystal | Percent mortality |
| --- | --- | --- |
| AB52 | – | 50 |
| AB59 | – | 71 |
| AB68 | + | 60 |
| AB78 | – | 100 |
| AB122 | – | 57 |
| AB218 | – | 64 |
| AB256 | – | 64 |

Isolates AB59 and AB256 have been deposited in the Agricultural Research Service, Patent Culture Collection (NRRL), Northern Regional Research Center, 1815 North University Street, Peoria Ill. 61604, USA, and given the Accession Numbers NRRL B-21228 and NRRL B-21230, respectively.

Example 20

Identification of Novel VIP1/VIP2 like Genes by Hybridization

To identify strains containing genes related to those found in the VIP1A(a)/VIP2A(a) region of AB78, a collection of Bacillus strains was screened by hybridization. Independent cultures of 463 Bacillus strains were grown in wells of 96 well microtiter dishes (five plates total) until the cultures sporulated. Of the strains tested, 288 were categorized as *Bacillus thuringiensis*, and 175 were categorized as other Bacillus species based on the presence or absence of δ-endotoxin crystals. For each microtiter dish, a 96-pin colony stamper was used to transfer approximately 10 μl of spore culture to two 150 mm plates containing L-agar. Inoculated plates were grown 4–8 hours at 30° C., then chilled to 4° C. Colonies were transferred to nylon filters, and the cells lysed by standard methods known in the art. The filters were hybridized to a DNA probe generated from DNA fragments containing both VIP1A(a) and VIP2A(a) DNA sequences. Hybridization was performed overnight at 65° C. using the hybridization conditions of Church and Gilbert (Church, G. M., and W. Gilbert, PNAS, 81:1991–1995 (1984)). Filters were washed with 2× SSC containing 0.1% SDS at 65° C. and exposed to X-Ray film.

Of the 463 Bacillus strains screened, 55 strains were identified that hybridized to the VIP1A(a)/VIP2A(a) probe. DNA was isolated from 22 of these strains, and analyzed using a Southern blot with VIP1A(a)/VIP2A(a) DNA as probes. These strains were grouped into 8 classes based on their Southern blot pattern. Each class differed in Southern blot pattern from AB78. One class had a pattern identical to that of the VIP1A(a)/VIP2A(a) homologs from *Bacillus thuringiensis var tenebrionis* (see below). Each of the 22 strains was tested for activity against western corn rootworm (WCRW). Three strains, AB433, AB434, and AB435 were found to be active on WCRW. Western blot analysis using VIP2A(a) antisera revealed that strains AB6, AB433, AB434, AB435, AB444, and AB445 produce a protein(s) of equivalent size to VIP2A(a).

Notable among the strains identified was *Bacillus thuringiensis* strain AB6, (NRRL B-21060) which produced a VIP active against black cutworm (*Agrotis ipsilon*) as described in Example 15. Western blot analysis with polyclonal antisera to VIP2A(a) and polyclonal antisera to VIP1A(a) suggests that AB6 produces proteins similar to VIP2A(a) and VIP1A(a). Thus, AB6 may contain VIPs similar to VIP1A(a) and VIP2A(a), but with a different spectrum of insecticidal activity.

Example 21

Cloning of a VIP1A(a)/VIP2A(a) Homolog from *Bacillus thuringiensis* Var. *tenebriones*.

Several previously characterized Bacillus strains were tested for presence of DNA similar to VIP1A(a)/VIP2A(a) by Southern blot analysis. DNA from Bacillus strains AB78, AB188, GC91, HD-1 and ATCC 10876 was analyzed for presence of VIP1A(a)/VIP2A(a) like sequences. DNA from *Bt* strains GC91 and HD-1, and the *Bc* strain ATCC 10876 did not hybridize to VIP2A(a)/VIP1A(a) DNA, indicating they lack DNA sequences similar to VIP1A(a)/VIP2A(a) genes. Similarly, DNA from the insecticidal strain AB88 (Example 16) did not hybridize to VIP1A(a)/VIP2A(a) DNA region, suggesting that the VIP activity produced by this strain does not result from VIP1A(a)/VIP2A(a) homologs. In contrast, *Bacillus thuringiensis var tenebrionis* (*Btt*) contained sequences that hybridized to the VIP1A(a)/VIP2A (a) region. Further analysis confirmed that *Btt* contains VIP1A(a)/VIP2A(a) like sequences.

To characterize the *Btt* homologs of VIP2A(a) and VIP1A (a), the genes encoding these proteins were cloned. Southern blot analysis identified a 9.5 kb Eco RI restriction fragment likely to contain the coding regions for the homologs. Genomic DNA was digested with Eco RI, and DNA fragments of approximately 9.5 kb in length were gel-purified. This DNA was ligated into pBluescript SK(+) digested with Eco RI, and transformed into *E. coli* to generate a plasmid library. Approximately 10,000 colonies were screened by colony hybridization for the presence of VIP2A(a) homologous sequences. Twenty eight positive colonies were identified. All twenty eight clones are identical, and contain VIP1A(a)/VIP2A(a) homologs. Clone pCIB7100 has been deposited in the Agricultural Research Service, Patent Culture Collection (NRRL), Northern Regional Research Center, 1815 North University Street, Peoria Ill. 61604, USA, and given the Accession Number B-21322. Several subclones were constructed from pCIB7100. A 3.8 kb Xba I fragment from pCIB7100 was cloned into pBluescript SK(+) to yield pCIB7101. A 1.8 kb Hind III fragment and a 1.4 kb Hind III fragment from pCIB7100 were cloned into pBluescript SK(+) to yield pCIB7102 and pCIB7103, respectively. Subclones pCIB7101, pCIB7102 and pCIB7103 have been deposited in the Agricultural Research Service, Patent Culture Collection (NRRL), Northern Regional Research Center, 1815 North University Street, Peoria Ill. 61604, USA, and given the Accession Numbers B-21323, B-21324 and B-21325 respectively.

The DNA sequence of the region of pCIB7100 containing the VIP2A(a)/VIP1A(a) homologs was determined by the dideoxy chain termination method (Sanger et al., 1977, Proc. Natl. Acad. Sci. USA 74:5463–5467). Reactions were performed using PRISM Ready Reaction Dye Deoxy Terminator Cycle Sequencing Kits and PRISM Sequenase® Terminator Double-Stranded DNA Sequencing Kits, and analyzed on an ABI model 373 automated sequencer. Custom oligonucleotides were used as primers to determine the DNA sequence in certain regions. The DNA sequence of this region is shown in SEQ ID NO:19.

The 4 kb region shown in SEQ ID NO:19 contains two open readings frames (ORFs), which encode proteins with a high degree of similarity to VIP1A(a) and VIP2A(a) proteins from strain AB78. The amino acid sequence of the VIP2A(a) homolog, designated as VIP2A(b) using the standardized nomenclature, is found at SEQ ID NO:20 and the amino acid sequence of the VIP1A(a) homolog, designated as VIP1A(b) using the standardized nomenclature, is disclosed at SEQ ID NO:21. The VIP2A(b) protein exhibits 91% amino acid identity to VIP2A(a) from AB78. An alignment of the amino acid sequences of the two VIP2 proteins is provided in Table 19. The VIP1A(b) protein exhibits 77% amino acid identity to VIP1A(a) from AB78. An alignment of these two VIP1 proteins is provided in Table 20. The alignment shown in Table 20 discloses the similarity between VIP1A(b) and VIP1A(a) from AB78. This alignment reveals that the amino terminal regions of the two VIP1 proteins share higher amino acid identity in the amino-terminal region than in the carboxy terminal region. In fact, the amino terminal two thirds (up to aa 618 of the VIP1A(b) sequence shown in Table 20) of the two proteins exhibit 91% identity, while the carboxy-terminal third (from aa 619–833 of VIP1A(b)) exhibit only 35% identity.

Western blot analysis indicated that *Bacillus thuringiensis var tenebrionis* (*Btt*) produces both VIP1A(a) like and VIP2A(a) like proteins. However, these proteins do not appear to have activity against western corn rootworm. Bioassay for activity against western corn rootworm was performed using either a 24 h culture supernatant from *Btt* or *E. coli* clone pCIB7100 (which contains the entire region of the VIP1A(a)/VIP2A(a) homologs). No activity against western corn rootworm was detected in either case.

Given the similarity between the VIP2 proteins from *Btt* and AB78, the ability of VIP2A(b) from *Btt* to substitute for VIP2A(a) from AB78 was tested. Cells containing pCIB6206 (which produces AB78 VIP1A(a) but not VIP2A (a) protein) were mixed with *Btt* culture supernatant, and tested for activity against western corn rootworm. While neither *Btt* culture supernatant nor cells containing pCIB6206 had activity on WCRW, the mixture of *Btt* and pCIB6206 gave high activity against WCRW. Furthermore, additional bioassay showed that the *Btt* clone pCIB7100, which contains the *Btt* VIP1A(b)/VIP2A(b) genes in *E. coli*, also confers activity against WCRW when mixed with pCIB6206. Thus, the VIP2A(b) protein produced by *Btt* is functionally equivalent to the VIP2A(a) protein produced by AB78.

Thus, the ability to identify new strains with insecticidal activity by using VIP DNA as hybridization probes has been demonstrated. Furthermore, Bacillus strains that contain VIP1A(a)/VIP2A(a) like sequences, produce VIP1A(a)/ VIP2A(a) like protein, yet demonstrate toxicity toward different insect pests. Similar methods can identify many more members of the VIP1/VIP2 family. Furthermore, use of similar methods can identify homologs of other varieties of VIPs (for example, the VIPs from AB88).

TABLE 19

Alignment of VIP2 Amino Acid Sequences from *Bacillus thuringiensis* var. *tenebrionis*
(VIP2A(b) vs. AB78 (VIP2A(a))

```
Btt    1  MQR ME G KL F VVS KT L Q VVT RT VLL S T VYS I T LL NN VVI KA D Q L NI NS Q S K  50   SEQ ID NO:20
          | . | | | | | | | :  | | | .  | | | | |  :  | | | | | | | :  | | .  | | | |     | | | | :  | | | | | | | |
AB78   1  MKR ME G KL F MVS KK L Q VVT KT VLL S T VF S I S LL NN E VI KA E Q L NI NS Q S K  50   SEQ ID NO:2

51  YT NL Q NL KI P D NA E D F KE D KG KA KE WG KE KG E E WR P P AT E KG E MNN F L D N 100
          | | | | | | | | | . | . . | | | | | | | | :  | | | | | | | | | | :  -  | | :    . | | | | | .  | | | | | | |
      51  YT NL Q NL KI T D KV E D F KE D KE KA KE WG KE KE KE WK L T AT E KG KMNN F L D N 100

101  KND I  KT NY KE I T F S MAGS CE D E I KD L E E I D KI F D KA NL S S S I I T YKN V E P 150
          | | | |   | | | | | | | | | | | | |   | | | | | | | .  | | | | :  | | | .  | | | .  | | | | | | | | |
     101  KND I  XT NY KE I T F S MAGS F E D E I KD L KE I D KM F D KT NL S NS I I T YKN V E P 150

151  AT I  G F NKS L T E GNT I NS D AMA Q F KE Q F L G KD MKF D S YL D YHL T A Q Q VS S K 200
          . | | | | | | | | | | | | | | | | | | | | | | | | | | :  :  | :  | | | | | | | | | | | | | | | | |
     151  T T I  G F NKS L T E GNT I NS D AMA Q F KE Q F L D R D I KF D S YL D T HL T A Q Q VS S K 200

201  KR VI  L KVT VP S GKGS T T P T KA G VI L NN N E YKML I D NG YVL HVD KVS KVVK 250
          . | | | | | | | | | | | | | | | | | | | | | | | | | | | .  | | | | | | | | | :  :  | | | | | | | | |
     201  E R VI  L KVT VP S GKGS T T P T KA G VI L NNS E YKML I D NG YMV HVD KVS KVVK 250

251  KG ME CL Q VE GT L KKS L D F KND I NA E AHS WG MKI YE D WA KN L T AS Q R E A L D 300
          | | :  | | | | :  | | | | | | | | | | | | | | | | | | | | | |   | | :  | | | :  | | .  | | | | | | |
     251  KG VE CL Q I  E GT L KKS L D F KND I NA E AHS WG MKN YE E WA KD L T D S Q R E A L D 300
```

TABLE 19-continued

Alignment of VIP2 Amino Acid Sequences from *Bacillus thuringiensis* var. *tenebrionis* (VIP2A(b) vs. AB78 (VIP2A(a)))

```
301 G Y A R Q D Y K E I N N Y L R N Q G G S G N E K L D A Q L K N I S D A L G K K P I P E N I T V Y R W 350
    | | | | | | | | | | | | | | | | | | | | | | | | | :   | | | | | | | | | | | | | | | | | | | | | |
301 G Y A R Q D Y K E I N N Y L R N Q G G S G N E K L D A Q I   K N I S D A L G K K P I P E N I T V Y R W 350

351 C G M P E F G Y Q I S D P L P S L K D F E E Q F L N T I K E D K G Y M S T S L S S E R L A A F G S R 400
    | | | | | | | | | | | | | | | | | | | | | | | | | | | | | | | | | | | | | | | | | | | | | | | | | |
351 C G M P E F G Y Q I S D P L P S L K D F E E Q F L N T I K E D K G Y M S T S L S S E R L A A F G S R 400

401 K I I L R L A V P K G S T G A Y L S A I G G F A S E K E I L L D K S K Y H I D K A T E V I I K G V 450
    | | | | | |   | | | | | | | | | | | | | | | | | | | | | | | | | | | | | | | | · | | | | | | | | |
401 K I I L R L Q V P K G S T G A Y L S A I G G F A S E K E I L L D K S K Y H I D K V T E V I I K G V 450

451 K R Y V V D A T L L T N 462
    | | | | | | | | | | | |
451 K R Y V V D A T L L T N 462
```

TABLE 21

Alignment of VIP1 Amino Acid Sequences from *Bacillus thuringiensis* var. *tenebrionis* (VIP1A(b) vs. AB78 (VIP1A(a)))

```
Btt    1 M K N M K K K L A S V V T C M L L A P M F L N G N V N A V N A D S K I N Q I S T T Q E N Q Q K E M D  50  SEQ ID NO:21
         | | | | | | | | | | | | |   | | | |   | | | | | | | | | | | | | · | | | | | | | · | | | | | | | |
Ab78   1 M K N M K K K L A S V V T C T L L A P M F L N G N V N A V Y A D S K T N Q I S T T Q K N Q Q K E M D  50  SEQ ID NO:5

51 R K G L L G Y Y F K G K D F N N L T M F A P T R D N T L M Y D Q Q T A N A L L D K K Q Q E Y Q S I R 100
         | | | | | | | | | | | | | · | | | | | | | | | | | | · | | : | | | | | | |   | | | | | | | | | | |
      51 R K G L L G Y Y F K G K D F S N L T M F A P T R D S T L I Y D Q Q T A N K L L D K K Q Q E Y Q S I R 100

101 W I G L I Q R K E T G D F T F N L S K D E Q A I I E I D G K I I S N K G K E K Q V V H L E K E K L V 150
         | | | | | | · | | | | | | | | | | · | | | | | | | | | : | | | | | | | | | | | | | | | | | : | | |
     101 W I G L I Q S K E T G D F T F N L S E D E Q A I I E I N G K I I S N K G K E K Q V V H L E K G K L V 150

151 P I K I E Y Q S D T K F N I D S K T F K E L K L F K I D S Q N Q S Q Q V Q . . . L R N P E F N K K E 197
         | | | | | | | | | | | | | | | | | | | | | | | | | | | | | · | | | |       | | | | | | | | |
     151 P I K I E Y Q S D T K F N I D S K T F K E L K L F K I D S Q N Q P Q Q V Q Q D E L R N P E F N K K E 200

198 S Q E F L A K A S K T N L F K Q K M K R D I D E D T D T D G D S I P D L W E E N G Y T I Q N K V A V 247
         | | | | | | | : : | | · | | | · | | | : | | | | | | | | | | | | | | | | | | | | | | | : : | |
     201 S Q E F L A K P S K I N L F T Q K M K R E I D E D T D T D G D S I P D L W E E N G Y T I Q N R I A V 250

248 K W D D S L A S K G Y T K F V S N P L D S H T V G D P Y T D Y E K A A R D L D L S N A K E T F N P L 297
         | | | | | | | | | | | | | | | | | | : | | | | | | | | | | | | | | | | | | | | | | | | | | | | | |
     251 K W D D S L A S K G Y T K F V S N P L E S H T V G D P Y T D Y E K A A R D L D L S N A K E T F N P L 300

298 V A A F P S V N V S M E K V I L S P N E N L S N S V E S H S S T N W S Y T N T E G A S I E A G G P 347
         | | | | | | | | | | | | | | | | | | | | | | | | | | | | | | | | | | | | | | | : | | |     | |
     301 V A A F P S V N V S M E K V I L S P N E N L S N S V E S H S S T N W S Y T N T E G A S V E A G I G P 350

348 L G L S F G V S V T Y Q H S E T V A Q E W G T S T G N T S Q F N T A S A G Y L N A N V R Y N N V G T 397
         | : | | | | | · | | | | | | | | | | | | | | | | | | | | | | | | | | | | | | | | | | | | | | | |
     351 K G I S F G V S V N Y Q H S E T V A Q E W G T S T G N T S Q F N T A S A G Y L N A N V R Y N N V G T 400

398 G A I Y D V K P T T S F V L N N N T I A T I T A K S N S T A L R I S P G D S Y P E I G E N A I A I T 447
         | | | | | | | | | | | | | | : | | | | | | | | | | | | · | | | | : | | | ·   | : | : | | | |
     401 G A I Y D V K P T T S F V L N N D T I A T I T A K S N S T A L N I S P G E S Y P K K G Q N G I A I T 450

448 S M D D F N S H P I T L N K Q Q V N Q L I N N K P I M L E T D Q T D G V Y K I R D T H G N I V T G G 497
         | | | | | | | | | | | | · | | : · | : | | | | : | | | | : | | | | | | | | | : | | | | | | | | |
     451 S M D D F N S H P I T L N K K Q V D N L L N N K P M M L E T N Q T D G V Y K I K D T H G N I V T G G 500

498 E W N G V T Q Q I K A K T A S I I V D D G K Q V A E K R V A A K D Y G H P E D K T P P 1 T L K D T L 547
         | | | | | · | | | | | | | | | | | | | | | : : · · | | | | | | | | | | : | | | | | · | | | | · |
     501 E W N G V I Q Q I K A K T A S I I V D D G E R V A E K R V A A K D Y E N P E D K T P S L T L K D A L 550

548 K L S Y P D E I K E T N G L L Y Y D D K P I Y E S S V M T Y L D E N T A K E V K K Q I N D T T G K F 597
         | | | | | | | | | | : | | | | | | : | | | | | | | | | | | | | | | | | | | | | : : | | | | | | |
     551 K L S Y P D E I K E I E G L L Y Y K N K P I Y E S S V M T Y L D E N T A K E V T K Q L N D T T G K F 600

Btt  598 K D V N H L Y D V K L T P K M N F T I K M A S L Y D G A E N N H N S L G T W Y L T Y N V A G G N T G 647  SEQ ID NO:21
         | | | · | | | | | | | | | | | | | · | : ·     | | | · | | · | · | | : | · |     |   | · | | | · |
Ab78 601 K D V S H L Y D V K L T P K M N V T I K L S I L Y D N A E S N D N S I G K W T N T N I V S G G N N G 650  SEQ ID NO:5

648 K R Q Y R S A H S C A H V A L S S E A K K K L N Q N A N Y Y L S M Y M K A D S T T E P T I E V A G E 697
         | : | | · | · :     | : : ·   | · · |   · | · | | | · |   : | | | : | | | | · · · | : · · | · | |
     651 K K Q Y S S N N P D A N L T L N T D A Q E K L N K N R D Y Y I S L Y M K S E K N T Q C E I T I D G E 700
```

TABLE 21-continued

Alignment of VIP1 Amino Acid Sequences from *Bacillus thuringiensis* var. *tenebrionis*
(VIP1A(b) vs. AB78 (VIP1A(a)))

```
698  KS AI TS KK VKL NN QNYQR VDI L VKNS E RNP MDKI YI RGNGT TNVYGDDVT 747
        : || . | . | . : | . : | | . | : | | : . . |   . . | | : . . : . | : . | : . . . : :  || : .
701  I YP I TT KT VNVNKDNYKRL DI I AHNI KS NP I S S L HI KT NDE I TL F WD DI S 750

748  I P E VS AI  NP AS L S DE E I  QE I  F KDS TI  E YGN P S F VADAVT F K . . . . . . . . . 788
     | . : | . . | . | . . | . | . | | . : | : .   . | . . : : :   | : . . .   . . . :
751  I T D VAS I  KP E NL T DS E I  KQ I  YS R YGI  KL E DGI  L I  DKK GGI  HYGE FI  N EA S 800

789  . NI KP L QN Y VKE YE I  YHK. . . . . . . S HR YE KKT VF DI  MG VH YE YS I  A RE Q 830
       | | . | | | | | | . . | . :     . .           | . . | . . . . : :     . : . : : : .   . . .
801  F NI  E P L QN Y VT KYKVT YS S E L GQ NVS DTL E S DKI  YKDGT I  KF DF T KYS KN 850

831  K K A 833
     . . :
851  E Q G 851
```

Example 22

Fusion of VIP Proteins to Make a Single Polypeptide

VIP proteins may occur in nature as single polypeptides, or as two or more interacting polypeptides. When an active VIP is comprised of two or more interacting protein chains, these protein chains can be produced as a single polypeptide chain from a gene resulting from the fusion of the two (or more) VIP coding regions. The genes encoding the two chains are fused by merging the coding regions of the genes to produce a single open reading frame encoding both VIP polypeptides. The composite polypeptides can be fused to produce the smaller polypeptide as the $NH_2$ terminus of the fusion protein, or they can be fused to produce the larger of the polypeptides as the $NH_2$ terminus of the fusion protein. A linker region can optionally be used between the two polypeptide domains. Such linkers are known in the art. This linker can optionally be designed to contain protease cleavage sites such that once the single fused polypeptide is ingested by the target insect it is cleaved in the linker region to liberate the two polypeptide components of the active VIP molecule.

VIP1A(a) and VIP2A(a) from *B. cereus* strain AB78 are fused to make a single polypeptide by fusing their coding regions. The resulting DNA has the sequence given in SEQ ID NO:22 with the encoded protein given in SEQ ID NO:23. In like manner, other fusion proteins may be produced.

The fusion of the genes encoding VIP1A(a) and VIP2A(a) is accomplished using standard techniques of molecular biology. The nucleotides deleted between the VIP1A(a) and VIP2A(a) coding regions are deleted using known mutagenesis techniques or, alternatively, the coding regions are fused using PCR techniques.

The fused VIP polypeptides can be expressed in other organisms using a synthetic gene, or partially synthetic gene, optimized for expression in the alternative host. For instance, to express the fused VIP polypeptide from above in maize, one makes a synthetic gene using the maize preferred codons for each amino acid, see for example U.S. Pat. No. 5,625,136 herein incorporated by reference. Synthetic DNA sequences created according to these methods are disclosed in SEQ ID NO:17 (maize optimized version of the 100 kDa VIP1A(a) coding sequence), SEQ ID NO:18 (maize optimized version of the 80 kDa VIP1A(a) coding sequence) and SEQ ID NO:24 (maize optimized version of the VIP2A(a) coding sequence).

Synthetic VIP1 and VIP2 genes optimized for expression in maize can be fused using PCR techniques, or the synthetic genes can be designed to be fused at a common restriction site. Alternatively, the synthetic fusion gene can be designed to encode a single polypeptide comprised of both VIP1 and VIP2 domains.

Addition of a peptide linker between the VIP1 and VIP2 domains of the fusion protein can be accomplished by PCR mutagenesis, use of a synthetic DNA linker encoding the linker peptide, or other methods known in the art.

The fused VIP polypeptides can be comprised of one or more binding domains. If more than one binding domain is used in the fusion, multiple target pests are controlled using such a fusion. The other binding domains can be obtained by using all or part of other VIPs; *Bacillus thuringiensis* endotoxins, or parts thereof; or other proteins capable of binding to the target pest or appropriate biding domains derived from such binding proteins.

One example of a fusion construction comprising a maize optimized DNA sequence encoding a single polypeptide chain fusion having VIP2A(a) at the N-terminal end and VIP1A(a) at the C-terminal end is provided by pCIB5531. A DNA sequence encoding a linker with the peptide sequence PSTPPTPSPSTPPTPS (SEQ ID NO:47) has been inserted between the two coding regions. The sequence encoding this linker and relevant cloning sites is 5'-CCC GGG CCT TCT ACT CCC CCA ACT CCC TCT CCT AGC ACG CCT CCG ACA CCT AGC GAT ATC GGA TC C-3' (SEQ ID NO:48). Oligonucleotides were synthesized to represent both the upper and lower strands and cloned into a pUC vector following hybridization and phosphorylation using standard procedures. The stop codon in VIP2A(a) was removed using PCR and replaced by the BglII restriction site with a SmaI site. A translation fusion was made by ligating the Bam HI/PstI fragment of the VIP2A(a) gene from pCIB5522 (see Example 24), a PCR fragment containing the PstI-end fragment of the VIP2A(a) gene (identical to that used to construct pCIB5522), a synthetic linker having ends that would ligate with a blunt site at the 5' end and with BamHI at the 3' end and the modified synthetic VIP1A(a) gene from pCIB5526 described below (See SEQ ID NO:35). The fusion was obtained by a four way ligation that resulted in a plasmid containing the VIP2A(a) gene without a translation stop codon, with a linker and the VIP1A(a) coding region without the Bacillus secretion signal. The DNA sequence for this construction is disclosed in SEQ ID NO:49, which encodes the fusion protein disclosed in SEQ ID NO:50. A single polypeptide fusion where VIP1A(a) is at the N-terminal end and VIP2A(a) is at the C-terminal end can be made in a similar fashion. Furthermore, either one or both genes can be linked in a translation fusion with or without a linker at either the 5' or the 3' end to other molecules like toxin encoding genes or reporter genes.

Example 23

Targeting of VIP2 to Plant Organelles

Various mechanisms for targeting gene products are known to exist in plants and the sequences controlling the functioning of these mechanisms have been characterized in some detail. For example, the targeting of gene products to the chloroplast is controlled by a signal sequence found at the amino-terminal end of various proteins. This signal is cleaved during chloroplast import, yielding the mature protein (e.g. Comai et al. *J. Biol. Chem.* 263: 15104–15109 (1988)). These signal sequences can be fused to heterologous gene products such as VIP2 to effect the import of those products into the chloroplast (van den Broeck et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products such as VIP2 to these organelles. Examples of such sequences are the nuclear-encoded ATPases and specific aspartate amino transferase isoforms for mitochondria. Similarly, targeting to cellular protein bodies has been described by Rogers et al. (*Proc. Natl. Acad. Sci. USA* 82: 6512–6516 (1985)).

By the fusion of the appropriate targeting sequences described above to coding sequences of interest such as VIP2 it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino-terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the start codon ATG, or alternatively replacement of some amino acids within the coding sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) *Methods in Chloroplast Molecular Biology*, Elsevier. pp 1081–1091 (1982); Wasmann et al. Mol. Gen. Genet. 205: 446–453 (1986)). These construction techniques are well known in the art and are equally applicable to mitochondria and peroxisomes.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

A DNA sequence encoding a secretion signal is present in the native Bacillus VIP2 gene. This signal is not present in the mature protein which has the N-terminal sequence of LKITDKVEDF (amino acid residues 57 to 66 of SEQ ID NO:2). It is possible to engineer VIP2 to be secreted out of the plant cell or to be targeted to subcellular organelles such as the endoplasmic reticulum, vacuole, mitochondria or plastids including chloroplasts. Hybrid proteins made by fusion of a secretion signal peptide to a marker gene have been successfully targeted into the secretion pathway. (Itirriaga G. et al., *The Plant Cell*, 1: 381–390 (1989), Denecke et al., *The Plant Cell*, 2:51–59 (1990). Amino-terminal sequences have been identified that are responsible for targeting to the ER, the apoplast, and extracellular secretion from aleurone cells (Koehler & Ho, *Plant Cell* 2: 769–783 (1990)).

The presence of additional signals are required for the protein to be retained in the endoplasmic reticulum or the vacuole. The peptide sequence KDEL/HDEL at the carboxy-terminal of a protein is required for its retention in the endoplasmic reticulum (reviewed by Pelham, *Annual Review Cell Biol.*, 5:1–23 (1989). The signals for retention of proteins in the vacuole have also been characterized. Vacuolar targeting signals may be present either at the amino-terminal portion, (Holwerda et al., *The Plant Cell*, 4:307–318 (1992), Nakamura et al., *Plant Physiol.*, 101:1–5 (1993)), carboxy- terminal portion, or in the internal sequence of the targeted protein. (Tague et al., *The Plant Cell*, 4:307–318 (1992), Saalbach et al., *The Plant Cell*, 3:695–708 (1991)). Additionally, amino-terminal sequences in conjunction with carboxy-terminal sequences are responsible for vacuolar targeting of gene products (Shinshi et al. *Plant Molec. Biol.* 14: 357–368 (1990)). Similarly, proteins may be targeted to the mitochondria or plastids using specific carboxy terminal signal peptide fusions (Heijne et al., *Eur. J. Biochem.*, 180:535–545 (1989), Archer and Keegstra, *Plant Molecular Biology*, 23:1105–1115 (1993)).

In order to target VIP2, either for secretion or to the various subcellular organelles, a maize optimized DNA sequence encoding a known signal peptide(s) may be designed to be at the 5' or the 3' end of the gene as required. To secrete VIP2 out of the cell, a DNA sequence encoding the eukaryotic secretion signal peptide MGWSWIFLFLLS-GAAGVHCL (SEQ ID NO:25) from U.S. patent application Ser. No. 08/267,641 or any other described in the literature (Itirriaga et al., *The Plant Cell*, 1:381–390 (1989), Denecke, et al., *The Plant Cell*, 2:51–59 (1990)) may be added to the 5' end of either the complete VIP2 gene sequence or to the sequence truncated to encode the mature protein or the gene truncated to nucleotide 286 or encoding a protein to start at amino acid residue 94 (methionine). To target VIP2 to be retained in the endoplasmic reticulum, a DNA sequence encoding the ER signal peptide KDEL/HDEL, in addition to the secretion signal, can be added to the 3' end of the gene. For vacuolar targeting a DNA sequence encoding the signal peptide SSSSFADSNPIRVTDRAAST (SEQ ID NO:3; Holwerda et al., *The Plant Cell*, 4:307–318 (1992)) can be designed to be adjacent to the secretion signal or a sequence encoding a carboxyl signal peptide as described by Dombrowski et al., *The Plant Cell*, 5:587–596 (1993) or a functional variation may be inserted at the 3' end of the gene. Similarly, VIP2 can be designed to be targeted to either the mitochondria or the plastids, including the chloroplasts, by inserting sequences in the VIP2 sequence described that would encode the required targeting signals. The bacterial secretion signal present in VIP2 may be retained or removed from the final construction.

One example of a construction which incorporates a eukaryotic secretion signal fused to a coding sequence for a VIP is provided by pCIB5528. Oligonucleotides corresponding to both the upper and lower strand of sequences encoding the secretion signal peptide of SEQ ID NO:25 was synthesized and has the sequence 5'-GGATCCACC ATG GGC TGG AGC TGG ATC TTC CTG TTC CTG CTG AGC GGC GCC GCG GGC GTG CAC TGC CTGCAG-3' (SEQ ID NO:41). When hybridized, the 5' end of the secretion signal resembled "sticky-ends" corresponding to restriction sites BamHI and PstI. The oligonucleotide was hybridized and phosphorylated and ligated into pCIB5527 (construction described in Example 23A) which had been digested with BarmHI/PstI using standard procedures. The resulting maize optimized coding sequence is disclosed in SEQ ID NO:42 which encodes the protein disclosed in SEQ ID NO:43. This encoded protein comprises the eukaryotic secretion signal in place of the Bacillus secretion signal.

One example of a construction which incorporates a vacuolar targetting signal fused to a coding sequence for a VIP is provided by pCIB5533. Oligonucleotides corresponding to both the upper and lower strand of sequences encoding the vacuolar targetting peptide of SEQ ID NO:3 was synthesized and has the sequence 5'-CCG CGG GCG TGC ACT GCC TCA GCA GCA GCA GCT TCG CCG ACA GCA ACC CCA TCC GCG TGA CCG ACC GCG CCG CCA GCA CCC TGC AG-3' (SEQ ID NO:44). When hybridized, the 5' end of the vacuolar targetting signal resembled "sticky-ends" corresponding to restriction sites SacII and PstI. The oligonucleotide was hybridized and phosphorylated and ligated into pCIB5528 (construction described above) which had been digested with SacII/PstI using standard procedures. The resulting maize optimized coding sequence is disclosed in SEQ ID NO:45 which encodes the protein disclosed in SEQ ID NO:46. This encoded protein comprises the vacuolar targetting peptide in addition to the eukaryotic secretion signal.

The VIP1 gene can also be designed to be secreted or targeted to subcellular organelles by similar procedures.

Example 23

Removal of Bacillus Secretion Signal from VIP1A(a) and VIP2A(a)

VIP1A(a) and VIP2A(a) are secreted during the growth of strain AB78. The nature of peptide sequences that act as secretion signals has been described in the literature (Simonen and Palva, Microbiological reviews, pg. 109–137 (1993)). Following the information in the above publication, the putative secretion signal was identified in both genes. In VIP1A(a) this signal is composed of amino acids 1–33 (See SEQ ID NO:5). Processing of the secretion signal probably occurs after the serine at amino acid 33. The secretion signal in VIP2A(a) was identified as amino acids 1–49 (See SEQ ID NO:2). N-terminal peptide analysis of the secreted mature VIP2A(a) protein revealed the N-terminal sequence LKITDKVEDFKEDK. This sequence is found beginning at amino acid 57 in SEQ ID NO:2. The genes encoding these proteins have been modified by removal of the Bacillus secretion signals.

A maize optimized VIP1A(a) coding region was constructed which had the sequences encoding the first 33 amino acids, i.e., the secretion signal, removed from its 5' end. This modification was obtained by PCR using an forward primer that contained the sequence 5'-GGA TCC ACC ATG AAG ACC AAC CAG ATC AGC-3' (SEQ ID NO:33), which hybridizes with the maize optimized gene (SEQ ID NO:26) at nucleotide position 100,and added a BamHI restriction site and a eukaryotic translation start site consensus including a start codon. The reverse primer that contained the sequence 5'-AAG CTT CAG CTC CTT G-3' (SEQ ID NO:34) hybridizes on the complementary strand at nucelotide position 507. A 527 bp amplification product was obtained containing the restriction sites BamHI at the 5' end and HindIII site at the 3' end. The amplification product was cloned into a T- vector (described in Example 24, below) and sequenced to ensure the correct DNA sequence. The BamHI/HindIII fragment was then obtained by restriction digest and used to replace the BamHI/HindIII fragment of the maize optimized VIP1A(a) gene cloned in the root-preferred promoter cassette. The construct obtained was designated pCIB5526. The maize optimized coding region for VIP1A(a) with the Bacillus secretion signal removed is disclosed as SEQ ID NO:35 and the encoded protein is disclosed as SEQ ID NO:36.

The gene encoding the processed form of VIP2A(a), i.e., a coding region with the secretion signal removed, was constructed by a procedure similar to that described for that used to construct the processed form of VIP1A(a), above. The modification was obtained by PCR using the forward primer 5'-GGA TCC ACC ATG CTG CAG AAC CTG AAG ATC AC-3' (SEQ ID NO:37). This primer hybridizes at nucleotide position 150 of the maize optimized VIP2A(a) gene (SEQ ID NO:27). A silent mutation has been inserted at nucleotide position 15 of this primer to obtain a PstI restriction site. The reverse primer has the sequence 5'-AAG CTT CCA CTC CTT CTC-3' (SEQ ID NO:38). A 259 bp product was obtained with HindIII restriction site at the 3' end. The amplification product was cloned into a T- vector, sequenced and ligated to a BamHI/HindIII digested root-preferred promoter cassette containing the maize optimized VIP2A(a). The construct obtained was designated pCIB5527. The maize optimized coding region for VIP2A(a) with the Bacillus secretion signal removed is disclosed as SEQ ID NO:39 and the encoded protein is disclosed as SEQ ID NO:40.

Example 24

Construction and Cloning of the VIP1A(a) and VIP2A(a) Maize Optimized Genes

Design

The maize optimized genes were designed by reverse translation of the native VIP1A(a) and VIP2A(a) protein sequences using codons that are used most often in maize (Murray et al., Nucleic Acid Research, 17:477–498 (1989)). To facilitate cloning, the DNA sequence was further modified to incorporate unique restriction sites at intervals of every 200–360 nucleotides. VIP1A(a) was designed to be cloned in 11 such fragments and VIP2A(a) was cloned in 5 fragments. Following cloning of the individual fragments, adjacent fragments were joined using the restriction sites common to both fragments, to obtain the complete gene. To clone each fragment, oligonucleotides (50–85 nucleotides) were designed to represent both the upper and the lower strand of the DNA. The upper oligo of the first oligo pair was designed to have a 15 bp single stranded region at the 3' end which was homologous to a similar single stranded region of the lower strand of the next oligo pair to direct the orientation and sequence of the various oligo pairs within a given fragment. The oligos are also designed such that when the all the oligos representing a fragment are hybridized, the ends have single stranded regions corresponding to the particular restriction site to be formed. The structure of each oligomer was examined for stable secondary structures such as hairpin loops using the OLIGO program from NBI Inc. Whenever neccesary, nucleotides were changed to decrease the stability of the secondary structure without changing the amino acid sequence of the protein. A plant ribosomal binding site consensus sequence, TAAACAATG (Joshi et al., Nucleic Acid Res., 15:6643–6653 (1987)) or eukaryotic ribosomal binding site concensus sequence CCACCATG (Kozak,

*Nucleic Acid Research*, 12:857–872 (1984)) was inserted at the translational start codon of the gene.

Cloning

Oligos were synthesized by IDT Inc., and were supplied as lyophilized powders. They were resuspended at a concentration of 200 μM. To 30 μl of each oligo formamide was added a final concentration of 25–50% and the sample was boiled for two minutes before separation on a premade 10% polyacryamide/urea gel obtained from Novex. After electrophoresis, the oligo was detected by UV shadowing by placing the gel on a TLC plate containing a fluorescent indicator and exposing it to UV light. The region containing DNA of the correct size was excised and extracted from the polyacryamide by an overnight incubation of the minced gel fragment in a buffer containing 0.4M LiCl, 0.1 mM EDTA. The DNA was separated from the gel residue by centrifugation through a Millipore UFMC filter. The extracted DNA was ethanol precipitated by the addition of 2 volumes of absolute alcohol. After centrifugation, the precipitate was resuspended in $dH_2O$ at a concentration of 2.5 μM. Fragments were cloned either by hybridization of the oligos and ligation with the appropriate vector or by amplification of the hybridized fragment using a equimolar mixture of all the oligos for a particular fragment as a template and end-specific PCR primers.

Cloning by hybridization and ligation

Homologous double stranded oligo pairs were obtained by mixing 5 μl of the upper and of the lower oligo for each oligo pair with buffer containing 1× polynucleotide kinase (PNK) buffer (70 mM Tris-HCl (pH 7.6), 10 mM $MgCl_2$, 5 mM dithiothreitol (DTT)), 50 mM KCl, and 5% formamide in a final volume of 50 μl. The oligos were boiled for 10 minutes and slow cooled to 37° C. or room temperature. 10 μl was removed for analysis on a 4% agarose in a TAE buffer system (Metaphore®; FMC). Each hybridized oligo pair was kinased by the addition of ATP at a final concentration of 1 mM, BSA at a final concentration of 100 μg per ml and 200 units of polynucleotide kinase and 1 μl of 10× PNK buffer in a volume of 10 μl. Following hybridization and phosphorylation, the reaction was incubated at 37° C. for 2 hours to overnight. 10 μl of each of the oligo pairs for a particular fragment, were mixed in a final volume of 50 μl. The oligo pairs were hybridized by heating at 80° C. for 10 minutes and slow cooling to 37° C. 2 μl of oligos was mixed with about 100 ng of an appropriate vector and ligated using a buffer containing 50 mM Tris-HCl (pH 7.8), 10 mM $MgCl_2$, 10 mM DTT, 1 mM ATP. The reaction was incubated at room temp. for 2 hours to overnight and transformed into DH5α strain of *E. coli*, plated on L- plates containing ampicillin at a concentration of 100 μg/ml using standard procedures. Positive clones were further characterized and confirmed by PCR miniscreen described in detail in U.S. Pat. No. 5,625,136 using the universal primers "Reverse" and M13 "-20" as primers. Positive clones were identified by digestion of DNA with appropriate enzymes followed by sequencing. Recombinants that had the expected DNA sequence were then selected for further work.

PCR Amplification and cloning into T- vector

PCR amplification was carried out by using a mixture of all the oligomers that represented the upper and the lower strand of a particular fragment (final concentration 5 mM each) as template, specific end primers for the particular fragment (final concentration 2 mM) 200 μM of each dATP, dTTP, dCTP and dGTP, 10 mM Tris-HCl (pH 8.3), 50 mM KCl, 1.5 mM $MgCl_2$, 0.01% gelatin and 5 units of Taq polymerase in a final reaction volume of 50 μl. The amplification reaction was carried out in a Perkin Elmer thermocycler 9600 by incubation at 95° C. for 1 min (1 cycle), followed by 20 cycles of 95° C. for 45 sec., 50° C. for 30 sec. Finally the reaction was incubated for 5 min at 72° C. before analyzing the product. 10 μl of the reaction was analyzed on a 2.5% Nusieve (FMC) agarose gel in a TAE buffer system. The correct size fragment was gel purified and used for cloning into a PCR cloning vector or T-vector. T-vector construction was as described by Marchuk et al., *Nucleic Acid Research*, 19:1154 (1991). pBluescriptsk+ (Stratagene®, Calif.) was used as the parent vector. Transformation and identification of the correct clone was carried out as described above.

Fragments 1, 3, 4, 5, 6, 8, and 9 of VIP1A(a) and fragments 2 and 4 of VIP2A(a) were obtained by cloning of PCR amplification products; whereas, fragments 2, 7, 10 and 11 of VIP1A(a) and fragments 1, 3, and 5 of VIP2A(a) were obtained by hybridization/ligation.

Once fragments with the desired sequence were obtained, the complete gene was assembled by cloning together adjacent fragments. The complete gene was resequenced and tested for activity against WCRW before moving it into plant expression vectors containing the root preferred promoter (disclosed in U.S. Pat. No. 5,466,785, herein incorporated by reference) and the rice actin promoter.

One such plant expression vector is pCIB5521. The maize optimized VIP1A(a) coding region (SEQ ID NO:26) was cloned in a plant expression vector containing the root preferred promoter at the 5' of the gene with the PEP Carboxylase intron #9 followed by the 35S terminator at the 3' end. The plasmid also contains sequences for ampicillin resistance from the plasmid pUC19. Another plant expression vector is pCIB5522, which contains the maize optimized VIP2A(a) coding region (SEQ ID NO:27) fused to the root preferred promoter at the 5' of the gene with the PEP Carboxylase intron #9 followed by the 35S terminator at the 3' end.

Example 25

NAD Affinity Chromatography

A purification strategy was used based on the affinity of VIP2 for the substrate NAD. The supernatant from the pH 3.5 sodium citrate buffer treatment described in Example 4 was dialyzed in 20 mM TRIS pH 7.5 overnight. The neutralized supernatant was added to an equal volume of washed NAD agarose and incubated with gentle rocking at 4° C. overnight. The resin and protein solution were added to a 10 ml disposable polypropylene column and the protein solution allowed to flow out. The column was washed with 5 column volumes of 20 mM TRIS pH 7.5 then washed with 2–5 column volumes of 20 mM TRIS pH 7.5, 100 mM NaCl, followed by 2–5 column volumes of 20 mM TRIS 7.5. The VIP proteins were eluted in 20 mM TRIS pH 7.5 supplemented with 5 mM NAD. Approximately 3 column volumes of the effluent were collected and concentrated in a Centricon -10. Yield is typically about 7–15 μg of protein per ml of resin.

When the purified proteins were analyzed by SDS-PAGE followed by silver staining, two polypeptides were visible, one with Mr of approximately 80,000 and one with Mr of approximately 45,000. N-terminal sequencing revealed that the Mr 80,000 protein corresponded to a proteolytically processed form of VIP1A(A) and the Mr 45,000 form corresponded to a proteolytically processed form of VIP2A (a). The co-purification of VIP1A(a) with VIP2A(a) indicates that the two proteins probably form a complex and have protein-protein interacting regions. VIP1A(a) and VIP2A(a) proteins purified in this manner were biologically active against western corn rootworm.

Example 26

Expression of Maize Optimized VIP1(a) and VIP2A(a)

*E. coli* strains containing different plasmids comprising VIP genes were assayed for expression of VIPs. *E. coli* strains harboring the individual plasmids were grown overnight in L-broth and expressed protein was extracted from the culture as described in Example 3, above. Protein expression was assayed by Western Blot analysis using antibodies developed using standard methods known in the art, similar to those described in Example 12, above. Also, insecticidal activity of the expressed proteins were tested against Western corn rootworm according to the method in Example 3, above. The results of the *E. coli* expression assays are described below.

| Extract of *E. coli* Strain Harboring Indicated Plasmid | Assay No. 1 % Mortality | Assay No. 2 % Mortality | Protein Detected |
|---|---|---|---|
| Control | 0 | 0 | no |
| pCIB5521 (maize optimized VIP1A(a)) | 47 | 27 | yes |
| pCIB5522 (maize optimized VIP2A(a)) | 7 | 7 | yes |
| pCIB6024 (native VIP2A(a)) | 13 | 13 | yes |
| pCIB6206 (native VIP1A(a)) | 27 | 40 | yes |
| Extracts pCIB5521 + pCIB5522 combined | 87 | 47 | |
| Extracts pCIB5521 + pCIB6024 combined | 93 | 100 | |
| Extracts pCIB5522 + pCIB6206 combined | 100 | 100 | |
| Extracts pCIB6024 + pCIB6206 combined | 100 | 100 | |

The DNA from these plasmids was used to transiently express the VIPs in a maize protoplast expression system. Protoplasts were isolated from maize 2717 Line 6 suspension cultures by digestion of the cell walls using Cellulase RS and Macerase R10 in appropriate buffer. Protoplasts were recovered by sieving and centrifugation. Protoplasts were transformed by a standard direct gene transfer method using approximately 75 μg plasmid DNA and PEG-40. Treated protoplasts were incubated overnight in the dark at room temperature. Analysis of VIP expression was accomplished on protoplast explants by Western blot analysis and insecticidal activity against Western corn rootworm as described above for the expression in *E. coli*. The results of the maize protoplast expression assays are described below.

| Extract Tested | Assay No. 1 % Mortality | Assay No. 2 % Mortality | Protein Detected |
|---|---|---|---|
| No DNA control | 0 | 10 | no |
| pCIB5521 (p) (maize optimized VIP1A(a)) | 20 (0) | 30 | yes |
| pCIB5522 (p) (maize optmizied VIP2A(a)) | 20 (0) | 20 | yes |
| Extracts pCIB5521 (p) + pCIB5522 (p) combined | 87 (82) | 90 | |
| Extracts pCIB5521 (p) + pCIB5522 (e) combined | 100 | — | |
| Extracts pCIB5522 (p) + pCIB5521 (e) combined | 53 (36) | — | |
| Extracts pCIB5521 (p) + pCIB6024 (e) combined | 100 | — | |
| Extracts pCIB5522 (p) + pCIB6206 (e) combined | 100 | — | |
| pCIB6024(e) (native VIP2A(a)) | 0 | — | yes |
| pCIB6206(e) (native VIP1A(a)) | 20 | — | yes |
| pCIB5521 + pCIB5522 (plasmids delivered by cotransformation) | 100 | 100 | yes |

(p) = extract of protoplast culture transformed with indicated plasmid
(e) = extract of *E. coli* strain harboring indicated plasmid The expression data obtained with both *E. coli* and maize protoplasts show that the maize optimized VIP1A(a) and VIP2A(a) genes make the same protein as the native VIP1A (a) and VIP2A(a) genes, respectively, and that the proteins encoded by the maize optimized genes are functionally equivalent to the proteins encoded by the native genes.

All publications and Pat. applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following deposits have been made at Agricultural Research Service, Patent Culture Collection (NRRL), Northern Regional Research Center, 1815 North University Street, Peoria, Ill. 61604, USA:

| | |
|---|---|
| 1. *E. coli* PL2 | Accession No. NRRL B-21221N |
| 2. *E. coli* pCIB6022 | Accession No. NRRL B-21222 |
| 3. *E. coli* pCIB6023 | Accession No. NRRL B-21223N |
| 4. *Bacillus thuringiensis* HD73-78VIP | Accession No. NRRL B-21224 |
| 5. *Bacillus thuringiensis* AB88 | Accession No. NRRL B-21225 |
| 6. *Bacillus thuringiensis* AB359 | Accession No. NRRL B-21226 |
| 7. *Bacillus thuringiensis* AB289 | Accession No. NRRL B-21227 |
| 8. *Bacillus* sp. AB59 | Accession No. NRRL B-21228 |
| 9. *Bacillus* sp. AB294 | Accession No. NRRL B-21229 |
| 10. *Bacillus* sp. AB256 | Accession No. NRRL B-21230 |
| 11. *E. coli* PS-4 | Accession No. NRRL B-21059 |
| 12. *E. coli* P3-12 | Accession No. NRRL B-21061 |
| 13. *Bacillus cereus* AB78 | Accession No. NRRL B-21058 |
| 14. *Bacillus thuringiensis* AB6 | Accession No. NRRL B-21060 |
| 15. *E. coli* pCIB6202 | Accession No. NRRL B-21321 |
| 16. *E. coli* pCIB7100 | Accession No. NRRL B-21322 |
| 17. *E. coli* pCIB7101 | Accession No. NRRL B-21323 |
| 18. *E. coli* pCIB7102 | Accession No. NRRL B-21324 |
| 19. *E. coli* pCIB7102 | Accession No. NRRL B-21325 |
| 20. *E. coli* pCIB7104 | Accession No. NRRL B-21422 |
| 21. *E. coli* pCIB7107 | Accession No. NRRL B-21423 |
| 22. *E. coli* pCIB7108 | Accession No. NRRL B-21438 |
| 23. *Bacillus thuringiensis* AB424 | Accession No. NRRL B-21439 |

Although the foregoing invention has been described in some detail by way of illustration and example for purposes of clarity of understanding, it will be obvious that certain changes and modifications may be practiced within the scope of the appended claims.

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
( A ) LENGTH: 6049 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Bacillus cereus
( B ) STRAIN: AB78
( C ) INDIVIDUAL ISOLATE: NRRL B- 21058

( i x ) FEATURE:
( A ) NAME/KEY: CDS
( B ) LOCATION: 1082..2467
( D ) OTHER INFORMATION: /product="VIP2A(a)"

( i x ) FEATURE:
( A ) NAME/KEY: misc_feature
( B ) LOCATION: 2475..5126
( D ) OTHER INFORMATION: /note= "Coding sequence for the 100 kd VIP1A(a) protein. This coding sequence is repeated in SEQ ID NO:4 and translated separately."

( x i ) SEQUENCE DESCRIPTION: SEQ ID NO:1:

ATCGATACAA TGTTGTTTTA CTTAGACCGG TAGTCTCTGT AATTTGTTTA ATGCTATATT 60

CTTTACTTTG ATACATTTTA ATAGCCATTT CAACCTTATC AGTATGTTTT TGTGGTCTTC 120

CTCCTTTTTT TCCACGAGCT CTAGCTGCGT TTAATCCTGT TTTGGTACGT TCGCTAATAA 180

TATCTCTTTC TAATTCTGCA ATACTTGCCA TCATTCGAAA GAAGAATTTC CCCATAGCAT 240

TAGAGGTATC AATGTTGTCA TGAATAGAAA TAAAATCTAC ACCTAGCTCT TTGAATTTTT 300

CACTTAACTC AATTAGGTGT TTTGTAGAGC GAGAAATTCG ATCAAGTTTG TAAACAACTA 360

TCTTATCGCC TTTACGTAAT ACTTTTAGCA ACTCTTCGAG TTGAGGGCGC TCTTTTTTTA 420

TTCCTGTTAT TTTCTCCTGA TATAGCCTTT CTACACCATA TTGTTGCAAA GCATCTATTT 480

GCATATCGAG ATTTTGTTCT TCTGTGCTGA CACGAGCATA ACCAAAAATC AAATTGGTTT 540

CACTTCCTAT CTAAATATAT CTATTAAAAT AGCACCAAAA ACCTTATTAA ATTAAAATAA 600

GGAACTTTGT TTTTGGATAT GGATTTTGGT ACTCAATATG GATGAGTTTT TAACGCTTTT 660

GTTAAAAAAC AAACAAGTGC CATAAACGGT CGTTTTTGGG ATGACATAAT AAATAATCTG 720

TTTGATTAAC CTAACCTTGT ATCCTTACAG CCCAGTTTTA TTTGTACTTC AACTGACTGA 780

ATATGAAAAC AACATGAAGG TTTCATAAAA TTTATATATT TTCCATAACG GATGCTCTAT 840

CTTTAGGTTA TAGTTAAATT ATAAGAAAAA AACAAACGGA GGGAGTGAAA AAAAGCATCT 900

TCTCTATAAT TTTACAGGCT CTTTAATAAG AAGGGGGGAG ATTAGATAAT AAATATGAAT 960

ATCTATCTAT AATTGTTTGC TTCTACAATA ACTTATCTAA CTTTCATATA CAACAACAAA 1020

ACAGACTAAA TCCAGATTGT ATATTCATTT TCAGTTGTTC CTTTATAAAA TAATTTCATA 1080

A ATG AAA AGA ATG GAG GGA AAG TTG TTT ATG GTG TCA AAA AAA TTA 1126
Met Lys Arg Met Glu Gly Lys Leu Phe Met Val Ser Lys Lys Leu
1 5 10 15

CAA GTA GTT ACT AAA ACT GTA TTG CTT AGT ACA GTT TTC TCT ATA TCT 1174
Gln Val Val Thr Lys Thr Val Leu Leu Ser Thr Val Phe Ser Ile Ser
20 25 30

TTA TTA AAT AAT GAA GTG ATA AAA GCT GAA CAA TTA AAT ATA AAT TCT 1222
Leu Leu Asn Asn Glu Val Ile Lys Ala Glu Gln Leu Asn Ile Asn Ser
35 40 45

CAA AGT AAA TAT ACT AAC TTG CAA AAT CTA AAA ATC ACT GAC AAG GTA 1270
Gln Ser Lys Tyr Thr Asn Leu Gln Asn Leu Lys Ile Thr Asp Lys Val
50 55 60

```
GAG  GAT  TTT  AAA  GAA  GAT  AAG  GAA  AAA  GCG  AAA  GAA  TGG  GGG  AAA  GAA              1318
Glu  Asp  Phe  Lys  Glu  Asp  Lys  Glu  Lys  Ala  Lys  Glu  Trp  Gly  Lys  Glu
          65                  70                  75

AAA  GAA  AAA  GAG  TGG  AAA  CTA  ACT  GCT  ACT  GAA  AAA  GGA  AAA  ATG  AAT              1366
Lys  Glu  Lys  Glu  Trp  Lys  Leu  Thr  Ala  Thr  Glu  Lys  Gly  Lys  Met  Asn
 80                  85                  90                                  95

AAT  TTT  TTA  GAT  AAT  AAA  AAT  GAT  ATA  AAG  ACA  AAT  TAT  AAA  GAA  ATT              1414
Asn  Phe  Leu  Asp  Asn  Lys  Asn  Asp  Ile  Lys  Thr  Asn  Tyr  Lys  Glu  Ile
                         100                 105                      110

ACT  TTT  TCT  ATG  GCA  GGC  TCA  TTT  GAA  GAT  GAA  ATA  AAA  GAT  TTA  AAA              1462
Thr  Phe  Ser  Met  Ala  Gly  Ser  Phe  Glu  Asp  Glu  Ile  Lys  Asp  Leu  Lys
                    115                 120                      125

GAA  ATT  GAT  AAG  ATG  TTT  GAT  AAA  ACC  AAT  CTA  TCA  AAT  TCT  ATT  ATC              1510
Glu  Ile  Asp  Lys  Met  Phe  Asp  Lys  Thr  Asn  Leu  Ser  Asn  Ser  Ile  Ile
               130                 135                      140

ACC  TAT  AAA  AAT  GTG  GAA  CCG  ACA  ACA  ATT  GGA  TTT  AAT  AAA  TCT  TTA              1558
Thr  Tyr  Lys  Asn  Val  Glu  Pro  Thr  Thr  Ile  Gly  Phe  Asn  Lys  Ser  Leu
          145                 150                      155

ACA  GAA  GGT  AAT  ACG  ATT  AAT  TCT  GAT  GCA  ATG  GCA  CAG  TTT  AAA  GAA              1606
Thr  Glu  Gly  Asn  Thr  Ile  Asn  Ser  Asp  Ala  Met  Ala  Gln  Phe  Lys  Glu
160                      165                 170                           175

CAA  TTT  TTA  GAT  AGG  GAT  ATT  AAG  TTT  GAT  AGT  TAT  CTA  GAT  ACG  CAT              1654
Gln  Phe  Leu  Asp  Arg  Asp  Ile  Lys  Phe  Asp  Ser  Tyr  Leu  Asp  Thr  His
                    180                 185                      190

TTA  ACT  GCT  CAA  CAA  GTT  TCC  AGT  AAA  GAA  AGA  GTT  ATT  TTG  AAG  GTT              1702
Leu  Thr  Ala  Gln  Gln  Val  Ser  Ser  Lys  Glu  Arg  Val  Ile  Leu  Lys  Val
               195                 200                      205

ACG  GTT  CCG  AGT  GGG  AAA  GGT  TCT  ACT  ACT  CCA  ACA  AAA  GCA  GGT  GTC              1750
Thr  Val  Pro  Ser  Gly  Lys  Gly  Ser  Thr  Thr  Pro  Thr  Lys  Ala  Gly  Val
          210                 215                      220

ATT  TTA  AAT  AAT  AGT  GAA  TAC  AAA  ATG  CTC  ATT  GAT  AAT  GGG  TAT  ATG              1798
Ile  Leu  Asn  Asn  Ser  Glu  Tyr  Lys  Met  Leu  Ile  Asp  Asn  Gly  Tyr  Met
225                      230                      235

GTC  CAT  GTA  GAT  AAG  GTA  TCA  AAA  GTG  GTG  AAA  AAA  GGG  GTG  GAG  TGC              1846
Val  His  Val  Asp  Lys  Val  Ser  Lys  Val  Val  Lys  Lys  Gly  Val  Glu  Cys
240                      245                 250                           255

TTA  CAA  ATT  GAA  GGG  ACT  TTA  AAA  AAG  AGT  CTT  GAC  TTT  AAA  AAT  GAT              1894
Leu  Gln  Ile  Glu  Gly  Thr  Leu  Lys  Lys  Ser  Leu  Asp  Phe  Lys  Asn  Asp
                    260                 265                      270

ATA  AAT  GCT  GAA  GCG  CAT  AGC  TGG  GGT  ATG  AAG  AAT  TAT  GAA  GAG  TGG              1942
Ile  Asn  Ala  Glu  Ala  His  Ser  Trp  Gly  Met  Lys  Asn  Tyr  Glu  Glu  Trp
               275                 280                      285

GCT  AAA  GAT  TTA  ACC  GAT  TCG  CAA  AGG  GAA  GCT  TTA  GAT  GGG  TAT  GCT              1990
Ala  Lys  Asp  Leu  Thr  Asp  Ser  Gln  Arg  Glu  Ala  Leu  Asp  Gly  Tyr  Ala
          290                 295                      300

AGG  CAA  GAT  TAT  AAA  GAA  ATC  AAT  AAT  TAT  TTA  AGA  AAT  CAA  GGC  GGA              2038
Arg  Gln  Asp  Tyr  Lys  Glu  Ile  Asn  Asn  Tyr  Leu  Arg  Asn  Gln  Gly  Gly
305                      310                      315

AGT  GGA  AAT  GAA  AAA  CTA  GAT  GCT  CAA  ATA  AAA  AAT  ATT  TCT  GAT  GCT              2086
Ser  Gly  Asn  Glu  Lys  Leu  Asp  Ala  Gln  Ile  Lys  Asn  Ile  Ser  Asp  Ala
320                      325                 330                           335

TTA  GGG  AAG  AAA  CCA  ATA  CCG  GAA  AAT  ATT  ACT  GTG  TAT  AGA  TGG  TGT              2134
Leu  Gly  Lys  Lys  Pro  Ile  Pro  Glu  Asn  Ile  Thr  Val  Tyr  Arg  Trp  Cys
                    340                 345                      350

GGC  ATG  CCG  GAA  TTT  GGT  TAT  CAA  ATT  AGT  GAT  CCG  TTA  CCT  TCT  TTA              2182
Gly  Met  Pro  Glu  Phe  Gly  Tyr  Gln  Ile  Ser  Asp  Pro  Leu  Pro  Ser  Leu
               355                 360                      365

AAA  GAT  TTT  GAA  GAA  CAA  TTT  TTA  AAT  ACA  ATC  AAA  GAA  GAC  AAA  GGA              2230
Lys  Asp  Phe  Glu  Glu  Gln  Phe  Leu  Asn  Thr  Ile  Lys  Glu  Asp  Lys  Gly
          370                 375                      380
```

```
TAT ATG AGT ACA AGC TTA TCG AGT GAA CGT CTT GCA GCT TTT GGA TCT       2278
Tyr Met Ser Thr Ser Leu Ser Ser Glu Arg Leu Ala Ala Phe Gly Ser
    385             390                 395

AGA AAA ATT ATA TTA CGA TTA CAA GTT CCG AAA GGA AGT ACG GGT GCG       2326
Arg Lys Ile Ile Leu Arg Leu Gln Val Pro Lys Gly Ser Thr Gly Ala
400             405                 410                 415

TAT TTA AGT GCC ATT GGT GGA TTT GCA AGT GAA AAA GAG ATC CTA CTT       2374
Tyr Leu Ser Ala Ile Gly Gly Phe Ala Ser Glu Lys Glu Ile Leu Leu
                420                 425                 430

GAT AAA GAT AGT AAA TAT CAT ATT GAT AAA GTA ACA GAG GTA ATT ATT       2422
Asp Lys Asp Ser Lys Tyr His Ile Asp Lys Val Thr Glu Val Ile Ile
                435                 440                 445

AAA GGT GTT AAG CGA TAT GTA GTG GAT GCA ACA TTA TTA ACA AAT           2467
Lys Gly Val Lys Arg Tyr Val Val Asp Ala Thr Leu Leu Thr Asn
450                 455                 460

TAAGGAGATG AAAAATATGA AGAAAAAGTT AGCAAGTGTT GTAACGTGTA CGTTATTAGC     2527
TCCTATGTTT TTGAATGGAA ATGTGAATGC TGTTTACGCA GACAGCAAAA CAAATCAAAT     2587
TTCTACAACA CAGAAAAATC AACAGAAAGA GATGGACCGA AAAGGATTAC TTGGGTATTA     2647
TTTCAAGGA AAAGATTTTA GTAATCTTAC TATGTTTGCA CCGACACGTG ATAGTACTCT      2707
TATTTATGAT CAACAAACAG CAAATAAACT ATTAGATAAA AACAACAAG AATATCAGTC      2767
TATTCGTTGG ATTGGTTTGA TTCAGAGTAA AGAACGGGA GATTTCACAT TTAACTTATC      2827
TGAGGATGAA CAGGCAATTA TAGAAATCAA TGGGAAAATT ATTTCTAATA AGGGAAAGA      2887
AAAGCAAGTT GTCCATTTAG AAAAAGGAAA ATTAGTTCCA ATCAAAATAG AGTATCAATC     2947
AGATACAAAA TTTAATATTG ACAGTAAAAC ATTTAAAGAA CTTAAATTAT TTAAAATAGA     3007
TAGTCAAAAC CAACCCCAGC AAGTCCAGCA AGATGAACTG AGAAATCCTG AATTTAACAA     3067
GAAAGAATCA CAGGAATTCT TAGCGAAACC ATCGAAAATA AATCTTTTCA CTCAAAAAAT     3127
GAAAAGGGAA ATTGATGAAG ACACGGATAC GGATGGGGAC TCTATTCCTG ACCTTTGGGA     3187
AGAAAATGGG TATACGATTC ACAATAGAAT CGCTGTAAAG TGGGACGATT CTCTAGCAAG     3247
TAAAGGGTAT ACGAAATTTG TTTCAAATCC ACTAGAAAGT CACACAGTTG GTGATCCTTA     3307
TACAGATTAT GAAAAGGCAG CAAGAGATCT AGATTTGTCA AATGCAAAGG AAACGTTTAA     3367
CCCATTGGTA GCTGCTTTTC AAGTGTGAA TGTTAGTATG GAAAAGGTGA TATTATCACC      3427
AAATGAAAAT TTATCCAATA GTGTAGAGTC TCATTCATCC ACGAATTGGT CTTATACAAA     3487
TACAGAAGGT GCTTCTGTTG AAGCGGGGAT TGGACCAAAA GGTATTTCGT TCGGAGTTAG     3547
CGTAAACTAT CAACACTCTG AAACAGTTGC ACAAGAATGG GAACATCTA CAGGAAATAC      3607
TTCGCAATTC AATACGGCTT CAGCGGGATA TTTAAATGCA AATGTTCGAT ATAACAATGT     3667
AGGAACTGGT GCCATCTACG ATGTAAAACC TACAACAAGT TTTGTATTAA ATAACGATAC     3727
TATCGCAACT ATTACGGCGA AATCTAATTC TACAGCCTTA AATATATCTC CTGGAGAAAG     3787
TTACCCGAAA AAAGGACAAA ATGGAATCGC AATAACATCA ATGGATGATT TAATTCCCA      3847
TCCGATTACA TTAAATAAAA AACAAGTAGA TAATCTGCTA ATAATAAAC CTATGATGTT      3907
GGAAACAAAC CAAACAGATG GTGTTTATAA GATAAAAGAT ACACATGGAA ATATAGTAAC     3967
TGGCGGAGAA TGGAATGGTG TCATACAACA AATCAAGGCT AAAACAGCGT CTATTATTGT     4027
GGATGATGGG GAACGTGTAG CAGAAAAACG TGTAGCGGCA AAAGATTATG AAAATCCAGA     4087
AGATAAAACA CCGTCTTTAA CTTTAAAAGA TGCCCTGAAG CTTTCATATC AGATGAAAT      4147
AAAAGAAATA GAGGGATTAT TATATTATAA AAACAAACCG ATATCGAAT CGAGCGTTAT      4207
GACTTACTTA GATGAAAAATA CAGCAAAAGA AGTGACCAAA CAATTAAATG ATACCACTGG    4267
```

| | | | | | |
|---|---|---|---|---|---|
| GAAATTTAAA | GATGTAAGTC | ATTTATATGA | TGTAAAACTG | ACTCCAAAAA | TGAATGTTAC | 4327 |
| AATCAAATTG | TCTATACTTT | ATGATAATGC | TGAGTCTAAT | GATAACTCAA | TTGGTAAATG | 4387 |
| GACAAACACA | AATATTGTTT | CAGGTGGAAA | TAACGGAAAA | AACAATATT  | CTTCTAATAA | 4447 |
| TCCGGATGCT | AATTTGACAT | TAAATACAGA | TGCTCAAGAA | AAATTAAATA | AAAATCGTGA | 4507 |
| CTATTATATA | AGTTTATATA | TGAAGTCAGA | AAAAAACACA | CAATGTGAGA | TTACTATAGA | 4567 |
| TGGGGAGATT | TATCCGATCA | CTACAAAAAC | AGTGAATGTG | AATAAAGACA | ATTACAAAAG | 4627 |
| ATTAGATATT | ATAGCTCATA | ATATAAAAG  | TAATCCAATT | TCTTCACTTC | ATATTAAAAC | 4687 |
| GAATGATGAA | ATAACTTTAT | TTTGGGATGA | TATTTCTATA | ACAGATGTAG | CATCAATAAA | 4747 |
| ACCGGAAAAT | TTAACAGATT | CAGAAATTAA | ACAGATTTAT | AGTAGGTATG | GTATTAAGTT | 4807 |
| AGAAGATGGA | ATCCTTATTG | ATAAAAAGG  | TGGGATTCAT | TATGGTGAAT | TTATTAATGA | 4867 |
| AGCTAGTTTT | AATATTGAAC | CATTGCAAAA | TTATGTGACC | AAATATGAAG | TTACTTATAG | 4927 |
| TAGTGAGTTA | GGACCAAACG | TGAGTGACAC | ACTTGAAAGT | GATAAAATTT | ACAAGGATGG | 4987 |
| GACAATTAAA | TTTGATTTTA | CCAAATATAG | TAAAAATGAA | CAAGGATTAT | TTTATGACAG | 5047 |
| TGGATTAAAT | TGGGACTTTA | AAATTAATGC | TATTACTTAT | GATGGTAAAG | AGATGAATGT | 5107 |
| TTTTCATAGA | TATAATAAAT | AGTTATTATA | TCTATGAAGC | TGGTGCTAAA | GATAGTGTAA | 5167 |
| AAGTTAATAT | ACTGTAGGAT | TGTAATAAAA | GTAATGGAAT | TGATATCGTA | CTTTGGAGTG | 5227 |
| GGGGATACTT | TGTAAATAGT | TCTATCAGAA | ACATTAGACT | AAGAAAAGTT | ACTACCCCCA | 5287 |
| CTTGAAAATG | AAGATTCAAC | TGATTACAAA | CAACCTGTTA | AATATTATAA | GGTTTTAACA | 5347 |
| AAATATTAAA | CTCTTTATGT | TAATACTGTA | ATATAAAGAG | TTTAATTGTA | TTCAAATGAA | 5407 |
| GCTTTCCCAC | AAAATTAGAC | TGATTATCTA | ATGAAATAAT | CAGTCTAATT | TTGTAGAACA | 5467 |
| GGTCTGGTAT | TATTGTACGT | GGTCACTAAA | AGATATCTAA | TATTATTGGG | CAAGGCGTTC | 5527 |
| CATGATTGAA | TCCTCGAATG | TCTTGCCCTT | TCATTTATT  | TAAGAAGGAT | TGTGGAGAAA | 5587 |
| TTATGGTTTA | GATAATGAAG | AAAGACTTCA | CTTCTAATTT | TGATGTTAA  | ATAAATCAAA | 5647 |
| ATTTGGCGAT | TCACATTGTT | TAATCCACTG | ATAAACATA  | CTGGAGTGTT | CTTAAAAAAT | 5707 |
| CAGCTTTTTT | CTTTATAAAA | TTTTGCTTAG | CGTACGAAAT | TCGTGTTTTG | TTGGTGGGAC | 5767 |
| CCCATGCCCA | TCAACTTAAG | AGTAAATTAG | TAATGAACTT | TCGTTCATCT | GGATTAAAAT | 5827 |
| AACCTCAAAT | TAGGACATGT | TTTTAAAAAT | AAGCAGACCA | AATAAGCCTA | GAATAGGTAT | 5887 |
| CATTTTTAAA | AATTATGCTG | CTTTCTTTTG | TTTTCCAAAT | CCATTATACT | CATAAGCAAC | 5947 |
| ACCCATAATG | TCAAAGACTG | TTTTTGTCTC | ATATCGATAA | GCTTGATATC | GAATTCCTGC | 6007 |
| AGCCCGGGGG | ATCCACTAGT | TCTAGAGCGG | CCGCCACCGC | GG | | 6049 |

( 2 ) INFORMATION FOR SEQ ID NO:2:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Lys | Arg | Met | Glu | Gly | Lys | Leu | Phe | Met | Val | Ser | Lys | Lys | Leu | Gln |
|---|---|---|---|---|---|---|---|---|---|---|---|---|---|---|---|
| 1 | | | | 5 | | | | | 10 | | | | | 15 | |

| Val | Val | Thr | Lys | Thr | Val | Leu | Leu | Ser | Thr | Val | Phe | Ser | Ile | Ser | Leu |
|---|---|---|---|---|---|---|---|---|---|---|---|---|---|---|---|
| | | | 20 | | | | | 25 | | | | | 30 | | |

| Leu | Asn | Asn | Glu | Val | Ile | Lys | Ala | Glu | Gln | Leu | Asn | Ile | Asn | Ser | Gln |
|---|---|---|---|---|---|---|---|---|---|---|---|---|---|---|---|

```
                    35                        40                         45
Ser  Lys  Tyr  Thr  Asn  Leu  Gln  Asn  Leu  Lys  Ile  Thr  Asp  Lys  Val  Glu
          50                       55                       60

Asp  Phe  Lys  Glu  Asp  Lys  Glu  Lys  Ala  Lys  Glu  Trp  Gly  Lys  Glu  Lys
 65                       70                       75                        80

Glu  Lys  Glu  Trp  Lys  Leu  Thr  Ala  Thr  Glu  Lys  Gly  Lys  Met  Asn  Asn
                85                       90                             95

Phe  Leu  Asp  Asn  Lys  Asn  Asp  Ile  Lys  Thr  Asn  Tyr  Lys  Glu  Ile  Thr
               100                      105                      110

Phe  Ser  Met  Ala  Gly  Ser  Phe  Glu  Asp  Glu  Ile  Lys  Asp  Leu  Lys  Glu
               115                      120                      125

Ile  Asp  Lys  Met  Phe  Asp  Lys  Thr  Asn  Leu  Ser  Asn  Ser  Ile  Ile  Thr
          130                      135                      140

Tyr  Lys  Asn  Val  Glu  Pro  Thr  Thr  Ile  Gly  Phe  Asn  Lys  Ser  Leu  Thr
145                      150                      155                      160

Glu  Gly  Asn  Thr  Ile  Asn  Ser  Asp  Ala  Met  Ala  Gln  Phe  Lys  Glu  Gln
                    165                      170                      175

Phe  Leu  Asp  Arg  Asp  Ile  Lys  Phe  Asp  Ser  Tyr  Leu  Asp  Thr  His  Leu
               180                      185                      190

Thr  Ala  Gln  Gln  Val  Ser  Ser  Glu  Arg  Val  Ile  Leu  Lys  Val  Thr
               195                      200                      205

Val  Pro  Ser  Gly  Lys  Gly  Ser  Thr  Thr  Pro  Thr  Lys  Ala  Gly  Val  Ile
     210                      215                      220

Leu  Asn  Asn  Ser  Glu  Tyr  Lys  Met  Leu  Ile  Asp  Asn  Gly  Tyr  Met  Val
225                      230                      235                      240

His  Val  Asp  Lys  Val  Ser  Lys  Val  Val  Lys  Lys  Gly  Val  Glu  Cys  Leu
               245                      250                      255

Gln  Ile  Glu  Gly  Thr  Leu  Lys  Lys  Ser  Leu  Asp  Phe  Lys  Asn  Asp  Ile
               260                      265                      270

Asn  Ala  Glu  Ala  His  Ser  Trp  Gly  Met  Lys  Asn  Tyr  Glu  Glu  Trp  Ala
               275                      280                      285

Lys  Asp  Leu  Thr  Asp  Ser  Gln  Arg  Glu  Ala  Leu  Asp  Gly  Tyr  Ala  Arg
290                      295                      300

Gln  Asp  Tyr  Lys  Glu  Ile  Asn  Asn  Tyr  Leu  Arg  Asn  Gln  Gly  Gly  Ser
305                      310                      315                      320

Gly  Asn  Glu  Lys  Leu  Asp  Ala  Gln  Ile  Lys  Asn  Ile  Ser  Asp  Ala  Leu
               325                      330                      335

Gly  Lys  Lys  Pro  Ile  Pro  Glu  Asn  Ile  Thr  Val  Tyr  Arg  Trp  Cys  Gly
               340                      345                      350

Met  Pro  Glu  Phe  Gly  Tyr  Gln  Ile  Ser  Asp  Pro  Leu  Pro  Ser  Leu  Lys
               355                      360                      365

Asp  Phe  Glu  Glu  Gln  Phe  Leu  Asn  Thr  Ile  Lys  Glu  Asp  Lys  Gly  Tyr
     370                      375                      380

Met  Ser  Thr  Ser  Leu  Ser  Ser  Glu  Arg  Leu  Ala  Ala  Phe  Gly  Ser  Arg
385                      390                      395                      400

Lys  Ile  Ile  Leu  Arg  Leu  Gln  Val  Pro  Lys  Gly  Ser  Thr  Gly  Ala  Tyr
               405                      410                      415

Leu  Ser  Ala  Ile  Gly  Gly  Phe  Ala  Ser  Glu  Lys  Glu  Ile  Leu  Leu  Asp
               420                      425                      430

Lys  Asp  Ser  Lys  Tyr  His  Ile  Asp  Lys  Val  Thr  Glu  Val  Ile  Ile  Lys
          435                      440                      445

Gly  Val  Lys  Arg  Tyr  Val  Val  Asp  Ala  Thr  Leu  Leu  Thr  Asn
450                      455                      460
```

( 2 ) INFORMATION FOR SEQ ID NO:3:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..20
( D ) OTHER INFORMATION: /note= "Signal peptide for vacuolar targetting"

( x i ) SEQUENCE DESCRIPTION: SEQ ID NO:3:

```
Ser Ser Ser Ser Phe Ala Asp Ser Asn Pro Ile Arg Val Thr Asp Arg
1               5                   10                  15

Ala Ala Ser Thr
            20
```

( 2 ) INFORMATION FOR SEQ ID NO:4:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus cereus
( B ) STRAIN: AB78
( C ) INDIVIDUAL ISOLATE: NRRL B- 21058

( i x ) FEATURE:
( A ) NAME/KEY: CDS
( B ) LOCATION: 1..2652
( D ) OTHER INFORMATION: /product="100 kDa protein VIP1A(a)"
/ note= "This sequence is identical to the portion of SEQ ID NO:1 between and including nucleotide 2475 to 5126."

( x i ) SEQUENCE DESCRIPTION: SEQ ID NO:4:

```
ATG AAA AAT ATG AAG AAA AAG TTA GCA AGT GTT GTA ACG TGT ACG TTA      48
Met Lys Asn Met Lys Lys Lys Leu Ala Ser Val Val Thr Cys Thr Leu
        465                 470                 475

TTA GCT CCT ATG TTT TTG AAT GGA AAT GTG AAT GCT GTT TAC GCA GAC      96
Leu Ala Pro Met Phe Leu Asn Gly Asn Val Asn Ala Val Tyr Ala Asp
    480                 485                 490

AGC AAA ACA AAT CAA ATT TCT ACA ACA CAG AAA AAT CAA CAG AAA GAG     144
Ser Lys Thr Asn Gln Ile Ser Thr Thr Gln Lys Asn Gln Gln Lys Glu
495                 500                 505                 510

ATG GAC CGA AAA GGA TTA CTT GGG TAT TAT TTC AAA GGA AAA GAT TTT     192
Met Asp Arg Lys Gly Leu Leu Gly Tyr Tyr Phe Lys Gly Lys Asp Phe
                515                 520                 525

AGT AAT CTT ACT ATG TTT GCA CCG ACA CGT GAT AGT ACT CTT ATT TAT     240
Ser Asn Leu Thr Met Phe Ala Pro Thr Arg Asp Ser Thr Leu Ile Tyr
            530                 535                 540

GAT CAA CAA ACA GCA AAT AAA CTA TTA GAT AAA AAA CAA CAA GAA TAT     288
Asp Gln Gln Thr Ala Asn Lys Leu Leu Asp Lys Lys Gln Gln Glu Tyr
        545                 550                 555

CAG TCT ATT CGT TGG ATT GGT TTG ATT CAG AGT AAA GAA ACG GGA GAT     336
Gln Ser Ile Arg Trp Ile Gly Leu Ile Gln Ser Lys Glu Thr Gly Asp
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 560 |     |     |     |     | 565 |     |     |     |     | 570 |     |     |      |
| TTC | ACA | TTT | AAC | TTA | TCT | GAG | GAT | GAA | CAG | GCA | ATT | ATA | GAA | ATC | AAT | 384  |
| Phe | Thr | Phe | Asn | Leu | Ser | Glu | Asp | Glu | Gln | Ala | Ile | Ile | Glu | Ile | Asn |      |
| 575 |     |     |     |     | 580 |     |     |     |     | 585 |     |     |     |     | 590 |      |
| GGG | AAA | ATT | ATT | TCT | AAT | AAA | GGG | AAA | GAA | AAG | CAA | GTT | GTC | CAT | TTA | 432  |
| Gly | Lys | Ile | Ile | Ser | Asn | Lys | Gly | Lys | Glu | Lys | Gln | Val | Val | His | Leu |      |
|     |     |     |     | 595 |     |     |     |     | 600 |     |     |     |     | 605 |     |      |
| GAA | AAA | GGA | AAA | TTA | GTT | CCA | ATC | AAA | ATA | GAG | TAT | CAA | TCA | GAT | ACA | 480  |
| Glu | Lys | Gly | Lys | Leu | Val | Pro | Ile | Lys | Ile | Glu | Tyr | Gln | Ser | Asp | Thr |      |
|     |     |     | 610 |     |     |     |     | 615 |     |     |     |     | 620 |     |     |      |
| AAA | TTT | AAT | ATT | GAC | AGT | AAA | ACA | TTT | AAA | GAA | CTT | AAA | TTA | TTT | AAA | 528  |
| Lys | Phe | Asn | Ile | Asp | Ser | Lys | Thr | Phe | Lys | Glu | Leu | Lys | Leu | Phe | Lys |      |
|     |     |     |     | 625 |     |     |     |     | 630 |     |     |     |     | 635 |     |      |
| ATA | GAT | AGT | CAA | AAC | CAA | CCC | CAG | CAA | GTC | CAG | CAA | GAT | GAA | CTG | AGA | 576  |
| Ile | Asp | Ser | Gln | Asn | Gln | Pro | Gln | Gln | Val | Gln | Gln | Asp | Glu | Leu | Arg |      |
|     |     |     | 640 |     |     |     |     | 645 |     |     |     |     | 650 |     |     |      |
| AAT | CCT | GAA | TTT | AAC | AAG | AAA | GAA | TCA | CAG | GAA | TTC | TTA | GCG | AAA | CCA | 624  |
| Asn | Pro | Glu | Phe | Asn | Lys | Lys | Glu | Ser | Gln | Glu | Phe | Leu | Ala | Lys | Pro |      |
| 655 |     |     |     |     | 660 |     |     |     |     | 665 |     |     |     |     | 670 |      |
| TCG | AAA | ATA | AAT | CTT | TTC | ACT | CAA | AAA | ATG | AAA | AGG | GAA | ATT | GAT | GAA | 672  |
| Ser | Lys | Ile | Asn | Leu | Phe | Thr | Gln | Lys | Met | Lys | Arg | Glu | Ile | Asp | Glu |      |
|     |     |     |     | 675 |     |     |     |     | 680 |     |     |     |     | 685 |     |      |
| GAC | ACG | GAT | ACG | GAT | GGG | GAC | TCT | ATT | CCT | GAC | CTT | TGG | GAA | GAA | AAT | 720  |
| Asp | Thr | Asp | Thr | Asp | Gly | Asp | Ser | Ile | Pro | Asp | Leu | Trp | Glu | Glu | Asn |      |
|     |     |     | 690 |     |     |     |     | 695 |     |     |     |     | 700 |     |     |      |
| GGG | TAT | ACG | ATT | CAA | AAT | AGA | ATC | GCT | GTA | AAG | TGG | GAC | GAT | TCT | CTA | 768  |
| Gly | Tyr | Thr | Ile | Gln | Asn | Arg | Ile | Ala | Val | Lys | Trp | Asp | Asp | Ser | Leu |      |
|     |     |     |     | 705 |     |     |     |     | 710 |     |     |     |     | 715 |     |      |
| GCA | AGT | AAA | GGG | TAT | ACG | AAA | TTT | GTT | TCA | AAT | CCA | CTA | GAA | AGT | CAC | 816  |
| Ala | Ser | Lys | Gly | Tyr | Thr | Lys | Phe | Val | Ser | Asn | Pro | Leu | Glu | Ser | His |      |
| 720 |     |     |     |     | 725 |     |     |     |     | 730 |     |     |     |     |     |      |
| ACA | GTT | GGT | GAT | CCT | TAT | ACA | GAT | TAT | GAA | AAG | GCA | GCA | AGA | GAT | CTA | 864  |
| Thr | Val | Gly | Asp | Pro | Tyr | Thr | Asp | Tyr | Glu | Lys | Ala | Ala | Arg | Asp | Leu |      |
| 735 |     |     |     |     | 740 |     |     |     |     | 745 |     |     |     |     | 750 |      |
| GAT | TTG | TCA | AAT | GCA | AAG | GAA | ACG | TTT | AAC | CCA | TTG | GTA | GCT | GCT | TTT | 912  |
| Asp | Leu | Ser | Asn | Ala | Lys | Glu | Thr | Phe | Asn | Pro | Leu | Val | Ala | Ala | Phe |      |
|     |     |     |     | 755 |     |     |     |     | 760 |     |     |     |     | 765 |     |      |
| CCA | AGT | GTG | AAT | GTT | AGT | ATG | GAA | AAG | GTG | ATA | TTA | TCA | CCA | AAT | GAA | 960  |
| Pro | Ser | Val | Asn | Val | Ser | Met | Glu | Lys | Val | Ile | Leu | Ser | Pro | Asn | Glu |      |
|     |     |     | 770 |     |     |     |     | 775 |     |     |     |     | 780 |     |     |      |
| AAT | TTA | TCC | AAT | AGT | GTA | GAG | TCT | CAT | TCA | TCC | ACG | AAT | TGG | TCT | TAT | 1008 |
| Asn | Leu | Ser | Asn | Ser | Val | Glu | Ser | His | Ser | Ser | Thr | Asn | Trp | Ser | Tyr |      |
|     |     |     |     | 785 |     |     |     |     | 790 |     |     |     |     | 795 |     |      |
| ACA | AAT | ACA | GAA | GGT | GCT | TCT | GTT | GAA | GCG | GGG | ATT | GGA | CCA | AAA | GGT | 1056 |
| Thr | Asn | Thr | Glu | Gly | Ala | Ser | Val | Glu | Ala | Gly | Ile | Gly | Pro | Lys | Gly |      |
|     |     | 800 |     |     |     |     | 805 |     |     |     |     | 810 |     |     |     |      |
| ATT | TCG | TTC | GGA | GTT | AGC | GTA | AAC | TAT | CAA | CAC | TCT | GAA | ACA | GTT | GCA | 1104 |
| Ile | Ser | Phe | Gly | Val | Ser | Val | Asn | Tyr | Gln | His | Ser | Glu | Thr | Val | Ala |      |
| 815 |     |     |     |     | 820 |     |     |     |     | 825 |     |     |     |     | 830 |      |
| CAA | GAA | TGG | GGA | ACA | TCT | ACA | GGA | AAT | ACT | TCG | CAA | TTC | AAT | ACG | GCT | 1152 |
| Gln | Glu | Trp | Gly | Thr | Ser | Thr | Gly | Asn | Thr | Ser | Gln | Phe | Asn | Thr | Ala |      |
|     |     |     |     | 835 |     |     |     |     | 840 |     |     |     |     | 845 |     |      |
| TCA | GCG | GGA | TAT | TTA | AAT | GCA | AAT | GTT | CGA | TAT | AAC | AAT | GTA | GGA | ACT | 1200 |
| Ser | Ala | Gly | Tyr | Leu | Asn | Ala | Asn | Val | Arg | Tyr | Asn | Asn | Val | Gly | Thr |      |
|     |     |     | 850 |     |     |     |     | 855 |     |     |     |     | 860 |     |     |      |
| GGT | GCC | ATC | TAC | GAT | GTA | AAA | CCT | ACA | ACA | AGT | TTT | GTA | TTA | AAT | AAC | 1248 |
| Gly | Ala | Ile | Tyr | Asp | Val | Lys | Pro | Thr | Thr | Ser | Phe | Val | Leu | Asn | Asn |      |
|     |     |     |     | 865 |     |     |     |     | 870 |     |     |     |     | 875 |     |      |
| GAT | ACT | ATC | GCA | ACT | ATT | ACG | GCG | AAA | TCT | AAT | TCT | ACA | GCC | TTA | AAT | 1296 |
| Asp | Thr | Ile | Ala | Thr | Ile | Thr | Ala | Lys | Ser | Asn | Ser | Thr | Ala | Leu | Asn |      |

```
                        880                             885                             890
ATA   TCT   CCT   GGA   GAA   AGT   TAC   CCG   AAA   AAA   GGA   CAA   AAT   GGA   ATC   GCA    1344
Ile   Ser   Pro   Gly   Glu   Ser   Tyr   Pro   Lys   Lys   Gly   Gln   Asn   Gly   Ile   Ala
895                     900                             905                             910

ATA   ACA   TCA   ATG   GAT   GAT   TTT   AAT   TCC   CAT   CCG   ATT   ACA   TTA   AAT   AAA    1392
Ile   Thr   Ser   Met   Asp   Asp   Phe   Asn   Ser   His   Pro   Ile   Thr   Leu   Asn   Lys
                  915                           920                            925

AAA   CAA   GTA   GAT   AAT   CTG   CTA   AAT   AAT   AAA   CCT   ATG   ATG   TTG   GAA   ACA    1440
Lys   Gln   Val   Asp   Asn   Leu   Leu   Asn   Asn   Lys   Pro   Met   Met   Leu   Glu   Thr
                        930                            935                            940

AAC   CAA   ACA   GAT   GGT   GTT   TAT   AAG   ATA   AAA   GAT   ACA   CAT   GGA   AAT   ATA    1488
Asn   Gln   Thr   Asp   Gly   Val   Tyr   Lys   Ile   Lys   Asp   Thr   His   Gly   Asn   Ile
            945                            950                            955

GTA   ACT   GGC   GGA   GAA   TGG   AAT   GGT   GTC   ATA   CAA   CAA   ATC   AAG   GCT   AAA    1536
Val   Thr   Gly   Gly   Glu   Trp   Asn   Gly   Val   Ile   Gln   Gln   Ile   Lys   Ala   Lys
      960                            965                            970

ACA   GCG   TCT   ATT   ATT   GTG   GAT   GAT   GGG   GAA   CGT   GTA   GCA   GAA   AAA   CGT    1584
Thr   Ala   Ser   Ile   Ile   Val   Asp   Asp   Gly   Glu   Arg   Val   Ala   Glu   Lys   Arg
975                           980                            985                            990

GTA   GCG   GCA   AAA   GAT   TAT   GAA   AAT   CCA   GAA   GAT   AAA   ACA   CCG   TCT   TTA    1632
Val   Ala   Ala   Lys   Asp   Tyr   Glu   Asn   Pro   Glu   Asp   Lys   Thr   Pro   Ser   Leu
                        995                            1000                           1005

ACT   TTA   AAA   GAT   GCC   CTG   AAG   CTT   TCA   TAT   CCA   GAT   GAA   ATA   AAA   GAA    1680
Thr   Leu   Lys   Asp   Ala   Leu   Lys   Leu   Ser   Tyr   Pro   Asp   Glu   Ile   Lys   Glu
                  1010                          1015                           1020

ATA   GAG   GGA   TTA   TTA   TAT   TAT   AAA   AAC   AAA   CCG   ATA   TAC   GAA   TCG   AGC    1728
Ile   Glu   Gly   Leu   Leu   Tyr   Tyr   Lys   Asn   Lys   Pro   Ile   Tyr   Glu   Ser   Ser
                  1025                          1030                           1035

GTT   ATG   ACT   TAC   TTA   GAT   GAA   AAT   ACA   GCA   AAA   GAA   GTG   ACC   AAA   CAA    1776
Val   Met   Thr   Tyr   Leu   Asp   Glu   Asn   Thr   Ala   Lys   Glu   Val   Thr   Lys   Gln
1040                          1045                           1050

TTA   AAT   GAT   ACC   ACT   GGG   AAA   TTT   AAA   GAT   GTA   AGT   CAT   TTA   TAT   GAT    1824
Leu   Asn   Asp   Thr   Thr   Gly   Lys   Phe   Lys   Asp   Val   Ser   His   Leu   Tyr   Asp
1055                          1060                           1065                           1070

GTA   AAA   CTG   ACT   CCA   AAA   ATG   AAT   GTT   ACA   ATC   AAA   TTG   TCT   ATA   CTT    1872
Val   Lys   Leu   Thr   Pro   Lys   Met   Asn   Val   Thr   Ile   Lys   Leu   Ser   Ile   Leu
                        1075                           1080                           1085

TAT   GAT   AAT   GCT   GAG   TCT   AAT   GAT   AAC   TCA   ATT   GGT   AAA   TGG   ACA   AAC    1920
Tyr   Asp   Asn   Ala   Glu   Ser   Asn   Asp   Asn   Ser   Ile   Gly   Lys   Trp   Thr   Asn
                  1090                          1095                           1100

ACA   AAT   ATT   GTT   TCA   GGT   GGA   AAT   AAC   GGA   AAA   AAA   CAA   TAT   TCT   TCT    1968
Thr   Asn   Ile   Val   Ser   Gly   Gly   Asn   Asn   Gly   Lys   Lys   Gln   Tyr   Ser   Ser
                  1105                          1110                           1115

AAT   AAT   CCG   GAT   GCT   AAT   TTG   ACA   TTA   AAT   ACA   GAT   GCT   CAA   GAA   AAA    2016
Asn   Asn   Pro   Asp   Ala   Asn   Leu   Thr   Leu   Asn   Thr   Asp   Ala   Gln   Glu   Lys
            1120                          1125                           1130

TTA   AAT   AAA   AAT   CGT   GAC   TAT   TAT   ATA   AGT   TTA   TAT   ATG   AAG   TCA   GAA    2064
Leu   Asn   Lys   Asn   Arg   Asp   Tyr   Tyr   Ile   Ser   Leu   Tyr   Met   Lys   Ser   Glu
1135                          1140                           1145                           1150

AAA   AAC   ACA   CAA   TGT   GAG   ATT   ACT   ATA   GAT   GGG   GAG   ATT   TAT   CCG   ATC    2112
Lys   Asn   Thr   Gln   Cys   Glu   Ile   Thr   Ile   Asp   Gly   Glu   Ile   Tyr   Pro   Ile
                        1155                           1160                           1165

ACT   ACA   AAA   ACA   GTG   AAT   GTG   AAT   AAA   GAC   AAT   TAC   AAA   AGA   TTA   GAT    2160
Thr   Thr   Lys   Thr   Val   Asn   Val   Asn   Lys   Asp   Asn   Tyr   Lys   Arg   Leu   Asp
                  1170                          1175                           1180

ATT   ATA   GCT   CAT   AAT   ATA   AAA   AGT   AAT   CCA   ATT   TCT   TCA   CTT   CAT   ATT    2208
Ile   Ile   Ala   His   Asn   Ile   Lys   Ser   Asn   Pro   Ile   Ser   Ser   Leu   His   Ile
            1185                          1190                           1195

AAA   ACG   AAT   GAT   GAA   ATA   ACT   TTA   TTT   TGG   GAT   GAT   ATT   TCT   ATA   ACA    2256
Lys   Thr   Asn   Asp   Glu   Ile   Thr   Leu   Phe   Trp   Asp   Asp   Ile   Ser   Ile   Thr
```

| | | | | | | | | | | | | | | | | |
|---|---|---|---|---|---|---|---|---|---|---|---|---|---|---|---|---|
| | | 1200 | | | | 1205 | | | | | 1210 | | | | | |
| GAT | GTA | GCA | TCA | ATA | AAA | CCG | GAA | AAT | TTA | ACA | GAT | TCA | GAA | ATT | AAA | 2304 |
| Asp | Val | Ala | Ser | Ile | Lys | Pro | Glu | Asn | Leu | Thr | Asp | Ser | Glu | Ile | Lys | |
| 1215 | | | | 1220 | | | | | | 1225 | | | | | 1230 | |
| CAG | ATT | TAT | AGT | AGG | TAT | GGT | ATT | AAG | TTA | GAA | GAT | GGA | ATC | CTT | ATT | 2352 |
| Gln | Ile | Tyr | Ser | Arg | Tyr | Gly | Ile | Lys | Leu | Glu | Asp | Gly | Ile | Leu | Ile | |
| | | | | 1235 | | | | | | 1240 | | | | | 1245 | |
| GAT | AAA | AAA | GGT | GGG | ATT | CAT | TAT | GGT | GAA | TTT | ATT | AAT | GAA | GCT | AGT | 2400 |
| Asp | Lys | Lys | Gly | Gly | Ile | His | Tyr | Gly | Glu | Phe | Ile | Asn | Glu | Ala | Ser | |
| | | | | 1250 | | | | | | 1255 | | | | | 1260 | |
| TTT | AAT | ATT | GAA | CCA | TTG | CAA | AAT | TAT | GTG | ACC | AAA | TAT | GAA | GTT | ACT | 2448 |
| Phe | Asn | Ile | Glu | Pro | Leu | Gln | Asn | Tyr | Val | Thr | Lys | Tyr | Glu | Val | Thr | |
| | | | | 1265 | | | | | | 1270 | | | | | 1275 | |
| TAT | AGT | AGT | GAG | TTA | GGA | CCA | AAC | GTG | AGT | GAC | ACA | CTT | GAA | AGT | GAT | 2496 |
| Tyr | Ser | Ser | Glu | Leu | Gly | Pro | Asn | Val | Ser | Asp | Thr | Leu | Glu | Ser | Asp | |
| | | | | 1280 | | | | | | 1285 | | | | | 1290 | |
| AAA | ATT | TAC | AAG | GAT | GGG | ACA | ATT | AAA | TTT | GAT | TTT | ACC | AAA | TAT | AGT | 2544 |
| Lys | Ile | Tyr | Lys | Asp | Gly | Thr | Ile | Lys | Phe | Asp | Phe | Thr | Lys | Tyr | Ser | |
| 1295 | | | | | | 1300 | | | | | 1305 | | | | 1310 | |
| AAA | AAT | GAA | CAA | GGA | TTA | TTT | TAT | GAC | AGT | GGA | TTA | AAT | TGG | GAC | TTT | 2592 |
| Lys | Asn | Glu | Gln | Gly | Leu | Phe | Tyr | Asp | Ser | Gly | Leu | Asn | Trp | Asp | Phe | |
| | | | | 1315 | | | | | | 1320 | | | | | 1325 | |
| AAA | ATT | AAT | GCT | ATT | ACT | TAT | GAT | GGT | AAA | GAG | ATG | AAT | GTT | TTT | CAT | 2640 |
| Lys | Ile | Asn | Ala | Ile | Thr | Tyr | Asp | Gly | Lys | Glu | Met | Asn | Val | Phe | His | |
| | | | | 1330 | | | | | | 1335 | | | | | 1340 | |
| AGA | TAT | AAT | AAA | TAG | | | | | | | | | | | | 2655 |
| Arg | Tyr | Asn | Lys | | | | | | | | | | | | | |
| | | | | 1345 | | | | | | | | | | | | |

(2) INFORMATION FOR SEQ ID NO:5:

(i) SEQUENCE CHARACTERISTICS:
        (A) LENGTH: 884 amino acids
        (B) TYPE: amino acid
        (D) TOPOLOGY: linear (ii) MOLECULE TYPE: protein (xi) SEQUENCE DESCRIPTION: SEQ ID NO:5:

| | | | | | | | | | | | | | | |
|---|---|---|---|---|---|---|---|---|---|---|---|---|---|---|
| Met | Lys | Asn | Met | Lys | Lys | Lys | Leu | Ala | Ser | Val | Val | Thr | Cys | Thr | Leu |
| 1 | | | | 5 | | | | | 10 | | | | | 15 | |
| Leu | Ala | Pro | Met | Phe | Leu | Asn | Gly | Asn | Val | Asn | Ala | Val | Tyr | Ala | Asp |
| | | | 20 | | | | | 25 | | | | | 30 | | |
| Ser | Lys | Thr | Asn | Gln | Ile | Ser | Thr | Thr | Gln | Lys | Asn | Gln | Gln | Lys | Glu |
| | | | 35 | | | | 40 | | | | | 45 | | | |
| Met | Asp | Arg | Lys | Gly | Leu | Leu | Gly | Tyr | Tyr | Phe | Lys | Gly | Lys | Asp | Phe |
| | 50 | | | | | 55 | | | | | 60 | | | | |
| Ser | Asn | Leu | Thr | Met | Phe | Ala | Pro | Thr | Arg | Asp | Ser | Thr | Leu | Ile | Tyr |
| 65 | | | | | 70 | | | | 75 | | | | | | 80 |
| Asp | Gln | Gln | Thr | Ala | Asn | Lys | Leu | Leu | Asp | Lys | Lys | Gln | Gln | Glu | Tyr |
| | | | | 85 | | | | | 90 | | | | | 95 | |
| Gln | Ser | Ile | Arg | Trp | Ile | Gly | Leu | Ile | Gln | Ser | Lys | Glu | Thr | Gly | Asp |
| | | | 100 | | | | | 105 | | | | | 110 | | |
| Phe | Thr | Phe | Asn | Leu | Ser | Glu | Asp | Glu | Gln | Ala | Ile | Ile | Glu | Ile | Asn |
| | | | 115 | | | | | 120 | | | | | 125 | | |
| Gly | Lys | Ile | Ile | Ser | Asn | Lys | Gly | Lys | Glu | Lys | Gln | Val | Val | His | Leu |
| | | | 130 | | | | 135 | | | | | 140 | | | |
| Glu | Lys | Gly | Lys | Leu | Val | Pro | Ile | Lys | Ile | Glu | Tyr | Gln | Ser | Asp | Thr |
| 145 | | | | | 150 | | | | 155 | | | | | | 160 |

```
Lys  Phe  Asn  Ile  Asp  Ser  Lys  Thr  Phe  Lys  Glu  Leu  Lys  Leu  Phe  Lys
              165                     170                    175

Ile  Asp  Ser  Gln  Asn  Gln  Pro  Gln  Val  Gln  Gln  Asp  Glu  Leu  Arg
              180                     185                    190

Asn  Pro  Glu  Phe  Asn  Lys  Lys  Glu  Ser  Gln  Glu  Phe  Leu  Ala  Lys  Pro
              195                     200                    205

Ser  Lys  Ile  Asn  Leu  Phe  Thr  Gln  Lys  Met  Lys  Arg  Glu  Ile  Asp  Glu
         210                    215                    220

Asp  Thr  Asp  Thr  Asp  Gly  Asp  Ser  Ile  Pro  Asp  Leu  Trp  Glu  Glu  Asn
225                        230                    235                         240

Gly  Tyr  Thr  Ile  Gln  Asn  Arg  Ile  Ala  Val  Lys  Trp  Asp  Asp  Ser  Leu
                   245                        250                    255

Ala  Ser  Lys  Gly  Tyr  Thr  Lys  Phe  Val  Ser  Asn  Pro  Leu  Glu  Ser  His
                   260                    265                    270

Thr  Val  Gly  Asp  Pro  Tyr  Thr  Asp  Tyr  Glu  Lys  Ala  Ala  Arg  Asp  Leu
              275                    280                    285

Asp  Leu  Ser  Asn  Ala  Lys  Glu  Thr  Phe  Asn  Pro  Leu  Val  Ala  Ala  Phe
         290                    295                    300

Pro  Ser  Val  Asn  Val  Ser  Met  Glu  Lys  Val  Ile  Leu  Ser  Pro  Asn  Glu
305                        310                    315                         320

Asn  Leu  Ser  Asn  Ser  Val  Glu  Ser  His  Ser  Ser  Thr  Asn  Trp  Ser  Tyr
                   325                    330                    335

Thr  Asn  Thr  Glu  Gly  Ala  Ser  Val  Glu  Ala  Gly  Ile  Gly  Pro  Lys  Gly
                   340                    345                    350

Ile  Ser  Phe  Gly  Val  Ser  Val  Asn  Tyr  Gln  His  Ser  Glu  Thr  Val  Ala
              355                    360                    365

Gln  Glu  Trp  Gly  Thr  Ser  Thr  Gly  Asn  Thr  Ser  Gln  Phe  Asn  Thr  Ala
370                        375                    380

Ser  Ala  Gly  Tyr  Leu  Asn  Ala  Asn  Val  Arg  Tyr  Asn  Asn  Val  Gly  Thr
385                        390                    395                         400

Gly  Ala  Ile  Tyr  Asp  Val  Lys  Pro  Thr  Thr  Ser  Phe  Val  Leu  Asn  Asn
              405                    410                    415

Asp  Thr  Ile  Ala  Thr  Ile  Thr  Ala  Lys  Ser  Asn  Ser  Thr  Ala  Leu  Asn
              420                    425                    430

Ile  Ser  Pro  Gly  Glu  Ser  Tyr  Pro  Lys  Lys  Gly  Gln  Asn  Gly  Ile  Ala
              435                    440                    445

Ile  Thr  Ser  Met  Asp  Asp  Phe  Asn  Ser  His  Pro  Ile  Thr  Leu  Asn  Lys
              450                    455                    460

Lys  Gln  Val  Asp  Asn  Leu  Leu  Asn  Asn  Lys  Pro  Met  Met  Leu  Glu  Thr
465                        470                    475                         480

Asn  Gln  Thr  Asp  Gly  Val  Tyr  Lys  Ile  Lys  Asp  Thr  His  Gly  Asn  Ile
                   485                    490                    495

Val  Thr  Gly  Gly  Glu  Trp  Asn  Gly  Val  Ile  Gln  Gln  Ile  Lys  Ala  Lys
                   500                    505                    510

Thr  Ala  Ser  Ile  Ile  Val  Asp  Asp  Gly  Glu  Arg  Val  Ala  Glu  Lys  Arg
              515                    520                    525

Val  Ala  Ala  Lys  Asp  Tyr  Glu  Asn  Pro  Glu  Asp  Lys  Thr  Pro  Ser  Leu
              530                    535                    540

Thr  Leu  Lys  Asp  Ala  Leu  Lys  Leu  Ser  Tyr  Pro  Asp  Glu  Ile  Lys  Glu
545                        550                    555                         560

Ile  Glu  Gly  Leu  Leu  Tyr  Tyr  Lys  Asn  Lys  Pro  Ile  Tyr  Glu  Ser  Ser
                   565                    570                    575

Val  Met  Thr  Tyr  Leu  Asp  Glu  Asn  Thr  Ala  Lys  Glu  Val  Thr  Lys  Gln
              580                    585                    590
```

-continued

Leu Asn Asp Thr Thr Gly Lys Phe Lys Asp Val Ser His Leu Tyr Asp
595 600 605

Val Lys Leu Thr Pro Lys Met Asn Val Thr Ile Lys Leu Ser Ile Leu
610 615 620

Tyr Asp Asn Ala Glu Ser Asn Asp Asn Ser Ile Gly Lys Trp Thr Asn
625 630 635 640

Thr Asn Ile Val Ser Gly Gly Asn Asn Gly Lys Lys Gln Tyr Ser Ser
645 650 655

Asn Asn Pro Asp Ala Asn Leu Thr Leu Asn Thr Asp Ala Gln Glu Lys
660 665 670

Leu Asn Lys Asn Arg Asp Tyr Tyr Ile Ser Leu Tyr Met Lys Ser Glu
675 680 685

Lys Asn Thr Gln Cys Glu Ile Thr Ile Asp Gly Glu Ile Tyr Pro Ile
690 695 700

Thr Thr Lys Thr Val Asn Val Asn Lys Asp Asn Tyr Lys Arg Leu Asp
705 710 715 720

Ile Ile Ala His Asn Ile Lys Ser Asn Pro Ile Ser Ser Leu His Ile
725 730 735

Lys Thr Asn Asp Glu Ile Thr Leu Phe Trp Asp Asp Ile Ser Ile Thr
740 745 750

Asp Val Ala Ser Ile Lys Pro Glu Asn Leu Thr Asp Ser Glu Ile Lys
755 760 765

Gln Ile Tyr Ser Arg Tyr Gly Ile Lys Leu Glu Asp Gly Ile Leu Ile
770 775 780

Asp Lys Lys Gly Gly Ile His Tyr Gly Glu Phe Ile Asn Glu Ala Ser
785 790 795 800

Phe Asn Ile Glu Pro Leu Gln Asn Tyr Val Thr Lys Tyr Glu Val Thr
805 810 815

Tyr Ser Ser Glu Leu Gly Pro Asn Val Ser Asp Thr Leu Glu Ser Asp
820 825 830

Lys Ile Tyr Lys Asp Gly Thr Ile Lys Phe Asp Phe Thr Lys Tyr Ser
835 840 845

Lys Asn Glu Gln Gly Leu Phe Tyr Asp Ser Gly Leu Asn Trp Asp Phe
850 855 860

Lys Ile Asn Ala Ile Thr Tyr Asp Gly Lys Glu Met Asn Val Phe His
865 870 875 880

Arg Tyr Asn Lys ( 2 ) INFORMATION FOR SEQ ID NO:6:

( i ) SEQUENCE CHARACTERISTICS:
( A ) LENGTH: 2004 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus cereus
( B ) STRAIN: AB78
( C ) INDIVIDUAL ISOLATE: NRRL B- 21058

( i x ) FEATURE:
( A ) NAME/KEY: CDS
( B ) LOCATION: 1..2001

( D ) OTHER INFORMATION: /product="80 kDa protein VIP1A(a)"
/ note= "This sequence is identical to that found in SEQ ID NO:1 between and including nucleotide positions 3126 and 5126"

( x i ) SEQUENCE DESCRIPTION: SEQ ID NO:6:

| ATG | AAA | AGG | GAA | ATT | GAT | GAA | GAC | ACG | GAT | ACG | GAT | GGG | GAC | TCT | ATT | 48 |
|---|---|---|---|---|---|---|---|---|---|---|---|---|---|---|---|---|
| Met | Lys | Arg | Glu | Ile | Asp | Glu | Asp | Thr | Asp | Thr | Asp | Gly | Asp | Ser | Ile | |
| 885 | | | | 890 | | | | | 895 | | | | | | 900 | |

| CCT | GAC | CTT | TGG | GAA | GAA | AAT | GGG | TAT | ACG | ATT | CAA | AAT | AGA | ATC | GCT | 96 |
|---|---|---|---|---|---|---|---|---|---|---|---|---|---|---|---|---|
| Pro | Asp | Leu | Trp | Glu | Glu | Asn | Gly | Tyr | Thr | Ile | Gln | Asn | Arg | Ile | Ala | |
| | | | | 905 | | | | | 910 | | | | | 915 | | |

| GTA | AAG | TGG | GAC | GAT | TCT | CTA | GCA | AGT | AAA | GGG | TAT | ACG | AAA | TTT | GTT | 144 |
|---|---|---|---|---|---|---|---|---|---|---|---|---|---|---|---|---|
| Val | Lys | Trp | Asp | Asp | Ser | Leu | Ala | Ser | Lys | Gly | Tyr | Thr | Lys | Phe | Val | |
| | | | 920 | | | | | 925 | | | | | 930 | | | |

| TCA | AAT | CCA | CTA | GAA | AGT | CAC | ACA | GTT | GGT | GAT | CCT | TAT | ACA | GAT | TAT | 192 |
|---|---|---|---|---|---|---|---|---|---|---|---|---|---|---|---|---|
| Ser | Asn | Pro | Leu | Glu | Ser | His | Thr | Val | Gly | Asp | Pro | Tyr | Thr | Asp | Tyr | |
| | | 935 | | | | | 940 | | | | | 945 | | | | |

| GAA | AAG | GCA | GCA | AGA | GAT | CTA | GAT | TTG | TCA | AAT | GCA | AAG | GAA | ACG | TTT | 240 |
|---|---|---|---|---|---|---|---|---|---|---|---|---|---|---|---|---|
| Glu | Lys | Ala | Ala | Arg | Asp | Leu | Asp | Leu | Ser | Asn | Ala | Lys | Glu | Thr | Phe | |
| | 950 | | | | | 955 | | | | | 960 | | | | | |

| AAC | CCA | TTG | GTA | GCT | GCT | TTT | CCA | AGT | GTG | AAT | GTT | AGT | ATG | GAA | AAG | 288 |
|---|---|---|---|---|---|---|---|---|---|---|---|---|---|---|---|---|
| Asn | Pro | Leu | Val | Ala | Ala | Phe | Pro | Ser | Val | Asn | Val | Ser | Met | Glu | Lys | |
| 965 | | | | | 970 | | | | | 975 | | | | | 980 | |

| GTG | ATA | TTA | TCA | CCA | AAT | GAA | AAT | TTA | TCC | AAT | AGT | GTA | GAG | TCT | CAT | 336 |
|---|---|---|---|---|---|---|---|---|---|---|---|---|---|---|---|---|
| Val | Ile | Leu | Ser | Pro | Asn | Glu | Asn | Leu | Ser | Asn | Ser | Val | Glu | Ser | His | |
| | | | | 985 | | | | | 990 | | | | | 995 | | |

| TCA | TCC | ACG | AAT | TGG | TCT | TAT | ACA | AAT | ACA | GAA | GGT | GCT | TCT | GTT | GAA | 384 |
|---|---|---|---|---|---|---|---|---|---|---|---|---|---|---|---|---|
| Ser | Ser | Thr | Asn | Trp | Ser | Tyr | Thr | Asn | Thr | Glu | Gly | Ala | Ser | Val | Glu | |
| | | | 1000 | | | | | 1005 | | | | | 1010 | | | |

| GCG | GGG | ATT | GGA | CCA | AAA | GGT | ATT | TCG | TTC | GGA | GTT | AGC | GTA | AAC | TAT | 432 |
|---|---|---|---|---|---|---|---|---|---|---|---|---|---|---|---|---|
| Ala | Gly | Ile | Gly | Pro | Lys | Gly | Ile | Ser | Phe | Gly | Val | Ser | Val | Asn | Tyr | |
| | | 1015 | | | | | 1020 | | | | | 1025 | | | | |

| CAA | CAC | TCT | GAA | ACA | GTT | GCA | CAA | GAA | TGG | GGA | ACA | TCT | ACA | GGA | AAT | 480 |
|---|---|---|---|---|---|---|---|---|---|---|---|---|---|---|---|---|
| Gln | His | Ser | Glu | Thr | Val | Ala | Gln | Glu | Trp | Gly | Thr | Ser | Thr | Gly | Asn | |
| | 1030 | | | | | 1035 | | | | | 1040 | | | | | |

| ACT | TCG | CAA | TTC | AAT | ACG | GCT | TCA | GCG | GGA | TAT | TTA | AAT | GCA | AAT | GTT | 528 |
|---|---|---|---|---|---|---|---|---|---|---|---|---|---|---|---|---|
| Thr | Ser | Gln | Phe | Asn | Thr | Ala | Ser | Ala | Gly | Tyr | Leu | Asn | Ala | Asn | Val | |
| 1045 | | | | | 1050 | | | | | 1055 | | | | | 1060 | |

| CGA | TAT | AAC | AAT | GTA | GGA | ACT | GGT | GCC | ATC | TAC | GAT | GTA | AAA | CCT | ACA | 576 |
|---|---|---|---|---|---|---|---|---|---|---|---|---|---|---|---|---|
| Arg | Tyr | Asn | Asn | Val | Gly | Thr | Gly | Ala | Ile | Tyr | Asp | Val | Lys | Pro | Thr | |
| | | | | 1065 | | | | | 1070 | | | | | 1075 | | |

| ACA | AGT | TTT | GTA | TTA | AAT | AAC | GAT | ACT | ATC | GCA | ACT | ATT | ACG | GCG | AAA | 624 |
|---|---|---|---|---|---|---|---|---|---|---|---|---|---|---|---|---|
| Thr | Ser | Phe | Val | Leu | Asn | Asn | Asp | Thr | Ile | Ala | Thr | Ile | Thr | Ala | Lys | |
| | | | 1080 | | | | | 1085 | | | | | 1090 | | | |

| TCT | AAT | TCT | ACA | GCC | TTA | AAT | ATA | TCT | CCT | GGA | GAA | AGT | TAC | CCG | AAA | 672 |
|---|---|---|---|---|---|---|---|---|---|---|---|---|---|---|---|---|
| Ser | Asn | Ser | Thr | Ala | Leu | Asn | Ile | Ser | Pro | Gly | Glu | Ser | Tyr | Pro | Lys | |
| | | 1095 | | | | | 1100 | | | | | 1105 | | | | |

| AAA | GGA | CAA | AAT | GGA | ATC | GCA | ATA | ACA | TCA | ATG | GAT | GAT | TTT | AAT | TCC | 720 |
|---|---|---|---|---|---|---|---|---|---|---|---|---|---|---|---|---|
| Lys | Gly | Gln | Asn | Gly | Ile | Ala | Ile | Thr | Ser | Met | Asp | Asp | Phe | Asn | Ser | |
| | 1110 | | | | | 1115 | | | | | 1120 | | | | | |

| CAT | CCG | ATT | ACA | TTA | AAT | AAA | AAA | CAA | GTA | GAT | AAT | CTG | CTA | AAT | AAT | 768 |
|---|---|---|---|---|---|---|---|---|---|---|---|---|---|---|---|---|
| His | Pro | Ile | Thr | Leu | Asn | Lys | Lys | Gln | Val | Asp | Asn | Leu | Leu | Asn | Asn | |
| 1125 | | | | | 1130 | | | | | 1135 | | | | | 1140 | |

| AAA | CCT | ATG | ATG | TTG | GAA | ACA | AAC | CAA | ACA | GAT | GGT | GTT | TAT | AAG | ATA | 816 |
|---|---|---|---|---|---|---|---|---|---|---|---|---|---|---|---|---|
| Lys | Pro | Met | Met | Leu | Glu | Thr | Asn | Gln | Thr | Asp | Gly | Val | Tyr | Lys | Ile | |
| | | | | 1145 | | | | | 1150 | | | | | 1155 | | |

| AAA | GAT | ACA | CAT | GGA | AAT | ATA | GTA | ACT | GGC | GGA | GAA | TGG | AAT | GGT | GTC | 864 |
|---|---|---|---|---|---|---|---|---|---|---|---|---|---|---|---|---|
| Lys | Asp | Thr | His | Gly | Asn | Ile | Val | Thr | Gly | Gly | Glu | Trp | Asn | Gly | Val | |
| | | | 1160 | | | | | 1165 | | | | | 1170 | | | |

| ATA | CAA | CAA | ATC | AAG | GCT | AAA | ACA | GCG | TCT | ATT | ATT | GTG | GAT | GAT | GGG | 912 |

```
Ile Gln Gln Ile Lys Ala Lys Thr Ala Ser Ile Ile Val Asp Asp Gly
            1175                1180                1185

GAA CGT GTA GCA GAA AAA CGT GTA GCG GCA AAA GAT TAT GAA AAT CCA        960
Glu Arg Val Ala Glu Lys Arg Val Ala Ala Lys Asp Tyr Glu Asn Pro
1190                1195                1200

GAA GAT AAA ACA CCG TCT TTA ACT TTA AAA GAT GCC CTG AAG CTT TCA        1008
Glu Asp Lys Thr Pro Ser Leu Thr Leu Lys Asp Ala Leu Lys Leu Ser
1205                1210                1215                1220

TAT CCA GAT GAA ATA AAA GAA ATA GAG GGA TTA TTA TAT TAT AAA AAC        1056
Tyr Pro Asp Glu Ile Lys Glu Ile Glu Gly Leu Leu Tyr Tyr Lys Asn
                1225                1230                1235

AAA CCG ATA TAC GAA TCG AGC GTT ATG ACT TAC TTA GAT GAA AAT ACA        1104
Lys Pro Ile Tyr Glu Ser Ser Val Met Thr Tyr Leu Asp Glu Asn Thr
            1240                1245                1250

GCA AAA GAA GTG ACC AAA CAA TTA AAT GAT ACC ACT GGG AAA TTT AAA        1152
Ala Lys Glu Val Thr Lys Gln Leu Asn Asp Thr Thr Gly Lys Phe Lys
1255                1260                1265

GAT GTA AGT CAT TTA TAT GAT GTA AAA CTG ACT CCA AAA ATG AAT GTT        1200
Asp Val Ser His Leu Tyr Asp Val Lys Leu Thr Pro Lys Met Asn Val
1270                1275                1280

ACA ATC AAA TTG TCT ATA CTT TAT GAT AAT GCT GAG TCT AAT GAT AAC        1248
Thr Ile Lys Leu Ser Ile Leu Tyr Asp Asn Ala Glu Ser Asn Asp Asn
1285                1290                1295                1300

TCA ATT GGT AAA TGG ACA AAC ACA AAT ATT GTT TCA GGT GGA AAT AAC        1296
Ser Ile Gly Lys Trp Thr Asn Thr Asn Ile Val Ser Gly Gly Asn Asn
                1305                1310                1315

GGA AAA AAA CAA TAT TCT TCT AAT AAT CCG GAT GCT AAT TTG ACA TTA        1344
Gly Lys Lys Gln Tyr Ser Ser Asn Asn Pro Asp Ala Asn Leu Thr Leu
            1320                1325                1330

AAT ACA GAT GCT CAA GAA AAA TTA AAT AAA AAT CGT GAC TAT TAT ATA        1392
Asn Thr Asp Ala Gln Glu Lys Leu Asn Lys Asn Arg Asp Tyr Tyr Ile
            1335                1340                1345

AGT TTA TAT ATG AAG TCA GAA AAA AAC ACA CAA TGT GAG ATT ACT ATA        1440
Ser Leu Tyr Met Lys Ser Glu Lys Asn Thr Gln Cys Glu Ile Thr Ile
1350                1355                1360

GAT GGG GAG ATT TAT CCG ATC ACT ACA AAA ACA GTG AAT GTG AAT AAA        1488
Asp Gly Glu Ile Tyr Pro Ile Thr Thr Lys Thr Val Asn Val Asn Lys
1365                1370                1375                1380

GAC AAT TAC AAA AGA TTA GAT ATT ATA GCT CAT AAT ATA AAA AGT AAT        1536
Asp Asn Tyr Lys Arg Leu Asp Ile Ile Ala His Asn Ile Lys Ser Asn
                1385                1390                1395

CCA ATT TCT TCA CTT CAT ATT AAA ACG AAT GAT GAA ATA ACT TTA TTT        1584
Pro Ile Ser Ser Leu His Ile Lys Thr Asn Asp Glu Ile Thr Leu Phe
            1400                1405                1410

TGG GAT GAT ATT TCT ATA ACA GAT GTA GCA TCA ATA AAA CCG GAA AAT        1632
Trp Asp Asp Ile Ser Ile Thr Asp Val Ala Ser Ile Lys Pro Glu Asn
            1415                1420                1425

TTA ACA GAT TCA GAA ATT AAA CAG ATT TAT AGT AGG TAT GGT ATT AAG        1680
Leu Thr Asp Ser Glu Ile Lys Gln Ile Tyr Ser Arg Tyr Gly Ile Lys
1430                1435                1440

TTA GAA GAT GGA ATC CTT ATT GAT AAA AAA GGT GGG ATT CAT TAT GGT        1728
Leu Glu Asp Gly Ile Leu Ile Asp Lys Lys Gly Gly Ile His Tyr Gly
1445                1450                1455                1460

GAA TTT ATT AAT GAA GCT AGT TTT AAT ATT GAA CCA TTG CCA AAT TAT        1776
Glu Phe Ile Asn Glu Ala Ser Phe Asn Ile Glu Pro Leu Pro Asn Tyr
                1465                1470                1475

GTG ACC AAA TAT GAA GTT ACT TAT AGT AGT GAG TTA GGA CCA AAC GTG        1824
Val Thr Lys Tyr Glu Val Thr Tyr Ser Ser Glu Leu Gly Pro Asn Val
            1480                1485                1490

AGT GAC ACA CTT GAA AGT GAT AAA ATT TAC AAG GAT GGG ACA ATT AAA        1872
```

```
Ser  Asp  Thr  Leu  Glu  Ser  Asp  Lys  Ile  Tyr  Lys  Asp  Gly  Thr  Ile  Lys
          1495            1500                    1505

TTT  GAT  TTT  ACC  AAA  TAT  AGT  AAA  AAT  GAA  CAA  GGA  TTA  TTT  TAT  GAC      1920
Phe  Asp  Phe  Thr  Lys  Tyr  Ser  Lys  Asn  Glu  Gln  Gly  Leu  Phe  Tyr  Asp
          1510            1515                    1520

AGT  GGA  TTA  AAT  TGG  GAC  TTT  AAA  ATT  AAT  GCT  ATT  ACT  TAT  GAT  GGT      1968
Ser  Gly  Leu  Asn  Trp  Asp  Phe  Lys  Ile  Asn  Ala  Ile  Thr  Tyr  Asp  Gly
1525                      1530                    1535                      1540

AAA  GAG  ATG  AAT  GTT  TTT  CAT  AGA  TAT  AAT  AAA  TAG                           2004
Lys  Glu  Met  Asn  Val  Phe  His  Arg  Tyr  Asn  Lys
                    1545                     1550
```

( 2 ) INFORMATION FOR SEQ ID NO:7:

( i ) SEQUENCE CHARACTERISTICS:
        ( A ) LENGTH: 667 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Lys  Arg  Glu  Ile  Asp  Glu  Asp  Thr  Asp  Thr  Asp  Gly  Asp  Ser  Ile
 1                    5                   10                         15

Pro  Asp  Leu  Trp  Glu  Glu  Asn  Gly  Tyr  Thr  Ile  Gln  Asn  Arg  Ile  Ala
               20                   25                         30

Val  Lys  Trp  Asp  Asp  Ser  Leu  Ala  Ser  Lys  Gly  Tyr  Thr  Lys  Phe  Val
               35                   40                         45

Ser  Asn  Pro  Leu  Glu  Ser  His  Thr  Val  Gly  Asp  Pro  Tyr  Thr  Asp  Tyr
      50                        55                        60

Glu  Lys  Ala  Ala  Arg  Asp  Leu  Asp  Leu  Ser  Asn  Ala  Lys  Glu  Thr  Phe
 65                    70                        75                         80

Asn  Pro  Leu  Val  Ala  Ala  Phe  Pro  Ser  Val  Asn  Val  Ser  Met  Glu  Lys
                    85                   90                         95

Val  Ile  Leu  Ser  Pro  Asn  Glu  Asn  Leu  Ser  Asn  Ser  Val  Glu  Ser  His
               100                  105                        110

Ser  Ser  Thr  Asn  Trp  Ser  Tyr  Thr  Asn  Thr  Glu  Gly  Ala  Ser  Val  Glu
          115                       120                        125

Ala  Gly  Ile  Gly  Pro  Lys  Gly  Ile  Ser  Phe  Gly  Val  Ser  Val  Asn  Tyr
     130                       135                        140

Gln  His  Ser  Glu  Thr  Val  Ala  Gln  Glu  Trp  Gly  Thr  Ser  Thr  Gly  Asn
145                      150                       155                       160

Thr  Ser  Gln  Phe  Asn  Thr  Ala  Ser  Ala  Gly  Tyr  Leu  Asn  Ala  Asn  Val
                    165                       170                       175

Arg  Tyr  Asn  Asn  Val  Gly  Thr  Gly  Ala  Ile  Tyr  Asp  Val  Lys  Pro  Thr
               180                       185                       190

Thr  Ser  Phe  Val  Leu  Asn  Asn  Asp  Thr  Ile  Ala  Thr  Ile  Thr  Ala  Lys
          195                       200                       205

Ser  Asn  Ser  Thr  Ala  Leu  Asn  Ile  Ser  Pro  Gly  Glu  Ser  Tyr  Pro  Lys
     210                       215                       220

Lys  Gly  Gln  Asn  Gly  Ile  Ala  Ile  Thr  Ser  Met  Asp  Asp  Phe  Asn  Ser
225                       230                       235                       240

His  Pro  Ile  Thr  Leu  Asn  Lys  Lys  Gln  Val  Asp  Asn  Leu  Leu  Asn  Asn
                    245                       250                       255

Lys  Pro  Met  Met  Leu  Glu  Thr  Asn  Gln  Thr  Asp  Gly  Val  Tyr  Lys  Ile
               260                       265                       270

Lys  Asp  Thr  His  Gly  Asn  Ile  Val  Thr  Gly  Gly  Glu  Trp  Asn  Gly  Val
          275                       280                       285
```

| | | | | | | | | | | | | | | |
|---|---|---|---|---|---|---|---|---|---|---|---|---|---|---|
| Ile | Gln | Gln | Ile | Lys | Ala | Lys | Thr | Ala | Ser | Ile | Ile | Val | Asp | Asp | Gly |
| | 290 | | | | 295 | | | | | 300 | | | | | |
| Glu | Arg | Val | Ala | Glu | Lys | Arg | Val | Ala | Ala | Lys | Asp | Tyr | Glu | Asn | Pro |
| 305 | | | | | 310 | | | | | 315 | | | | | 320 |
| Glu | Asp | Lys | Thr | Pro | Ser | Leu | Thr | Leu | Lys | Asp | Ala | Leu | Lys | Leu | Ser |
| | | | | 325 | | | | | 330 | | | | | 335 | |
| Tyr | Pro | Asp | Glu | Ile | Lys | Glu | Ile | Glu | Gly | Leu | Leu | Tyr | Tyr | Lys | Asn |
| | | | 340 | | | | | 345 | | | | | 350 | | |
| Lys | Pro | Ile | Tyr | Glu | Ser | Ser | Val | Met | Thr | Tyr | Leu | Asp | Glu | Asn | Thr |
| | | 355 | | | | | 360 | | | | | 365 | | | |
| Ala | Lys | Glu | Val | Thr | Lys | Gln | Leu | Asn | Asp | Thr | Thr | Gly | Lys | Phe | Lys |
| | 370 | | | | | 375 | | | | | 380 | | | | |
| Asp | Val | Ser | His | Leu | Tyr | Asp | Val | Lys | Leu | Thr | Pro | Lys | Met | Asn | Val |
| 385 | | | | | 390 | | | | | 395 | | | | | 400 |
| Thr | Ile | Lys | Leu | Ser | Ile | Leu | Tyr | Asp | Asn | Ala | Glu | Ser | Asn | Asp | Asn |
| | | | | 405 | | | | | 410 | | | | | 415 | |
| Ser | Ile | Gly | Lys | Trp | Thr | Asn | Thr | Asn | Ile | Val | Ser | Gly | Gly | Asn | Asn |
| | | | 420 | | | | | 425 | | | | | 430 | | |
| Gly | Lys | Lys | Gln | Tyr | Ser | Ser | Asn | Asn | Pro | Asp | Ala | Asn | Leu | Thr | Leu |
| | | 435 | | | | | 440 | | | | | 445 | | | |
| Asn | Thr | Asp | Ala | Gln | Glu | Lys | Leu | Asn | Lys | Asn | Arg | Asp | Tyr | Tyr | Ile |
| | 450 | | | | | 455 | | | | | 460 | | | | |
| Ser | Leu | Tyr | Met | Lys | Ser | Glu | Lys | Asn | Thr | Gln | Cys | Glu | Ile | Thr | Ile |
| 465 | | | | | 470 | | | | | 475 | | | | | 480 |
| Asp | Gly | Glu | Ile | Tyr | Pro | Ile | Thr | Thr | Lys | Thr | Val | Asn | Val | Asn | Lys |
| | | | | 485 | | | | | 490 | | | | | 495 | |
| Asp | Asn | Tyr | Lys | Arg | Leu | Asp | Ile | Ile | Ala | His | Asn | Ile | Lys | Ser | Asn |
| | | | 500 | | | | | 505 | | | | | 510 | | |
| Pro | Ile | Ser | Ser | Leu | His | Ile | Lys | Thr | Asn | Asp | Glu | Ile | Thr | Leu | Phe |
| | | 515 | | | | | 520 | | | | | 525 | | | |
| Trp | Asp | Asp | Ile | Ser | Ile | Thr | Asp | Val | Ala | Ser | Ile | Lys | Pro | Glu | Asn |
| | 530 | | | | | 535 | | | | | 540 | | | | |
| Leu | Thr | Asp | Ser | Glu | Ile | Lys | Gln | Ile | Tyr | Ser | Arg | Tyr | Gly | Ile | Lys |
| 545 | | | | | 550 | | | | | 555 | | | | | 560 |
| Leu | Glu | Asp | Gly | Ile | Leu | Ile | Asp | Lys | Lys | Gly | Gly | Ile | His | Tyr | Gly |
| | | | | 565 | | | | | 570 | | | | | 575 | |
| Glu | Phe | Ile | Asn | Glu | Ala | Ser | Phe | Asn | Ile | Glu | Pro | Leu | Pro | Asn | Tyr |
| | | | 580 | | | | | 585 | | | | | 590 | | |
| Val | Thr | Lys | Tyr | Glu | Val | Thr | Tyr | Ser | Ser | Glu | Leu | Gly | Pro | Asn | Val |
| | | 595 | | | | | 600 | | | | | 605 | | | |
| Ser | Asp | Thr | Leu | Glu | Ser | Asp | Lys | Ile | Tyr | Lys | Asp | Gly | Thr | Ile | Lys |
| | 610 | | | | | 615 | | | | | 620 | | | | |
| Phe | Asp | Phe | Thr | Lys | Tyr | Ser | Lys | Asn | Glu | Gln | Gly | Leu | Phe | Tyr | Asp |
| 625 | | | | | 630 | | | | | 635 | | | | | 640 |
| Ser | Gly | Leu | Asn | Trp | Asp | Phe | Lys | Ile | Asn | Ala | Ile | Thr | Tyr | Asp | Gly |
| | | | | 645 | | | | | 650 | | | | | 655 | |
| Lys | Glu | Met | Asn | Val | Phe | His | Arg | Tyr | Asn | Lys | | | | | |
| | | | 660 | | | | | 665 | | | | | | | |

( 2 ) INFORMATION FOR SEQ ID NO:8:

( i ) SEQUENCE CHARACTERISTICS:
( A ) LENGTH: 16 amino acids
( B ) TYPE: amino acid
( C ) STRANDEDNESS: single ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
                    ( A ) ORGANISM: Bacillus cereus
                    ( B ) STRAIN: AB78
                    ( C ) INDIVIDUAL ISOLATE: NRRL B- 21058

( i x ) FEATURE:
( A ) NAME/KEY: Peptide
( B ) LOCATION: 1..16
( D ) OTHER INFORMATION: /note= "N-terminal sequence of protein purified from strain AB78"

( x i ) SEQUENCE DESCRIPTION: SEQ ID NO:8:

Lys Arg Glu Ile Asp Glu Asp Thr Asp Thr Asx Gly Asp Ser Ile Pro
1 5 10 15

( 2 ) INFORMATION FOR SEQ ID NO:9:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 1..21
( D ) OTHER INFORMATION: /note= "Oligonucleotide probe based on amino acids 3 to 9 of SEQ ID NO:8, using codon usage of Bacillus thuringiensis"

( x i ) SEQUENCE DESCRIPTION: SEQ ID NO:9:

GAAATTGATC AAGATACNGA T 21

( 2 ) INFORMATION FOR SEQ ID NO:10:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
( A ) ORGANISM: Bacillus thuringiensis
( B ) STRAIN: AB88

( i x ) FEATURE:
( A ) NAME/KEY: Peptide
( B ) LOCATION: 1..14
( D ) OTHER INFORMATION: /note= "N-terminal amino acid sequence of protein known as anion exchange fraction 23 ( smaller )"

( x i ) SEQUENCE DESCRIPTION: SEQ ID NO:10:

Xaa Glu Pro Phe Val Ser Ala Xaa Xaa Xaa Gln Xaa Xaa Xaa
1 5 10

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: Bacillus thuringiensis ( x i ) SEQUENCE DESCRIPTION: SEQ ID NO:11:

Xaa Glu Tyr Glu Asn Val Glu Pro Phe Val Ser Ala Xaa
1                5                                    10

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: Bacillus thurigiensis ( x i ) SEQUENCE DESCRIPTION: SEQ ID NO:12:

Met Asn Lys Asn Asn Thr Lys Leu Pro Thr Arg Ala Leu Pro
1                5                                    10

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Bacillus thuringiensis
        ( B ) STRAIN: AB88

( i x ) FEATURE:
        ( A ) NAME/KEY: Peptide
        ( B ) LOCATION: 1..15
        ( D ) OTHER INFORMATION: /note= "N-terminal amino acid
            sequence of 35 kDa VIP active against Agrotis ipsilon"

( x i ) SEQUENCE DESCRIPTION: SEQ ID NO:13:

Ala Leu Ser Glu Asn Thr Gly Lys Asp Gly Gly Tyr Ile Val Pro
1                5                            10                      15

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: Bacillus thuringiensis ( x i ) SEQUENCE DESCRIPTION: SEQ ID NO:14:

Met Asp Asn Asn Pro Asn Ile Asn Glu

```
            1               5
```

( 2 ) INFORMATION FOR SEQ ID NO:15:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
  ( A ) NAME/KEY: Peptide
  ( B ) LOCATION: 1..9
  ( D ) OTHER INFORMATION: /note= "N-terminal sequence of 80
   kDa delta- endotoxin"

( x i ) SEQUENCE DESCRIPTION: SEQ ID NO:15:

```
Met   Asp   Asn   Asn   Pro   Asn   Ile   Asn   Glu
1                       5
```

( 2 ) INFORMATION FOR SEQ ID NO:16:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
  ( A ) ORGANISM: Bacillus thuringiensis ( i x ) FEATURE:
  ( A ) NAME/KEY: Peptide
  ( B ) LOCATION: 1..11
  ( D ) OTHER INFORMATION: /note= "N-terminal sequence from 60
   kDa delta- endotoxin"

( x i ) SEQUENCE DESCRIPTION: SEQ ID NO:16:

```
Met   Asn   Val   Leu   Asn   Ser   Gly   Arg   Thr   Thr   Ile
1                       5                       1 0
```

( 2 ) INFORMATION FOR SEQ ID NO:17:

( i ) SEQUENCE CHARACTERISTICS:
  ( A ) LENGTH: 2655 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: misc_feature
  ( B ) LOCATION: 1..2652
  ( D ) OTHER INFORMATION: /note= "Maize optimized DNA
   sequence for 100 kd VIP1A(a) protein from AB78"

( x i ) SEQUENCE DESCRIPTION: SEQ ID NO:17:

```
ATGAAGAACA TGAAGAAGAA GCTGGCCAGC GTGGTGACCT GCACCCTGCT GGCCCCCATG    60
TTCCTGAACG GCAACGTGAA CGCCGTGTAC GCCGACAGCA AGACCAACCA GATCAGCACC   120
ACCCAGAAGA ACCAGCAGAA GGAGATGGAC CGCAAGGGCC TGCTGGGCTA CTACTTCAAG   180
GGCAAGGACT TCAGCAACCT GACCATGTTC GCCCCCACGC GTGACAGCAC CCTGATCTAC   240
GACCAGCAGA CCGCCAACAA GCTGCTGGAC AAGAAGCAGC AGGAGTACCA GAGCATCCGC   300
TGGATCGGCC TGATCCAGAG CAAGGAGACC GGCGACTTCA CCTTCAACCT GAGCGAGGAC   360
GAGCAGGCCA TCATCGAGAT CAACGGCAAG ATCATCAGCA ACAAGGGCAA GGAGAAGCAG   420
GTGGTGCACC TGGAGAAGGG CAAGCTGGTG CCCATCAAGA TCGAGTACCA GAGCGACACC   480
AAGTTCAACA TCGACAGCAA GACCTTCAAG GAGCTGAAGC TTTTCAAGAT CGACAGCCAG   540
AACCAGCCCC AGCAGGTGCA GCAGGACGAG CTGCGCAACC CCGAGTTCAA CAAGAAGGAG   600
AGCCAGGAGT TCCTGGCCAA GCCCAGCAAG ATCAACCTGT TCACCCAGCA GATGAAGCGC   660
GAGATCGACG AGGACACCGA CACCGACGGC GACAGCATCC CCGACCTGTG GGAGGAGAAC   720
GGCTACACCA TCCAGAACCG CATCGCCGTG AAGTGGGACG ACAGCCTGGC TAGCAAGGGC   780
TACACCAAGT TCGTGAGCAA CCCCCTGGAG AGCCACACCG TGGGCGACCC CTACACCGAC   840
TACGAGAAGG CCGCCCGCGA CCTGGACCTG AGCAACGCCA AGGAGACCTT CAACCCCCTG   900
GTGGCCGCCT TCCCCAGCGT GAACGTGAGC ATGGAGAAGG TGATCCTGAG CCCCAACGAG   960
AACCTGAGCA ACAGCGTGGA GAGCCACTCG AGCACCAACT GGAGCTACAC CAACACCGAG  1020
GGCGCCAGCG TGGAGGCCGG CATCGGTCCC AAGGGCATCA GCTTCGGCGT GAGCGTGAAC  1080
TACCAGCACA GCGAGACCGT GGCCCAGGAG TGGGGCACCA GCACCGGCAA CACCAGCCAG  1140
TTCAACACCG CCAGCGCCGG CTACCTGAAC GCCAACGTGC GCTACAACAA CGTGGGCACC  1200
GGCGCCATCT ACGACGTGAA GCCCACCACC AGCTTCGTGC TGAACAACGA CACCATCGCC  1260
ACCATCACCG CCAAGTCGAA TTCCACCGCC CTGAACATCA GCCCGGCGA GAGCTACCCC  1320
AAGAAGGGCC AGAACGGCAT CGCCATCACC AGCATGGACG ACTTCAACAG CCACCCCATC  1380
ACCCTGAACA AGAAGCAGGT GGACAACCTG CTGAACAACA AGCCATGAT GCTGGAGACC  1440
AACCAGACCG ACGGCGTCTA CAAGATCAAG GACACCCACG GCAACATCGT GACCGGCGGC  1500
GAGTGGAACG GCGTGATCCA GCAGATCAAG GCCAAGACCG CCAGCATCAT CGTCGACGAC  1560
GGCGAGCGCG TGGCCGAGAA GCGCGTGGCC GCCAAGGACT ACGAGAACCC CGAGGACAAG  1620
ACCCCCAGCC TGACCCTGAA GGACGCCCTG AAGCTGAGCT ACCCCGACGA GATCAAGGAG  1680
ATCGAGGGCC TGCTGTACTA CAAGAACAAG CCCATCTACG AGAGCAGCGT GATGACCTAT  1740
CTAGACGAGA ACACCGCCAA GGAGGTGACC AAGCAGCTGA ACGACACCAC CGGCAAGTTC  1800
AAGGACGTGA GCCACCTGTA CGACGTGAAG CTGACCCCCA AGATGAACGT GACCATCAAG  1860
CTGAGCATCC TGTACGACAA CGCCGAGAGC AACGACAACA GCATCGGCAA GTGGACCAAC  1920
ACCAACATCG TGAGCGGCGG CAACAACGGC AAGAAGCAGT ACAGCAGCAA CAACCCCGAC  1980
GCCAACCTGA CCCTGAACAC CGACGCCCAG GAGAAGCTGA CAAGAACCG GACTACTAC  2040
ATCAGCCTGT ACATGAAGAG CGAGAAGAAC ACCCAGTGCG AGATCACCAT CGACGGCGAG  2100
ATATACCCCA TCACCACCAA GACCGTGAAC GTGAACAAGG ACAACTACAA GCGCCTGGAC  2160
ATCATCGCCC ACAACATCAA GAGCAACCCC ATCAGCAGCC TGCACATCAA GACCAACGAC  2220
GAGATCACCC TGTTCTGGGA CGACATATCG ATTACCGACG TCGCCAGCAT CAAGCCCGAG  2280
AACCTGACCG ACAGCGAGAT CAAGCAGATA TACAGTCGCT ACGGCATCAA GCTGGAGGAC  2340
GGCATCCTGA TCGACAAGAA GGGCGGCATC CACTACGGCG AGTTCATCAA CGAGGCCAGC  2400
```

| TTCAACATCG | AGCCCCTGCA | GAACTACGTG | ACCAAGTACG | AGGTGACCTA | CAGCAGCGAG | 2460 |
| CTGGGCCCCA | ACGTGAGCGA | CACCCTGGAG | AGCGACAAGA | TTTACAAGGA | CGGCACCATC | 2520 |
| AAGTTCGACT | TCACCAAGTA | CAGCAAGAAC | GAGCAGGGCC | TGTTCTACGA | CAGCGGCCTG | 2580 |
| AACTGGGACT | TCAAGATCAA | CGCCATCACC | TACGACGGCA | AGGAGATGAA | CGTGTTCCAC | 2640 |
| CGCTACAACA | AGTAG | | | | | 2655 |

( 2 ) INFORMATION FOR SEQ ID NO:18:

( i ) SEQUENCE CHARACTERISTICS:
        ( A ) LENGTH: 2004 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..2004
        ( D ) OTHER INFORMATION: /note= "Maize optimized DNA
            sequence for VIP1A(a) 80 kd protein from AB78"

( x i ) SEQUENCE DESCRIPTION: SEQ ID NO:18:

ATGAAGCGCG AGATCGACGA GGACACCGAC ACCGACGGCG ACAGCATCCC CGACCTGTGG 60

GAGGAGAACG GCTACACCAT CCAGAACCGC ATCGCCGTGA AGTGGGACGA CAGCCTGGCT 120

AGCAAGGGCT ACACCAAGTT CGTGAGCAAC CCCCTGGAGA GCCACACCGT GGGCGACCCC 180

TACACCGACT ACGAGAAGGC CGCCCGCGAC CTGGACCTGA GCAACGCCAA GGAGACCTTC 240

AACCCCCTGG TGGCCGCCTT CCCCAGCGTG AACGTGAGCA TGGAGAAGGT GATCCTGAGC 300

CCCAACGAGA ACCTGAGCAA CAGCGTGGAG AGCCACTCGA GCACCAACTG GAGCTACACC 360

AACACCGAGG GCGCCAGCGT GGAGGCCGGC ATCGGTCCCA AGGGCATCAG CTTCGGCGTG 420

AGCGTGAACT ACCAGCACAG CGAGACCGTG GCCCAGGAGT GGGGCACCAG CACCGGCAAC 480

ACCAGCCAGT TCAACACCGC CAGCGCCGGC TACCTGAACG CCAACGTGCG CTACAACAAC 540

GTGGGCACCG GCGCCATCTA CGACGTGAAG CCCACCACCA GCTTCGTGCT GAACAACGAC 600

ACCATCGCCA CCATCACCGC CAAGTCGAAT TCCACCGCCC TGAACATCAG CCCCGGCGAG 660

AGCTACCCCA AGAAGGGCCA GAACGGCATC GCCATCACCA GCATGGACGA CTTCAACAGC 720

CACCCCATCA CCCTGAACAA GAAGCAGGTG GACAACCTGC TGAACAACAA GCCCATGATG 780

CTGGAGACCA ACCAGACCGA CGGCGTCTAC AAGATCAAGG ACACCCACGG CAACATCGTG 840

ACCGGCGGCG AGTGGAACGG CGTGATCCAG CAGATCAAGG CCAAGACCGC CAGCATCATC 900

GTCGACGACG GCGAGCGCGT GGCCGAGAAG CGCGTGGCCG CCAAGGACTA CGAGAACCCC 960

GAGGACAAGA CCCCCAGCCT GACCCTGAAG GACGCCCTGA AGCTGAGCTA CCCCGACGAG 1020

ATCAAGGAGA TCGAGGGCCT GCTGTACTAC AAGAACAAGC CCATCTACGA GAGCAGCGTG 1080

ATGACCTATC TAGACGAGAA CACCGCCAAG GAGGTGACCA AGCAGCTGAA CGACACCACC 1140

GGCAAGTTCA AGGACGTGAG CCACCTGTAC GACGTGAAGC TGACCCCCAA GATGAACGTG 1200

ACCATCAAGC TGAGCATCCT GTACGACAAC GCCGAGAGCA ACGACAACAG CATCGGCAAG 1260

TGGACCAACA CCAACATCGT GAGCGGCGGC AACAACGGCA AGAAGCAGTA CAGCAGCAAC 1320

AACCCCGACG CCAACCTGAC CCTGAACACC GACGCCCAGG AGAAGCTGAA CAAGAACCGC 1380

GACTACTACA TCAGCCTGTA CATGAAGAGC GAGAAGAACA CCCAGTGCGA GATCACCATC 1440

```
GACGGCGAGA TATACCCCAT CACCACCAAG ACCGTGAACG TGAACAAGGA CAACTACAAG    1500

CGCCTGGACA TCATCGCCCA CAACATCAAG AGCAACCCCA TCAGCAGCCT GCACATCAAG    1560

ACCAACGACG AGATCACCCT GTTCTGGGAC GACATATCGA TTACCGACGT CGCCAGCATC    1620

AAGCCCGAGA ACCTGACCGA CAGCGAGATC AAGCAGATAT ACAGTCGCTA CGGCATCAAG    1680

CTGGAGGACG GCATCCTGAT CGACAAGAAG GGCGGCATCC ACTACGGCGA GTTCATCAAC    1740

GAGGCCAGCT TCAACATCGA GCCCCTGCAG AACTACGTGA CCAAGTACGA GGTGACCTAC    1800

AGCAGCGAGC TGGGCCCCAA CGTGAGCGAC ACCCTGGAGA GCGACAAGAT TTACAAGGAC    1860

GGCACCATCA AGTTCGACTT CACCAAGTAC AGCAAGAACG AGCAGGGCCT GTTCTACGAC    1920

AGCGGCCTGA ACTGGGACTT CAAGATCAAC GCCATCACCT ACGACGGCAA GGAGATGAAC    1980

GTGTTCCACC GCTACAACAA GTAG                                           2004
```

( 2 ) INFORMATION FOR SEQ ID NO:19:

( i ) SEQUENCE CHARACTERISTICS:
( A ) LENGTH: 4074 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1386
( D ) OTHER INFORMATION: /product="VIP2A(b) from Btt"

( i x ) FEATURE:
( A ) NAME/KEY: CDS
( B ) LOCATION: 1394..3895
( D ) OTHER INFORMATION: /product="VIP1A(b) from Btt"

( i x ) FEATURE:
( A ) NAME/KEY: misc_feature
( B ) LOCATION: 1..4074
( D ) OTHER INFORMATION: /note= "Cloned DNA sequence from Btt which contains the genes for both VIP1A(b) and VIP2A(b)"

( x i ) SEQUENCE DESCRIPTION: SEQ ID NO:19:

```
ATG CAA AGA ATG GAG GGA AAG TTG TTT GTG GTG TCA AAA ACA TTA CAA       48
Met Gln Arg Met Glu Gly Lys Leu Phe Val Val Ser Lys Thr Leu Gln
        670                     675                 680

GTA GTT ACT AGA ACT GTA TTG CTT AGT ACA GTT TAC TCT ATA ACT TTA       96
Val Val Thr Arg Thr Val Leu Leu Ser Thr Val Tyr Ser Ile Thr Leu
    685                 690                 695

TTA AAT AAT GTA GTG ATA AAA GCT GAC CAA TTA AAT ATA AAT TCT CAA      144
Leu Asn Asn Val Val Ile Lys Ala Asp Gln Leu Asn Ile Asn Ser Gln
700                 705                 710                 715

AGT AAA TAT ACT AAC TTG CAA AAT CTA AAA ATC CCT GAT AAT GCA GAG      192
Ser Lys Tyr Thr Asn Leu Gln Asn Leu Lys Ile Pro Asp Asn Ala Glu
                720                 725                 730

GAT TTT AAA GAA GAT AAG GGG AAA GCG AAA GAA TGG GGG AAA GAG AAA      240
Asp Phe Lys Glu Asp Lys Gly Lys Ala Lys Glu Trp Gly Lys Glu Lys
            735                 740                 745

GGG GAA GAG TGG AGG CCT CCT GCT ACT GAG AAA GGA GAA ATG AAT AAT      288
Gly Glu Glu Trp Arg Pro Pro Ala Thr Glu Lys Gly Glu Met Asn Asn
        750                 755                 760

TTT TTA GAT AAT AAA AAT GAT ATA AAG ACC AAT TAT AAA GAA ATT ACT      336
Phe Leu Asp Asn Lys Asn Asp Ile Lys Thr Asn Tyr Lys Glu Ile Thr
    765                 770                 775

TTT TCT ATG GCA GGT TCA TGT GAA GAT GAA ATA AAA GAT TTA GAA GAA      384
```

|  |  |  |  |  |  |  |  |  |  |  |  |  |  |  |  |
|---|---|---|---|---|---|---|---|---|---|---|---|---|---|---|---|
| Phe | Ser | Met | Ala | Gly | Ser | Cys | Glu | Asp | Glu | Ile | Lys | Asp | Leu | Glu | Glu |
| 780 |  |  |  | 785 |  |  |  |  | 790 |  |  |  |  |  | 795 |

| ATT | GAT | AAG | ATC | TTT | GAT | AAA | GCC | AAT | CTC | TCG | AGT | TCT | ATT | ATC | ACC | 432 |
|---|---|---|---|---|---|---|---|---|---|---|---|---|---|---|---|---|
| Ile | Asp | Lys | Ile | Phe | Asp | Lys | Ala | Asn | Leu | Ser | Ser | Ser | Ile | Ile | Thr |  |
|  |  |  |  | 800 |  |  |  |  | 805 |  |  |  |  |  | 810 |  |

| TAT | AAA | AAT | GTG | GAA | CCA | GCA | ACA | ATT | GGA | TTT | AAT | AAA | TCT | TTA | ACA | 480 |
|---|---|---|---|---|---|---|---|---|---|---|---|---|---|---|---|---|
| Tyr | Lys | Asn | Val | Glu | Pro | Ala | Thr | Ile | Gly | Phe | Asn | Lys | Ser | Leu | Thr |  |
|  |  |  | 815 |  |  |  |  | 820 |  |  |  |  | 825 |  |  |  |

| GAA | GGT | AAT | ACG | ATT | AAT | TCT | GAT | GCA | ATG | GCA | CAG | TTT | AAA | GAA | CAA | 528 |
|---|---|---|---|---|---|---|---|---|---|---|---|---|---|---|---|---|
| Glu | Gly | Asn | Thr | Ile | Asn | Ser | Asp | Ala | Met | Ala | Gln | Phe | Lys | Glu | Gln |  |
|  |  | 830 |  |  |  |  | 835 |  |  |  |  | 840 |  |  |  |  |

| TTT | TTA | GGT | AAG | GAT | ATG | AAG | TTT | GAT | AGT | TAT | CTA | GAT | ACT | CAT | TTA | 576 |
|---|---|---|---|---|---|---|---|---|---|---|---|---|---|---|---|---|
| Phe | Leu | Gly | Lys | Asp | Met | Lys | Phe | Asp | Ser | Tyr | Leu | Asp | Thr | His | Leu |  |
|  | 845 |  |  |  |  | 850 |  |  |  |  | 855 |  |  |  |  |  |

| ACT | GCT | CAA | CAA | GTT | TCC | AGT | AAA | AAA | AGA | GTT | ATT | TTG | AAG | GTT | ACG | 624 |
|---|---|---|---|---|---|---|---|---|---|---|---|---|---|---|---|---|
| Thr | Ala | Gln | Gln | Val | Ser | Ser | Lys | Lys | Arg | Val | Ile | Leu | Lys | Val | Thr |  |
| 860 |  |  |  |  | 865 |  |  |  |  | 870 |  |  |  |  | 875 |  |

| GTT | CCG | AGT | GGG | AAA | GGT | TCT | ACT | ACT | CCA | ACA | AAA | GCA | GGT | GTC | ATT | 672 |
|---|---|---|---|---|---|---|---|---|---|---|---|---|---|---|---|---|
| Val | Pro | Ser | Gly | Lys | Gly | Ser | Thr | Thr | Pro | Thr | Lys | Ala | Gly | Val | Ile |  |
|  |  |  |  | 880 |  |  |  |  | 885 |  |  |  |  | 890 |  |  |

| TTA | AAC | AAT | AAT | GAA | TAC | AAA | ATG | CTC | ATT | GAT | AAT | GGG | TAT | GTG | CTC | 720 |
|---|---|---|---|---|---|---|---|---|---|---|---|---|---|---|---|---|
| Leu | Asn | Asn | Asn | Glu | Tyr | Lys | Met | Leu | Ile | Asp | Asn | Gly | Tyr | Val | Leu |  |
|  |  |  | 895 |  |  |  |  | 900 |  |  |  |  | 905 |  |  |  |

| CAT | GTA | GAT | AAG | GTA | TCA | AAA | GTA | GTA | AAA | AAA | GGG | ATG | GAG | TGC | TTA | 768 |
|---|---|---|---|---|---|---|---|---|---|---|---|---|---|---|---|---|
| His | Val | Asp | Lys | Val | Ser | Lys | Val | Val | Lys | Lys | Gly | Met | Glu | Cys | Leu |  |
|  |  | 910 |  |  |  |  | 915 |  |  |  |  | 920 |  |  |  |  |

| CAA | GTT | GAA | GGG | ACT | TTA | AAA | AAG | AGT | CTC | GAC | TTT | AAA | AAT | GAT | ATA | 816 |
|---|---|---|---|---|---|---|---|---|---|---|---|---|---|---|---|---|
| Gln | Val | Glu | Gly | Thr | Leu | Lys | Lys | Ser | Leu | Asp | Phe | Lys | Asn | Asp | Ile |  |
|  | 925 |  |  |  |  | 930 |  |  |  |  | 935 |  |  |  |  |  |

| AAT | GCT | GAA | GCG | CAT | AGC | TGG | GGG | ATG | AAA | ATT | TAT | GAA | GAC | TGG | GCT | 864 |
|---|---|---|---|---|---|---|---|---|---|---|---|---|---|---|---|---|
| Asn | Ala | Glu | Ala | His | Ser | Trp | Gly | Met | Lys | Ile | Tyr | Glu | Asp | Trp | Ala |  |
| 940 |  |  |  |  | 945 |  |  |  |  | 950 |  |  |  |  | 955 |  |

| AAA | AAT | TTA | ACC | GCT | TCG | CAA | AGG | GAA | GCT | TTA | GAT | GGG | TAT | GCT | AGG | 912 |
|---|---|---|---|---|---|---|---|---|---|---|---|---|---|---|---|---|
| Lys | Asn | Leu | Thr | Ala | Ser | Gln | Arg | Glu | Ala | Leu | Asp | Gly | Tyr | Ala | Arg |  |
|  |  |  |  | 960 |  |  |  |  | 965 |  |  |  |  | 970 |  |  |

| CAA | GAT | TAT | AAA | GAA | ATC | AAT | AAT | TAT | TTG | CGC | AAT | CAA | GGC | GGG | AGT | 960 |
|---|---|---|---|---|---|---|---|---|---|---|---|---|---|---|---|---|
| Gln | Asp | Tyr | Lys | Glu | Ile | Asn | Asn | Tyr | Leu | Arg | Asn | Gln | Gly | Gly | Ser |  |
|  |  | 975 |  |  |  |  | 980 |  |  |  |  | 985 |  |  |  |  |

| GGA | AAT | GAA | AAG | CTG | GAT | GCC | CAA | TTA | AAA | AAT | ATT | TCT | GAT | GCT | TTA | 1008 |
|---|---|---|---|---|---|---|---|---|---|---|---|---|---|---|---|---|
| Gly | Asn | Glu | Lys | Leu | Asp | Ala | Gln | Leu | Lys | Asn | Ile | Ser | Asp | Ala | Leu |  |
|  |  | 990 |  |  |  |  | 995 |  |  |  |  | 1000 |  |  |  |  |

| GGG | AAG | AAA | CCC | ATA | CCA | GAA | AAT | ATT | ACC | GTG | TAT | AGA | TGG | TGT | GGC | 1056 |
|---|---|---|---|---|---|---|---|---|---|---|---|---|---|---|---|---|
| Gly | Lys | Lys | Pro | Ile | Pro | Glu | Asn | Ile | Thr | Val | Tyr | Arg | Trp | Cys | Gly |  |
|  | 1005 |  |  |  |  | 1010 |  |  |  |  | 1015 |  |  |  |  |  |

| ATG | CCG | GAA | TTT | GGT | TAT | CAA | ATT | AGT | GAT | CCG | TTA | CCT | TCT | TTA | AAA | 1104 |
|---|---|---|---|---|---|---|---|---|---|---|---|---|---|---|---|---|
| Met | Pro | Glu | Phe | Gly | Tyr | Gln | Ile | Ser | Asp | Pro | Leu | Pro | Ser | Leu | Lys |  |
| 1020 |  |  |  |  | 1025 |  |  |  |  | 1030 |  |  |  |  | 1035 |  |

| GAT | TTT | GAA | GAA | CAA | TTT | TTA | AAT | ACA | ATT | AAA | GAA | GAC | AAA | GGG | TAT | 1152 |
|---|---|---|---|---|---|---|---|---|---|---|---|---|---|---|---|---|
| Asp | Phe | Glu | Glu | Gln | Phe | Leu | Asn | Thr | Ile | Lys | Glu | Asp | Lys | Gly | Tyr |  |
|  |  |  |  | 1040 |  |  |  |  | 1045 |  |  |  |  | 1050 |  |  |

| ATG | AGT | ACA | AGC | TTA | TCG | AGT | GAA | CGT | CTT | GCA | GCT | TTT | GGA | TCT | AGA | 1200 |
|---|---|---|---|---|---|---|---|---|---|---|---|---|---|---|---|---|
| Met | Ser | Thr | Ser | Leu | Ser | Ser | Glu | Arg | Leu | Ala | Ala | Phe | Gly | Ser | Arg |  |
|  |  |  | 1055 |  |  |  |  | 1060 |  |  |  |  | 1065 |  |  |  |

| AAA | ATT | ATA | TTA | CGC | TTA | CAA | GTT | CCG | AAA | GGA | AGT | ACG | GGG | GCG | TAT | 1248 |
|---|---|---|---|---|---|---|---|---|---|---|---|---|---|---|---|---|
| Lys | Ile | Ile | Leu | Arg | Leu | Gln | Val | Pro | Lys | Gly | Ser | Thr | Gly | Ala | Tyr |  |
|  |  | 1070 |  |  |  |  | 1075 |  |  |  |  | 1080 |  |  |  |  |

| TTA | AGT | GCC | ATT | GGT | GGA | TTT | GCA | AGT | GAA | AAA | GAG | ATC | CTA | CTT | GAT | 1296 |
|---|---|---|---|---|---|---|---|---|---|---|---|---|---|---|---|---|
| Leu | Ser | Ala | Ile | Gly | Gly | Phe | Ala | Ser | Glu | Lys | Glu | Ile | Leu | Leu | Asp |  |
|  | 1085 |  |  |  |  | 1090 |  |  |  |  | 1095 |  |  |  |  |  |

| AAA | GAT | AGT | AAA | TAT | CAT | ATT | GAT | AAA | GCA | ACA | GAG | GTA | ATC | ATT | AAA | 1344 |
|---|---|---|---|---|---|---|---|---|---|---|---|---|---|---|---|---|

|     |     |     |     |     |     |     |     |     |     |     |     |     |     |     |      |
| --- | --- | --- | --- | --- | --- | --- | --- | --- | --- | --- | --- | --- | --- | --- | ---- |
| Lys | Asp | Ser | Lys | Tyr | His | Ile | Asp | Lys | Ala | Thr | Glu | Val | Ile | Ile | Lys  |
| 1100 |    |     |     |     | 1105|     |     |     | 1110|     |     |     |     |     | 1115 |
| GGT | GTT | AAG | CGA | TAT | GTA | GTG | GAT | GCA | ACA | TTA | TTA | ACA | AAT |     | 1386 |
| Gly | Val | Lys | Arg | Tyr | Val | Val | Asp | Ala | Thr | Leu | Leu | Thr | Asn |     |      |
|     |     |     |     | 1120|     |     |     |     | 1125|     |     |     |     |     |      |
| TAAGGAG | ATG | AAA | AAT | ATG | AAG | AAA | AAG | TTA | GCA | AGT | GTT | GTA | ACC | TGT | 1435 |
|     | Met | Lys | Asn | Met | Lys | Lys | Lys | Leu | Ala | Ser | Val | Val | Thr | Cys |      |
|     | 1   |     |     |     | 5   |     |     |     |     | 10  |     |     |     |     |      |
| ATG | TTA | TTA | GCT | CCT | ATG | TTT | TTG | AAT | GGA | AAT | GTG | AAT | GCT | GTT | AAC  | 1483 |
| Met | Leu | Leu | Ala | Pro | Met | Phe | Leu | Asn | Gly | Asn | Val | Asn | Ala | Val | Asn  |
| 15  |     |     |     |     | 20  |     |     |     |     | 25  |     |     |     |     | 30   |
| GCG | GAT | AGT | AAA | ATA | AAT | CAG | ATT | TCT | ACA | ACG | CAG | GAA | AAC | CAA | CAG  | 1531 |
| Ala | Asp | Ser | Lys | Ile | Asn | Gln | Ile | Ser | Thr | Thr | Gln | Glu | Asn | Gln | Gln  |
|     |     |     |     | 35  |     |     |     |     | 40  |     |     |     |     | 45  |      |
| AAA | GAG | ATG | GAC | CGA | AAG | GGA | TTA | TTG | GGA | TAT | TAT | TTC | AAA | GGA | AAA  | 1579 |
| Lys | Glu | Met | Asp | Arg | Lys | Gly | Leu | Leu | Gly | Tyr | Tyr | Phe | Lys | Gly | Lys  |
|     |     |     | 50  |     |     |     |     | 55  |     |     |     |     | 60  |     |      |
| GAT | TTT | AAT | AAT | CTT | ACT | ATG | TTT | GCA | CCG | ACA | CGT | GAT | AAT | ACC | CTT  | 1627 |
| Asp | Phe | Asn | Asn | Leu | Thr | Met | Phe | Ala | Pro | Thr | Arg | Asp | Asn | Thr | Leu  |
|     |     | 65  |     |     |     |     | 70  |     |     |     |     | 75  |     |     |      |
| ATG | TAT | GAC | CAA | CAA | ACA | GCG | AAT | GCA | TTA | TTA | GAT | AAA | AAA | CAA | CAA  | 1675 |
| Met | Tyr | Asp | Gln | Gln | Thr | Ala | Asn | Ala | Leu | Leu | Asp | Lys | Lys | Gln | Gln  |
|     | 80  |     |     |     |     | 85  |     |     |     |     | 90  |     |     |     |      |
| GAA | TAT | CAG | TCC | ATT | CGT | TGG | ATT | GGT | TTG | ATT | CAG | CGT | AAA | GAA | ACG  | 1723 |
| Glu | Tyr | Gln | Ser | Ile | Arg | Trp | Ile | Gly | Leu | Ile | Gln | Arg | Lys | Glu | Thr  |
| 95  |     |     |     |     | 100 |     |     |     |     | 105 |     |     |     |     | 110  |
| GGC | GAT | TTC | ACA | TTT | AAC | TTA | TCA | AAG | GAT | GAA | CAG | GCA | ATT | ATA | GAA  | 1771 |
| Gly | Asp | Phe | Thr | Phe | Asn | Leu | Ser | Lys | Asp | Glu | Gln | Ala | Ile | Ile | Glu  |
|     |     |     |     | 115 |     |     |     |     | 120 |     |     |     |     | 125 |      |
| ATC | GAT | GGG | AAA | ATC | ATT | TCT | AAT | AAA | GGG | AAA | GAA | AAG | CAA | GTT | GTC  | 1819 |
| Ile | Asp | Gly | Lys | Ile | Ile | Ser | Asn | Lys | Gly | Lys | Glu | Lys | Gln | Val | Val  |
|     |     |     | 130 |     |     |     |     | 135 |     |     |     |     | 140 |     |      |
| CAT | TTA | GAA | AAA | GAA | AAA | TTA | GTT | CCA | ATC | AAA | ATA | GAG | TAT | CAA | TCA  | 1867 |
| His | Leu | Glu | Lys | Glu | Lys | Leu | Val | Pro | Ile | Lys | Ile | Glu | Tyr | Gln | Ser  |
|     |     | 145 |     |     |     |     | 150 |     |     |     |     | 155 |     |     |      |
| GAT | ACG | AAA | TTT | AAT | ATT | GAT | AGT | AAA | ACA | TTT | AAA | GAA | CTT | AAA | TTA  | 1915 |
| Asp | Thr | Lys | Phe | Asn | Ile | Asp | Ser | Lys | Thr | Phe | Lys | Glu | Leu | Lys | Leu  |
|     | 160 |     |     |     |     | 165 |     |     |     |     | 170 |     |     |     |      |
| TTT | AAA | ATA | GAT | AGT | CAA | AAC | CAA | TCT | CAA | CAA | GTT | CAA | CTG | AGA | AAC  | 1963 |
| Phe | Lys | Ile | Asp | Ser | Gln | Asn | Gln | Ser | Gln | Gln | Val | Gln | Leu | Arg | Asn  |
| 175 |     |     |     |     | 180 |     |     |     |     | 185 |     |     |     |     | 190  |
| CCT | GAA | TTT | AAC | AAA | AAA | GAA | TCA | CAG | GAA | TTT | TTA | GCA | AAA | GCA | TCA  | 2011 |
| Pro | Glu | Phe | Asn | Lys | Lys | Glu | Ser | Gln | Glu | Phe | Leu | Ala | Lys | Ala | Ser  |
|     |     |     |     | 195 |     |     |     |     | 200 |     |     |     |     | 205 |      |
| AAA | ACA | AAC | CTT | TTT | AAG | CAA | AAA | ATG | AAA | AGA | GAT | ATT | GAT | GAA | GAT  | 2059 |
| Lys | Thr | Asn | Leu | Phe | Lys | Gln | Lys | Met | Lys | Arg | Asp | Ile | Asp | Glu | Asp  |
|     |     |     | 210 |     |     |     |     | 215 |     |     |     |     | 220 |     |      |
| ACG | GAT | ACA | GAT | GGA | GAC | TCC | ATT | CCT | GAT | CTT | TGG | GAA | GAA | AAT | GGG  | 2107 |
| Thr | Asp | Thr | Asp | Gly | Asp | Ser | Ile | Pro | Asp | Leu | Trp | Glu | Glu | Asn | Gly  |
|     |     | 225 |     |     |     |     | 230 |     |     |     |     | 235 |     |     |      |
| TAC | ACG | ATT | CAA | AAT | AAA | GTT | GCT | GTC | AAA | TGG | GAT | GAT | TCG | CTA | GCA  | 2155 |
| Tyr | Thr | Ile | Gln | Asn | Lys | Val | Ala | Val | Lys | Trp | Asp | Asp | Ser | Leu | Ala  |
|     | 240 |     |     |     |     | 245 |     |     |     |     | 250 |     |     |     |      |
| AGT | AAG | GGA | TAT | ACA | AAA | TTT | GTT | TCG | AAT | CCA | TTA | GAC | AGC | CAC | ACA  | 2203 |
| Ser | Lys | Gly | Tyr | Thr | Lys | Phe | Val | Ser | Asn | Pro | Leu | Asp | Ser | His | Thr  |
| 255 |     |     |     |     | 260 |     |     |     |     | 265 |     |     |     |     | 270  |
| GTT | GGC | GAT | CCC | TAT | ACT | GAT | TAT | GAA | AAG | GCC | GCA | AGG | GAT | TTA | GAT  | 2251 |
| Val | Gly | Asp | Pro | Tyr | Thr | Asp | Tyr | Glu | Lys | Ala | Ala | Arg | Asp | Leu | Asp  |
|     |     |     | 275 |     |     |     |     | 280 |     |     |     |     | 285 |     |      |
| TTA | TCA | AAT | GCA | AAG | GAA | ACG | TTC | AAC | CCA | TTG | GTA | GCT | GCT | TTT | CCA  | 2299 |

|     |     |     |     |     |     |     |     |     |     |     |     |     |     |     |      |
|-----|-----|-----|-----|-----|-----|-----|-----|-----|-----|-----|-----|-----|-----|-----|------|
| Leu | Ser | Asn | Ala | Lys | Glu | Thr | Phe | Asn | Pro | Leu | Val | Ala | Ala | Phe | Pro  |
|     |     |     | 290 |     |     |     |     | 295 |     |     |     | 300 |     |     |      |
| AGT | GTG | AAT | GTT | AGT | ATG | GAA | AAG | GTG | ATA | TTA | TCA | CCA | AAT | GAA | AAT  | 2347 |
| Ser | Val | Asn | Val | Ser | Met | Glu | Lys | Val | Ile | Leu | Ser | Pro | Asn | Glu | Asn  |
|     |     | 305 |     |     |     | 310 |     |     |     |     | 315 |     |     |     |      |
| TTA | TCC | AAT | AGT | GTA | GAG | TCT | CAT | TCA | TCC | ACG | AAT | TGG | TCT | TAT | ACG  | 2395 |
| Leu | Ser | Asn | Ser | Val | Glu | Ser | His | Ser | Ser | Thr | Asn | Trp | Ser | Tyr | Thr  |
|     | 320 |     |     |     |     | 325 |     |     |     |     | 330 |     |     |     |      |
| AAT | ACA | GAA | GGA | GCT | TCC | ATT | GAA | GCT | GGT | GGC | GGT | CCA | TTA | GGC | CTT  | 2443 |
| Asn | Thr | Glu | Gly | Ala | Ser | Ile | Glu | Ala | Gly | Gly | Gly | Pro | Leu | Gly | Leu  |
| 335 |     |     |     |     | 340 |     |     |     |     | 345 |     |     |     |     | 350  |
| TCT | TTT | GGC | GTG | AGT | GTT | ACT | TAT | CAA | CAC | TCT | GAA | ACA | GTT | GCA | CAA  | 2491 |
| Ser | Phe | Gly | Val | Ser | Val | Thr | Tyr | Gln | His | Ser | Glu | Thr | Val | Ala | Gln  |
|     |     |     |     | 355 |     |     |     |     | 360 |     |     |     |     | 365 |      |
| GAA | TGG | GGA | ACA | TCT | ACA | GGA | AAT | ACT | TCA | CAA | TTC | AAT | ACG | GCT | TCA  | 2539 |
| Glu | Trp | Gly | Thr | Ser | Thr | Gly | Asn | Thr | Ser | Gln | Phe | Asn | Thr | Ala | Ser  |
|     |     |     | 370 |     |     |     |     | 375 |     |     |     |     | 380 |     |      |
| GCG | GGA | TAT | TTA | AAT | GCA | AAT | GTT | CGG | TAT | AAC | AAT | GTA | GGG | ACT | GGT  | 2587 |
| Ala | Gly | Tyr | Leu | Asn | Ala | Asn | Val | Arg | Tyr | Asn | Asn | Val | Gly | Thr | Gly  |
|     |     | 385 |     |     |     |     | 390 |     |     |     |     | 395 |     |     |      |
| GCC | ATC | TAT | GAT | GTA | AAA | CCT | ACA | ACA | AGT | TTT | GTA | TTA | AAT | AAC | AAT  | 2635 |
| Ala | Ile | Tyr | Asp | Val | Lys | Pro | Thr | Thr | Ser | Phe | Val | Leu | Asn | Asn | Asn  |
| 400 |     |     |     |     | 405 |     |     |     |     | 410 |     |     |     |     |      |
| ACC | ATC | GCA | ACG | ATT | ACA | GCA | AAA | TCA | AAT | TCA | ACA | GCT | TTA | CGT | ATA  | 2683 |
| Thr | Ile | Ala | Thr | Ile | Thr | Ala | Lys | Ser | Asn | Ser | Thr | Ala | Leu | Arg | Ile  |
| 415 |     |     |     |     | 420 |     |     |     |     | 425 |     |     |     |     | 430  |
| TCT | CCG | GGG | GAT | AGT | TAT | CCA | GAA | ATA | GGA | GAA | AAC | GCT | ATT | GCG | ATT  | 2731 |
| Ser | Pro | Gly | Asp | Ser | Tyr | Pro | Glu | Ile | Gly | Glu | Asn | Ala | Ile | Ala | Ile  |
|     |     |     |     | 435 |     |     |     |     | 440 |     |     |     |     | 445 |      |
| ACA | TCT | ATG | GAT | GAT | TTT | AAT | TCT | CAT | CCA | ATT | ACA | TTA | AAT | AAA | CAA  | 2779 |
| Thr | Ser | Met | Asp | Asp | Phe | Asn | Ser | His | Pro | Ile | Thr | Leu | Asn | Lys | Gln  |
|     |     |     | 450 |     |     |     |     | 455 |     |     |     |     | 460 |     |      |
| CAG | GTA | AAT | CAA | TTG | ATA | AAT | AAT | AAG | CCA | ATT | ATG | CTA | GAG | ACA | GAC  | 2827 |
| Gln | Val | Asn | Gln | Leu | Ile | Asn | Asn | Lys | Pro | Ile | Met | Leu | Glu | Thr | Asp  |
|     |     | 465 |     |     |     |     | 470 |     |     |     |     | 475 |     |     |      |
| CAA | ACA | GAT | GGT | GTT | TAT | AAA | ATA | AGA | GAT | ACA | CAT | GGA | AAT | ATT | GTA  | 2875 |
| Gln | Thr | Asp | Gly | Val | Tyr | Lys | Ile | Arg | Asp | Thr | His | Gly | Asn | Ile | Val  |
|     |     | 480 |     |     |     | 485 |     |     |     |     | 490 |     |     |     |      |
| ACT | GGT | GGA | GAA | TGG | AAT | GGT | GTA | ACA | CAA | CAA | ATT | AAA | GCA | AAA | ACA  | 2923 |
| Thr | Gly | Gly | Glu | Trp | Asn | Gly | Val | Thr | Gln | Gln | Ile | Lys | Ala | Lys | Thr  |
| 495 |     |     |     |     | 500 |     |     |     |     | 505 |     |     |     |     | 510  |
| GCG | TCT | ATT | ATT | GTG | GAT | GAC | GGG | AAA | CAG | GTA | GCA | GAA | AAA | CGT | GTG  | 2971 |
| Ala | Ser | Ile | Ile | Val | Asp | Asp | Gly | Lys | Gln | Val | Ala | Glu | Lys | Arg | Val  |
|     |     |     |     | 515 |     |     |     |     | 520 |     |     |     |     | 525 |      |
| GCG | GCA | AAA | GAT | TAT | GGT | CAT | CCA | GAA | GAT | AAA | ACA | CCA | CCT | TTA | ACT  | 3019 |
| Ala | Ala | Lys | Asp | Tyr | Gly | His | Pro | Glu | Asp | Lys | Thr | Pro | Pro | Leu | Thr  |
|     |     |     |     | 530 |     |     |     | 535 |     |     |     |     | 540 |     |      |
| TTA | AAA | GAT | ACC | CTG | AAG | CTT | TCA | TAC | CCA | GAT | GAA | ATA | AAA | GAA | ACT  | 3067 |
| Leu | Lys | Asp | Thr | Leu | Lys | Leu | Ser | Tyr | Pro | Asp | Glu | Ile | Lys | Glu | Thr  |
|     |     | 545 |     |     |     |     | 550 |     |     |     |     | 555 |     |     |      |
| AAT | GGA | TTG | TTG | TAC | TAT | GAT | GAC | AAA | CCA | ATC | TAT | GAA | TCG | AGT | GTC  | 3115 |
| Asn | Gly | Leu | Leu | Tyr | Tyr | Asp | Asp | Lys | Pro | Ile | Tyr | Glu | Ser | Ser | Val  |
|     | 560 |     |     |     |     | 565 |     |     |     |     | 570 |     |     |     |      |
| ATG | ACT | TAT | CTG | GAT | GAA | AAT | ACG | GCA | AAA | GAA | GTC | AAA | AAA | CAA | ATA  | 3163 |
| Met | Thr | Tyr | Leu | Asp | Glu | Asn | Thr | Ala | Lys | Glu | Val | Lys | Lys | Gln | Ile  |
| 575 |     |     |     |     | 580 |     |     |     |     | 585 |     |     |     |     | 590  |
| AAT | GAT | ACA | ACC | GGA | AAA | TTT | AAG | GAT | GTA | AAT | CAC | TTA | TAT | GAT | GTA  | 3211 |
| Asn | Asp | Thr | Thr | Gly | Lys | Phe | Lys | Asp | Val | Asn | His | Leu | Tyr | Asp | Val  |
|     |     |     |     | 595 |     |     |     |     | 600 |     |     |     |     | 605 |      |
| AAA | CTG | ACT | CCA | AAA | ATG | AAT | TTT | ACG | ATT | AAA | ATG | GCT | TCC | TTG | TAT  | 3259 |

| | | | | | | | | | | | | | | | |
|---|---|---|---|---|---|---|---|---|---|---|---|---|---|---|---|
| Lys | Leu | Thr | Pro<br>610 | Lys | Met | Asn | Phe | Thr<br>615 | Ile | Lys | Met | Ala | Ser<br>620 | Leu | Tyr |
| GAT | GGG | GCT | GAA | AAT | AAT | CAT | AAC | TCT | TTA | GGA | ACC | TGG | TAT | TTA | ACA |
| Asp | Gly | Ala<br>625 | Glu | Asn | Asn | His | Asn<br>630 | Ser | Leu | Gly | Thr | Trp<br>635 | Tyr | Leu | Thr |
| TAT | AAT | GTT | GCT | GGT | GGA | AAT | ACT | GGG | AAG | AGA | CAA | TAT | CGT | TCA | GCT |
| Tyr | Asn<br>640 | Val | Ala | Gly | Gly | Asn<br>645 | Thr | Gly | Lys | Arg | Gln<br>650 | Tyr | Arg | Ser | Ala |
| CAT | TCT | TGT | GCA | CAT | GTA | GCT | CTA | TCT | TCA | GAA | GCG | AAA | AAG | AAA | CTA |
| His<br>655 | Ser | Cys | Ala | His | Val<br>660 | Ala | Leu | Ser | Ser | Glu<br>665 | Ala | Lys | Lys | Lys | Leu<br>670 |
| AAT | CAA | AAT | GCG | AAT | TAC | TAT | CTT | AGC | ATG | TAT | ATG | AAG | GCT | GAT | TCT |
| Asn | Gln | Asn | Ala | Tyr<br>675 | Tyr | Leu | Ser | Met<br>680 | Tyr | Met | Lys | Ala | Asp<br>685 | Ser |
| ACT | ACG | GAA | CCT | ACA | ATA | GAA | GTA | GCT | GGG | GAA | AAA | TCT | GCA | ATA | ACA |
| Thr | Thr | Glu | Pro<br>690 | Thr | Ile | Glu | Val | Ala<br>695 | Gly | Glu | Lys | Ser | Ala<br>700 | Ile | Thr |
| AGT | AAA | AAA | GTA | AAA | TTA | AAT | AAT | CAA | AAT | TAT | CAA | AGA | GTT | GAT | ATT |
| Ser | Lys | Lys<br>705 | Val | Lys | Leu | Asn | Asn<br>710 | Gln | Asn | Tyr | Gln | Arg<br>715 | Val | Asp | Ile |
| TTA | GTG | AAA | AAT | TCT | GAA | AGA | AAT | CCA | ATG | GAT | AAA | ATA | TAT | ATA | AGA |
| Leu | Val | Lys<br>720 | Asn | Ser | Glu | Arg | Asn<br>725 | Pro | Met | Asp | Lys | Ile<br>730 | Tyr | Ile | Arg |
| GGA | AAT | GGC | ACG | ACA | AAT | GTT | TAT | GGG | GAT | GAT | GTT | ACT | ATC | CCA | GAG |
| Gly<br>735 | Asn | Gly | Thr | Thr | Asn<br>740 | Val | Tyr | Gly | Asp | Asp<br>745 | Val | Thr | Ile | Pro | Glu<br>750 |
| GTA | TCA | GCT | ATA | AAT | CCG | GCT | AGT | CTA | TCA | GAT | GAA | GAA | ATT | CAA | GAA |
| Val | Ser | Ala | Ile | Asn<br>755 | Pro | Ala | Ser | Leu | Ser<br>760 | Asp | Glu | Glu | Ile | Gln<br>765 | Glu |
| ATA | TTT | AAA | GAC | TCA | ACT | ATT | GAA | TAT | GGA | AAT | CCT | AGT | TTC | GTT | GCT |
| Ile | Phe | Lys | Asp<br>770 | Ser | Thr | Ile | Glu | Tyr<br>775 | Gly | Asn | Pro | Ser | Phe<br>780 | Val | Ala |
| GAT | GCC | GTA | ACA | TTT | AAA | AAT | ATA | AAA | CCT | TTA | CAA | AAT | TAT | GTA | AAG |
| Asp | Ala | Val<br>785 | Thr | Phe | Lys | Asn | Ile<br>790 | Lys | Pro | Leu | Gln | Asn<br>795 | Tyr | Val | Lys |
| GAA | TAT | GAA | ATA | TAT | CAT | AAA | TCT | CAT | CGA | TAT | GAA | AAG | AAA | ACG | GTC |
| Glu | Tyr<br>800 | Glu | Ile | Tyr | His | Lys<br>805 | Ser | His | Arg | Tyr | Glu<br>810 | Lys | Lys | Thr | Val |
| TTT | GAT | ATC | ATG | GGT | GTT | CAT | TAT | GAG | TAT | AGT | ATA | GCT | AGG | GAA | CAA |
| Phe<br>815 | Asp | Ile | Met | Gly | Val<br>820 | His | Tyr | Glu | Tyr | Ser<br>825 | Ile | Ala | Arg | Glu | Gln<br>830 |
| AAG | AAA | GCC | GCA | TAATTTAAA | AATAAACTC | GTTAGAGTTT | ATTTAGCATG | | | | | | | | |
| Lys | Lys | Ala | Ala | | | | | | | | | | | | |

| | |
|---|---|
| GAT GGG GCT GAA AAT AAT CAT AAC TCT TTA GGA ACC TGG TAT TTA ACA | 3307 |
| TAT AAT GTT GCT GGT GGA AAT ACT GGG AAG AGA CAA TAT CGT TCA GCT | 3355 |
| CAT TCT TGT GCA CAT GTA GCT CTA TCT TCA GAA GCG AAA AAG AAA CTA | 3403 |
| AAT CAA AAT GCG AAT TAC TAT CTT AGC ATG TAT ATG AAG GCT GAT TCT | 3451 |
| ACT ACG GAA CCT ACA ATA GAA GTA GCT GGG GAA AAA TCT GCA ATA ACA | 3499 |
| AGT AAA AAA GTA AAA TTA AAT AAT CAA AAT TAT CAA AGA GTT GAT ATT | 3547 |
| TTA GTG AAA AAT TCT GAA AGA AAT CCA ATG GAT AAA ATA TAT ATA AGA | 3595 |
| GGA AAT GGC ACG ACA AAT GTT TAT GGG GAT GAT GTT ACT ATC CCA GAG | 3643 |
| GTA TCA GCT ATA AAT CCG GCT AGT CTA TCA GAT GAA GAA ATT CAA GAA | 3691 |
| ATA TTT AAA GAC TCA ACT ATT GAA TAT GGA AAT CCT AGT TTC GTT GCT | 3739 |
| GAT GCC GTA ACA TTT AAA AAT ATA AAA CCT TTA CAA AAT TAT GTA AAG | 3787 |
| GAA TAT GAA ATA TAT CAT AAA TCT CAT CGA TAT GAA AAG AAA ACG GTC | 3835 |
| TTT GAT ATC ATG GGT GTT CAT TAT GAG TAT AGT ATA GCT AGG GAA CAA | 3883 |
| AAG AAA GCC GCA TAATTTAAA AATAAACTC GTTAGAGTTT ATTTAGCATG | 3935 |
| GTATTTTTAA GAATAATCAA TATGTTGAAC CGTTTGTAGC TGTTTTGGAA GGGAATTTCA | 3995 |
| TTTTATTTGG TCTCTTAAGT TGATGGGCAT GGGATATGTT CAGCATCCAA GCGTTTNGGG | 4055 |
| GGTTANAAAA TCCAATTTT | 4074 |

( 2 ) INFORMATION FOR SEQ ID NO:20:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| | | | | | | | | | | | | | | | |
|---|---|---|---|---|---|---|---|---|---|---|---|---|---|---|---|
| Met<br>1 | Gln | Arg | Met | Glu<br>5 | Gly | Lys | Leu | Phe | Val<br>10 | Val | Ser | Lys | Thr | Leu<br>15 | Gln |
| Val | Val | Thr | Arg | Thr | Val | Leu | Leu | Ser | Thr | Val | Tyr | Ser | Ile | Thr | Leu |

-continued

|  |  |  | 20 |  |  |  | 25 |  |  |  | 30 |  |  |
|---|---|---|---|---|---|---|---|---|---|---|---|---|---|
| Leu | Asn | Asn | Val | Val | Ile | Lys | Ala | Asp | Gln | Leu | Asn | Ile | Asn | Ser | Gln |
|  |  | 35 |  |  |  | 40 |  |  |  |  | 45 |  |  |
| Ser | Lys | Tyr | Thr | Asn | Leu | Gln | Asn | Leu | Lys | Ile | Pro | Asp | Asn | Ala | Glu |
|  | 50 |  |  |  | 55 |  |  |  | 60 |  |  |  |
| Asp | Phe | Lys | Glu | Asp | Lys | Gly | Lys | Ala | Lys | Glu | Trp | Gly | Lys | Glu | Lys |
| 65 |  |  |  | 70 |  |  |  | 75 |  |  |  | 80 |
| Gly | Glu | Glu | Trp | Arg | Pro | Pro | Ala | Thr | Glu | Lys | Gly | Glu | Met | Asn | Asn |
|  |  |  | 85 |  |  |  | 90 |  |  |  | 95 |
| Phe | Leu | Asp | Asn | Lys | Asn | Asp | Ile | Lys | Thr | Asn | Tyr | Lys | Glu | Ile | Thr |
|  |  | 100 |  |  |  | 105 |  |  |  | 110 |  |
| Phe | Ser | Met | Ala | Gly | Ser | Cys | Glu | Asp | Ile | Lys | Asp | Leu | Glu | Glu |
|  |  | 115 |  |  |  | 120 |  |  |  | 125 |  |  |
| Ile | Asp | Lys | Ile | Phe | Asp | Lys | Ala | Asn | Leu | Ser | Ser | Ile | Ile | Thr |
|  | 130 |  |  |  | 135 |  |  |  | 140 |  |  |  |
| Tyr | Lys | Asn | Val | Glu | Pro | Ala | Thr | Ile | Gly | Phe | Asn | Lys | Ser | Leu | Thr |
| 145 |  |  |  | 150 |  |  |  | 155 |  |  |  | 160 |
| Glu | Gly | Asn | Thr | Ile | Asn | Ser | Asp | Ala | Met | Ala | Gln | Phe | Lys | Glu | Gln |
|  |  |  | 165 |  |  |  | 170 |  |  |  | 175 |
| Phe | Leu | Gly | Lys | Asp | Met | Lys | Phe | Asp | Ser | Tyr | Leu | Asp | Thr | His | Leu |
|  |  | 180 |  |  |  | 185 |  |  |  | 190 |  |
| Thr | Ala | Gln | Gln | Val | Ser | Ser | Lys | Arg | Val | Ile | Leu | Lys | Val | Thr |
|  |  | 195 |  |  |  | 200 |  |  |  | 205 |  |  |
| Val | Pro | Ser | Gly | Lys | Gly | Ser | Thr | Thr | Pro | Thr | Lys | Ala | Gly | Val | Ile |
|  | 210 |  |  |  | 215 |  |  |  | 220 |  |  |  |
| Leu | Asn | Asn | Asn | Glu | Tyr | Lys | Met | Leu | Ile | Asp | Asn | Gly | Tyr | Val | Leu |
| 225 |  |  |  | 230 |  |  |  | 235 |  |  |  | 240 |
| His | Val | Asp | Lys | Val | Ser | Lys | Val | Val | Lys | Lys | Gly | Met | Glu | Cys | Leu |
|  |  |  | 245 |  |  |  | 250 |  |  |  | 255 |
| Gln | Val | Glu | Gly | Thr | Leu | Lys | Lys | Ser | Leu | Asp | Phe | Lys | Asn | Asp | Ile |
|  |  |  | 260 |  |  |  | 265 |  |  |  | 270 |
| Asn | Ala | Glu | Ala | His | Ser | Trp | Gly | Met | Lys | Ile | Tyr | Glu | Asp | Trp | Ala |
|  |  | 275 |  |  |  | 280 |  |  |  | 285 |  |
| Lys | Asn | Leu | Thr | Ala | Ser | Gln | Arg | Glu | Ala | Leu | Asp | Gly | Tyr | Ala | Arg |
|  | 290 |  |  |  | 295 |  |  |  | 300 |  |  |  |
| Gln | Asp | Tyr | Lys | Glu | Ile | Asn | Asn | Tyr | Leu | Arg | Asn | Gln | Gly | Gly | Ser |
| 305 |  |  |  | 310 |  |  |  | 315 |  |  |  | 320 |
| Gly | Asn | Glu | Lys | Leu | Asp | Ala | Gln | Leu | Lys | Asn | Ile | Ser | Asp | Ala | Leu |
|  |  |  | 325 |  |  |  | 330 |  |  |  | 335 |
| Gly | Lys | Lys | Pro | Ile | Pro | Glu | Asn | Ile | Thr | Val | Tyr | Arg | Trp | Cys | Gly |
|  |  |  | 340 |  |  |  | 345 |  |  |  | 350 |
| Met | Pro | Glu | Phe | Gly | Tyr | Gln | Ile | Ser | Asp | Pro | Leu | Pro | Ser | Leu | Lys |
|  |  | 355 |  |  |  | 360 |  |  |  | 365 |  |
| Asp | Phe | Glu | Glu | Gln | Phe | Leu | Asn | Thr | Ile | Lys | Glu | Asp | Lys | Gly | Tyr |
|  |  | 370 |  |  |  | 375 |  |  |  | 380 |  |
| Met | Ser | Thr | Ser | Leu | Ser | Ser | Glu | Arg | Leu | Ala | Ala | Phe | Gly | Ser | Arg |
| 385 |  |  |  | 390 |  |  |  | 395 |  |  |  | 400 |
| Lys | Ile | Ile | Leu | Arg | Leu | Gln | Val | Pro | Lys | Gly | Ser | Thr | Gly | Ala | Tyr |
|  |  |  | 405 |  |  |  | 410 |  |  |  | 415 |
| Leu | Ser | Ala | Ile | Gly | Gly | Phe | Ala | Ser | Glu | Lys | Glu | Ile | Leu | Leu | Asp |
|  |  |  | 420 |  |  |  | 425 |  |  |  | 430 |  |
| Lys | Asp | Ser | Lys | Tyr | His | Ile | Asp | Lys | Ala | Thr | Glu | Val | Ile | Ile | Lys |
|  |  | 435 |  |  |  | 440 |  |  |  | 445 |  |  |

```
Gly  Val  Lys  Arg  Tyr  Val  Val  Asp  Ala  Thr  Leu  Leu  Thr  Asn
450                      455                      460
```

(2) INFORMATION FOR SEQ ID NO:21:

(i) SEQUENCE CHARACTERISTICS:
      (A) LENGTH: 834 amino acids
      (B) TYPE: amino acid
      (D) TOPOLOGY: linear (ii) MOLECULE TYPE: protein (xi) SEQUENCE DESCRIPTION: SEQ ID NO:21:

```
Met  Lys  Asn  Met  Lys  Lys  Leu  Ala  Ser  Val  Val  Thr  Cys  Met  Leu
1                    5                    10                       15

Leu  Ala  Pro  Met  Phe  Leu  Asn  Gly  Asn  Val  Asn  Ala  Val  Asn  Ala  Asp
               20                    25                       30

Ser  Lys  Ile  Asn  Gln  Ile  Ser  Thr  Thr  Gln  Glu  Asn  Gln  Lys  Glu
               35                    40                       45

Met  Asp  Arg  Lys  Gly  Leu  Leu  Gly  Tyr  Tyr  Phe  Lys  Gly  Lys  Asp  Phe
     50                    55                        60

Asn  Asn  Leu  Thr  Met  Phe  Ala  Pro  Thr  Arg  Asp  Asn  Thr  Leu  Met  Tyr
65                        70                    75                          80

Asp  Gln  Gln  Thr  Ala  Asn  Ala  Leu  Leu  Asp  Lys  Lys  Gln  Gln  Glu  Tyr
                    85                        90                          95

Gln  Ser  Ile  Arg  Trp  Ile  Gly  Leu  Ile  Gln  Arg  Lys  Glu  Thr  Gly  Asp
               100                    105                      110

Phe  Thr  Phe  Asn  Leu  Ser  Lys  Asp  Glu  Gln  Ala  Ile  Ile  Glu  Ile  Asp
          115                        120                      125

Gly  Lys  Ile  Ile  Ser  Asn  Lys  Gly  Lys  Glu  Lys  Gln  Val  Val  His  Leu
     130                        135                      140

Glu  Lys  Glu  Lys  Leu  Val  Pro  Ile  Lys  Ile  Glu  Tyr  Gln  Ser  Asp  Thr
145                       150                      155                      160

Lys  Phe  Asn  Ile  Asp  Ser  Lys  Thr  Phe  Lys  Glu  Leu  Lys  Leu  Phe  Lys
               165                        170                      175

Ile  Asp  Ser  Gln  Asn  Gln  Ser  Gln  Gln  Val  Gln  Leu  Arg  Asn  Pro  Glu
               180                        185                      190

Phe  Asn  Lys  Lys  Glu  Ser  Gln  Glu  Phe  Leu  Ala  Lys  Ala  Ser  Lys  Thr
          195                        200                      205

Asn  Leu  Phe  Lys  Gln  Lys  Met  Lys  Arg  Asp  Ile  Asp  Glu  Asp  Thr  Asp
     210                       215                      220

Thr  Asp  Gly  Asp  Ser  Ile  Pro  Asp  Leu  Trp  Glu  Asn  Gly  Tyr  Thr
225                      230                    235                      240

Ile  Gln  Asn  Lys  Val  Ala  Val  Lys  Trp  Asp  Asp  Ser  Leu  Ala  Ser  Lys
               245                        250                      255

Gly  Tyr  Thr  Lys  Phe  Val  Ser  Asn  Pro  Leu  Asp  Ser  His  Thr  Val  Gly
               260                       265                      270

Asp  Pro  Tyr  Thr  Asp  Tyr  Glu  Lys  Ala  Ala  Arg  Asp  Leu  Asp  Leu  Ser
          275                       280                      285

Asn  Ala  Lys  Glu  Thr  Phe  Asn  Pro  Leu  Val  Ala  Ala  Phe  Pro  Ser  Val
     290                       295                      300

Asn  Val  Ser  Met  Glu  Lys  Val  Ile  Leu  Ser  Pro  Asn  Glu  Asn  Leu  Ser
305                       310                      315                      320

Asn  Ser  Val  Glu  Ser  His  Ser  Ser  Thr  Asn  Trp  Ser  Tyr  Thr  Asn  Thr
                    325                       330                      335

Glu  Gly  Ala  Ser  Ile  Glu  Ala  Gly  Gly  Gly  Pro  Leu  Gly  Leu  Ser  Phe
               340                       345                      350
```

| | | | | | | | | | | | | | | |
|---|---|---|---|---|---|---|---|---|---|---|---|---|---|---|
| Gly | Val | Ser 355 | Val | Thr | Tyr | Gln | His 360 | Ser | Glu | Thr | Val | Ala 365 | Gln | Glu | Trp |
| Gly | Thr 370 | Ser | Thr | Gly | Asn | Thr 375 | Ser | Gln | Phe | Asn | Thr 380 | Ala | Ser | Ala | Gly |
| Tyr 385 | Leu | Asn | Ala | Asn | Val 390 | Arg | Tyr | Asn | Asn | Val 395 | Gly | Thr | Gly | Ala | Ile 400 |
| Tyr | Asp | Val | Lys | Pro 405 | Thr | Thr | Ser | Phe | Val 410 | Leu | Asn | Asn | Asn | Thr 415 | Ile |
| Ala | Thr | Ile | Thr 420 | Ala | Lys | Ser | Asn | Ser 425 | Thr | Ala | Leu | Arg | Ile 430 | Ser | Pro |
| Gly | Asp | Ser 435 | Tyr | Pro | Glu | Ile | Gly 440 | Glu | Asn | Ala | Ile | Ala 445 | Ile | Thr | Ser |
| Met | Asp 450 | Asp | Phe | Asn | Ser | His 455 | Pro | Ile | Thr | Leu | Asn 460 | Lys | Gln | Gln | Val |
| Asn 465 | Gln | Leu | Ile | Asn | Asn 470 | Lys | Pro | Ile | Met | Leu 475 | Glu | Thr | Asp | Gln | Thr 480 |
| Asp | Gly | Val | Tyr | Lys 485 | Ile | Arg | Asp | Thr | His 490 | Gly | Asn | Ile | Val | Thr 495 | Gly |
| Gly | Glu | Trp | Asn 500 | Gly | Val | Thr | Gln | Gln 505 | Ile | Lys | Ala | Lys | Thr 510 | Ala | Ser |
| Ile | Ile | Val 515 | Asp | Asp | Gly | Lys | Gln 520 | Val | Ala | Glu | Lys | Arg 525 | Val | Ala | Ala |
| Lys | Asp 530 | Tyr | Gly | His | Pro | Glu 535 | Asp | Lys | Thr | Pro | Pro 540 | Leu | Thr | Leu | Lys |
| Asp 545 | Thr | Leu | Lys | Leu | Ser 550 | Tyr | Pro | Asp | Glu | Ile 555 | Lys | Glu | Thr | Asn | Gly 560 |
| Leu | Leu | Tyr | Tyr | Asp 565 | Asp | Lys | Pro | Ile | Tyr 570 | Glu | Ser | Ser | Val | Met 575 | Thr |
| Tyr | Leu | Asp | Glu 580 | Asn | Thr | Ala | Lys | Glu 585 | Val | Lys | Lys | Gln | Ile 590 | Asn | Asp |
| Thr | Thr | Gly 595 | Lys | Phe | Lys | Asp | Val 600 | Asn | His | Leu | Tyr | Asp 605 | Val | Lys | Leu |
| Thr | Pro 610 | Lys | Met | Asn | Phe | Thr 615 | Ile | Lys | Met | Ala | Ser 620 | Leu | Tyr | Asp | Gly |
| Ala 625 | Glu | Asn | Asn | His | Asn 630 | Ser | Leu | Gly | Thr | Trp 635 | Tyr | Leu | Thr | Tyr | Asn 640 |
| Val | Ala | Gly | Gly | Asn 645 | Thr | Gly | Lys | Arg | Gln 650 | Tyr | Arg | Ser | Ala | His 655 | Ser |
| Cys | Ala | His | Val 660 | Ala | Leu | Ser | Ser | Glu 665 | Ala | Lys | Lys | Lys | Leu 670 | Asn | Gln |
| Asn | Ala | Asn 675 | Tyr | Tyr | Leu | Ser | Met 680 | Tyr | Met | Lys | Ala | Asp 685 | Ser | Thr | Thr |
| Glu | Pro 690 | Thr | Ile | Glu | Val | Ala 695 | Gly | Glu | Lys | Ser | Ala 700 | Ile | Thr | Ser | Lys |
| Lys 705 | Val | Lys | Leu | Asn | Asn 710 | Gln | Asn | Tyr | Gln | Arg 715 | Val | Asp | Ile | Leu | Val 720 |
| Lys | Asn | Ser | Glu | Arg 725 | Asn | Pro | Met | Asp | Lys 730 | Ile | Tyr | Ile | Arg | Gly 735 | Asn |
| Gly | Thr | Thr | Asn 740 | Val | Tyr | Gly | Asp | Val 745 | Thr | Ile | Pro | Glu 750 | Val | Ser |
| Ala | Ile | Asn 755 | Pro | Ala | Ser | Leu | Ser 760 | Asp | Glu | Glu | Ile | Gln 765 | Glu | Ile | Phe |
| Lys | Asp | Ser | Thr | Ile | Glu | Tyr | Gly | Asn | Pro | Ser | Phe | Val | Ala | Asp | Ala |

|     |     |     |     | 770 |     |     |     |     | 775 |     |     |     |     | 780 |     |     |
| --- | --- | --- | --- | --- | --- | --- | --- | --- | --- | --- | --- | --- | --- | --- | --- | --- |
| Val | Thr | Phe | Lys | Asn | Ile | Lys | Pro | Leu | Gln | Asn | Tyr | Val | Lys | Glu | Tyr |     |
| 785 |     |     |     |     | 790 |     |     |     |     | 795 |     |     |     |     | 800 |     |
| Glu | Ile | Tyr | His | Lys | Ser | His | Arg | Tyr | Glu | Lys | Lys | Thr | Val | Phe | Asp |     |
|     |     |     |     | 805 |     |     |     |     | 810 |     |     |     |     | 815 |     |     |
| Ile | Met | Gly | Val | His | Tyr | Glu | Tyr | Ser | Ile | Ala | Arg | Glu | Gln | Lys | Lys |     |
|     |     |     | 820 |     |     |     |     | 825 |     |     |     |     | 830 |     |     |     |
| Ala | Ala |     |     |     |     |     |     |     |     |     |     |     |     |     |     |     |

( 2 ) INFORMATION FOR SEQ ID NO:22:

( i ) SEQUENCE CHARACTERISTICS:
        ( A ) LENGTH: 4041 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..4038
        ( D ) OTHER INFORMATION: /product="VIP1A(a)/VIP2A(a) fusion
            product"

( x i ) SEQUENCE DESCRIPTION: SEQ ID NO:22:

| ATG | AAA | AGA | ATG | GAG | GGA | AAG | TTG | TTT | ATG | GTG | TCA | AAA | AAA | TTA | CAA | 48  |
| --- | --- | --- | --- | --- | --- | --- | --- | --- | --- | --- | --- | --- | --- | --- | --- | --- |
| Met | Lys | Arg | Met | Glu | Gly | Lys | Leu | Phe | Met | Val | Ser | Lys | Lys | Leu | Gln |     |
| 835 |     |     |     |     | 840 |     |     |     |     | 845 |     |     |     |     | 850 |     |
| GTA | GTT | ACT | AAA | ACT | GTA | TTG | CTT | AGT | ACA | GTT | TTC | TCT | ATA | TCT | TTA | 96  |
| Val | Val | Thr | Lys | Thr | Val | Leu | Leu | Ser | Thr | Val | Phe | Ser | Ile | Ser | Leu |     |
|     |     |     |     | 855 |     |     |     |     | 860 |     |     |     |     | 865 |     |     |
| TTA | AAT | AAT | GAA | GTG | ATA | AAA | GCT | GAA | CAA | TTA | AAT | ATA | AAT | TCT | CAA | 144 |
| Leu | Asn | Asn | Glu | Val | Ile | Lys | Ala | Glu | Gln | Leu | Asn | Ile | Asn | Ser | Gln |     |
|     |     |     |     | 870 |     |     |     |     | 875 |     |     |     |     | 880 |     |     |
| AGT | AAA | TAT | ACT | AAC | TTG | CAA | AAT | CTA | AAA | ATC | ACT | GAC | AAG | GTA | GAG | 192 |
| Ser | Lys | Tyr | Thr | Asn | Leu | Gln | Asn | Leu | Lys | Ile | Thr | Asp | Lys | Val | Glu |     |
|     |     | 885 |     |     |     |     | 890 |     |     |     |     | 895 |     |     |     |     |
| GAT | TTT | AAA | GAA | GAT | AAG | GAA | AAA | GCG | AAA | GAA | TGG | GGG | AAA | GAA | AAA | 240 |
| Asp | Phe | Lys | Glu | Asp | Lys | Glu | Lys | Ala | Lys | Glu | Trp | Gly | Lys | Glu | Lys |     |
|     | 900 |     |     |     |     | 905 |     |     |     |     | 910 |     |     |     |     |     |
| GAA | AAA | GAG | TGG | AAA | CTA | ACT | GCT | ACT | GAA | AAA | GGA | AAA | ATG | AAT | AAT | 288 |
| Glu | Lys | Glu | Trp | Lys | Leu | Thr | Ala | Thr | Glu | Lys | Gly | Lys | Met | Asn | Asn |     |
| 915 |     |     |     |     | 920 |     |     |     |     | 925 |     |     |     |     | 930 |     |
| TTT | TTA | GAT | AAT | AAA | AAT | GAT | ATA | AAG | ACA | AAT | TAT | AAA | GAA | ATT | ACT | 336 |
| Phe | Leu | Asp | Asn | Lys | Asn | Asp | Ile | Lys | Thr | Asn | Tyr | Lys | Glu | Ile | Thr |     |
|     |     |     |     | 935 |     |     |     |     | 940 |     |     |     |     | 945 |     |     |
| TTT | TCT | ATG | GCA | GGC | TCA | TTT | GAA | GAT | GAA | ATA | AAA | GAT | TTA | AAA | GAA | 384 |
| Phe | Ser | Met | Ala | Gly | Ser | Phe | Glu | Asp | Glu | Ile | Lys | Asp | Leu | Lys | Glu |     |
|     |     |     | 950 |     |     |     |     | 955 |     |     |     |     | 960 |     |     |     |
| ATT | GAT | AAG | ATG | TTT | GAT | AAA | ACC | AAT | CTA | TCA | AAT | TCT | ATT | ATC | ACC | 432 |
| Ile | Asp | Lys | Met | Phe | Asp | Lys | Thr | Asn | Leu | Ser | Asn | Ser | Ile | Ile | Thr |     |
|     |     | 965 |     |     |     |     | 970 |     |     |     |     | 975 |     |     |     |     |
| TAT | AAA | AAT | GTG | GAA | CCG | ACA | ACA | ATT | GGA | TTT | AAT | AAA | TCT | TTA | ACA | 480 |
| Tyr | Lys | Asn | Val | Glu | Pro | Thr | Thr | Ile | Gly | Phe | Asn | Lys | Ser | Leu | Thr |     |
|     | 980 |     |     |     |     | 985 |     |     |     |     | 990 |     |     |     |     |     |
| GAA | GGT | AAT | ACG | ATT | AAT | TCT | GAT | GCA | ATG | GCA | CAG | TTT | AAA | GAA | CAA | 528 |
| Glu | Gly | Asn | Thr | Ile | Asn | Ser | Asp | Ala | Met | Ala | Gln | Phe | Lys | Glu | Gln |     |
| 995 |     |     |     |     | 1000|     |     |     |     | 1005|     |     |     |     | 1010|     |
| TTT | TTA | GAT | AGG | GAT | ATT | AAG | TTT | GAT | AGT | TAT | CTA | GAT | ACG | CAT | TTA | 576 |
| Phe | Leu | Asp | Arg | Asp | Ile | Lys | Phe | Asp | Ser | Tyr | Leu | Asp | Thr | His | Leu |     |
|     |     |     |     | 1015|     |     |     |     | 1020|     |     |     |     | 1025|     |     |

| | | | | | | | | | | | | | | | | |
|---|---|---|---|---|---|---|---|---|---|---|---|---|---|---|---|---|
| ACT | GCT | CAA | CAA | GTT | TCC | AGT | AAA | GAA | AGA | GTT | ATT | TTG | AAG | GTT | ACG | 624 |
| Thr | Ala | Gln | Gln | Val | Ser | Ser | Lys | Glu | Arg | Val | Ile | Leu | Lys | Val | Thr | |
| | | | 1030 | | | | 1035 | | | | | | 1040 | | | |
| GTT | CCG | AGT | GGG | AAA | GGT | TCT | ACT | ACT | CCA | ACA | AAA | GCA | GGT | GTC | ATT | 672 |
| Val | Pro | Ser | Gly | Lys | Gly | Ser | Thr | Thr | Pro | Thr | Lys | Ala | Gly | Val | Ile | |
| | | | 1045 | | | | 1050 | | | | | | 1055 | | | |
| TTA | AAT | AAT | AGT | GAA | TAC | AAA | ATG | CTC | ATT | GAT | AAT | GGG | TAT | ATG | GTC | 720 |
| Leu | Asn | Asn | Ser | Glu | Tyr | Lys | Met | Leu | Ile | Asp | Asn | Gly | Tyr | Met | Val | |
| | | | 1060 | | | | 1065 | | | | | | 1070 | | | |
| CAT | GTA | GAT | AAG | GTA | TCA | AAA | GTG | GTG | AAA | AAA | GGG | GTG | GAG | TGC | TTA | 768 |
| His | Val | Asp | Lys | Val | Ser | Lys | Val | Val | Lys | Lys | Gly | Val | Glu | Cys | Leu | |
| 1075 | | | | 1080 | | | | | 1085 | | | | | | 1090 | |
| CAA | ATT | GAA | GGG | ACT | TTA | AAA | AAG | AGT | CTT | GAC | TTT | AAA | AAT | GAT | ATA | 816 |
| Gln | Ile | Glu | Gly | Thr | Leu | Lys | Lys | Ser | Leu | Asp | Phe | Lys | Asn | Asp | Ile | |
| | | | | 1095 | | | | | 1100 | | | | | | 1105 | |
| AAT | GCT | GAA | GCG | CAT | AGC | TGG | GGT | ATG | AAG | AAT | TAT | GAA | GAG | TGG | GCT | 864 |
| Asn | Ala | Glu | Ala | His | Ser | Trp | Gly | Met | Lys | Asn | Tyr | Glu | Glu | Trp | Ala | |
| | | | | 1110 | | | | | 1115 | | | | | | 1120 | |
| AAA | GAT | TTA | ACC | GAT | TCG | CAA | AGG | GAA | GCT | TTA | GAT | GGG | TAT | GCT | AGG | 912 |
| Lys | Asp | Leu | Thr | Asp | Ser | Gln | Arg | Glu | Ala | Leu | Asp | Gly | Tyr | Ala | Arg | |
| | | | | 1125 | | | | | 1130 | | | | | | 1135 | |
| CAA | GAT | TAT | AAA | GAA | ATC | AAT | AAT | TAT | TTA | AGA | AAT | CAA | GGC | GGA | AGT | 960 |
| Gln | Asp | Tyr | Lys | Glu | Ile | Asn | Asn | Tyr | Leu | Arg | Asn | Gln | Gly | Gly | Ser | |
| | | | 1140 | | | | | 1145 | | | | | | 1150 | | |
| GGA | AAT | GAA | AAA | CTA | GAT | GCT | CAA | ATA | AAA | AAT | ATT | TCT | GAT | GCT | TTA | 1008 |
| Gly | Asn | Glu | Lys | Leu | Asp | Ala | Gln | Ile | Lys | Asn | Ile | Ser | Asp | Ala | Leu | |
| 1155 | | | | | 1160 | | | | | 1165 | | | | | 1170 | |
| GGG | AAG | AAA | CCA | ATA | CCG | GAA | AAT | ATT | ACT | GTG | TAT | AGA | TGG | TGT | GGC | 1056 |
| Gly | Lys | Lys | Pro | Ile | Pro | Glu | Asn | Ile | Thr | Val | Tyr | Arg | Trp | Cys | Gly | |
| | | | | 1175 | | | | | 1180 | | | | | | 1185 | |
| ATG | CCG | GAA | TTT | GGT | TAT | CAA | ATT | AGT | GAT | CCG | TTA | CCT | TCT | TTA | AAA | 1104 |
| Met | Pro | Glu | Phe | Gly | Tyr | Gln | Ile | Ser | Asp | Pro | Leu | Pro | Ser | Leu | Lys | |
| | | | | 1190 | | | | | 1195 | | | | | | 1200 | |
| GAT | TTT | GAA | GAA | CAA | TTT | TTA | AAT | ACA | ATC | AAA | GAA | GAC | AAA | GGA | TAT | 1152 |
| Asp | Phe | Glu | Glu | Gln | Phe | Leu | Asn | Thr | Ile | Lys | Glu | Asp | Lys | Gly | Tyr | |
| | | | | 1205 | | | | | 1210 | | | | | | 1215 | |
| ATG | AGT | ACA | AGC | TTA | TCG | AGT | GAA | CGT | CTT | GCA | GCT | TTT | GGA | TCT | AGA | 1200 |
| Met | Ser | Thr | Ser | Leu | Ser | Ser | Glu | Arg | Leu | Ala | Ala | Phe | Gly | Ser | Arg | |
| | | | 1220 | | | | | 1225 | | | | | | 1230 | | |
| AAA | ATT | ATA | TTA | CGA | TTA | CAA | GTT | CCG | AAA | GGA | AGT | ACG | GGT | GCG | TAT | 1248 |
| Lys | Ile | Ile | Leu | Arg | Leu | Gln | Val | Pro | Lys | Gly | Ser | Thr | Gly | Ala | Tyr | |
| 1235 | | | | | 1240 | | | | | 1245 | | | | | 1250 | |
| TTA | AGT | GCC | ATT | GGT | GGA | TTT | GCA | AGT | GAA | AAA | GAG | ATC | CTA | CTT | GAT | 1296 |
| Leu | Ser | Ala | Ile | Gly | Gly | Phe | Ala | Ser | Glu | Lys | Glu | Ile | Leu | Leu | Asp | |
| | | | | 1255 | | | | | 1260 | | | | | | 1265 | |
| AAA | GAT | AGT | AAA | TAT | CAT | ATT | GAT | AAA | GTA | ACA | GAG | GTA | ATT | ATT | AAA | 1344 |
| Lys | Asp | Ser | Lys | Tyr | His | Ile | Asp | Lys | Val | Thr | Glu | Val | Ile | Ile | Lys | |
| | | | 1270 | | | | | 1275 | | | | | | 1280 | | |
| GGT | GTT | AAG | CGA | TAT | GTA | GTG | GAT | GCA | ACA | TTA | TTA | ACA | AAT | ATG | AAA | 1392 |
| Gly | Val | Lys | Arg | Tyr | Val | Val | Asp | Ala | Thr | Leu | Leu | Thr | Asn | Met | Lys | |
| | | | 1285 | | | | | 1290 | | | | | | 1295 | | |
| AAT | ATG | AAG | AAA | AAG | TTA | GCA | AGT | GTT | GTA | ACG | TGT | ACG | TTA | TTA | GCT | 1440 |
| Asn | Met | Lys | Lys | Lys | Leu | Ala | Ser | Val | Val | Thr | Cys | Thr | Leu | Leu | Ala | |
| | | | 1300 | | | | | 1305 | | | | | | 1310 | | |
| CCT | ATG | TTT | TTG | AAT | GGA | AAT | GTG | AAT | GCT | GTT | TAC | GCA | GAC | AGC | AAA | 1488 |
| Pro | Met | Phe | Leu | Asn | Gly | Asn | Val | Asn | Ala | Val | Tyr | Ala | Asp | Ser | Lys | |
| 1315 | | | | | 1320 | | | | | 1325 | | | | | 1330 | |
| ACA | AAT | CAA | ATT | TCT | ACA | ACA | CAG | AAA | AAT | CAA | CAG | AAA | GAG | ATG | GAC | 1536 |
| Thr | Asn | Gln | Ile | Ser | Thr | Thr | Gln | Lys | Asn | Gln | Gln | Lys | Glu | Met | Asp | |
| | | | | 1335 | | | | | 1340 | | | | | | 1345 | |

| | | | | | | | | | | | | | | | | |
|---|---|---|---|---|---|---|---|---|---|---|---|---|---|---|---|---|
| CGA | AAA | GGA | TTA | CTT | GGG | TAT | TAT | TTC | AAA | GGA | AAA | GAT | TTT | AGT | AAT | 1584 |
| Arg | Lys | Gly | Leu | Leu | Gly | Tyr | Tyr | Phe | Lys | Gly | Lys | Asp | Phe | Ser | Asn | |
| | | | 1350 | | | | 1355 | | | | | 1360 | | | | |
| CTT | ACT | ATG | TTT | GCA | CCG | ACA | CGT | GAT | AGT | ACT | CTT | ATT | TAT | GAT | CAA | 1632 |
| Leu | Thr | Met | Phe | Ala | Pro | Thr | Arg | Asp | Ser | Thr | Leu | Ile | Tyr | Asp | Gln | |
| | | 1365 | | | | 1370 | | | | | 1375 | | | | | |
| CAA | ACA | GCA | AAT | AAA | CTA | TTA | GAT | AAA | AAA | CAA | CAA | GAA | TAT | CAG | TCT | 1680 |
| Gln | Thr | Ala | Asn | Lys | Leu | Leu | Asp | Lys | Lys | Gln | Gln | Glu | Tyr | Gln | Ser | |
| | 1380 | | | | 1385 | | | | | 1390 | | | | | | |
| ATT | CGT | TGG | ATT | GGT | TTG | ATT | CAG | AGT | AAA | GAA | ACG | GGA | GAT | TTC | ACA | 1728 |
| Ile | Arg | Trp | Ile | Gly | Leu | Ile | Gln | Ser | Lys | Glu | Thr | Gly | Asp | Phe | Thr | |
| 1395 | | | | 1400 | | | | 1405 | | | | | 1410 | | | |
| TTT | AAC | TTA | TCT | GAG | GAT | GAA | CAG | GCA | ATT | ATA | GAA | ATC | AAT | GGG | AAA | 1776 |
| Phe | Asn | Leu | Ser | Glu | Asp | Glu | Gln | Ala | Ile | Ile | Glu | Ile | Asn | Gly | Lys | |
| | | | | 1415 | | | | 1420 | | | | | 1425 | | | |
| ATT | ATT | TCT | AAT | AAA | GGG | AAA | GAA | AAG | CAA | GTT | GTC | CAT | TTA | GAA | AAA | 1824 |
| Ile | Ile | Ser | Asn | Lys | Gly | Lys | Glu | Lys | Gln | Val | Val | His | Leu | Glu | Lys | |
| | | | 1430 | | | | 1435 | | | | | 1440 | | | | |
| GGA | AAA | TTA | GTT | CCA | ATC | AAA | ATA | GAG | TAT | CAA | TCA | GAT | ACA | AAA | TTT | 1872 |
| Gly | Lys | Leu | Val | Pro | Ile | Lys | Ile | Glu | Tyr | Gln | Ser | Asp | Thr | Lys | Phe | |
| | | | 1445 | | | | 1450 | | | | | 1455 | | | | |
| AAT | ATT | GAC | AGT | AAA | ACA | TTT | AAA | GAA | CTT | AAA | TTA | TTT | AAA | ATA | GAT | 1920 |
| Asn | Ile | Asp | Ser | Lys | Thr | Phe | Lys | Glu | Leu | Lys | Leu | Phe | Lys | Ile | Asp | |
| | 1460 | | | | 1465 | | | | | 1470 | | | | | | |
| AGT | CAA | AAC | CAA | CCC | CAG | CAA | GTC | CAG | CAA | GAT | GAA | CTG | AGA | AAT | CCT | 1968 |
| Ser | Gln | Asn | Gln | Pro | Gln | Gln | Val | Gln | Gln | Asp | Glu | Leu | Arg | Asn | Pro | |
| 1475 | | | | 1480 | | | | 1485 | | | | | 1490 | | | |
| GAA | TTT | AAC | AAG | AAA | GAA | TCA | CAG | GAA | TTC | TTA | GCG | AAA | CCA | TCG | AAA | 2016 |
| Glu | Phe | Asn | Lys | Lys | Glu | Ser | Gln | Glu | Phe | Leu | Ala | Lys | Pro | Ser | Lys | |
| | | | | 1495 | | | | 1500 | | | | | 1505 | | | |
| ATA | AAT | CTT | TTC | ACT | CAA | AAA | ATG | AAA | AGG | GAA | ATT | GAT | GAA | GAC | ACG | 2064 |
| Ile | Asn | Leu | Phe | Thr | Gln | Lys | Met | Lys | Arg | Glu | Ile | Asp | Glu | Asp | Thr | |
| | | | 1510 | | | | 1515 | | | | | 1520 | | | | |
| GAT | ACG | GAT | GGG | GAC | TCT | ATT | CCT | GAC | CTT | TGG | GAA | GAA | AAT | GGG | TAT | 2112 |
| Asp | Thr | Asp | Gly | Asp | Ser | Ile | Pro | Asp | Leu | Trp | Glu | Glu | Asn | Gly | Tyr | |
| | | | 1525 | | | | 1530 | | | | | 1535 | | | | |
| ACG | ATT | CAA | AAT | AGA | ATC | GCT | GTA | AAG | TGG | GAC | GAT | TCT | CTA | GCA | AGT | 2160 |
| Thr | Ile | Gln | Asn | Arg | Ile | Ala | Val | Lys | Trp | Asp | Asp | Ser | Leu | Ala | Ser | |
| | 1540 | | | | 1545 | | | | | 1550 | | | | | | |
| AAA | GGG | TAT | ACG | AAA | TTT | GTT | TCA | AAT | CCA | CTA | GAA | AGT | CAC | ACA | GTT | 2208 |
| Lys | Gly | Tyr | Thr | Lys | Phe | Val | Ser | Asn | Pro | Leu | Glu | Ser | His | Thr | Val | |
| 1555 | | | | 1560 | | | | 1565 | | | | | 1570 | | | |
| GGT | GAT | CCT | TAT | ACA | GAT | TAT | GAA | AAG | GCA | GCA | AGA | GAT | CTA | GAT | TTG | 2256 |
| Gly | Asp | Pro | Tyr | Thr | Asp | Tyr | Glu | Lys | Ala | Ala | Arg | Asp | Leu | Asp | Leu | |
| | | | 1575 | | | | 1580 | | | | | 1585 | | | | |
| TCA | AAT | GCA | AAG | GAA | ACG | TTT | AAC | CCA | TTG | GTA | GCT | GCT | TTT | CCA | AGT | 2304 |
| Ser | Asn | Ala | Lys | Glu | Thr | Phe | Asn | Pro | Leu | Val | Ala | Ala | Phe | Pro | Ser | |
| | | | 1590 | | | | 1595 | | | | | 1600 | | | | |
| GTG | AAT | GTT | AGT | ATG | GAA | AAG | GTG | ATA | TTA | TCA | CCA | AAT | GAA | AAT | TTA | 2352 |
| Val | Asn | Val | Ser | Met | Glu | Lys | Val | Ile | Leu | Ser | Pro | Asn | Glu | Asn | Leu | |
| | | | 1605 | | | | 1610 | | | | | 1615 | | | | |
| TCC | AAT | AGT | GTA | GAG | TCT | CAT | TCA | TCC | ACG | AAT | TGG | TCT | TAT | ACA | AAT | 2400 |
| Ser | Asn | Ser | Val | Glu | Ser | His | Ser | Ser | Thr | Asn | Trp | Ser | Tyr | Thr | Asn | |
| | | 1620 | | | | 1625 | | | | | 1630 | | | | | |
| ACA | GAA | GGT | GCT | TCT | GTT | GAA | GCG | GGG | ATT | GGA | CCA | AAA | GGT | ATT | TCG | 2448 |
| Thr | Glu | Gly | Ala | Ser | Val | Glu | Ala | Gly | Ile | Gly | Pro | Lys | Gly | Ile | Ser | |
| 1635 | | | | 1640 | | | | 1645 | | | | | 1650 | | | |
| TTC | GGA | GTT | AGC | GTA | AAC | TAT | CAA | CAC | TCT | GAA | ACA | GTT | GCA | CAA | GAA | 2496 |
| Phe | Gly | Val | Ser | Val | Asn | Tyr | Gln | His | Ser | Glu | Thr | Val | Ala | Gln | Glu | |
| | | | 1655 | | | | 1660 | | | | | 1665 | | | | |

```
TGG GGA ACA TCT ACA GGA AAT ACT TCG CAA TTC AAT ACG GCT TCA GCG       2544
Trp Gly Thr Ser Thr Gly Asn Thr Ser Gln Phe Asn Thr Ala Ser Ala
        1670                1675                1680

GGA TAT TTA AAT GCA AAT GTT CGA TAT AAC AAT GTA GGA ACT GGT GCC       2592
Gly Tyr Leu Asn Ala Asn Val Arg Tyr Asn Asn Val Gly Thr Gly Ala
        1685                1690                1695

ATC TAC GAT GTA AAA CCT ACA ACA AGT TTT GTA TTA AAT AAC GAT ACT       2640
Ile Tyr Asp Val Lys Pro Thr Thr Ser Phe Val Leu Asn Asn Asp Thr
        1700                1705                1710

ATC GCA ACT ATT ACG GCG AAA TCT AAT TCT ACA GCC TTA AAT ATA TCT       2688
Ile Ala Thr Ile Thr Ala Lys Ser Asn Ser Thr Ala Leu Asn Ile Ser
        1715                1720                1725            1730

CCT GGA GAA AGT TAC CCG AAA AAA GGA CAA AAT GGA ATC GCA ATA ACA       2736
Pro Gly Glu Ser Tyr Pro Lys Lys Gly Gln Asn Gly Ile Ala Ile Thr
                    1735                1740                1745

TCA ATG GAT GAT TTT AAT TCC CAT CCG ATT ACA TTA AAT AAA AAA CAA       2784
Ser Met Asp Asp Phe Asn Ser His Pro Ile Thr Leu Asn Lys Lys Gln
                1750                1755                1760

GTA GAT AAT CTG CTA AAT AAT AAA CCT ATG ATG TTG GAA ACA AAC CAA       2832
Val Asp Asn Leu Leu Asn Asn Lys Pro Met Met Leu Glu Thr Asn Gln
        1765                1770                1775

ACA GAT GGT GTT TAT AAG ATA AAA GAT ACA CAT GGA AAT ATA GTA ACT       2880
Thr Asp Gly Val Tyr Lys Ile Lys Asp Thr His Gly Asn Ile Val Thr
        1780                1785                1790

GGC GGA GAA TGG AAT GGT GTC ATA CAA CAA ATC AAG GCT AAA ACA GCG       2928
Gly Gly Glu Trp Asn Gly Val Ile Gln Gln Ile Lys Ala Lys Thr Ala
1795                1800                1805                1810

TCT ATT ATT GTG GAT GAT GGG GAA CGT GTA GCA GAA AAA CGT GTA GCG       2976
Ser Ile Ile Val Asp Asp Gly Glu Arg Val Ala Glu Lys Arg Val Ala
                1815                1820                1825

GCA AAA GAT TAT GAA AAT CCA GAA GAT AAA ACA CCG TCT TTA ACT TTA       3024
Ala Lys Asp Tyr Glu Asn Pro Glu Asp Lys Thr Pro Ser Leu Thr Leu
                    1830                1835                1840

AAA GAT GCC CTG AAG CTT TCA TAT CCA GAT GAA ATA AAA GAA ATA GAG       3072
Lys Asp Ala Leu Lys Leu Ser Tyr Pro Asp Glu Ile Lys Glu Ile Glu
            1845                1850                1855

GGA TTA TTA TAT TAT AAA AAC AAA CCG ATA TAC GAA TCG AGC GTT ATG       3120
Gly Leu Leu Tyr Tyr Lys Asn Lys Pro Ile Tyr Glu Ser Ser Val Met
1860                1865                1870

ACT TAC TTA GAT GAA AAT ACA GCA AAA GAA GTG ACC AAA CAA TTA AAT       3168
Thr Tyr Leu Asp Glu Asn Thr Ala Lys Glu Val Thr Lys Gln Leu Asn
1875                1880                1885                1890

GAT ACC ACT GGG AAA TTT AAA GAT GTA AGT CAT TTA TAT GAT GTA AAA       3216
Asp Thr Thr Gly Lys Phe Lys Asp Val Ser His Leu Tyr Asp Val Lys
                1895                1900                1905

CTG ACT CCA AAA ATG AAT GTT ACA ATC AAA TTG TCT ATA CTT TAT GAT       3264
Leu Thr Pro Lys Met Asn Val Thr Ile Lys Leu Ser Ile Leu Tyr Asp
                1910                1915                1920

AAT GCT GAG TCT AAT GAT AAC TCA ATT GGT AAA TGG ACA AAC ACA AAT       3312
Asn Ala Glu Ser Asn Asp Asn Ser Ile Gly Lys Trp Thr Asn Thr Asn
        1925                1930                1935

ATT GTT TCA GGT GGA AAT AAC GGA AAA AAA CAA TAT TCT TCT AAT AAT       3360
Ile Val Ser Gly Gly Asn Asn Gly Lys Lys Gln Tyr Ser Ser Asn Asn
        1940                1945                1950

CCG GAT GCT AAT TTG ACA TTA AAT ACA GAT GCT CAA GAA AAA TTA AAT       3408
Pro Asp Ala Asn Leu Thr Leu Asn Thr Asp Ala Gln Glu Lys Leu Asn
1955                1960                1965                1970

AAA AAT CGT GAC TAT TAT ATA AGT TTA TAT ATG AAG TCA GAA AAA AAC       3456
Lys Asn Arg Asp Tyr Tyr Ile Ser Leu Tyr Met Lys Ser Glu Lys Asn
                1975                1980                1985
```

| | | | | | | | | | | | | | | | | |
|---|---|---|---|---|---|---|---|---|---|---|---|---|---|---|---|---|
| ACA | CAA | TGT | GAG | ATT | ACT | ATA | GAT | GGG | GAG | ATT | TAT | CCG | ATC | ACT | ACA | 3504 |
| Thr | Gln | Cys | Glu | Ile | Thr | Ile | Asp | Gly | Glu | Ile | Tyr | Pro | Ile | Thr | Thr | |
| | | | | 1990 | | | | 1995 | | | | | 2000 | | | |
| AAA | ACA | GTG | AAT | GTG | AAT | AAA | GAC | AAT | TAC | AAA | AGA | TTA | GAT | ATT | ATA | 3552 |
| Lys | Thr | Val | Asn | Val | Asn | Lys | Asp | Asn | Tyr | Lys | Arg | Leu | Asp | Ile | Ile | |
| | | 2005 | | | | 2010 | | | | | 2015 | | | | | |
| GCT | CAT | AAT | ATA | AAA | AGT | AAT | CCA | ATT | TCT | TCA | CTT | CAT | ATT | AAA | ACG | 3600 |
| Ala | His | Asn | Ile | Lys | Ser | Asn | Pro | Ile | Ser | Ser | Leu | His | Ile | Lys | Thr | |
| | 2020 | | | | | 2025 | | | | | 2030 | | | | | |
| AAT | GAT | GAA | ATA | ACT | TTA | TTT | TGG | GAT | GAT | ATT | TCT | ATA | ACA | GAT | GTA | 3648 |
| Asn | Asp | Glu | Ile | Thr | Leu | Phe | Trp | Asp | Asp | Ile | Ser | Ile | Thr | Asp | Val | |
| 2035 | | | | | 2040 | | | | | 2045 | | | | | 2050 | |
| GCA | TCA | ATA | AAA | CCG | GAA | AAT | TTA | ACA | GAT | TCA | GAA | ATT | AAA | CAG | ATT | 3696 |
| Ala | Ser | Ile | Lys | Pro | Glu | Asn | Leu | Thr | Asp | Ser | Glu | Ile | Lys | Gln | Ile | |
| | | | | 2055 | | | | | 2060 | | | | | 2065 | | |
| TAT | AGT | AGG | TAT | GGT | ATT | AAG | TTA | GAA | GAT | GGA | ATC | CTT | ATT | GAT | AAA | 3744 |
| Tyr | Ser | Arg | Tyr | Gly | Ile | Lys | Leu | Glu | Asp | Gly | Ile | Leu | Ile | Asp | Lys | |
| | | | 2070 | | | | | 2075 | | | | | 2080 | | | |
| AAA | GGT | GGG | ATT | CAT | TAT | GGT | GAA | TTT | ATT | AAT | GAA | GCT | AGT | TTT | AAT | 3792 |
| Lys | Gly | Gly | Ile | His | Tyr | Gly | Glu | Phe | Ile | Asn | Glu | Ala | Ser | Phe | Asn | |
| | | | 2085 | | | | | 2090 | | | | | 2095 | | | |
| ATT | GAA | CCA | TTG | CAA | AAT | TAT | GTG | ACC | AAA | TAT | GAA | GTT | ACT | TAT | AGT | 3840 |
| Ile | Glu | Pro | Leu | Gln | Asn | Tyr | Val | Thr | Lys | Tyr | Glu | Val | Thr | Tyr | Ser | |
| | | | 2100 | | | | | 2105 | | | | | 2110 | | | |
| AGT | GAG | TTA | GGA | CCA | AAC | GTG | AGT | GAC | ACA | CTT | GAA | AGT | GAT | AAA | ATT | 3888 |
| Ser | Glu | Leu | Gly | Pro | Asn | Val | Ser | Asp | Thr | Leu | Glu | Ser | Asp | Lys | Ile | |
| 2115 | | | | | 2120 | | | | | 2125 | | | | | 2130 | |
| TAC | AAG | GAT | GGG | ACA | ATT | AAA | TTT | GAT | TTT | ACC | AAA | TAT | AGT | AAA | AAT | 3936 |
| Tyr | Lys | Asp | Gly | Thr | Ile | Lys | Phe | Asp | Phe | Thr | Lys | Tyr | Ser | Lys | Asn | |
| | | | | 2135 | | | | | 2140 | | | | | 2145 | | |
| GAA | CAA | GGA | TTA | TTT | TAT | GAC | AGT | GGA | TTA | AAT | TGG | GAC | TTT | AAA | ATT | 3984 |
| Glu | Gln | Gly | Leu | Phe | Tyr | Asp | Ser | Gly | Leu | Asn | Trp | Asp | Phe | Lys | Ile | |
| | | | | 2150 | | | | | 2155 | | | | | 2160 | | |
| AAT | GCT | ATT | ACT | TAT | GAT | GGT | AAA | GAG | ATG | AAT | GTT | TTT | CAT | AGA | TAT | 4032 |
| Asn | Ala | Ile | Thr | Tyr | Asp | Gly | Lys | Glu | Met | Asn | Val | Phe | His | Arg | Tyr | |
| | | | 2165 | | | | | 2170 | | | | | 2175 | | | |
| AAT | AAA | TAG | | | | | | | | | | | | | | 4041 |
| Asn | Lys | | | | | | | | | | | | | | | |
| | 2180 | | | | | | | | | | | | | | | |

( 2 ) INFORMATION FOR SEQ ID NO:23:

( i ) SEQUENCE CHARACTERISTICS:
        ( A ) LENGTH: 1346 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Met | Lys | Arg | Met | Glu | Gly | Lys | Leu | Phe | Met | Val | Ser | Lys | Lys | Leu | Gln |
| 1 | | | | 5 | | | | | 10 | | | | | 15 | |
| Val | Val | Thr | Lys | Thr | Val | Leu | Leu | Ser | Thr | Val | Phe | Ser | Ile | Ser | Leu |
| | | | 20 | | | | | 25 | | | | | 30 | | |
| Leu | Asn | Asn | Glu | Val | Ile | Lys | Ala | Glu | Gln | Leu | Asn | Ile | Asn | Ser | Gln |
| | | | 35 | | | | 40 | | | | | 45 | | | |
| Ser | Lys | Tyr | Thr | Asn | Leu | Gln | Asn | Leu | Lys | Ile | Thr | Asp | Lys | Val | Glu |
| | 50 | | | | | 55 | | | | | 60 | | | | |
| Asp | Phe | Lys | Glu | Asp | Lys | Glu | Lys | Ala | Lys | Glu | Trp | Gly | Lys | Glu | Lys |
| 65 | | | | | 70 | | | | | 75 | | | | | 80 |
| Glu | Lys | Glu | Trp | Lys | Leu | Thr | Ala | Thr | Glu | Lys | Gly | Lys | Met | Asn | Asn |

-continued

|  |  |  | 85 |  |  |  | 90 |  |  |  | 95 |  |  |
|---|---|---|---|---|---|---|---|---|---|---|---|---|---|
| Phe | Leu | Asp | Asn | Lys | Asn | Asp | Ile | Lys | Thr | Asn | Tyr | Lys | Glu | Ile | Thr |
|  |  |  | 100 |  |  |  | 105 |  |  |  | 110 |  |  |
| Phe | Ser | Met | Ala | Gly | Ser | Phe | Glu | Asp | Ile | Lys | Asp | Leu | Lys | Glu |
|  |  |  | 115 |  |  |  | 120 |  |  |  | 125 |  |  |
| Ile | Asp | Lys | Met | Phe | Asp | Lys | Thr | Asn | Leu | Ser | Asn | Ser | Ile | Ile | Thr |
|  |  |  | 130 |  |  |  | 135 |  |  |  | 140 |  |  |
| Tyr | Lys | Asn | Val | Glu | Pro | Thr | Thr | Ile | Gly | Phe | Asn | Lys | Ser | Leu | Thr |
| 145 |  |  |  |  | 150 |  |  |  | 155 |  |  |  |  | 160 |
| Glu | Gly | Asn | Thr | Ile | Asn | Ser | Asp | Ala | Met | Ala | Gln | Phe | Lys | Glu | Gln |
|  |  |  | 165 |  |  |  | 170 |  |  |  | 175 |  |  |
| Phe | Leu | Asp | Arg | Asp | Ile | Lys | Phe | Asp | Ser | Tyr | Leu | Asp | Thr | His | Leu |
|  |  |  | 180 |  |  |  | 185 |  |  |  | 190 |  |  |
| Thr | Ala | Gln | Gln | Val | Ser | Ser | Glu | Arg | Val | Ile | Leu | Lys | Val | Thr |
|  |  |  | 195 |  |  |  | 200 |  |  |  | 205 |  |  |
| Val | Pro | Ser | Gly | Lys | Gly | Ser | Thr | Thr | Pro | Thr | Lys | Ala | Gly | Val | Ile |
|  |  |  | 210 |  |  |  | 215 |  |  |  | 220 |  |  |
| Leu | Asn | Asn | Ser | Glu | Tyr | Lys | Met | Leu | Ile | Asp | Asn | Gly | Tyr | Met | Val |
| 225 |  |  |  |  | 230 |  |  |  | 235 |  |  |  |  | 240 |
| His | Val | Asp | Lys | Val | Ser | Lys | Val | Val | Lys | Lys | Gly | Val | Glu | Cys | Leu |
|  |  |  | 245 |  |  |  | 250 |  |  |  | 255 |  |  |
| Gln | Ile | Glu | Gly | Thr | Leu | Lys | Lys | Ser | Leu | Asp | Phe | Lys | Asn | Asp | Ile |
|  |  |  | 260 |  |  |  | 265 |  |  |  | 270 |  |  |
| Asn | Ala | Glu | Ala | His | Ser | Trp | Gly | Met | Lys | Asn | Tyr | Glu | Glu | Trp | Ala |
|  |  |  | 275 |  |  |  | 280 |  |  |  | 285 |  |  |
| Lys | Asp | Leu | Thr | Asp | Ser | Gln | Arg | Glu | Ala | Leu | Asp | Gly | Tyr | Ala | Arg |
|  |  |  | 290 |  |  |  | 295 |  |  |  | 300 |  |  |
| Gln | Asp | Tyr | Lys | Glu | Ile | Asn | Asn | Tyr | Leu | Arg | Asn | Gln | Gly | Gly | Ser |
| 305 |  |  |  |  | 310 |  |  |  | 315 |  |  |  |  | 320 |
| Gly | Asn | Glu | Lys | Leu | Asp | Ala | Gln | Ile | Lys | Asn | Ile | Ser | Asp | Ala | Leu |
|  |  |  | 325 |  |  |  | 330 |  |  |  | 335 |  |  |
| Gly | Lys | Lys | Pro | Ile | Pro | Glu | Asn | Ile | Thr | Val | Tyr | Arg | Trp | Cys | Gly |
|  |  |  | 340 |  |  |  | 345 |  |  |  | 350 |  |  |
| Met | Pro | Glu | Phe | Gly | Tyr | Gln | Ile | Ser | Asp | Pro | Leu | Pro | Ser | Leu | Lys |
|  |  |  | 355 |  |  |  | 360 |  |  |  | 365 |  |  |
| Asp | Phe | Glu | Glu | Gln | Phe | Leu | Asn | Thr | Ile | Lys | Glu | Asp | Lys | Gly | Tyr |
|  |  |  | 370 |  |  |  | 375 |  |  |  | 380 |  |  |
| Met | Ser | Thr | Ser | Leu | Ser | Ser | Glu | Arg | Leu | Ala | Ala | Phe | Gly | Ser | Arg |
| 385 |  |  |  |  | 390 |  |  |  | 395 |  |  |  |  | 400 |
| Lys | Ile | Ile | Leu | Arg | Leu | Gln | Val | Pro | Lys | Gly | Ser | Thr | Gly | Ala | Tyr |
|  |  |  | 405 |  |  |  | 410 |  |  |  | 415 |  |  |
| Leu | Ser | Ala | Ile | Gly | Gly | Phe | Ala | Ser | Glu | Lys | Glu | Ile | Leu | Leu | Asp |
|  |  |  | 420 |  |  |  | 425 |  |  |  | 430 |  |  |
| Lys | Asp | Ser | Lys | Tyr | His | Ile | Asp | Lys | Val | Thr | Glu | Val | Ile | Ile | Lys |
|  |  |  | 435 |  |  |  | 440 |  |  |  | 445 |  |  |
| Gly | Val | Lys | Arg | Tyr | Val | Val | Asp | Ala | Thr | Leu | Leu | Thr | Asn | Met | Lys |
|  |  |  | 450 |  |  |  | 455 |  |  |  | 460 |  |  |
| Asn | Met | Lys | Lys | Lys | Leu | Ala | Ser | Val | Val | Thr | Cys | Thr | Leu | Leu | Ala |
| 465 |  |  |  |  | 470 |  |  |  | 475 |  |  |  |  | 480 |
| Pro | Met | Phe | Leu | Asn | Gly | Asn | Val | Asn | Ala | Val | Tyr | Ala | Asp | Ser | Lys |
|  |  |  | 485 |  |  |  | 490 |  |  |  | 495 |  |  |
| Thr | Asn | Gln | Ile | Ser | Thr | Thr | Gln | Lys | Asn | Gln | Gln | Lys | Glu | Met | Asp |
|  |  |  | 500 |  |  |  | 505 |  |  |  | 510 |  |  |

| | | | | | | | | | | | | | | |
|---|---|---|---|---|---|---|---|---|---|---|---|---|---|---|
|Arg|Lys|Gly|Leu|Leu|Gly|Tyr|Tyr|Phe|Lys|Gly|Lys|Asp|Phe|Ser|Asn|
| | |515| | | |520| | | |525| | | | |
|Leu|Thr|Met|Phe|Ala|Pro|Thr|Arg|Asp|Ser|Thr|Leu|Ile|Tyr|Asp|Gln|
|530| | | | |535| | | | |540| | | | |
|Gln|Thr|Ala|Asn|Lys|Leu|Leu|Asp|Lys|Lys|Gln|Gln|Glu|Tyr|Gln|Ser|
|545| | | | |550| | | | |555| | | | |560|
|Ile|Arg|Trp|Ile|Gly|Leu|Ile|Gln|Ser|Lys|Glu|Thr|Gly|Asp|Phe|Thr|
| | | | |565| | | | |570| | | | |575| |
|Phe|Asn|Leu|Ser|Glu|Asp|Glu|Gln|Ala|Ile|Ile|Glu|Ile|Asn|Gly|Lys|
| | | |580| | | | |585| | | | |590| | |
|Ile|Ile|Ser|Asn|Lys|Gly|Lys|Glu|Lys|Gln|Val|Val|His|Leu|Glu|Lys|
| | |595| | | | |600| | | | |605| | | |
|Gly|Lys|Leu|Val|Pro|Ile|Lys|Ile|Glu|Tyr|Gln|Ser|Asp|Thr|Lys|Phe|
| |610| | | | |615| | | | |620| | | | |
|Asn|Ile|Asp|Ser|Lys|Thr|Phe|Lys|Glu|Leu|Lys|Leu|Phe|Lys|Ile|Asp|
|625| | | | |630| | | | |635| | | | |640|
|Ser|Gln|Asn|Gln|Pro|Gln|Gln|Val|Gln|Gln|Asp|Glu|Leu|Arg|Asn|Pro|
| | | | |645| | | | |650| | | | |655| |
|Glu|Phe|Asn|Lys|Lys|Glu|Ser|Gln|Glu|Phe|Leu|Ala|Lys|Pro|Ser|Lys|
| | | |660| | | | |665| | | | |670| | |
|Ile|Asn|Leu|Phe|Thr|Gln|Lys|Met|Lys|Arg|Glu|Ile|Asp|Glu|Asp|Thr|
| | |675| | | | |680| | | | |685| | | |
|Asp|Thr|Asp|Gly|Asp|Ser|Ile|Pro|Asp|Leu|Trp|Glu|Glu|Asn|Gly|Tyr|
|690| | | | |695| | | | |700| | | | | |
|Thr|Ile|Gln|Asn|Arg|Ile|Ala|Val|Lys|Trp|Asp|Asp|Ser|Leu|Ala|Ser|
|705| | | | |710| | | | |715| | | | |720|
|Lys|Gly|Tyr|Thr|Lys|Phe|Val|Ser|Asn|Pro|Leu|Glu|Ser|His|Thr|Val|
| | | | |725| | | | |730| | | | |735| |
|Gly|Asp|Pro|Tyr|Thr|Asp|Tyr|Glu|Lys|Ala|Ala|Arg|Asp|Leu|Asp|Leu|
| | | |740| | | | |745| | | | |750| | |
|Ser|Asn|Ala|Lys|Glu|Thr|Phe|Asn|Pro|Leu|Val|Ala|Ala|Phe|Pro|Ser|
| | |755| | | | |760| | | | |765| | | |
|Val|Asn|Val|Ser|Met|Glu|Lys|Val|Ile|Leu|Ser|Pro|Asn|Glu|Asn|Leu|
| |770| | | | |775| | | | |780| | | | |
|Ser|Asn|Ser|Val|Glu|Ser|His|Ser|Ser|Thr|Asn|Trp|Ser|Tyr|Thr|Asn|
|785| | | | |790| | | | |795| | | | |800|
|Thr|Glu|Gly|Ala|Ser|Val|Glu|Ala|Gly|Ile|Gly|Pro|Lys|Gly|Ile|Ser|
| | | | |805| | | | |810| | | | |815| |
|Phe|Gly|Val|Ser|Val|Asn|Tyr|Gln|His|Ser|Glu|Thr|Val|Ala|Gln|Glu|
| | | |820| | | | |825| | | | |830| | |
|Trp|Gly|Thr|Ser|Thr|Gly|Asn|Thr|Ser|Gln|Phe|Asn|Thr|Ala|Ser|Ala|
| | |835| | | | |840| | | | |845| | | |
|Gly|Tyr|Leu|Asn|Ala|Asn|Val|Arg|Tyr|Asn|Asn|Val|Gly|Thr|Gly|Ala|
| |850| | | | |855| | | | |860| | | | |
|Ile|Tyr|Asp|Val|Lys|Pro|Thr|Thr|Ser|Phe|Val|Leu|Asn|Asn|Asp|Thr|
|865| | | | |870| | | | |875| | | | |880|
|Ile|Ala|Thr|Ile|Thr|Ala|Lys|Ser|Asn|Ser|Thr|Ala|Leu|Asn|Ile|Ser|
| | | | |885| | | | |890| | | | |895| |
|Pro|Gly|Glu|Ser|Tyr|Pro|Lys|Lys|Gly|Gln|Asn|Gly|Ile|Ala|Ile|Thr|
| | | |900| | | | |905| | | | |910| | |
|Ser|Met|Asp|Asp|Phe|Asn|Ser|His|Pro|Ile|Thr|Leu|Asn|Lys|Lys|Gln|
| | |915| | | | |920| | | | |925| | | |
|Val|Asp|Asn|Leu|Leu|Asn|Asn|Lys|Pro|Met|Met|Leu|Glu|Thr|Asn|Gln|
|930| | | | |935| | | | |940| | | | | |

Thr Asp Gly Val Tyr Lys Ile Lys Asp Thr His Gly Asn Ile Val Thr
945                 950                 955                 960

Gly Gly Glu Trp Asn Gly Val Ile Gln Gln Ile Lys Ala Lys Thr Ala
            965                 970                 975

Ser Ile Ile Val Asp Asp Gly Glu Arg Val Ala Glu Lys Arg Val Ala
                980                 985                 990

Ala Lys Asp Tyr Glu Asn Pro Glu Asp Lys Thr Pro Ser Leu Thr Leu
        995                 1000                1005

Lys Asp Ala Leu Lys Leu Ser Tyr Pro Asp Glu Ile Lys Glu Ile Glu
        1010                1015                1020

Gly Leu Leu Tyr Tyr Lys Asn Lys Pro Ile Tyr Glu Ser Ser Val Met
1025                1030                1035                1040

Thr Tyr Leu Asp Glu Asn Thr Ala Lys Glu Val Thr Lys Gln Leu Asn
            1045                1050                1055

Asp Thr Thr Gly Lys Phe Lys Asp Val Ser His Leu Tyr Asp Val Lys
                1060                1065                1070

Leu Thr Pro Lys Met Asn Val Thr Ile Lys Leu Ser Ile Leu Tyr Asp
            1075                1080                1085

Asn Ala Glu Ser Asn Asp Asn Ser Ile Gly Lys Trp Thr Asn Thr Asn
        1090                1095                1100

Ile Val Ser Gly Gly Asn Asn Gly Lys Lys Gln Tyr Ser Ser Asn Asn
1105                1110                1115                1120

Pro Asp Ala Asn Leu Thr Leu Asn Thr Asp Ala Gln Glu Lys Leu Asn
            1125                1130                1135

Lys Asn Arg Asp Tyr Tyr Ile Ser Leu Tyr Met Lys Ser Glu Lys Asn
            1140                1145                1150

Thr Gln Cys Glu Ile Thr Ile Asp Gly Glu Ile Tyr Pro Ile Thr Thr
            1155                1160                1165

Lys Thr Val Asn Val Asn Lys Asp Asn Tyr Lys Arg Leu Asp Ile Ile
        1170                1175                1180

Ala His Asn Ile Lys Ser Asn Pro Ile Ser Ser Leu His Ile Lys Thr
1185                1190                1195                1200

Asn Asp Glu Ile Thr Leu Phe Trp Asp Asp Ile Ser Ile Thr Asp Val
            1205                1210                1215

Ala Ser Ile Lys Pro Glu Asn Leu Thr Asp Ser Glu Ile Lys Gln Ile
        1220                1225                1230

Tyr Ser Arg Tyr Gly Ile Lys Leu Glu Asp Gly Ile Leu Ile Asp Lys
            1235                1240                1245

Lys Gly Gly Ile His Tyr Gly Glu Phe Ile Asn Glu Ala Ser Phe Asn
        1250                1255                1260

Ile Glu Pro Leu Gln Asn Tyr Val Thr Lys Tyr Glu Val Thr Tyr Ser
1265                1270                1275                1280

Ser Glu Leu Gly Pro Asn Val Ser Asp Thr Leu Glu Ser Asp Lys Ile
            1285                1290                1295

Tyr Lys Asp Gly Thr Ile Lys Phe Asp Phe Thr Lys Tyr Ser Lys Asn
            1300                1305                1310

Glu Gln Gly Leu Phe Tyr Asp Ser Gly Leu Asn Trp Asp Phe Lys Ile
            1315                1320                1325

Asn Ala Ile Thr Tyr Asp Gly Lys Glu Met Asn Val Phe His Arg Tyr
            1330                1335                1340

Asn Lys
1345

( 2 ) INFORMATION FOR SEQ ID NO:24:

( i ) SEQUENCE CHARACTERISTICS:
( A ) LENGTH: 1399 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 1..1386
( D ) OTHER INFORMATION: /note= "Maize optimized DNA sequence for VIP2A(a) protein from AB78"

( x i ) SEQUENCE DESCRIPTION: SEQ ID NO:24:

ATGAAGCGCA TGGAGGGCAA GCTGTTCATG GTGAGCAAGA AGCTCCAGGT GGTGACCAAG 60

ACCGTGCTGC TGAGCACCGT GTTCAGCATC AGCCTGCTGA ACAACGAGGT GATCAAGGCC 120

GAGCAGCTGA ACATCAACAG CCAGAGCAAG TACACCAACC TCCAGAACCT GAAGATCACC 180

GACAAGGTGG AGGACTTCAA GGAGGACAAG GAGAAGGCCA AGGAGTGGGG CAAGGAGAAG 240

GAGAAGGAGT GGAAGCTTAC CGCCACCGAG AAGGGCAAGA TGAACAACTT CCTGGACAAC 300

AAGAACGACA TCAAGACCAA CTACAAGGAG ATCACCTTCA GCATGGCCGG CAGCTTCGAG 360

GACGAGATCA AGGACCTGAA GGAGATCGAC AAGATGTTCG ACAAGACCAA CCTGAGCAAC 420

AGCATCATCA CCTACAAGAA CGTGGAGCCC ACCACCATCG GCTTCAACAA GAGCCTGACC 480

GAGGGCAACA CCATCAACAG CGACGCCATG GCCCAGTTCA AGGAGCAGTT CCTGGACCGC 540

GACATCAAGT TCGACAGCTA CCTGGACACC CACCTGACCG CCCAGCAGGT GAGCAGCAAG 600

GAGCGCGTGA TCCTGAAGGT GACCGTCCCC AGCGGCAAGG GCAGCACCAC CCCCACCAAG 660

GCCGGCGTGA TCCTGAACAA CAGCGAGTAC AAGATGCTGA TCGACAACGG CTACATGGTG 720

CACGTGGACA AGGTGAGCAA GGTGGTGAAG AAGGGCGTGG AGTGCCTCCA GATCGAGGGC 780

ACCCTGAAGA AGAGTCTAGA CTTCAAGAAC GACATCAACG CCGAGGCCCA CAGCTGGGGC 840

ATGAAGAACT ACGAGGAGTG GGCCAAGGAC CTGACCGACA GCCAGCGCGA GGCCCTGGAC 900

GGCTACGCCC GCCAGGACTA CAAGGAGATC AACAACTACC TGCGCAACCA GGGCGGCAGC 960

GGCAACGAGA AGCTGGACGC CCAGATCAAG AACATCAGCG ACGCCCTGGG CAAGAAGCCC 1020

ATCCCCGAGA ACATCACCGT GTACCGCTGG TGCGGCATGC CCGAGTTCGG CTACCAGATC 1080

AGCGACCCCC TGCCCAGCCT GAAGGACTTC GAGGAGCAGT TCCTGAACAC CATCAAGGAG 1140

GACAAGGGCT ACATGAGCAC CAGCCTGAGC AGCGAGCGCC TGGCCGCCTT CGGCAGCCGC 1200

AAGATCATCC TGCGCCTGCA GGTGCCCAAG GGCAGCACCG GCGCCTACCT GAGCGCCATC 1260

GGCGGCTTCG CCAGCGAGAA GGAGATCCTG CTGGACAAGG ACAGCAAGTA CCACATCGAC 1320

AAGGTGACCG AGGTGATCAT CAAGGGCGTG AAGCGCTACG TGGTGGACGC CACCCTGCTG 1380

ACCAACTAGA TCTGAGCTC 1399

( 2 ) INFORMATION FOR SEQ ID NO:25:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..19

(D) OTHER INFORMATION: /note= "Secretion signal peptide to secrete VIP2 out of a cell"

(xi) SEQUENCE DESCRIPTION: SEQ ID NO:25:

| Gly | Trp | Ser | Trp | Ile | Phe | Leu | Phe | Leu | Leu | Ser | Gly | Ala | Ala | Gly | Val |
|---|---|---|---|---|---|---|---|---|---|---|---|---|---|---|---|
| 1 | | | | 5 | | | | | 10 | | | | | 15 | |

His Cys Leu (2) INFORMATION FOR SEQ ID NO:26:

(i) SEQUENCE CHARACTERISTICS:
  (A) LENGTH: 2655 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "Synthetic DNA"

(iii) HYPOTHETICAL: NO (ix) FEATURE:
  (A) NAME/KEY: misc_feature
  (B) LOCATION: 1..2655
  (D) OTHER INFORMATION: /note= "maize optimized DNA sequence encoding VIP1A(a)"

(xi) SEQUENCE DESCRIPTION: SEQ ID NO:26:

| | | | | | | |
|---|---|---|---|---|---|---|
| ATGAAGAACA | TGAAGAAGAA | GCTGGCCAGC | GTGGTGACCT | GCACCCTGCT | GGCCCCCATG | 60 |
| TTCCTGAACG | GCAACGTGAA | CGCCGTGTAC | GCCGACAGCA | AGACCAACCA | GATCAGCACC | 120 |
| ACCCAGAAGA | ACCAGCAGAA | GGAGATGGAC | CGCAAGGGCC | TGCTGGGCTA | CTACTTCAAG | 180 |
| GGCAAGGACT | TCAGCAACCT | GACCATGTTC | GCCCCCACGC | GTGACAGCAC | CCTGATCTAC | 240 |
| GACCAGCAGA | CCGCCAACAA | GCTGCTGGAC | AAGAAGCAGC | AGGAGTACCA | GAGCATCCGC | 300 |
| TGGATCGGCC | TGATCCAGAG | CAAGGAGACC | GGCGACTTCA | CCTTCAACCT | GAGCGAGGAC | 360 |
| GAGCAGGCCA | TCATCGAGAT | CAACGGCAAG | ATCATCAGCA | ACAAGGGCAA | GGAGAAGCAG | 420 |
| GTGGTGCACC | TGGAGAAGGG | CAAGCTGGTG | CCCATCAAGA | TCGAGTACCA | GAGCGACACC | 480 |
| AAGTTCAACA | TCGACAGCAA | GACCTTCAAG | GAGCTGAAGC | TTTTCAAGAT | CGACAGCCAG | 540 |
| AACCAGCCCC | AGCAGGTGCA | GCAGGACGAG | CTGCGCAACC | CCGAGTTCAA | CAAGAAGGAG | 600 |
| AGCCAGGAGT | TCCTGGCCAA | GCCCAGCAAG | ATCAACCTGT | TCACCCAGCA | GATGAAGCGC | 660 |
| GAGATCGACG | AGGACACCGA | CACCGACGGC | GACAGCATCC | CCGACCTGTG | GGAGGAGAAC | 720 |
| GGCTACACCA | TCCAGAACCG | CATCGCCGTG | AAGTGGGACG | ACAGCCTGGC | TAGCAAGGGC | 780 |
| TACACCAAGT | TCGTGAGCAA | CCCCCTGGAG | AGCCACACCG | TGGGCGACCC | CTACACCGAC | 840 |
| TACGAGAAGG | CCGCCCGCGA | CCTGGACCTG | AGCAACGCCA | AGGAGACCTT | CAACCCCCTG | 900 |
| GTGGCCGCCT | TCCCCAGCGT | GAACGTGAGC | ATGGAGAAGG | TGATCCTGAG | CCCCAACGAG | 960 |
| AACCTGAGCA | CAGCGTGGA | GAGCCACTCG | AGCACCAACT | GGAGCTACAC | CAACACCGAG | 1020 |
| GGCGCCAGCG | TGGAGGCCGG | CATCGGTCCC | AAGGGCATCA | GCTTCGGCGT | GAGCGTGAAC | 1080 |
| TACCAGCACA | GCGAGACCGT | GGCCCAGGAG | TGGGGCACCA | GCACCGGCAA | CACCAGCCAG | 1140 |
| TTCAACACCG | CCAGCGCCGG | CTACCTGAAC | GCCAACGTGC | GCTACAACAA | CGTGGGCACC | 1200 |
| GGCGCCATCT | ACGACGTGAA | GCCCACCACC | AGCTTCGTGC | TGAACAACGA | CACCATCGCC | 1260 |
| ACCATCACCG | CCAAGTCGAA | TTCCACCGCC | CTGAACATCA | GCCCCGGCGA | GAGCTACCCC | 1320 |
| AAGAAGGGCC | AGAACGGCAT | CGCCATCACC | AGCATGGACG | ACTTCAACAG | CCACCCCATC | 1380 |
| ACCCTGAACA | AGAAGCAGGT | GGACAACCTG | CTGAACAACA | AGCCCATGAT | GCTGGAGACC | 1440 |

-continued

| | | | | | | |
|---|---|---|---|---|---|---|
| AACCAGACCG | ACGGCGTCTA | CAAGATCAAG | GACACCCACG | GCAACATCGT | GACGGGCGGC | 1500 |
| GAGTGGAACG | GCGTGATCCA | GCAGATCAAG | GCCAAGACCG | CCAGCATCAT | CGTCGACGAC | 1560 |
| GGCGAGCGCG | TGGCCGAGAA | GCGCGTGGCC | GCCAAGGACT | ACGAGAACCC | CGAGGACAAG | 1620 |
| ACCCCCAGCC | TGACCCTGAA | GGACGCCCTG | AAGCTGAGCT | ACCCCGACGA | GATCAAGGAG | 1680 |
| ATCGAGGGCT | TGCTGTACTA | CAAGAACAAG | CCCATCTACG | AGAGCAGCGT | GATGACCTAT | 1740 |
| CTAGACGAGA | ACACCGCCAA | GGAGGTGACC | AAGCAGCTGA | ACGACACCAC | CGGCAAGTTC | 1800 |
| AAGGACGTGA | GCCACCTGTA | CGACGTGAAG | CTGACCCCCA | AGATGAACGT | GACCATCAAG | 1860 |
| CTGAGCATCC | TGTACGACAA | CGCCGAGAGC | AACGACAACA | GCATCGGCAA | GTGGACCAAC | 1920 |
| ACCAACATCG | TGAGCGGCGG | CAACAACGGC | AAGAAGCAGT | ACAGCAGCAA | CAACCCCGAC | 1980 |
| GCCAACCTGA | CCCTGAACAC | CGACGCCCAG | GAGAAGCTGA | ACAAGAACCG | CGACTACTAC | 2040 |
| ATCAGCCTGT | ACATGAAGAG | CGAGAAGAAC | ACCCAGTGCG | AGATCACCAT | CGACGGCGAG | 2100 |
| ATATACCCCA | TCACCACCAA | GACCGTGAAC | GTGAACAAGG | ACAACTACAA | GCGCCTGGAC | 2160 |
| ATCATCGCCC | ACAACATCAA | GAGCAACCCC | ATCAGCAGCC | TGCACATCAA | GACCAACGAC | 2220 |
| GAGATCACCC | TGTTCTGGGA | CGACATATCG | ATTACCGACG | TCGCCAGCAT | CAAGCCCGAG | 2280 |
| AACCTGACCG | ACAGCGAGAT | CAAGCAGATA | TACAGTCGCT | ACGGCATCAA | GCTGGAGGAC | 2340 |
| GGCATCCTGA | TCGACAAGAA | AGGCGGCATC | CACTACGGCG | AGTTCATCAA | CGAGGCCAGC | 2400 |
| TTCAACATCG | AGCCCCTGCA | GAACTACGTG | ACCAAGTACG | AGGTGACCTA | CAGCAGCGAG | 2460 |
| CTGGGCCCCA | ACGTGAGCGA | CACCCTGGAG | AGCGACAAGA | TTTACAAGGA | CGGCACCATC | 2520 |
| AAGTTCGACT | TCACCAAGTA | CAGCAAGAAC | GAGCAGGGCC | TGTTCTACGA | CAGCGGCCTG | 2580 |
| AACTGGGACT | TCAAGATCAA | CGCCATCACC | TACGACGGCA | AGGAGATGAA | CGTGTTCCAC | 2640 |
| CGCTACAACA | AGTAG | | | | | 2655 |

(2) INFORMATION FOR SEQ ID NO:27:

(i) SEQUENCE CHARACTERISTICS:
(A) LENGTH: 1389 base pairs
(B) TYPE: nucleic acid
(C) STRANDEDNESS: single
(D) TOPOLOGY: linear (ii) MOLECULE TYPE: other nucleic acid
(A) DESCRIPTION: /desc = “Synthetic DNA”

(iii) HYPOTHETICAL: NO (ix) FEATURE:
(A) NAME/KEY: misc_feature
(B) LOCATION: 1..1389
(D) OTHER INFORMATION: /note= “maize optimized DNA sequence encoding VIP2A(a)”

(xi) SEQUENCE DESCRIPTION: SEQ ID NO:27:

| | | | | | | |
|---|---|---|---|---|---|---|
| ATGAAGCGCA | TGGAGGGCAA | GCTGTTCATG | GTGAGCAAGA | AGCTCCAGGT | GGTGACCAAG | 60 |
| ACCGTGCTGC | TGAGCACCGT | GTTCAGCATC | AGCCTGCTGA | ACAACGAGGT | GATCAAGGCC | 120 |
| GAGCAGCTGA | ACATCAACAG | CCAGAGCAAG | TACACCAACC | TCCAGAACCT | GAAGATCACC | 180 |
| GACAAGGTGG | AGGACTTCAA | GGAGGACAAG | GAGAAGGCCA | AGGAGTGGGG | CAAGGAGAAG | 240 |
| GAGAAGGAGT | GGAAGCTTAC | CGCCACCGAG | AAGGGCAAGA | TGAACAACTT | CCTGGACAAC | 300 |
| AAGAACGACA | TCAAGACCAA | CTACAAGGAG | ATCACCTTCA | GCATAGCCGG | CAGCTTCGAG | 360 |
| GACGAGATCA | AGGACCTGAA | GGAGATCGAC | AAGATGTTCG | ACAAGACCAA | CCTGAGCAAC | 420 |
| AGCATCATCA | CCTACAAGAA | CGTGGAGCCC | ACCACCATCG | GCTTCAACAA | GAGCCTGACC | 480 |

| | | | | | |
|---|---|---|---|---|---|
| GAGGGCAACA | CCATCAACAG | CGACGCCATG | GCCCAGTTCA | AGGAGCAGTT | CCTGGACCGC | 540 |
| GACATCAAGT | TCGACAGCTA | CCTGGACACC | CACCTGACCG | CCCAGCAGGT | GAGCAGCAAG | 600 |
| GAGCGCGTGA | TCCTGAAGGT | GACCGTCCCC | AGCGGCAAGG | GCAGCACCAC | CCCCACCAAG | 660 |
| GCCGGCGTGA | TCCTGAACAA | CAGCGAGTAC | AAGATGCTGA | TCGACAACGG | CTACATGGTG | 720 |
| CACGTGGACA | AGGTGAGCAA | GGTGGTGAAG | AAGGGCGTGG | AGTGCCTCCA | GATCGAGGGC | 780 |
| ACCCTGAAGA | AGAGTCTAGA | CTTCAAGAAC | GACATCAACG | CCGAGGCCCA | CAGCTGGGGC | 840 |
| ATGAAGAACT | ACGAGGAGTG | GGCCAAGGAC | CTGACCGACA | GCCAGCGCGA | GGCCCTGGAC | 900 |
| GGCTACGCCC | GCCAGGACTA | CAAGGAGATC | AACAACTACC | TGCGCAACCA | GGGCGGCAGC | 960 |
| GGCAACGAGA | AGCTGGACGC | CCAGATCAAG | AACATCAGCG | ACGCCCTGGG | CAAGAAGCCC | 1020 |
| ATCCCCGAGA | ACATCACCGT | GTACCGCTGG | TGCGGCATGC | CCGAGTTCGG | CTACCAGATC | 1080 |
| AGCGACCCCC | TGCCCAGCCT | GAAGGACTTC | GAGGAGCAGT | TCCTGAACAC | CATCAAGGAG | 1140 |
| GACAAGGGCT | ACATGAGCAC | CAGCCTGAGC | AGCGAGCGCC | TGGCCGCCTT | CGGCAGCCGC | 1200 |
| AAGATCATCC | TGCGCCTGCA | GGTGCCCAAG | GGCAGCACTG | GTGCCTACCT | GAGCGCCATC | 1260 |
| GGCGGCTTCG | CCAGCGAGAA | GGAGATCCTG | CTGGATAAGG | ACAGCAAGTA | CCACATCGAC | 1320 |
| AAGGTGACCG | AGGTGATCAT | CAAGGGCGTG | AAGCGCTACG | TGGTGGACGC | CACCCTGCTG | 1380 |
| ACCAACTAG | | | | | | 1389 |

(2) INFORMATION FOR SEQ ID NO:28:

(i) SEQUENCE CHARACTERISTICS:
        (A) LENGTH: 2378 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 9..2375
        (D) OTHER INFORMATION: /note= "Native DNA sequence
            encoding VIP3A(a) protein from AB88 as contained in
            pCIB7104"

(xi) SEQUENCE DESCRIPTION: SEQ ID NO:28:

```
AGATGAAC ATG AAC AAG AAT AAT ACT AAA TTA AGC ACA AGA GCC TTA CCA        50
         Met Asn Lys Asn Asn Thr Lys Leu Ser Thr Arg Ala Leu Pro
           1               5                  10

AGT TTT ATT GAT TAT TTT AAT GGC ATT TAT GGA TTT GCC ACT GGT ATC         98
Ser Phe Ile Asp Tyr Phe Asn Gly Ile Tyr Gly Phe Ala Thr Gly Ile
 15              20                  25                  30

AAA GAC ATT ATG AAC ATG ATT TTT AAA ACG GAT ACA GGT GGT GAT CTA        146
Lys Asp Ile Met Asn Met Ile Phe Lys Thr Asp Thr Gly Gly Asp Leu
                 35                  40                  45

ACC CTA GAC GAA ATT TTA AAG AAT CAG CAG TTA CTA AAT GAT ATT TCT        194
Thr Leu Asp Glu Ile Leu Lys Asn Gln Gln Leu Leu Asn Asp Ile Ser
                50                  55                  60

GGT AAA TTG GAT GGG GTG AAT GGA AGC TTA AAT GAT CTT ATC GCA CAG        242
Gly Lys Leu Asp Gly Val Asn Gly Ser Leu Asn Asp Leu Ile Ala Gln
             65                  70                  75

GGA AAC TTA AAT ACA GAA TTA TCT AAG GAA ATA TTA AAA ATT GCA AAT        290
Gly Asn Leu Asn Thr Glu Leu Ser Lys Glu Ile Leu Lys Ile Ala Asn
         80                  85                  90

GAA CAA AAT CAA GTT TTA AAT GAT GTT AAT AAC AAA CTC GAT GCG ATA        338
Glu Gln Asn Gln Val Leu Asn Asp Val Asn Asn Lys Leu Asp Ala Ile
```

|  | 95 |  |  |  | 100 |  |  |  | 105 |  |  |  | 110 |  |  |  |
|---|---|---|---|---|---|---|---|---|---|---|---|---|---|---|---|---|
| AAT | ACG | ATG | CTT | CGG | GTA | TAT | CTA | CCT | AAA | ATT | ACC | TCT | ATG | TTG | AGT | 386 |
| Asn | Thr | Met | Leu | Arg | Val | Tyr | Leu | Pro | Lys | Ile | Thr | Ser | Met | Leu | Ser |  |
|  |  |  |  | 115 |  |  |  |  | 120 |  |  |  |  | 125 |  |  |
| GAT | GTA | ATG | AAA | CAA | AAT | TAT | GCG | CTA | AGT | CTG | CAA | ATA | GAA | TAC | TTA | 434 |
| Asp | Val | Met | Lys | Gln | Asn | Tyr | Ala | Leu | Ser | Leu | Gln | Ile | Glu | Tyr | Leu |  |
|  |  |  | 130 |  |  |  |  | 135 |  |  |  |  | 140 |  |  |  |
| AGT | AAA | CAA | TTG | CAA | GAG | ATT | TCT | GAT | AAG | TTG | GAT | ATT | ATT | AAT | GTA | 482 |
| Ser | Lys | Gln | Leu | Gln | Glu | Ile | Ser | Asp | Lys | Leu | Asp | Ile | Ile | Asn | Val |  |
|  |  | 145 |  |  |  |  | 150 |  |  |  |  | 155 |  |  |  |  |
| AAT | GTA | CTT | ATT | AAC | TCT | ACA | CTT | ACT | GAA | ATT | ACA | CCT | GCG | TAT | CAA | 530 |
| Asn | Val | Leu | Ile | Asn | Ser | Thr | Leu | Thr | Glu | Ile | Thr | Pro | Ala | Tyr | Gln |  |
|  | 160 |  |  |  |  | 165 |  |  |  |  | 170 |  |  |  |  |  |
| AGG | ATT | AAA | TAT | GTG | AAC | GAA | AAA | TTT | GAG | GAA | TTA | ACT | TTT | GCT | ACA | 578 |
| Arg | Ile | Lys | Tyr | Val | Asn | Glu | Lys | Phe | Glu | Glu | Leu | Thr | Phe | Ala | Thr |  |
| 175 |  |  |  |  | 180 |  |  |  |  | 185 |  |  |  |  | 190 |  |
| GAA | ACT | AGT | TCA | AAA | GTA | AAA | AAG | GAT | GGC | TCT | CCT | GCA | GAT | ATT | CTT | 626 |
| Glu | Thr | Ser | Ser | Lys | Val | Lys | Lys | Asp | Gly | Ser | Pro | Ala | Asp | Ile | Leu |  |
|  |  |  |  | 195 |  |  |  |  | 200 |  |  |  |  | 205 |  |  |
| GAT | GAG | TTA | ACT | GAG | TTA | ACT | GAA | CTA | GCG | AAA | AGT | GTA | ACA | AAA | AAT | 674 |
| Asp | Glu | Leu | Thr | Glu | Leu | Thr | Glu | Leu | Ala | Lys | Ser | Val | Thr | Lys | Asn |  |
|  |  |  | 210 |  |  |  |  | 215 |  |  |  |  | 220 |  |  |  |
| GAT | GTG | GAT | GGT | TTT | GAA | TTT | TAC | CTT | AAT | ACA | TTC | CAC | GAT | GTA | ATG | 722 |
| Asp | Val | Asp | Gly | Phe | Glu | Phe | Tyr | Leu | Asn | Thr | Phe | His | Asp | Val | Met |  |
|  |  | 225 |  |  |  |  | 230 |  |  |  |  | 235 |  |  |  |  |
| GTA | GGA | AAT | AAT | TTA | TTC | GGG | CGT | TCA | GCT | TTA | AAA | ACT | GCA | TCG | GAA | 770 |
| Val | Gly | Asn | Asn | Leu | Phe | Gly | Arg | Ser | Ala | Leu | Lys | Thr | Ala | Ser | Glu |  |
|  | 240 |  |  |  |  | 245 |  |  |  |  | 250 |  |  |  |  |  |
| TTA | ATT | ACT | AAA | GAA | AAT | GTG | AAA | ACA | AGT | GGC | AGT | GAG | GTC | GGA | AAT | 818 |
| Leu | Ile | Thr | Lys | Glu | Asn | Val | Lys | Thr | Ser | Gly | Ser | Glu | Val | Gly | Asn |  |
| 255 |  |  |  |  | 260 |  |  |  |  | 265 |  |  |  |  | 270 |  |
| GTT | TAT | AAC | TTC | TTA | ATT | GTA | TTA | ACA | GCT | CTG | CAA | GCC | CAA | GCT | TTT | 866 |
| Val | Tyr | Asn | Phe | Leu | Ile | Val | Leu | Thr | Ala | Leu | Gln | Ala | Gln | Ala | Phe |  |
|  |  |  |  | 275 |  |  |  |  | 280 |  |  |  |  | 285 |  |  |
| CTT | ACT | TTA | ACA | ACA | TGC | CGA | AAA | TTA | TTA | GGC | TTA | GCA | GAT | ATT | GAT | 914 |
| Leu | Thr | Leu | Thr | Thr | Cys | Arg | Lys | Leu | Leu | Gly | Leu | Ala | Asp | Ile | Asp |  |
|  |  |  | 290 |  |  |  |  | 295 |  |  |  |  | 300 |  |  |  |
| TAT | ACT | TCT | ATT | ATG | AAT | GAA | CAT | TTA | AAT | AAG | GAA | AAA | GAG | GAA | TTT | 962 |
| Tyr | Thr | Ser | Ile | Met | Asn | Glu | His | Leu | Asn | Lys | Glu | Lys | Glu | Glu | Phe |  |
|  |  | 305 |  |  |  |  | 310 |  |  |  |  | 315 |  |  |  |  |
| AGA | GTA | AAC | ATC | CTC | CCT | ACA | CTT | TCT | AAT | ACT | TTT | TCT | AAT | CCT | AAT | 1010 |
| Arg | Val | Asn | Ile | Leu | Pro | Thr | Leu | Ser | Asn | Thr | Phe | Ser | Asn | Pro | Asn |  |
|  | 320 |  |  |  |  | 325 |  |  |  |  | 330 |  |  |  |  |  |
| TAT | GCA | AAA | GTT | AAA | GGA | AGT | GAT | GAA | GAT | GCA | AAG | ATG | ATT | GTG | GAA | 1058 |
| Tyr | Ala | Lys | Val | Lys | Gly | Ser | Asp | Glu | Asp | Ala | Lys | Met | Ile | Val | Glu |  |
| 335 |  |  |  |  | 340 |  |  |  |  | 345 |  |  |  |  | 350 |  |
| GCT | AAA | CCA | GGA | CAT | GCA | TTG | ATT | GGG | TTT | GAA | ATT | AGT | AAT | GAT | TCA | 1106 |
| Ala | Lys | Pro | Gly | His | Ala | Leu | Ile | Gly | Phe | Glu | Ile | Ser | Asn | Asp | Ser |  |
|  |  |  |  | 355 |  |  |  |  | 360 |  |  |  |  | 365 |  |  |
| ATT | ACA | GTA | TTA | AAA | GTA | TAT | GAG | GCT | AAG | CTA | AAA | CAA | AAT | TAT | CAA | 1154 |
| Ile | Thr | Val | Leu | Lys | Val | Tyr | Glu | Ala | Lys | Leu | Lys | Gln | Asn | Tyr | Gln |  |
|  |  |  | 370 |  |  |  |  | 375 |  |  |  |  | 380 |  |  |  |
| GTC | GAT | AAG | GAT | TCC | TTA | TCG | GAA | GTT | ATT | TAT | GGT | GAT | ATG | GAT | AAA | 1202 |
| Val | Asp | Lys | Asp | Ser | Leu | Ser | Glu | Val | Ile | Tyr | Gly | Asp | Met | Asp | Lys |  |
|  |  | 385 |  |  |  |  | 390 |  |  |  |  | 395 |  |  |  |  |
| TTA | TTG | TGC | CCA | GAT | CAA | TCT | GAA | CAA | ATC | TAT | TAT | ACA | AAT | AAC | ATA | 1250 |
| Leu | Leu | Cys | Pro | Asp | Gln | Ser | Glu | Gln | Ile | Tyr | Tyr | Thr | Asn | Asn | Ile |  |
|  | 400 |  |  |  |  | 405 |  |  |  |  | 410 |  |  |  |  |  |
| GTA | TTT | CCA | AAT | GAA | TAT | GTA | ATT | ACT | AAA | ATT | GAT | TTC | ACT | AAA | AAA | 1298 |
| Val | Phe | Pro | Asn | Glu | Tyr | Val | Ile | Thr | Lys | Ile | Asp | Phe | Thr | Lys | Lys |  |

| | | | | | | | | | | | | | | | | |
|---|---|---|---|---|---|---|---|---|---|---|---|---|---|---|---|---|
| 415 | | | | | 420 | | | | | 425 | | | | | 430 | |
| ATG | AAA | ACT | TTA | AGA | TAT | GAG | GTA | ACA | GCG | AAT | TTT | TAT | GAT | TCT | TCT | 1346 |
| Met | Lys | Thr | Leu | Arg | Tyr | Glu | Val | Thr | Ala | Asn | Phe | Tyr | Asp | Ser | Ser | |
| | | | | 435 | | | | | 440 | | | | | 445 | | |
| ACA | GGA | GAA | ATT | GAC | TTA | AAT | AAG | AAA | AAA | GTA | GAA | TCA | AGT | GAA | GCG | 1394 |
| Thr | Gly | Glu | Ile | Asp | Leu | Asn | Lys | Lys | Lys | Val | Glu | Ser | Ser | Glu | Ala | |
| | | | | 450 | | | | | 455 | | | | | 460 | | |
| GAG | TAT | AGA | ACG | TTA | AGT | GCT | AAT | GAT | GAT | GGG | GTG | TAT | ATG | CCG | TTA | 1442 |
| Glu | Tyr | Arg | Thr | Leu | Ser | Ala | Asn | Asp | Asp | Gly | Val | Tyr | Met | Pro | Leu | |
| | | 465 | | | | | 470 | | | | | 475 | | | | |
| GGT | GTC | ATC | AGT | GAA | ACA | TTT | TTG | ACT | CCG | ATT | AAT | GGG | TTT | GGC | CTC | 1490 |
| Gly | Val | Ile | Ser | Glu | Thr | Phe | Leu | Thr | Pro | Ile | Asn | Gly | Phe | Gly | Leu | |
| | | 480 | | | | | 485 | | | | | 490 | | | | |
| CAA | GCT | GAT | GAA | AAT | TCA | AGA | TTA | ATT | ACT | TTA | ACA | TGT | AAA | TCA | TAT | 1538 |
| Gln | Ala | Asp | Glu | Asn | Ser | Arg | Leu | Ile | Thr | Leu | Thr | Cys | Lys | Ser | Tyr | |
| 495 | | | | | 500 | | | | | 505 | | | | | 510 | |
| TTA | AGA | GAA | CTA | CTG | CTA | GCA | ACA | GAC | TTA | AGC | AAT | AAA | GAA | ACT | AAA | 1586 |
| Leu | Arg | Glu | Leu | Leu | Leu | Ala | Thr | Asp | Leu | Ser | Asn | Lys | Glu | Thr | Lys | |
| | | | | 515 | | | | | 520 | | | | | 525 | | |
| TTG | ATC | GTC | CCG | CCA | AGT | GGT | TTT | ATT | AGC | AAT | ATT | GTA | GAG | AAC | GGG | 1634 |
| Leu | Ile | Val | Pro | Pro | Ser | Gly | Phe | Ile | Ser | Asn | Ile | Val | Glu | Asn | Gly | |
| | | | 530 | | | | | 535 | | | | | 540 | | | |
| TCC | ATA | GAA | GAG | GAC | AAT | TTA | GAG | CCG | TGG | AAA | GCA | AAT | AAT | AAG | AAT | 1682 |
| Ser | Ile | Glu | Glu | Asp | Asn | Leu | Glu | Pro | Trp | Lys | Ala | Asn | Asn | Lys | Asn | |
| | | 545 | | | | | 550 | | | | | 555 | | | | |
| GCG | TAT | GTA | GAT | CAT | ACA | GGC | GGA | GTG | AAT | GGA | ACT | AAA | GCT | TTA | TAT | 1730 |
| Ala | Tyr | Val | Asp | His | Thr | Gly | Gly | Val | Asn | Gly | Thr | Lys | Ala | Leu | Tyr | |
| | | 560 | | | | | 565 | | | | | 570 | | | | |
| GTT | CAT | AAG | GAC | GGA | GGA | ATT | TCA | CAA | TTT | ATT | GGA | GAT | AAG | TTA | AAA | 1778 |
| Val | His | Lys | Asp | Gly | Gly | Ile | Ser | Gln | Phe | Ile | Gly | Asp | Lys | Leu | Lys | |
| 575 | | | | | 580 | | | | | 585 | | | | | 590 | |
| CCG | AAA | ACT | GAG | TAT | GTA | ATC | CAA | TAT | ACT | GTT | AAA | GGA | AAA | CCT | TCT | 1826 |
| Pro | Lys | Thr | Glu | Tyr | Val | Ile | Gln | Tyr | Thr | Val | Lys | Gly | Lys | Pro | Ser | |
| | | | | 595 | | | | | 600 | | | | | 605 | | |
| ATT | CAT | TTA | AAA | GAT | GAA | AAT | ACT | GGA | TAT | ATT | CAT | TAT | GAA | GAT | ACA | 1874 |
| Ile | His | Leu | Lys | Asp | Glu | Asn | Thr | Gly | Tyr | Ile | His | Tyr | Glu | Asp | Thr | |
| | | | 610 | | | | | 615 | | | | | 620 | | | |
| AAT | AAT | AAT | TTA | GAA | GAT | TAT | CAA | ACT | ATT | AAT | AAA | CGT | TTT | ACT | ACA | 1922 |
| Asn | Asn | Asn | Leu | Glu | Asp | Tyr | Gln | Thr | Ile | Asn | Lys | Arg | Phe | Thr | Thr | |
| | | 625 | | | | | 630 | | | | | 635 | | | | |
| GGA | ACT | GAT | TTA | AAG | GGA | GTG | TAT | TTA | ATT | TTA | AAA | AGT | CAA | AAT | GGA | 1970 |
| Gly | Thr | Asp | Leu | Lys | Gly | Val | Tyr | Leu | Ile | Leu | Lys | Ser | Gln | Asn | Gly | |
| | | 640 | | | | | 645 | | | | | 650 | | | | |
| GAT | GAA | GCT | TGG | GGA | GAT | AAC | TTT | ATT | ATT | TTG | GAA | ATT | AGT | CCT | TCT | 2018 |
| Asp | Glu | Ala | Trp | Gly | Asp | Asn | Phe | Ile | Ile | Leu | Glu | Ile | Ser | Pro | Ser | |
| 655 | | | | | 660 | | | | | 665 | | | | | 670 | |
| GAA | AAG | TTA | TTA | AGT | CCA | GAA | TTA | ATT | AAT | ACA | AAT | AAT | TGG | ACG | AGT | 2066 |
| Glu | Lys | Leu | Leu | Ser | Pro | Glu | Leu | Ile | Asn | Thr | Asn | Asn | Trp | Thr | Ser | |
| | | | | 675 | | | | | 680 | | | | | 685 | | |
| ACG | GGA | TCA | ACT | AAT | ATT | AGC | GGT | AAT | ACA | CTC | ACT | CTT | TAT | CAG | GGA | 2114 |
| Thr | Gly | Ser | Thr | Asn | Ile | Ser | Gly | Asn | Thr | Leu | Thr | Leu | Tyr | Gln | Gly | |
| | | | 690 | | | | | 695 | | | | | 700 | | | |
| GGA | CGA | GGG | ATT | CTA | AAA | CAA | AAC | CTT | CAA | TTA | GAT | AGT | TTT | TCA | ACT | 2162 |
| Gly | Arg | Gly | Ile | Leu | Lys | Gln | Asn | Leu | Gln | Leu | Asp | Ser | Phe | Ser | Thr | |
| | | 705 | | | | | 710 | | | | | 715 | | | | |
| TAT | AGA | GTG | TAT | TTT | TCT | GTG | TCC | GGA | GAT | GCT | AAT | GTA | AGG | ATT | AGA | 2210 |
| Tyr | Arg | Val | Tyr | Phe | Ser | Val | Ser | Gly | Asp | Ala | Asn | Val | Arg | Ile | Arg | |
| | | 720 | | | | | 725 | | | | | 730 | | | | |
| AAT | TCT | AGG | GAA | GTG | TTA | TTT | GAA | AAA | AGA | TAT | ATG | AGC | GGT | GCT | AAA | 2258 |
| Asn | Ser | Arg | Glu | Val | Leu | Phe | Glu | Lys | Arg | Tyr | Met | Ser | Gly | Ala | Lys | |

| | | | | | | | | | | | | | | | | |
|---|---|---|---|---|---|---|---|---|---|---|---|---|---|---|---|---|
|735| | | |740| | | |745| | | |750| | | | |
|GAT|GTT|TCT|GAA|ATG|TTC|ACT|ACA|AAA|TTT|GAG|AAA|GAT|AAC|TTT|TAT|2306|
|Asp|Val|Ser|Glu|Met|Phe|Thr|Thr|Lys|Phe|Glu|Lys|Asp|Asn|Phe|Tyr| |
| | | | |755| | | |760| | | | |765| | | |
|ATA|GAG|CTT|TCT|CAA|GGG|AAT|AAT|TTA|TAT|GGT|GGT|CCT|ATT|GTA|CAT|2354|
|Ile|Glu|Leu|Ser|Gln|Gly|Asn|Asn|Leu|Tyr|Gly|Gly|Pro|Ile|Val|His| |
| | | |770| | | |775| | | | |780| | | | |
|TTT|TAC|GAT|GTC|TCT|ATT|AAG|TAA| | | | | | | | |2378|
|Phe|Tyr|Asp|Val|Ser|Ile|Lys| | | | | | | | | | |
| | |785| | | | | | | | | | | | | | |

( 2 ) INFORMATION FOR SEQ ID NO:29:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Met  Asn  Lys  Asn  Asn  Thr  Lys  Leu  Ser  Thr  Arg  Ala  Leu  Pro  Ser  Phe
 1                   5                        10                       15

Ile  Asp  Tyr  Phe  Asn  Gly  Ile  Tyr  Gly  Phe  Ala  Thr  Gly  Ile  Lys  Asp
              20                       25                       30

Ile  Met  Asn  Met  Ile  Phe  Lys  Thr  Asp  Thr  Gly  Gly  Asp  Leu  Thr  Leu
         35                        40                       45

Asp  Glu  Ile  Leu  Lys  Asn  Gln  Gln  Leu  Leu  Asn  Asp  Ile  Ser  Gly  Lys
      50                       55                       60

Leu  Asp  Gly  Val  Asn  Gly  Ser  Leu  Asn  Asp  Leu  Ile  Ala  Gln  Gly  Asn
65                        70                       75                       80

Leu  Asn  Thr  Glu  Leu  Ser  Lys  Glu  Ile  Leu  Lys  Ile  Ala  Asn  Glu  Gln
                   85                       90                       95

Asn  Gln  Val  Leu  Asn  Asp  Val  Asn  Asn  Lys  Leu  Asp  Ala  Ile  Asn  Thr
              100                      105                      110

Met  Leu  Arg  Val  Tyr  Leu  Pro  Lys  Ile  Thr  Ser  Met  Leu  Ser  Asp  Val
         115                      120                      125

Met  Lys  Gln  Asn  Tyr  Ala  Leu  Ser  Leu  Gln  Ile  Glu  Tyr  Leu  Ser  Lys
     130                      135                      140

Gln  Leu  Gln  Glu  Ile  Ser  Asp  Lys  Leu  Asp  Ile  Ile  Asn  Val  Asn  Val
145                       150                      155                      160

Leu  Ile  Asn  Ser  Thr  Leu  Thr  Glu  Ile  Thr  Pro  Ala  Tyr  Gln  Arg  Ile
                    165                      170                      175

Lys  Tyr  Val  Asn  Glu  Lys  Phe  Glu  Glu  Leu  Thr  Phe  Ala  Thr  Glu  Thr
               180                      185                      190

Ser  Ser  Lys  Val  Lys  Lys  Asp  Gly  Ser  Pro  Ala  Asp  Ile  Leu  Asp  Glu
          195                      200                      205

Leu  Thr  Glu  Leu  Thr  Glu  Leu  Ala  Lys  Ser  Val  Thr  Lys  Asn  Asp  Val
     210                      215                      220

Asp  Gly  Phe  Glu  Phe  Tyr  Leu  Asn  Thr  Phe  His  Asp  Val  Met  Val  Gly
225                      230                      235                      240

Asn  Asn  Leu  Phe  Gly  Arg  Ser  Ala  Leu  Lys  Thr  Ala  Ser  Glu  Leu  Ile
               245                      250                      255

Thr  Lys  Glu  Asn  Val  Lys  Thr  Ser  Gly  Ser  Glu  Val  Gly  Asn  Val  Tyr
               260                      265                      270

Asn  Phe  Leu  Ile  Val  Leu  Thr  Ala  Leu  Gln  Ala  Gln  Ala  Phe  Leu  Thr
          275                      280                      285
```

-continued

| | | | | | | | | | | | | | | |
|---|---|---|---|---|---|---|---|---|---|---|---|---|---|---|
| Leu | Thr 290 | Thr | Cys | Arg | Lys | Leu 295 | Leu | Gly | Leu | Ala | Asp 300 | Ile | Asp | Tyr | Thr |
| Ser 305 | Ile | Met | Asn | Glu | His 310 | Leu | Asn | Lys | Glu | Lys 315 | Glu | Glu | Phe | Arg | Val 320 |
| Asn | Ile | Leu | Pro | Thr 325 | Leu | Ser | Asn | Thr | Phe 330 | Ser | Asn | Pro | Asn | Tyr 335 | Ala |
| Lys | Val | Lys | Gly 340 | Ser | Asp | Glu | Asp | Ala | Lys 345 | Met | Ile | Val | Glu 350 | Ala | Lys |
| Pro | Gly | His | Ala 355 | Leu | Ile | Gly | Phe 360 | Glu | Ile | Ser | Asn | Asp 365 | Ser | Ile | Thr |
| Val | Leu 370 | Lys | Val | Tyr | Glu | Ala 375 | Lys | Leu | Lys | Gln | Asn 380 | Tyr | Gln | Val | Asp |
| Lys 385 | Asp | Ser | Leu | Ser | Glu 390 | Val | Ile | Tyr | Gly | Asp 395 | Met | Asp | Lys | Leu | Leu 400 |
| Cys | Pro | Asp | Gln | Ser 405 | Glu | Gln | Ile | Tyr | Tyr 410 | Thr | Asn | Asn | Ile | Val 415 | Phe |
| Pro | Asn | Glu | Tyr 420 | Val | Ile | Thr | Lys | Ile 425 | Asp | Phe | Thr | Lys | Lys 430 | Met | Lys |
| Thr | Leu | Arg 435 | Tyr | Glu | Val | Thr | Ala 440 | Asn | Phe | Tyr | Asp | Ser 445 | Ser | Thr | Gly |
| Glu | Ile 450 | Asp | Leu | Asn | Lys | Lys 455 | Lys | Val | Glu | Ser | Ser 460 | Glu | Ala | Glu | Tyr |
| Arg 465 | Thr | Leu | Ser | Ala | Asn 470 | Asp | Asp | Gly | Val | Tyr 475 | Met | Pro | Leu | Gly | Val 480 |
| Ile | Ser | Glu | Thr | Phe 485 | Leu | Thr | Pro | Ile | Asn 490 | Gly | Phe | Gly | Leu | Gln 495 | Ala |
| Asp | Glu | Asn | Ser 500 | Arg | Leu | Ile | Thr | Leu 505 | Thr | Cys | Lys | Ser | Tyr 510 | Leu | Arg |
| Glu | Leu | Leu 515 | Leu | Ala | Thr | Asp | Leu 520 | Ser | Asn | Lys | Glu | Thr 525 | Lys | Leu | Ile |
| Val | Pro 530 | Pro | Ser | Gly | Phe | Ile 535 | Ser | Asn | Ile | Val | Glu 540 | Asn | Gly | Ser | Ile |
| Glu 545 | Glu | Asp | Asn | Leu | Glu 550 | Pro | Trp | Lys | Ala | Asn 555 | Asn | Lys | Asn | Ala | Tyr 560 |
| Val | Asp | His | Thr | Gly 565 | Gly | Val | Asn | Gly | Thr 570 | Lys | Ala | Leu | Tyr | Val 575 | His |
| Lys | Asp | Gly | Gly 580 | Ile | Ser | Gln | Phe | Ile 585 | Gly | Asp | Lys | Leu | Lys 590 | Pro | Lys |
| Thr | Glu | Tyr 595 | Val | Ile | Gln | Tyr | Thr 600 | Val | Lys | Gly | Lys | Pro 605 | Ser | Ile | His |
| Leu | Lys 610 | Asp | Glu | Asn | Thr | Gly 615 | Tyr | Ile | His | Tyr | Glu 620 | Asp | Thr | Asn | Asn |
| Asn 625 | Leu | Glu | Asp | Tyr | Gln 630 | Thr | Ile | Asn | Lys | Arg 635 | Phe | Thr | Thr | Gly | Thr 640 |
| Asp | Leu | Lys | Gly | Val 645 | Tyr | Leu | Ile | Leu | Lys 650 | Ser | Gln | Asn | Gly | Asp 655 | Glu |
| Ala | Trp | Gly | Asp 660 | Asn | Phe | Ile | Ile | Leu 665 | Glu | Ile | Ser | Pro | Ser 670 | Glu | Lys |
| Leu | Leu | Ser 675 | Pro | Glu | Leu | Ile | Asn 680 | Thr | Asn | Asn | Trp | Thr 685 | Ser | Thr | Gly |
| Ser | Thr 690 | Asn | Ile | Ser | Gly | Asn 695 | Thr | Leu | Thr | Leu | Tyr 700 | Gln | Gly | Gly | Arg |
| Gly 705 | Ile | Leu | Lys | Gln | Asn 710 | Leu | Gln | Leu | Asp | Ser 715 | Phe | Ser | Thr | Tyr | Arg 720 |

| Val | Tyr | Phe | Ser | Val | Ser | Gly | Asp | Ala | Asn | Val | Arg | Ile | Arg | Asn | Ser |
|-----|-----|-----|-----|-----|-----|-----|-----|-----|-----|-----|-----|-----|-----|-----|-----|
|     |     |     |     | 725 |     |     |     |     | 730 |     |     |     |     | 735 |     |

| Arg | Glu | Val | Leu | Phe | Glu | Lys | Arg | Tyr | Met | Ser | Gly | Ala | Lys | Asp | Val |
|-----|-----|-----|-----|-----|-----|-----|-----|-----|-----|-----|-----|-----|-----|-----|-----|
|     |     |     | 740 |     |     |     |     | 745 |     |     |     |     | 750 |     |     |

| Ser | Glu | Met | Phe | Thr | Thr | Lys | Phe | Glu | Lys | Asp | Asn | Phe | Tyr | Ile | Glu |
|-----|-----|-----|-----|-----|-----|-----|-----|-----|-----|-----|-----|-----|-----|-----|-----|
|     |     | 755 |     |     |     |     | 760 |     |     |     |     | 765 |     |     |     |

| Leu | Ser | Gln | Gly | Asn | Asn | Leu | Tyr | Gly | Gly | Pro | Ile | Val | His | Phe | Tyr |
|-----|-----|-----|-----|-----|-----|-----|-----|-----|-----|-----|-----|-----|-----|-----|-----|
|     | 770 |     |     |     |     | 775 |     |     |     |     | 780 |     |     |     |     |

| Asp | Val | Ser | Ile | Lys |
|-----|-----|-----|-----|-----|
| 785 |     |     |     |     |

( 2 ) INFORMATION FOR SEQ ID NO:30:

( i ) SEQUENCE CHARACTERISTICS:
        ( A ) LENGTH: 2403 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature
        ( B ) LOCATION: 11..2389
        ( D ) OTHER INFORMATION: /note= "maize optimized DNA
            sequence encoding VIP3A(a)"

( x i ) SEQUENCE DESCRIPTION: SEQ ID NO:30:

```
GGATCCACCA  ATGAACATGA  ACAAGAACAA  CACCAAGCTG  AGCACCCGCG  CCCTGCCGAG      60
CTTCATCGAC  TACTTCAACG  GCATCTACGG  CTTCGCCACC  GGCATCAAGG  ACATCATGAA     120
CATGATCTTC  AAGACCGACA  CCGGCGGCGA  CCTGACCCTG  GACGAGATCC  TGAAGAACCA     180
GCAGCTGCTG  AACGACATCA  GCGGCAAGCT  GGACGGCGTG  AACGGCAGCC  TGAACGACCT     240
GATCGCCCAG  GGCAACCTGA  ACACCGAGCT  GAGCAAGGAG  ATCCTTAAGA  TCGCCAACGA     300
GCAGAACCAG  GTGCTGAACG  ACGTGAACAA  CAAGCTGGAC  GCCATCAACA  CCATGCTGCG     360
CGTGTACCTG  CCGAAGATCA  CCAGCATGCT  GAGCGACGTG  ATGAAGCAGA  ACTACGCCCT     420
GAGCCTGCAG  ATCGAGTACC  TGAGCAAGCA  GCTGCAGGAG  ATCAGCGACA  GCTGGACAT      480
CATCAACGTG  AACGTCCTGA  TCAACAGCAC  CCTGACCGAG  ATCACCCCGG  CCTACCAGCG     540
CATCAAGTAC  GTGAACGAGA  AGTTCGAAGA  GCTGACCTTC  GCCACCGAGA  CCAGCAGCAA     600
GGTGAAGAAG  GACGGCAGCC  CGGCCGACAT  CCTGGACGAG  CTGACCGAGC  TGACCGAGCT     660
GGCCAAGAGC  GTGACCAAGA  ACGACGTGGA  CGGCTTCGAG  TTCTACCTGA  ACACCTTCCA     720
CGACGTGATG  GTGGGCAACA  ACCTGTTCGG  CCGCAGCGCC  CTGAAGACCG  CCAGCGAGCT     780
GATCACCAAG  GAGAACGTGA  AGACCAGCGG  CAGCGAGGTG  GGCAACGTGT  ACAACTTCCT     840
GATCGTGCTG  ACCGCCCTGC  AGGCCCAGGC  CTTCCTGACC  CTGACCACCT  GTCGCAAGCT     900
GCTGGGCCTG  GCCGACATCG  ACTACACCAG  CATCATGAAC  GAGCACTTGA  CAAGGAGAA     960
GGAGGAGTTC  CGCGTGAACA  TCCTGCCGAC  CCTGAGCAAC  ACCTTCAGCA  ACCCGAACTA    1020
CGCCAAGGTG  AAGGGCAGCG  ACGAGGACGC  CAAGATGATC  GTGGAGGCTA  AGCCGGGCCA    1080
CGCGTTGATC  GGCTTCGAGA  TCAGCAACGA  CAGCATCACC  GTGCTGAAGG  TGTACGAGGC    1140
CAAGCTGAAG  CAGAACTACC  AGGTGGACAA  GGACAGCTTG  AGCGAGGTGA  TCTACGGCGA    1200
CATGGACAAG  CTGCTGTGTC  CGGACCAGAG  CGAGCAAATC  TACTACACCA  ACAACATCGT    1260
```

-continued

| | | | | | |
|---|---|---|---|---|---|
| GTTCCCGAAC | GAGTACGTGA | TCACCAAGAT | CGACTTCACC | AAGAAGATGA | AGACCCTGCG | 1320 |
| CTACGAGGTG | ACCGCCAACT | TCTACGACAG | CAGCACCGGC | GAGATCGACC | TGAACAAGAA | 1380 |
| GAAGGTGGAG | AGCAGCGAGG | CCGAGTACCG | CACCCTGAGC | GCGAACGACG | ACGGCGTCTA | 1440 |
| CATGCCACTG | GGCGTGATCA | GCGAGACCTT | CCTGACCCCG | ATCAACGGCT | TTGGCCTGCA | 1500 |
| GGCCGACGAG | AACAGCCGCC | TGATCACCCT | GACCTGTAAG | AGCTACCTGC | GCGAGCTGCT | 1560 |
| GCTAGCCACC | GACCTGAGCA | ACAAGGAGAC | CAAGCTGATC | GTGCCACCGA | GCGGCTTCAT | 1620 |
| CAGCAACATC | GTGGAGAACG | GCAGCATCGA | GGAGGACAAC | CTGGAGCCGT | GGAAGGCCAA | 1680 |
| CAACAAGAAC | GCCTACGTGG | ACCACACCGG | CGGCGTGAAC | GGCACCAAGG | CCCTGTACGT | 1740 |
| GCACAAGGAC | GGCGGCATCA | GCCAGTTCAT | CGGCGACAAG | CTGAAGCCGA | AGACCGAGTA | 1800 |
| CGTGATCCAG | TACACCGTGA | AGGGCAAGCC | ATCGATTCAC | CTGAAGGACG | AGAACACCGG | 1860 |
| CTACATCCAC | TACGAGGACA | CCAACAACAA | CCTGGAGGAC | TACCAGACCA | TCAACAAGCG | 1920 |
| CTTCACCACC | GGCACCGACC | TGAAGGGCGT | GTACCTGATC | CTGAAGAGCC | AGAACGGCGA | 1980 |
| CGAGGCCTGG | GGCGACAACT | TCATCATCCT | GGAGATCAGC | CCGAGCGAGA | AGCTGCTGAG | 2040 |
| CCCGGAGCTG | ATCAACACCA | ACAACTGGAC | CAGCACCGGC | AGCACCAACA | TCAGCGGCAA | 2100 |
| CACCCTGACC | CTGTACCAGG | GCGGCCGCGG | CATCCTGAAG | CAGAACCTGC | AGCTGGACAG | 2160 |
| CTTCAGCACC | TACCGCGTGT | ACTTCAGCGT | GAGCGGCGAC | GCCAACGTGC | GCATCCGCAA | 2220 |
| CAGCCGCGAG | GTGCTGTTCG | AGAAGAGGTA | CATGAGCGGC | GCCAAGGACG | TGAGCGAGAT | 2280 |
| GTTCACCACC | AAGTTCGAGA | AGGACAACTT | CTACATCGAG | CTGAGCCAGG | GCAACAACCT | 2340 |
| GTACGGCGGC | CCGATCGTGC | ACTTCTACGA | CGTGAGCATC | AAGTTAACGT | AGAGCTCAGA | 2400 |
| TCT | | | | | | 2403 |

( 2 ) INFORMATION FOR SEQ ID NO:31:

( i ) SEQUENCE CHARACTERISTICS:
          ( A ) LENGTH: 2612 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i x ) FEATURE:
          ( A ) NAME/KEY: CDS
          ( B ) LOCATION: 118..2484
          ( D ) OTHER INFORMATION: /note= "Native DNA sequence
               encoding VIP3A(b) from AB424"

( x i ) SEQUENCE DESCRIPTION: SEQ ID NO:31:

```
ATTGAAATTG ATAAAAAGTT ATGAGTGTTT AATAATCAGT AATTACCAAT AAAGAATTAA     60
GAATACAAGT TTACAAGAAA TAAGTGTTAC AAAAAATAGC TGAAAAGGAA GATGAAC       117

ATG AAC AAG AAT AAT ACT AAA TTA AGC ACA AGA GCC TTA CCA AGT TTT      165
Met Asn Lys Asn Asn Thr Lys Leu Ser Thr Arg Ala Leu Pro Ser Phe
790                 795                 800                 805

ATT GAT TAT TTC AAT GGC ATT TAT GGA TTT GCC ACT GGT ATC AAA GAC      213
Ile Asp Tyr Phe Asn Gly Ile Tyr Gly Phe Ala Thr Gly Ile Lys Asp
                810                 815                 820

ATT ATG AAC ATG ATT TTT AAA ACG GAT ACA GGT GGT GAT CTA ACC CTA      261
Ile Met Asn Met Ile Phe Lys Thr Asp Thr Gly Gly Asp Leu Thr Leu
            825                 830                 835

GAC GAA ATT TTA AAG AAT CAG CAG CTA CTA AAT GAT ATT TCT GGT AAA      309
Asp Glu Ile Leu Lys Asn Gln Gln Leu Leu Asn Asp Ile Ser Gly Lys
        840                 845                 850
```

| | | | | | | | | | | | | | | | | |
|---|---|---|---|---|---|---|---|---|---|---|---|---|---|---|---|---|
|TTG|GAT|GGG|GTG|AAT|GGA|AGC|TTA|AAT|GAT|CTT|ATC|GCA|CAG|GGA|AAC|357|
|Leu|Asp|Gly|Val|Asn|Gly|Ser|Leu|Asn|Asp|Leu|Ile|Ala|Gln|Gly|Asn| |
|855| | | | |860| | | |865| | | | | | | |

|TTA|AAT|ACA|GAA|TTA|TCT|AAG|GAA|ATA|TTA|AAA|ATT|GCA|AAT|GAA|CAA|405|
|---|---|---|---|---|---|---|---|---|---|---|---|---|---|---|---|---|
|Leu|Asn|Thr|Glu|Leu|Ser|Lys|Glu|Ile|Leu|Lys|Ile|Ala|Asn|Glu|Gln| |
|870| | | | |875| | | |880| | | | | |885| |

|AAT|CAA|GTT|TTA|AAT|GAT|GTT|AAT|AAC|AAA|CTC|GAT|GCG|ATA|AAT|ACG|453|
|---|---|---|---|---|---|---|---|---|---|---|---|---|---|---|---|---|
|Asn|Gln|Val|Leu|Asn|Asp|Val|Asn|Asn|Lys|Leu|Asp|Ala|Ile|Asn|Thr| |
| | | | |890| | | |895| | | | |900| | | |

|ATG|CTT|CGG|GTA|TAT|CTA|CCT|AAA|ATT|ACC|TCT|ATG|TTG|AGT|GAT|GTA|501|
|---|---|---|---|---|---|---|---|---|---|---|---|---|---|---|---|---|
|Met|Leu|Arg|Val|Tyr|Leu|Pro|Lys|Ile|Thr|Ser|Met|Leu|Ser|Asp|Val| |
| | | |905| | | |910| | | | |915| | | | |

|ATG|AAA|CAA|AAT|TAT|GCG|CTA|AGT|CTG|CAA|ATA|GAA|TAC|TTA|AGT|AAA|549|
|---|---|---|---|---|---|---|---|---|---|---|---|---|---|---|---|---|
|Met|Lys|Gln|Asn|Tyr|Ala|Leu|Ser|Leu|Gln|Ile|Glu|Tyr|Leu|Ser|Lys| |
| | | |920| | | |925| | | | |930| | | | |

|CAA|TTG|CAA|GAG|ATT|TCT|GAT|AAG|TTG|GAT|ATT|ATT|AAT|GTA|AAT|GTA|597|
|---|---|---|---|---|---|---|---|---|---|---|---|---|---|---|---|---|
|Gln|Leu|Gln|Glu|Ile|Ser|Asp|Lys|Leu|Asp|Ile|Ile|Asn|Val|Asn|Val| |
|935| | | | |940| | | |945| | | | | | | |

|CTT|ATT|AAC|TCT|ACA|CTT|ACT|GAA|ATT|ACA|CCT|GCG|TAT|CAA|AGG|ATT|645|
|---|---|---|---|---|---|---|---|---|---|---|---|---|---|---|---|---|
|Leu|Ile|Asn|Ser|Thr|Leu|Thr|Glu|Ile|Thr|Pro|Ala|Tyr|Gln|Arg|Ile| |
|950| | | | |955| | | |960| | | | | |965| |

|AAA|TAT|GTG|AAC|GAA|AAA|TTT|GAG|GAA|TTA|ACT|TTT|GCT|ACA|GAA|ACT|693|
|---|---|---|---|---|---|---|---|---|---|---|---|---|---|---|---|---|
|Lys|Tyr|Val|Asn|Glu|Lys|Phe|Glu|Glu|Leu|Thr|Phe|Ala|Thr|Glu|Thr| |
| | | | |970| | | |975| | | | |980| | | |

|AGT|TCA|AAA|GTA|AAA|AAG|GAT|GGC|TCT|CCT|GCA|GAT|ATT|CGT|GAT|GAG|741|
|---|---|---|---|---|---|---|---|---|---|---|---|---|---|---|---|---|
|Ser|Ser|Lys|Val|Lys|Lys|Asp|Gly|Ser|Pro|Ala|Asp|Ile|Arg|Asp|Glu| |
| | | |985| | | |990| | | | |995| | | | |

|TTA|ACT|GAG|TTA|ACT|GAA|CTA|GCG|AAA|AGT|GTA|ACA|AAA|AAT|GAT|GTG|789|
|---|---|---|---|---|---|---|---|---|---|---|---|---|---|---|---|---|
|Leu|Thr|Glu|Leu|Thr|Glu|Leu|Ala|Lys|Ser|Val|Thr|Lys|Asn|Asp|Val| |
| | | |1000| | | |1005| | | | |1010| | | | |

|GAT|GGT|TTT|GAA|TTT|TAC|CTT|AAT|ACA|TTC|CAC|GAT|GTA|ATG|GTA|GGA|837|
|---|---|---|---|---|---|---|---|---|---|---|---|---|---|---|---|---|
|Asp|Gly|Phe|Glu|Phe|Tyr|Leu|Asn|Thr|Phe|His|Asp|Val|Met|Val|Gly| |
| | | |1015| | | |1020| | | | |1025| | | | |

|AAT|AAT|TTA|TTC|GGG|CGT|TCA|GCT|TTA|AAA|ACT|GCA|TCG|GAA|TTA|ATT|885|
|---|---|---|---|---|---|---|---|---|---|---|---|---|---|---|---|---|
|Asn|Asn|Leu|Phe|Gly|Arg|Ser|Ala|Leu|Lys|Thr|Ala|Ser|Glu|Leu|Ile| |
|1030| | | | |1035| | | |1040| | | | | |1045| |

|ACT|AAA|GAA|AAT|GTG|AAA|ACA|AGT|GGC|AGT|GAG|GTC|GGA|AAT|GTT|TAT|933|
|---|---|---|---|---|---|---|---|---|---|---|---|---|---|---|---|---|
|Thr|Lys|Glu|Asn|Val|Lys|Thr|Ser|Gly|Ser|Glu|Val|Gly|Asn|Val|Tyr| |
| | | | |1050| | | |1055| | | | |1060| | | |

|AAC|TTC|CTA|ATT|GTA|TTA|ACA|GCT|CTG|CAA|GCA|AAA|GCT|TTT|CTT|ACT|981|
|---|---|---|---|---|---|---|---|---|---|---|---|---|---|---|---|---|
|Asn|Phe|Leu|Ile|Val|Leu|Thr|Ala|Leu|Gln|Ala|Lys|Ala|Phe|Leu|Thr| |
| | | | |1065| | | |1070| | | | |1075| | | |

|TTA|ACA|CCA|TGC|CGA|AAA|TTA|TTA|GGC|TTA|GCA|GAT|ATT|GAT|TAT|ACT|1029|
|---|---|---|---|---|---|---|---|---|---|---|---|---|---|---|---|---|
|Leu|Thr|Pro|Cys|Arg|Lys|Leu|Leu|Gly|Leu|Ala|Asp|Ile|Asp|Tyr|Thr| |
| | | |1080| | | |1085| | | | |1090| | | | |

|TCT|ATT|ATG|AAT|GAA|CAT|TTA|AAT|AAG|GAA|AAA|GAG|GAA|TTT|AGA|GTA|1077|
|---|---|---|---|---|---|---|---|---|---|---|---|---|---|---|---|---|
|Ser|Ile|Met|Asn|Glu|His|Leu|Asn|Lys|Glu|Lys|Glu|Glu|Phe|Arg|Val| |
|1095| | | | |1100| | | |1105| | | | | | | |

|AAC|ATC|CTC|CCT|ACA|CTT|TCT|AAT|ACT|TTT|TCT|AAT|CCT|AAT|TAT|GCA|1125|
|---|---|---|---|---|---|---|---|---|---|---|---|---|---|---|---|---|
|Asn|Ile|Leu|Pro|Thr|Leu|Ser|Asn|Thr|Phe|Ser|Asn|Pro|Asn|Tyr|Ala| |
|1110| | | | |1115| | | |1120| | | | | |1125| |

|AAA|GTT|AAA|GGA|AGT|GAT|GAA|GAT|GCA|AAG|ATG|ATT|GTG|GAA|GCT|AAA|1173|
|---|---|---|---|---|---|---|---|---|---|---|---|---|---|---|---|---|
|Lys|Val|Lys|Gly|Ser|Asp|Glu|Asp|Ala|Lys|Met|Ile|Val|Glu|Ala|Lys| |
| | | | |1130| | | |1135| | | | |1140| | | |

|CCA|GGA|CAT|GCA|TTG|ATT|GGG|TTT|GAA|ATT|AGT|AAT|GAT|TCA|ATT|ACA|1221|
|---|---|---|---|---|---|---|---|---|---|---|---|---|---|---|---|---|
|Pro|Gly|His|Ala|Leu|Ile|Gly|Phe|Glu|Ile|Ser|Asn|Asp|Ser|Ile|Thr| |
| | | |1145| | | |1150| | | | |1155| | | | |

|GTA|TTA|AAA|GTA|TAT|GAG|GCT|AAG|CTA|AAA|CAA|AAT|TAT|CAA|GTC|GAT|1269|
|---|---|---|---|---|---|---|---|---|---|---|---|---|---|---|---|---|
|Val|Leu|Lys|Val|Tyr|Glu|Ala|Lys|Leu|Lys|Gln|Asn|Tyr|Gln|Val|Asp| |
| | | |1160| | | |1165| | | | |1170| | | | |

```
AAG GAT TCC TTA TCG GAA GTT ATT TAT GGC GAT ATG GAT AAA TTA TTG              1317
Lys Asp Ser Leu Ser Glu Val Ile Tyr Gly Asp Met Asp Lys Leu Leu
        1175            1180            1185

TGC CCA GAT CAA TCT GGA CAA ATC TAT TAT ACA AAT AAC ATA GTA TTT              1365
Cys Pro Asp Gln Ser Gly Gln Ile Tyr Tyr Thr Asn Asn Ile Val Phe
1190            1195            1200                1205

CCA AAT GAA TAT GTA ATT ACT AAA ATT GAT TTC ACT AAA AAA ATG AAA              1413
Pro Asn Glu Tyr Val Ile Thr Lys Ile Asp Phe Thr Lys Lys Met Lys
            1210            1215            1220

ACT TTA AGA TAT GAG GTA ACA GCG AAT TTT TAT GAT TCT TCT ACA GGA              1461
Thr Leu Arg Tyr Glu Val Thr Ala Asn Phe Tyr Asp Ser Ser Thr Gly
        1225            1230            1235

GAA ATT GAC TTA AAT AAG AAA AAA GTA GAA TCA AGT GAA GCG GAG TAT              1509
Glu Ile Asp Leu Asn Lys Lys Lys Val Glu Ser Ser Glu Ala Glu Tyr
            1240            1245            1250

AGA ACG TTA AGT GCT AAT GAT GAT GGG GTG TAT ATG CCG TTA GGT GTC              1557
Arg Thr Leu Ser Ala Asn Asp Asp Gly Val Tyr Met Pro Leu Gly Val
        1255            1260            1265

ATC AGT GAA ACA TTT TTG ACT CCG ATT AAT GGG TTT GGC CTC CAA GCT              1605
Ile Ser Glu Thr Phe Leu Thr Pro Ile Asn Gly Phe Gly Leu Gln Ala
1270            1275            1280            1285

GAT GAA AAT TCA AGA TTA ATT ACT TTA ACA TGT AAA TCA TAT TTA AGA              1653
Asp Glu Asn Ser Arg Leu Ile Thr Leu Thr Cys Lys Ser Tyr Leu Arg
            1290            1295            1300

GAA CTA CTG CTA GCA ACA GAC TTA AGC AAT AAA GAA ACT AAA TTG ATC              1701
Glu Leu Leu Leu Ala Thr Asp Leu Ser Asn Lys Glu Thr Lys Leu Ile
        1305            1310            1315

GTC CCG CCA AGT GGT TTT ATT AGC AAT ATT GTA GAG AAC GGG TCC ATA              1749
Val Pro Pro Ser Gly Phe Ile Ser Asn Ile Val Glu Asn Gly Ser Ile
        1320            1325            1330

GAA GAG GAC AAT TTA GAG CCG TGG AAA GCA AAT AAT AAG AAT GCG TAT              1797
Glu Glu Asp Asn Leu Glu Pro Trp Lys Ala Asn Asn Lys Asn Ala Tyr
1335            1340            1345

GTA GAT CAT ACA GGC GGA GTG AAT GGA ACT AAA GCT TTA TAT GTT CAT              1845
Val Asp His Thr Gly Gly Val Asn Gly Thr Lys Ala Leu Tyr Val His
1350            1355            1360            1365

AAG GAC GGA GGA ATT TCA CAA TTT ATT GGA GAT AAG TTA AAA CCG AAA              1893
Lys Asp Gly Gly Ile Ser Gln Phe Ile Gly Asp Lys Leu Lys Pro Lys
            1370            1375            1380

ACT GAG TAT GTA ATC CAA TAT ACT GTT AAA GGA AAA CCT TCT ATT CAT              1941
Thr Glu Tyr Val Ile Gln Tyr Thr Val Lys Gly Lys Pro Ser Ile His
        1385            1390            1395

TTA AAA GAT GAA AAT ACT GGA TAT ATT CAT TAT GAA GAT ACA AAT AAT              1989
Leu Lys Asp Glu Asn Thr Gly Tyr Ile His Tyr Glu Asp Thr Asn Asn
    1400            1405            1410

AAT TTA GAA GAT TAT CAA ACT ATT AAT AAA CGT TTT ACT ACA GGA ACT              2037
Asn Leu Glu Asp Tyr Gln Thr Ile Asn Lys Arg Phe Thr Thr Gly Thr
        1415            1420            1425

GAT TTA AAG GGA GTG TAT TTA ATT TTA AAA AGT CAA AAT GGA GAT GAA              2085
Asp Leu Lys Gly Val Tyr Leu Ile Leu Lys Ser Gln Asn Gly Asp Glu
1430            1435            1440            1445

GCT TGG GGA GAT AAC TTT ATT ATT TTG GAA ATT AGT CCT TCT GAA AAG              2133
Ala Trp Gly Asp Asn Phe Ile Ile Leu Glu Ile Ser Pro Ser Glu Lys
                1450            1455            1460

TTA TTA AGT CCA GAA TTA ATT AAT ACA AAT AAT TGG ACG AGT ACG GGA              2181
Leu Leu Ser Pro Glu Leu Ile Asn Thr Asn Asn Trp Thr Ser Thr Gly
            1465            1470            1475

TCA ACT AAT ATT AGC GGT AAT ACA CTC ACT CTT TAT CAG GGA GGA CGA              2229
Ser Thr Asn Ile Ser Gly Asn Thr Leu Thr Leu Tyr Gln Gly Gly Arg
        1480            1485            1490
```

```
GGG ATT CTA AAA CAA AAC CTT CAA TTA GAT AGT TTT TCA ACT TAT AGA      2277
Gly Ile Leu Lys Gln Asn Leu Gln Leu Asp Ser Phe Ser Thr Tyr Arg
1495                1500                1505

GTG TAT TTC TCT GTG TCC GGA GAT GCT AAT GTA AGG ATT AGA AAT TCT      2325
Val Tyr Phe Ser Val Ser Gly Asp Ala Asn Val Arg Ile Arg Asn Ser
1510                1515                1520                1525

AGG GAA GTG TTA TTT GAA AAA AGA TAT ATG AGC GGT GCT AAA GAT GTT      2373
Arg Glu Val Leu Phe Glu Lys Arg Tyr Met Ser Gly Ala Lys Asp Val
                1530                1535                1540

TCT GAA ATG TTC ACT ACA AAA TTT GAG AAA GAT AAC TTC TAT ATA GAG      2421
Ser Glu Met Phe Thr Thr Lys Phe Glu Lys Asp Asn Phe Tyr Ile Glu
            1545                1550                1555

CTT TCT CAA GGG AAT AAT TTA TAT GGT GGT CCT ATT GTA CAT TTT TAC      2469
Leu Ser Gln Gly Asn Asn Leu Tyr Gly Gly Pro Ile Val His Phe Tyr
        1560                1565                1570

GAT GTC TCT ATT AAG TAAGATCGGG ATCTAATATT AACAGTTTTT AGAAGCTAAT      2524
Asp Val Ser Ile Lys
    1575

TCTTGTATAA TGTCCTTGAT TATGGAAAAA CACAATTTTG TTTGCTAAGA TGTATATATA    2584

GCTCACTCAT TAAAAGGCAA TCAAGCTT                                       2612
```

(2) INFORMATION FOR SEQ ID NO:32:

(i) SEQUENCE CHARACTERISTICS:
    (A) LENGTH: 789 amino acids
    (B) TYPE: amino acid
    (D) TOPOLOGY: linear (ii) MOLECULE TYPE: protein (xi) SEQUENCE DESCRIPTION: SEQ ID NO:32:

```
Met Asn Lys Asn Asn Thr Lys Leu Ser Thr Arg Ala Leu Pro Ser Phe
 1               5                  10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Asp Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
                100                 105                 110

Met Leu Arg Val Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
        130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Arg Asp Glu
        195                 200                 205
```

| | | | | | | | | | | | | | | |
|---|---|---|---|---|---|---|---|---|---|---|---|---|---|---|
| Leu | Thr 210 | Glu | Leu | Thr | Glu 215 | Leu | Ala | Lys | Ser | Val | Thr 220 | Lys | Asn | Asp | Val |
| Asp 225 | Gly | Phe | Glu | Phe | Tyr 230 | Leu | Asn | Thr | Phe | His 235 | Asp | Val | Met | Val | Gly 240 |
| Asn | Asn | Leu | Phe | Gly 245 | Arg | Ser | Ala | Leu | Lys 250 | Thr | Ala | Ser | Glu | Leu 255 | Ile |
| Thr | Lys | Glu | Asn 260 | Val | Lys | Thr | Ser | Gly 265 | Ser | Glu | Val | Gly | Asn 270 | Val | Tyr |
| Asn | Phe | Leu 275 | Ile | Val | Leu | Thr | Ala 280 | Leu | Gln | Ala | Lys | Ala 285 | Phe | Leu | Thr |
| Leu | Thr 290 | Pro | Cys | Arg | Lys 295 | Leu | Leu | Gly | Leu | Ala 300 | Asp | Ile | Asp | Tyr | Thr |
| Ser 305 | Ile | Met | Asn | Glu | His 310 | Leu | Asn | Lys | Glu | Lys 315 | Glu | Glu | Phe | Arg | Val 320 |
| Asn | Ile | Leu | Pro | Thr 325 | Leu | Ser | Asn | Thr | Phe 330 | Ser | Asn | Pro | Asn | Tyr 335 | Ala |
| Lys | Val | Lys | Gly 340 | Ser | Asp | Glu | Asp | Ala 345 | Lys | Met | Ile | Val | Glu 350 | Ala | Lys |
| Pro | Gly | His 355 | Ala | Leu | Ile | Gly | Phe 360 | Glu | Ile | Ser | Asn | Asp 365 | Ser | Ile | Thr |
| Val | Leu 370 | Lys | Val | Tyr | Glu | Ala 375 | Lys | Leu | Lys | Gln | Asn 380 | Tyr | Gln | Val | Asp |
| Lys 385 | Asp | Ser | Leu | Ser | Glu 390 | Val | Ile | Tyr | Gly | Asp 395 | Met | Asp | Lys | Leu | Leu 400 |
| Cys | Pro | Asp | Gln | Ser 405 | Gly | Gln | Ile | Tyr | Tyr 410 | Thr | Asn | Asn | Ile | Val 415 | Phe |
| Pro | Asn | Glu | Tyr 420 | Val | Ile | Thr | Lys | Ile 425 | Asp | Phe | Thr | Lys | Lys 430 | Met | Lys |
| Thr | Leu | Arg 435 | Tyr | Glu | Val | Thr | Ala 440 | Asn | Phe | Tyr | Asp | Ser 445 | Ser | Thr | Gly |
| Glu | Ile 450 | Asp | Leu | Asn | Lys | Lys 455 | Lys | Val | Glu | Ser | Ser 460 | Glu | Ala | Glu | Tyr |
| Arg 465 | Thr | Leu | Ser | Ala | Asn 470 | Asp | Asp | Gly | Val | Tyr 475 | Met | Pro | Leu | Gly | Val 480 |
| Ile | Ser | Glu | Thr | Phe 485 | Leu | Thr | Pro | Ile | Asn 490 | Gly | Phe | Gly | Leu | Gln 495 | Ala |
| Asp | Glu | Asn | Ser 500 | Arg | Leu | Ile | Thr | Leu 505 | Thr | Cys | Lys | Ser | Tyr 510 | Leu | Arg |
| Glu | Leu | Leu 515 | Leu | Ala | Thr | Asp | Leu 520 | Ser | Asn | Lys | Glu | Thr 525 | Lys | Leu | Ile |
| Val | Pro 530 | Pro | Ser | Gly | Phe | Ile 535 | Ser | Asn | Ile | Val | Glu 540 | Asn | Gly | Ser | Ile |
| Glu 545 | Glu | Asp | Asn | Leu | Glu 550 | Pro | Trp | Lys | Ala | Asn 555 | Asn | Lys | Asn | Ala | Tyr 560 |
| Val | Asp | His | Thr | Gly 565 | Gly | Val | Asn | Gly | Thr 570 | Lys | Ala | Leu | Tyr | Val 575 | His |
| Lys | Asp | Gly | Gly 580 | Ile | Ser | Gln | Phe | Ile 585 | Gly | Asp | Lys | Leu | Lys 590 | Pro | Lys |
| Thr | Glu | Tyr 595 | Val | Ile | Gln | Tyr | Thr 600 | Val | Lys | Gly | Lys | Pro 605 | Ser | Ile | His |
| Leu | Lys 610 | Asp | Glu | Asn | Thr | Gly 615 | Tyr | Ile | His | Tyr | Glu 620 | Asp | Thr | Asn | Asn |
| Asn 625 | Leu | Glu | Asp | Tyr | Gln 630 | Thr | Ile | Asn | Lys | Arg 635 | Phe | Thr | Thr | Gly | Thr 640 |

| Asp | Leu | Lys | Gly | Val | Tyr | Leu | Ile | Leu | Lys | Ser | Gln | Asn | Gly | Asp | Glu |
|-----|-----|-----|-----|-----|-----|-----|-----|-----|-----|-----|-----|-----|-----|-----|-----|
|     |     |     |     | 645 |     |     |     |     | 650 |     |     |     |     | 655 |     |

| Ala | Trp | Gly | Asp | Asn | Phe | Ile | Ile | Leu | Glu | Ile | Ser | Pro | Ser | Glu | Lys |
|-----|-----|-----|-----|-----|-----|-----|-----|-----|-----|-----|-----|-----|-----|-----|-----|
|     |     |     | 660 |     |     |     |     | 665 |     |     |     |     | 670 |     |     |

| Leu | Leu | Ser | Pro | Glu | Leu | Ile | Asn | Thr | Asn | Asn | Trp | Ser | Thr | Thr | Gly |
|-----|-----|-----|-----|-----|-----|-----|-----|-----|-----|-----|-----|-----|-----|-----|-----|
|     |     | 675 |     |     |     |     | 680 |     |     |     |     | 685 |     |     |     |

| Ser | Thr | Asn | Ile | Ser | Gly | Asn | Thr | Leu | Thr | Leu | Tyr | Gln | Gly | Gly | Arg |
|-----|-----|-----|-----|-----|-----|-----|-----|-----|-----|-----|-----|-----|-----|-----|-----|
|     | 690 |     |     |     |     | 695 |     |     |     |     | 700 |     |     |     |     |

| Gly | Ile | Leu | Lys | Gln | Asn | Leu | Gln | Leu | Asp | Ser | Phe | Ser | Thr | Tyr | Arg |
|-----|-----|-----|-----|-----|-----|-----|-----|-----|-----|-----|-----|-----|-----|-----|-----|
| 705 |     |     |     |     | 710 |     |     |     |     | 715 |     |     |     |     | 720 |

| Val | Tyr | Phe | Ser | Val | Ser | Gly | Asp | Ala | Asn | Val | Arg | Ile | Arg | Asn | Ser |
|-----|-----|-----|-----|-----|-----|-----|-----|-----|-----|-----|-----|-----|-----|-----|-----|
|     |     |     |     | 725 |     |     |     |     | 730 |     |     |     |     | 735 |     |

| Arg | Glu | Val | Leu | Phe | Glu | Lys | Arg | Tyr | Met | Ser | Gly | Ala | Lys | Asp | Val |
|-----|-----|-----|-----|-----|-----|-----|-----|-----|-----|-----|-----|-----|-----|-----|-----|
|     |     |     | 740 |     |     |     |     | 745 |     |     |     |     | 750 |     |     |

| Ser | Glu | Met | Phe | Thr | Thr | Lys | Phe | Glu | Lys | Asp | Asn | Phe | Tyr | Ile | Glu |
|-----|-----|-----|-----|-----|-----|-----|-----|-----|-----|-----|-----|-----|-----|-----|-----|
|     |     | 755 |     |     |     |     | 760 |     |     |     |     | 765 |     |     |     |

| Leu | Ser | Gln | Gly | Asn | Asn | Leu | Tyr | Gly | Gly | Pro | Ile | Val | His | Phe | Tyr |
|-----|-----|-----|-----|-----|-----|-----|-----|-----|-----|-----|-----|-----|-----|-----|-----|
|     | 770 |     |     |     |     | 775 |     |     |     |     | 780 |     |     |     |     |

| Asp | Val | Ser | Ile | Lys |
|-----|-----|-----|-----|-----|
| 785 |     |     |     |     |

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "forward primer used to make
            pCIB5526"

( i i i ) HYPOTHETICAL: NO ( x i ) SEQUENCE DESCRIPTION: SEQ ID NO:33:

GGATCCACCA TGAAGACCAA CCAGATCAGC                              30

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "reverse primer used to make
            pCIB5526"

( i i i ) HYPOTHETICAL: NO ( x i ) SEQUENCE DESCRIPTION: SEQ ID NO:34:

AAGCTTCAGC TCCTT                                            15

( 2 ) INFORMATION FOR SEQ ID NO:35:

( i ) SEQUENCE CHARACTERISTICS:
        ( A ) LENGTH: 2576 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

(iii) HYPOTHETICAL: NO (ix) FEATURE:
(A) NAME/KEY: CDS
(B) LOCATION: 9..2564
(D) OTHER INFORMATION: /note= "Maize optimized sequence encoding VIP1A(a) with the Bacillus secretion signal removed as contained in pCIB5526"

( x i ) SEQUENCE DESCRIPTION: SEQ ID NO:35:

```
GATCCACC ATG AAG ACC AAC CAG ATC AGC ACC ACC CAG AAG AAC CAG CAG       50
         Met Lys Thr Asn Gln Ile Ser Thr Thr Gln Lys Asn Gln Gln
                     825                 830                 835

AAG GAG ATG GAC CGC AAG GGC CTG CTG GGC TAC TAC TTC AAG GGC AAG        98
Lys Glu Met Asp Arg Lys Gly Leu Leu Gly Tyr Tyr Phe Lys Gly Lys
                840                 845                 850

GAC TTC AGC AAC CTG ACC ATG TTC GCC CCC ACG CGT GAC AGC ACC CTG       146
Asp Phe Ser Asn Leu Thr Met Phe Ala Pro Thr Arg Asp Ser Thr Leu
            855                 860                 865

ATC TAC GAC CAG CAG ACC GCC AAC AAG CTG CTG GAC AAG AAG CAG CAG       194
Ile Tyr Asp Gln Gln Thr Ala Asn Lys Leu Leu Asp Lys Lys Gln Gln
        870                 875                 880

GAG TAC CAG AGC ATC CGC TGG ATC GGC CTG ATC CAG AGC AAG GAG ACC       242
Glu Tyr Gln Ser Ile Arg Trp Ile Gly Leu Ile Gln Ser Lys Glu Thr
    885                 890                 895

GGC GAC TTC ACC TTC AAC CTG AGC GAG GAC GAG CAG GCC ATC ATC GAG       290
Gly Asp Phe Thr Phe Asn Leu Ser Glu Asp Glu Gln Ala Ile Ile Glu
900                 905                 910                 915

ATC AAC GGC AAG ATC ATC AGC AAC AAG GGC AAG GAG AAG CAG GTG GTG       338
Ile Asn Gly Lys Ile Ile Ser Asn Lys Gly Lys Glu Lys Gln Val Val
                920                 925                 930

CAC CTG GAG AAG GGC AAG CTG GTG CCC ATC AAG ATC GAG TAC CAG AGC       386
His Leu Glu Lys Gly Lys Leu Val Pro Ile Lys Ile Glu Tyr Gln Ser
            935                 940                 945

GAC ACC AAG TTC AAC ATC GAC AGC AAG ACC TTC AAG GAG CTG AAG CTT       434
Asp Thr Lys Phe Asn Ile Asp Ser Lys Thr Phe Lys Glu Leu Lys Leu
        950                 955                 960

TTC AAG ATC GAC AGC CAG AAC CAG CCC CAG CAG GTG CAG CAG GAC GAG       482
Phe Lys Ile Asp Ser Gln Asn Gln Pro Gln Gln Val Gln Gln Asp Glu
    965                 970                 975

CTG CGC AAC CCC GAG TTC AAC AAG AAG GAG AGC CAG GAG TTC CTG GCC       530
Leu Arg Asn Pro Glu Phe Asn Lys Lys Glu Ser Gln Glu Phe Leu Ala
980                 985                 990                 995

AAG CCC AGC AAG ATC AAC CTG TTC ACC CAG CAG ATG AAG CGC GAG ATC       578
Lys Pro Ser Lys Ile Asn Leu Phe Thr Gln Gln Met Lys Arg Glu Ile
                1000                1005                1010

GAC GAG GAC ACC GAC ACC GAC GGC GAC AGC ATC CCC GAC CTG TGG GAG       626
Asp Glu Asp Thr Asp Thr Asp Gly Asp Ser Ile Pro Asp Leu Trp Glu
            1015                1020                1025

GAG AAC GGC TAC ACC ATC CAG AAC CGC ATC GCC GTG AAG TGG GAC GAC       674
Glu Asn Gly Tyr Thr Ile Gln Asn Arg Ile Ala Val Lys Trp Asp Asp
        1030                1035                1040

AGC CTG GCT AGC AAG GGC TAC ACC AAG TTC GTG AGC AAC CCC CTG GAG       722
Ser Leu Ala Ser Lys Gly Tyr Thr Lys Phe Val Ser Asn Pro Leu Glu
    1045                1050                1055

AGC CAC ACC GTG GGC GAC CCC TAC ACC GAC TAC GAG AAG GCC GCC CGC       770
Ser His Thr Val Gly Asp Pro Tyr Thr Asp Tyr Glu Lys Ala Ala Arg
1060                1065                1070                1075

GAC CTG GAC CTG AGC AAC GCC AAG GAG ACC TTC AAC CCC CTG GTG GCC       818
Asp Leu Asp Leu Ser Asn Ala Lys Glu Thr Phe Asn Pro Leu Val Ala
                1080                1085                1090
```

| | | | | | | | | | | | | | | | | |
|---|---|---|---|---|---|---|---|---|---|---|---|---|---|---|---|---|
| GCC | TTC | CCC | AGC | GTG | AAC | GTG | AGC | ATG | GAG | AAG | GTG | ATC | CTG | AGC | CCC | 866 |
| Ala | Phe | Pro | Ser 1095 | Val | Asn | Val | Ser | Met 1100 | Glu | Lys | Val | Ile | Leu 1105 | Ser | Pro | |
| AAC | GAG | AAC | CTG | AGC | AAC | AGC | GTG | GAG | AGC | CAC | TCG | AGC | ACC | AAC | TGG | 914 |
| Asn | Glu | Asn | Leu 1110 | Ser | Asn | Ser | Val | Glu 1115 | Ser | His | Ser | Ser | Thr 1120 | Asn | Trp | |
| AGC | TAC | ACC | AAC | ACC | GAG | GGC | GCC | AGC | GTG | GAG | GCC | GGC | ATC | GGT | CCC | 962 |
| Ser | Tyr | Thr | Asn 1125 | Thr | Glu | Gly | Ala | Ser 1130 | Val | Glu | Ala | Gly | Ile 1135 | Gly | Pro | |
| AAG | GGC | ATC | AGC | TTC | GGC | GTG | AGC | GTG | AAC | TAC | CAG | CAC | AGC | GAG | ACC | 1010 |
| Lys | Gly | Ile | Ser 1140 | Phe | Gly | Val | Ser | Val 1145 | Asn | Tyr | Gln | His | Ser 1150 | Glu | Thr 1155 | |
| GTG | GCC | CAG | GAG | TGG | GGC | ACC | AGC | ACC | GGC | AAC | ACC | AGC | CAG | TTC | AAC | 1058 |
| Val | Ala | Gln | Glu | Trp | Gly | Thr | Ser | Thr | Gly | Asn | Thr | Ser | Gln | Phe | Asn | |
| | | | | | | 1160 | | | | | 1165 | | | | 1170 | |
| ACC | GCC | AGC | GCC | GGC | TAC | CTG | AAC | GCC | AAC | GTG | CGC | TAC | AAC | AAC | GTG | 1106 |
| Thr | Ala | Ser | Ala 1175 | Gly | Tyr | Leu | Asn | Ala 1180 | Asn | Val | Arg | Tyr | Asn 1185 | Asn | Val | |
| GGC | ACC | GGC | GCC | ATC | TAC | GAC | GTG | AAG | CCC | ACC | ACC | AGC | TTC | GTG | CTG | 1154 |
| Gly | Thr | Gly | Ala 1190 | Ile | Tyr | Asp | Val | Lys 1195 | Pro | Thr | Thr | Ser | Phe 1200 | Val | Leu | |
| AAC | AAC | GAC | ACC | ATC | GCC | ACC | ATC | ACC | GCC | AAG | TCG | AAT | TCC | ACC | GCC | 1202 |
| Asn | Asn | Asp | Thr 1205 | Ile | Ala | Thr | Ile | Thr 1210 | Ala | Lys | Ser | Asn | Ser 1215 | Thr | Ala | |
| CTG | AAC | ATC | AGC | CCC | GGC | GAG | AGC | TAC | CCC | AAG | AAG | GGC | CAG | AAC | GGC | 1250 |
| Leu | Asn | Ile | Ser | Pro | Gly | Glu | Ser | Tyr | Pro | Lys | Lys | Gly | Gln | Asn | Gly | |
| 1220 | | | | | 1225 | | | | | 1230 | | | | | 1235 | |
| ATC | GCC | ATC | ACC | AGC | ATG | GAC | GAC | TTC | AAC | AGC | CAC | CCC | ATC | ACC | CTG | 1298 |
| Ile | Ala | Ile | Thr | Ser | Met | Asp | Asp | Phe | Asn | Ser | His | Pro | Ile | Thr | Leu | |
| | | | 1240 | | | | | 1245 | | | | | 1250 | | | |
| AAC | AAG | AAG | CAG | GTG | GAC | AAC | CTG | CTG | AAC | AAC | AAG | CCC | ATG | ATG | CTG | 1346 |
| Asn | Lys | Lys | Gln | Val | Asp | Asn | Leu | Leu | Asn | Asn | Lys | Pro | Met | Met | Leu | |
| | | | 1255 | | | | | 1260 | | | | | 1265 | | | |
| GAG | ACC | AAC | CAG | ACC | GAC | GGC | GTC | TAC | AAG | ATC | AAG | GAC | ACC | CAC | GGC | 1394 |
| Glu | Thr | Asn | Gln | Thr | Asp | Gly | Val | Tyr | Lys | Ile | Lys | Asp | Thr | His | Gly | |
| | | | 1270 | | | | | 1275 | | | | | 1280 | | | |
| AAC | ATC | GTG | ACG | GGC | GGC | GAG | TGG | AAC | GGC | GTG | ATC | CAG | CAG | ATC | AAG | 1442 |
| Asn | Ile | Val | Thr | Gly | Gly | Glu | Trp | Asn | Gly | Val | Ile | Gln | Gln | Ile | Lys | |
| | 1285 | | | | | 1290 | | | | | 1295 | | | | | |
| GCC | AAG | ACC | GCC | AGC | ATC | ATC | GTC | GAC | GAC | GGC | GAG | CGC | GTG | GCC | GAG | 1490 |
| Ala | Lys | Thr | Ala | Ser | Ile | Ile | Val | Asp | Asp | Gly | Glu | Arg | Val | Ala | Glu | |
| 1300 | | | | | 1305 | | | | | 1310 | | | | | 1315 | |
| AAG | CGC | GTG | GCC | GCC | AAG | GAC | TAC | GAG | AAC | CCC | GAG | GAC | AAG | ACC | CCC | 1538 |
| Lys | Arg | Val | Ala | Ala | Lys | Asp | Tyr | Glu | Asn | Pro | Glu | Asp | Lys | Thr | Pro | |
| | | | 1320 | | | | | 1325 | | | | | 1330 | | | |
| AGC | CTG | ACC | CTG | AAG | GAC | GCC | CTG | AAG | CTG | AGC | TAC | CCC | GAC | GAG | ATC | 1586 |
| Ser | Leu | Thr | Leu | Lys | Asp | Ala | Leu | Lys | Leu | Ser | Tyr | Pro | Asp | Glu | Ile | |
| | | | 1335 | | | | | 1340 | | | | | 1345 | | | |
| AAG | GAG | ATC | GAG | GGC | TTG | CTG | TAC | TAC | AAG | AAC | AAG | CCC | ATC | TAC | GAG | 1634 |
| Lys | Glu | Ile | Glu | Gly | Leu | Leu | Tyr | Tyr | Lys | Asn | Lys | Pro | Ile | Tyr | Glu | |
| | | | 1350 | | | | | 1355 | | | | | 1360 | | | |
| AGC | AGC | GTG | ATG | ACC | TAT | CTA | GAC | GAG | AAC | ACC | GCC | AAG | GAG | GTG | ACC | 1682 |
| Ser | Ser | Val | Met | Thr | Tyr | Leu | Asp | Glu | Asn | Thr | Ala | Lys | Glu | Val | Thr | |
| | | | 1365 | | | | | 1370 | | | | | 1375 | | | |
| AAG | CAG | CTG | AAC | GAC | ACC | ACC | GGC | AAG | TTC | AAG | GAC | GTG | AGC | CAC | CTG | 1730 |
| Lys | Gln | Leu | Asn | Asp | Thr | Thr | Gly | Lys | Phe | Lys | Asp | Val | Ser | His | Leu | |
| 1380 | | | | | 1385 | | | | | 1390 | | | | | 1395 | |
| TAC | GAC | GTG | AAG | CTG | ACC | CCC | AAG | ATG | AAC | GTG | ACC | ATC | AAG | CTG | AGC | 1778 |
| Tyr | Asp | Val | Lys | Leu | Thr | Pro | Lys | Met | Asn | Val | Thr | Ile | Lys | Leu | Ser | |
| | | | 1400 | | | | | 1405 | | | | | 1410 | | | |

| | | | | | | | | | | | | | | | | |
|---|---|---|---|---|---|---|---|---|---|---|---|---|---|---|---|---|
| ATC | CTG | TAC | GAC | AAC | GCC | GAG | AGC | AAC | GAC | AAC | AGC | ATC | GGC | AAG | TGG | 1826 |
| Ile | Leu | Tyr | Asp | Asn | Ala | Glu | Ser | Asn | Asp | Asn | Ser | Ile | Gly | Lys | Trp | |
| | | | 1415 | | | | 1420 | | | | | 1425 | | | | |
| ACC | AAC | ACC | AAC | ATC | GTG | AGC | GGC | GGC | AAC | AAC | GGC | AAG | AAG | CAG | TAC | 1874 |
| Thr | Asn | Thr | Asn | Ile | Val | Ser | Gly | Gly | Asn | Asn | Gly | Lys | Lys | Gln | Tyr | |
| | | 1430 | | | | | 1435 | | | | | 1440 | | | | |
| AGC | AGC | AAC | AAC | CCC | GAC | GCC | AAC | CTG | ACC | CTG | AAC | ACC | GAC | GCC | CAG | 1922 |
| Ser | Ser | Asn | Asn | Pro | Asp | Ala | Asn | Leu | Thr | Leu | Asn | Thr | Asp | Ala | Gln | |
| | 1445 | | | | 1450 | | | | | 1455 | | | | | | |
| GAG | AAG | CTG | AAC | AAG | AAC | CGC | GAC | TAC | TAC | ATC | AGC | CTG | TAC | ATG | AAG | 1970 |
| Glu | Lys | Leu | Asn | Lys | Asn | Arg | Asp | Tyr | Tyr | Ile | Ser | Leu | Tyr | Met | Lys | |
| 1460 | | | | | 1465 | | | | | 1470 | | | | | 1475 | |
| AGC | GAG | AAG | AAC | ACC | CAG | TGC | GAG | ATC | ACC | ATC | GAC | GGC | GAG | ATA | TAC | 2018 |
| Ser | Glu | Lys | Asn | Thr | Gln | Cys | Glu | Ile | Thr | Ile | Asp | Gly | Glu | Ile | Tyr | |
| | | | | 1480 | | | | | 1485 | | | | | 1490 | | |
| CCC | ATC | ACC | ACC | AAG | ACC | GTG | AAC | GTG | AAC | AAG | GAC | AAC | TAC | AAG | CGC | 2066 |
| Pro | Ile | Thr | Thr | Lys | Thr | Val | Asn | Val | Asn | Lys | Asp | Asn | Tyr | Lys | Arg | |
| | | | 1495 | | | | | 1500 | | | | | 1505 | | | |
| CTG | GAC | ATC | ATC | GCC | CAC | AAC | ATC | AAG | AGC | AAC | CCC | ATC | AGC | AGC | CTG | 2114 |
| Leu | Asp | Ile | Ile | Ala | His | Asn | Ile | Lys | Ser | Asn | Pro | Ile | Ser | Ser | Leu | |
| | | 1510 | | | | | 1515 | | | | | 1520 | | | | |
| CAC | ATC | AAG | ACC | AAC | GAC | GAG | ATC | ACC | CTG | TTC | TGG | GAC | GAC | ATA | TCG | 2162 |
| His | Ile | Lys | Thr | Asn | Asp | Glu | Ile | Thr | Leu | Phe | Trp | Asp | Asp | Ile | Ser | |
| | 1525 | | | | | 1530 | | | | | 1535 | | | | | |
| ATT | ACC | GAC | GTC | GCC | AGC | ATC | AAG | CCC | GAG | AAC | CTG | ACC | GAC | AGC | GAG | 2210 |
| Ile | Thr | Asp | Val | Ala | Ser | Ile | Lys | Pro | Glu | Asn | Leu | Thr | Asp | Ser | Glu | |
| 1540 | | | | | 1545 | | | | | 1550 | | | | | 1555 | |
| ATC | AAG | CAG | ATA | TAC | AGT | CGC | TAC | GGC | ATC | AAG | CTG | GAG | GAC | GGC | ATC | 2258 |
| Ile | Lys | Gln | Ile | Tyr | Ser | Arg | Tyr | Gly | Ile | Lys | Leu | Glu | Asp | Gly | Ile | |
| | | | | 1560 | | | | | 1565 | | | | | 1570 | | |
| CTG | ATC | GAC | AAG | AAA | GGC | GGC | ATC | CAC | TAC | GGC | GAG | TTC | ATC | AAC | GAG | 2306 |
| Leu | Ile | Asp | Lys | Lys | Gly | Gly | Ile | His | Tyr | Gly | Glu | Phe | Ile | Asn | Glu | |
| | | | 1575 | | | | | 1580 | | | | | 1585 | | | |
| GCC | AGC | TTC | AAC | ATC | GAG | CCC | CTG | CAG | AAC | TAC | GTG | ACC | AAG | TAC | GAG | 2354 |
| Ala | Ser | Phe | Asn | Ile | Glu | Pro | Leu | Gln | Asn | Tyr | Val | Thr | Lys | Tyr | Glu | |
| | | 1590 | | | | | 1595 | | | | | 1600 | | | | |
| GTG | ACC | TAC | AGC | AGC | GAG | CTG | GGC | CCC | AAC | GTG | AGC | GAC | ACC | CTG | GAG | 2402 |
| Val | Thr | Tyr | Ser | Ser | Glu | Leu | Gly | Pro | Asn | Val | Ser | Asp | Thr | Leu | Glu | |
| | 1605 | | | | | 1610 | | | | | 1615 | | | | | |
| AGC | GAC | AAG | ATT | TAC | AAG | GAC | GGC | ACC | ATC | AAG | TTC | GAC | TTC | ACC | AAG | 2450 |
| Ser | Asp | Lys | Ile | Tyr | Lys | Asp | Gly | Thr | Ile | Lys | Phe | Asp | Phe | Thr | Lys | |
| 1620 | | | | | 1625 | | | | | 1630 | | | | | 1635 | |
| TAC | AGC | AAG | AAC | GAG | CAG | GGC | CTG | TTC | TAC | GAC | AGC | GGC | CTG | AAC | TGG | 2498 |
| Tyr | Ser | Lys | Asn | Glu | Gln | Gly | Leu | Phe | Tyr | Asp | Ser | Gly | Leu | Asn | Trp | |
| | | | | 1640 | | | | | 1645 | | | | | 1650 | | |
| GAC | TTC | AAG | ATC | AAC | GCC | ATC | ACC | TAC | GAC | GGC | AAG | GAG | ATG | AAC | GTG | 2546 |
| Asp | Phe | Lys | Ile | Asn | Ala | Ile | Thr | Tyr | Asp | Gly | Lys | Glu | Met | Asn | Val | |
| | | | 1655 | | | | | 1660 | | | | | 1665 | | | |
| TTC | CAC | CGC | TAC | AAC | AAG | TAGATCTGAG | CT | | | | | | | | | 2576 |
| Phe | His | Arg | Tyr | Asn | Lys | | | | | | | | | | | |
| | | 1670 | | | | | | | | | | | | | | |

( 2 ) INFORMATION FOR SEQ ID NO:36:

( i ) SEQUENCE CHARACTERISTICS:
        ( A ) LENGTH: 852 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Met  Lys  Thr  Asn  Gln  Ile  Ser  Thr  Thr  Gln  Lys  Asn  Gln  Gln  Lys  Glu
 1              5                        10                       15

Met  Asp  Arg  Lys  Gly  Leu  Leu  Gly  Tyr  Tyr  Phe  Lys  Gly  Lys  Asp  Phe
              20                        25                       30

Ser  Asn  Leu  Thr  Met  Phe  Ala  Pro  Thr  Arg  Asp  Ser  Thr  Leu  Ile  Tyr
              35                        40                       45

Asp  Gln  Gln  Thr  Ala  Asn  Lys  Leu  Leu  Asp  Lys  Lys  Gln  Gln  Glu  Tyr
         50                        55                       60

Gln  Ser  Ile  Arg  Trp  Ile  Gly  Leu  Ile  Gln  Ser  Lys  Glu  Thr  Gly  Asp
 65                        70                       75                       80

Phe  Thr  Phe  Asn  Leu  Ser  Glu  Asp  Glu  Gln  Ala  Ile  Ile  Glu  Ile  Asn
              85                        90                       95

Gly  Lys  Ile  Ile  Ser  Asn  Lys  Gly  Lys  Glu  Lys  Gln  Val  Val  His  Leu
             100                       105                      110

Glu  Lys  Gly  Lys  Leu  Val  Pro  Ile  Lys  Ile  Glu  Tyr  Gln  Ser  Asp  Thr
             115                       120                      125

Lys  Phe  Asn  Ile  Asp  Ser  Lys  Thr  Phe  Lys  Glu  Leu  Lys  Leu  Phe  Lys
         130                       135                      140

Ile  Asp  Ser  Gln  Asn  Gln  Pro  Gln  Gln  Val  Gln  Gln  Asp  Glu  Leu  Arg
145                       150                      155                      160

Asn  Pro  Glu  Phe  Asn  Lys  Lys  Glu  Ser  Gln  Glu  Phe  Leu  Ala  Lys  Pro
             165                       170                      175

Ser  Lys  Ile  Asn  Leu  Phe  Thr  Gln  Gln  Met  Lys  Arg  Glu  Ile  Asp  Glu
             180                       185                      190

Asp  Thr  Asp  Thr  Asp  Gly  Asp  Ser  Ile  Pro  Asp  Leu  Trp  Glu  Glu  Asn
         195                       200                      205

Gly  Tyr  Thr  Ile  Gln  Asn  Arg  Ile  Ala  Val  Lys  Trp  Asp  Asp  Ser  Leu
         210                       215                      220

Ala  Ser  Lys  Gly  Tyr  Thr  Lys  Phe  Val  Ser  Asn  Pro  Leu  Glu  Ser  His
225                       230                      235                      240

Thr  Val  Gly  Asp  Pro  Tyr  Thr  Asp  Tyr  Glu  Lys  Ala  Ala  Arg  Asp  Leu
             245                       250                      255

Asp  Leu  Ser  Asn  Ala  Lys  Glu  Thr  Phe  Asn  Pro  Leu  Val  Ala  Ala  Phe
             260                       265                      270

Pro  Ser  Val  Asn  Val  Ser  Met  Glu  Lys  Val  Ile  Leu  Ser  Pro  Asn  Glu
             275                       280                      285

Asn  Leu  Ser  Asn  Ser  Val  Glu  Ser  His  Ser  Ser  Thr  Asn  Trp  Ser  Tyr
             290                       295                      300

Thr  Asn  Thr  Glu  Gly  Ala  Ser  Val  Glu  Ala  Gly  Ile  Gly  Pro  Lys  Gly
305                       310                      315                      320

Ile  Ser  Phe  Gly  Val  Ser  Val  Asn  Tyr  Gln  His  Ser  Glu  Thr  Val  Ala
             325                       330                      335

Gln  Glu  Trp  Gly  Thr  Ser  Thr  Gly  Asn  Thr  Ser  Gln  Phe  Asn  Thr  Ala
             340                       345                      350

Ser  Ala  Gly  Tyr  Leu  Asn  Ala  Asn  Val  Arg  Tyr  Asn  Asn  Val  Gly  Thr
             355                       360                      365

Gly  Ala  Ile  Tyr  Asp  Val  Lys  Pro  Thr  Thr  Ser  Phe  Val  Leu  Asn  Asn
             370                       375                      380

Asp  Thr  Ile  Ala  Thr  Ile  Thr  Ala  Lys  Ser  Asn  Ser  Thr  Ala  Leu  Asn
385                       390                      395                      400

Ile  Ser  Pro  Gly  Glu  Ser  Tyr  Pro  Lys  Lys  Gly  Gln  Asn  Gly  Ile  Ala
             405                       410                      415

Ile  Thr  Ser  Met  Asp  Asp  Phe  Asn  Ser  His  Pro  Ile  Thr  Leu  Asn  Lys
             420                       425                      430
```

```
Lys Gln Val Asp Asn Leu Leu Asn Asn Lys Pro Met Met Leu Glu Thr
        435             440             445
Asn Gln Thr Asp Gly Val Tyr Lys Ile Lys Asp Thr His Gly Asn Ile
        450             455             460
Val Thr Gly Gly Glu Trp Asn Gly Val Ile Gln Ile Lys Ala Lys
465             470             475             480
Thr Ala Ser Ile Ile Val Asp Asp Gly Glu Arg Val Ala Glu Lys Arg
                485             490             495
Val Ala Ala Lys Asp Tyr Glu Asn Pro Glu Asp Lys Thr Pro Ser Leu
            500             505             510
Thr Leu Lys Asp Ala Leu Lys Leu Ser Tyr Pro Asp Glu Ile Lys Glu
            515             520             525
Ile Glu Gly Leu Leu Tyr Tyr Lys Asn Lys Pro Ile Tyr Glu Ser Ser
    530             535             540
Val Met Thr Tyr Leu Asp Glu Asn Thr Ala Lys Glu Val Thr Lys Gln
545             550             555             560
Leu Asn Asp Thr Thr Gly Lys Phe Lys Asp Val Ser His Leu Tyr Asp
                565             570             575
Val Lys Leu Thr Pro Lys Met Asn Val Thr Ile Lys Leu Ser Ile Leu
            580             585             590
Tyr Asp Asn Ala Glu Ser Asn Asp Asn Ser Ile Gly Lys Trp Thr Asn
            595             600             605
Thr Asn Ile Val Ser Gly Gly Asn Asn Gly Lys Lys Gln Tyr Ser Ser
    610             615             620
Asn Asn Pro Asp Ala Asn Leu Thr Leu Asn Thr Asp Ala Gln Glu Lys
625             630             635             640
Leu Asn Lys Asn Arg Asp Tyr Tyr Ile Ser Leu Tyr Met Lys Ser Glu
                645             650             655
Lys Asn Thr Gln Cys Glu Ile Thr Ile Asp Gly Glu Ile Tyr Pro Ile
            660             665             670
Thr Thr Lys Thr Val Asn Val Asn Lys Asp Asn Tyr Lys Arg Leu Asp
        675             680             685
Ile Ile Ala His Asn Ile Lys Ser Asn Pro Ile Ser Ser Leu His Ile
    690             695             700
Lys Thr Asn Asp Glu Ile Thr Leu Phe Trp Asp Asp Ile Ser Ile Thr
705             710             715             720
Asp Val Ala Ser Ile Lys Pro Glu Asn Leu Thr Asp Ser Glu Ile Lys
                725             730             735
Gln Ile Tyr Ser Arg Tyr Gly Ile Lys Leu Glu Asp Gly Ile Leu Ile
            740             745             750
Asp Lys Lys Gly Gly Ile His Tyr Gly Glu Phe Ile Asn Glu Ala Ser
        755             760             765
Phe Asn Ile Glu Pro Leu Gln Asn Tyr Val Thr Lys Tyr Glu Val Thr
770             775             780
Tyr Ser Ser Glu Leu Gly Pro Asn Val Ser Asp Thr Leu Glu Ser Asp
785             790             795             800
Lys Ile Tyr Lys Asp Gly Thr Ile Lys Phe Asp Phe Thr Lys Tyr Ser
                805             810             815
Lys Asn Glu Gln Gly Leu Phe Tyr Asp Ser Gly Leu Asn Trp Asp Phe
            820             825             830
Lys Ile Asn Ala Ile Thr Tyr Asp Gly Lys Glu Met Asn Val Phe His
        835             840             845
Arg Tyr Asn Lys
```

(2) INFORMATION FOR SEQ ID NO:37:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "forward primer used to make pCIB5527"

(iii) HYPOTHETICAL: NO (xi) SEQUENCE DESCRIPTION: SEQ ID NO:37:

```
GGATCCACCA TGCTGCAGAA CCTGAAGATC AC                                32
```

(2) INFORMATION FOR SEQ ID NO:38:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "reverse primer used to make pCIB5527"

(iii) HYPOTHETICAL: NO (xi) SEQUENCE DESCRIPTION: SEQ ID NO:38:

```
AAGCTTCCAC TCCTTCTC                                                18
```

(2) INFORMATION FOR SEQ ID NO:39:

(i) SEQUENCE CHARACTERISTICS:
        (A) LENGTH: 1241 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic DNA"

(iii) HYPOTHETICAL: NO (ix) FEATURE:
        (A) NAME/KEY: CDS
        (B) LOCATION: 9..1238
        (D) OTHER INFORMATION: /note= "Maize optimized DNA sequence encoding VIP2A(a) with the Bacillus secretion signal removed as contained in pCIB5527"

(xi) SEQUENCE DESCRIPTION: SEQ ID NO:39:

```
GATCCACC ATG CTG CAG AAC CTG AAG ATC ACC GAC AAG GTG GAG GAC TTC      50
         Met Leu Gln Asn Leu Lys Ile Thr Asp Lys Val Glu Asp Phe
                 855                     860                 865

AAG GAG GAC AAG GAG AAG GCC AAG GAG TGG GGC AAG GAG AAG GAG AAG       98
Lys Glu Asp Lys Glu Lys Ala Lys Glu Trp Gly Lys Glu Lys Glu Lys
            870                 875                 880

GAG TGG AAG CTT ACC GCC ACC GAG AAG GGC AAG ATG AAC AAC TTC CTG      146
Glu Trp Lys Leu Thr Ala Thr Glu Lys Gly Lys Met Asn Asn Phe Leu
        885                 890                 895

GAC AAC AAG AAC GAC ATC AAG ACC AAC TAC AAG GAG ATC ACC TTC AGC      194
Asp Asn Lys Asn Asp Ile Lys Thr Asn Tyr Lys Glu Ile Thr Phe Ser
    900                 905                 910

ATA GCC GGC AGC TTC GAG GAC GAG ATC AAG GAC CTG AAG GAG ATC GAC      242
```

| | | | | | | | | | | | | | | | |
|---|---|---|---|---|---|---|---|---|---|---|---|---|---|---|---|
| Ile | Ala | Gly | Ser | Phe | Glu | Asp | Glu | Ile | Lys | Asp | Leu | Lys | Glu | Ile | Asp |
| 915 | | | | 920 | | | | 925 | | | | | | | 930 |

| AAG | ATG | TTC | GAC | AAG | ACC | AAC | CTG | AGC | AAC | AGC | ATC | ATC | ACC | TAC | AAG | 290 |
|---|---|---|---|---|---|---|---|---|---|---|---|---|---|---|---|---|
| Lys | Met | Phe | Asp | Lys | Thr | Asn | Leu | Ser | Asn | Ser | Ile | Ile | Thr | Tyr | Lys | |
| | | | | 935 | | | | | 940 | | | | | 945 | | |

| AAC | GTG | GAG | CCC | ACC | ACC | ATC | GGC | TTC | AAC | AAG | AGC | CTG | ACC | GAG | GGC | 338 |
|---|---|---|---|---|---|---|---|---|---|---|---|---|---|---|---|---|
| Asn | Val | Glu | Pro | Thr | Thr | Ile | Gly | Phe | Asn | Lys | Ser | Leu | Thr | Glu | Gly | |
| | | | 950 | | | | | 955 | | | | | | 960 | | |

| AAC | ACC | ATC | AAC | AGC | GAC | GCC | ATG | GCC | CAG | TTC | AAG | GAG | CAG | TTC | CTG | 386 |
|---|---|---|---|---|---|---|---|---|---|---|---|---|---|---|---|---|
| Asn | Thr | Ile | Asn | Ser | Asp | Ala | Met | Ala | Gln | Phe | Lys | Glu | Gln | Phe | Leu | |
| | | 965 | | | | | 970 | | | | | 975 | | | | |

| GAC | CGC | GAC | ATC | AAG | TTC | GAC | AGC | TAC | CTG | GAC | ACC | CAC | CTG | ACC | GCC | 434 |
|---|---|---|---|---|---|---|---|---|---|---|---|---|---|---|---|---|
| Asp | Arg | Asp | Ile | Lys | Phe | Asp | Ser | Tyr | Leu | Asp | Thr | His | Leu | Thr | Ala | |
| | 980 | | | | | 985 | | | | | | 990 | | | | |

| CAG | CAG | GTG | AGC | AGC | AAG | GAG | CGC | GTG | ATC | CTG | AAG | GTG | ACC | GTC | CCC | 482 |
|---|---|---|---|---|---|---|---|---|---|---|---|---|---|---|---|---|
| Gln | Gln | Val | Ser | Ser | Lys | Glu | Arg | Val | Ile | Leu | Lys | Val | Thr | Val | Pro | |
| 995 | | | | | 1000 | | | | | 1005 | | | | | 1010 | |

| AGC | GGC | AAG | GGC | AGC | ACC | ACC | CCC | ACC | AAG | GCC | GGC | GTG | ATC | CTG | AAC | 530 |
|---|---|---|---|---|---|---|---|---|---|---|---|---|---|---|---|---|
| Ser | Gly | Lys | Gly | Ser | Thr | Thr | Pro | Thr | Lys | Ala | Gly | Val | Ile | Leu | Asn | |
| | | | | 1015 | | | | | 1020 | | | | | 1025 | | |

| AAC | AGC | GAG | TAC | AAG | ATG | CTG | ATC | GAC | AAC | GGC | TAC | ATG | GTG | CAC | GTG | 578 |
|---|---|---|---|---|---|---|---|---|---|---|---|---|---|---|---|---|
| Asn | Ser | Glu | Tyr | Lys | Met | Leu | Ile | Asp | Asn | Gly | Tyr | Met | Val | His | Val | |
| | | | | 1030 | | | | | 1035 | | | | | 1040 | | |

| GAC | AAG | GTG | AGC | AAG | GTG | GTG | AAG | AAG | GGC | GTG | GAG | TGC | CTC | CAG | ATC | 626 |
|---|---|---|---|---|---|---|---|---|---|---|---|---|---|---|---|---|
| Asp | Lys | Val | Ser | Lys | Val | Val | Lys | Lys | Gly | Val | Glu | Cys | Leu | Gln | Ile | |
| | | | 1045 | | | | | 1050 | | | | | 1055 | | | |

| GAG | GGC | ACC | CTG | AAG | AAG | AGT | CTA | GAC | TTC | AAG | AAC | GAC | ATC | AAC | GCC | 674 |
|---|---|---|---|---|---|---|---|---|---|---|---|---|---|---|---|---|
| Glu | Gly | Thr | Leu | Lys | Lys | Ser | Leu | Asp | Phe | Lys | Asn | Asp | Ile | Asn | Ala | |
| | | | 1060 | | | | | 1065 | | | | | 1070 | | | |

| GAG | GCC | CAC | AGC | TGG | GGC | ATG | AAG | AAC | TAC | GAG | GAG | TGG | GCC | AAG | GAC | 722 |
|---|---|---|---|---|---|---|---|---|---|---|---|---|---|---|---|---|
| Glu | Ala | His | Ser | Trp | Gly | Met | Lys | Asn | Tyr | Glu | Glu | Trp | Ala | Lys | Asp | |
| 1075 | | | | | 1080 | | | | | 1085 | | | | | 1090 | |

| CTG | ACC | GAC | AGC | CAG | CGC | GAG | GCC | CTG | GAC | GGC | TAC | GCC | CGC | CAG | GAC | 770 |
|---|---|---|---|---|---|---|---|---|---|---|---|---|---|---|---|---|
| Leu | Thr | Asp | Ser | Gln | Arg | Glu | Ala | Leu | Asp | Gly | Tyr | Ala | Arg | Gln | Asp | |
| | | | | 1095 | | | | | 1100 | | | | | 1105 | | |

| TAC | AAG | GAG | ATC | AAC | AAC | TAC | CTG | CGC | AAC | CAG | GGC | GGC | AGC | GGC | AAC | 818 |
|---|---|---|---|---|---|---|---|---|---|---|---|---|---|---|---|---|
| Tyr | Lys | Glu | Ile | Asn | Asn | Tyr | Leu | Arg | Asn | Gln | Gly | Gly | Ser | Gly | Asn | |
| | | | | 1110 | | | | | 1115 | | | | | 1120 | | |

| GAG | AAG | CTG | GAC | GCC | CAG | ATC | AAG | AAC | ATC | AGC | GAC | GCC | CTG | GGC | AAG | 866 |
|---|---|---|---|---|---|---|---|---|---|---|---|---|---|---|---|---|
| Glu | Lys | Leu | Asp | Ala | Gln | Ile | Lys | Asn | Ile | Ser | Asp | Ala | Leu | Gly | Lys | |
| | | | | 1125 | | | | | 1130 | | | | | 1135 | | |

| AAG | CCC | ATC | CCC | GAG | AAC | ATC | ACC | GTG | TAC | CGC | TGG | TGC | GGC | ATG | CCC | 914 |
|---|---|---|---|---|---|---|---|---|---|---|---|---|---|---|---|---|
| Lys | Pro | Ile | Pro | Glu | Asn | Ile | Thr | Val | Tyr | Arg | Trp | Cys | Gly | Met | Pro | |
| | | | 1140 | | | | | 1145 | | | | | 1150 | | | |

| GAG | TTC | GGC | TAC | CAG | ATC | AGC | GAC | CCC | CTG | CCC | AGC | CTG | AAG | GAC | TTC | 962 |
|---|---|---|---|---|---|---|---|---|---|---|---|---|---|---|---|---|
| Glu | Phe | Gly | Tyr | Gln | Ile | Ser | Asp | Pro | Leu | Pro | Ser | Leu | Lys | Asp | Phe | |
| 1155 | | | | | 1160 | | | | | 1165 | | | | | 1170 | |

| GAG | GAG | CAG | TTC | CTG | AAC | ACC | ATC | AAG | GAG | GAC | AAG | GGC | TAC | ATG | AGC | 1010 |
|---|---|---|---|---|---|---|---|---|---|---|---|---|---|---|---|---|
| Glu | Glu | Gln | Phe | Leu | Asn | Thr | Ile | Lys | Glu | Asp | Lys | Gly | Tyr | Met | Ser | |
| | | | | 1175 | | | | | 1180 | | | | | 1185 | | |

| ACC | AGC | CTG | AGC | AGC | GAG | CGC | CTG | GCC | GCC | TTC | GGC | AGC | CGC | AAG | ATC | 1058 |
|---|---|---|---|---|---|---|---|---|---|---|---|---|---|---|---|---|
| Thr | Ser | Leu | Ser | Ser | Glu | Arg | Leu | Ala | Ala | Phe | Gly | Ser | Arg | Lys | Ile | |
| | | | | 1190 | | | | | 1195 | | | | | 1200 | | |

| ATC | CTG | CGC | CTG | CAG | GTG | CCC | AAG | GGC | AGC | ACT | GGT | GCC | TAC | CTG | AGC | 1106 |
|---|---|---|---|---|---|---|---|---|---|---|---|---|---|---|---|---|
| Ile | Leu | Arg | Leu | Gln | Val | Pro | Lys | Gly | Ser | Thr | Gly | Ala | Tyr | Leu | Ser | |
| | | | 1205 | | | | | 1210 | | | | | 1215 | | | |

| GCC | ATC | GGC | GGC | TTC | GCC | AGC | GAG | AAG | GAG | ATC | CTG | CTG | GAT | AAG | GAC | 1154 |
|---|---|---|---|---|---|---|---|---|---|---|---|---|---|---|---|---|
| Ala | Ile | Gly | Gly | Phe | Ala | Ser | Glu | Lys | Glu | Ile | Leu | Leu | Asp | Lys | Asp | |
| | | | 1220 | | | | | 1225 | | | | | 1230 | | | |

| AGC | AAG | TAC | CAC | ATC | GAC | AAG | GTG | ACC | GAG | GTG | ATC | ATC | AAG | GGC | GTG | 1202 |

| Ser | Lys | Tyr | His | Ile | Asp | Lys | Val | Thr | Glu | Val | Ile | Ile | Lys | Gly | Val |
| --- | --- | --- | --- | --- | --- | --- | --- | --- | --- | --- | --- | --- | --- | --- | --- |
| 1235 | | | | | 1240 | | | | 1245 | | | | | | 1250 |

| AAG | CGC | TAC | GTG | GTG | GAC | GCC | ACC | CTG | CTG | ACC | AAC | TAG | | | 1241 |
| --- | --- | --- | --- | --- | --- | --- | --- | --- | --- | --- | --- | --- | --- | --- | --- |
| Lys | Arg | Tyr | Val | Val | Asp | Ala | Thr | Leu | Leu | Thr | Asn | | | | |
| | | | | 1255 | | | | | | 1260 | | | | | |

( 2 ) INFORMATION FOR SEQ ID NO:40:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

| Met | Leu | Gln | Asn | Leu | Lys | Ile | Thr | Asp | Lys | Val | Glu | Asp | Phe | Lys | Glu |
| --- | --- | --- | --- | --- | --- | --- | --- | --- | --- | --- | --- | --- | --- | --- | --- |
| 1 | | | | 5 | | | | | 10 | | | | | 15 | |
| Asp | Lys | Glu | Lys | Ala | Lys | Glu | Trp | Gly | Lys | Glu | Lys | Glu | Lys | Glu | Trp |
| | | | 20 | | | | | 25 | | | | | 30 | | |
| Lys | Leu | Thr | Ala | Thr | Glu | Lys | Gly | Lys | Met | Asn | Asn | Phe | Leu | Asp | Asn |
| | | | 35 | | | | | 40 | | | | | 45 | | |
| Lys | Asn | Asp | Ile | Lys | Thr | Asn | Tyr | Lys | Glu | Ile | Thr | Phe | Ser | Ile | Ala |
| | | 50 | | | | | 55 | | | | | 60 | | | |
| Gly | Ser | Phe | Glu | Asp | Glu | Ile | Lys | Asp | Leu | Lys | Glu | Ile | Asp | Lys | Met |
| 65 | | | | | 70 | | | | | 75 | | | | | 80 |
| Phe | Asp | Lys | Thr | Asn | Leu | Ser | Asn | Ser | Ile | Ile | Thr | Tyr | Lys | Asn | Val |
| | | | | 85 | | | | | 90 | | | | | 95 | |
| Glu | Pro | Thr | Thr | Ile | Gly | Phe | Asn | Lys | Ser | Leu | Thr | Glu | Gly | Asn | Thr |
| | | | 100 | | | | | 105 | | | | | 110 | | |
| Ile | Asn | Ser | Asp | Ala | Met | Ala | Gln | Phe | Lys | Glu | Gln | Phe | Leu | Asp | Arg |
| | | | 115 | | | | | 120 | | | | | 125 | | |
| Asp | Ile | Lys | Phe | Asp | Ser | Tyr | Leu | Asp | Thr | His | Leu | Thr | Ala | Gln | Gln |
| | | 130 | | | | | 135 | | | | | 140 | | | |
| Val | Ser | Ser | Lys | Glu | Arg | Val | Ile | Leu | Lys | Val | Thr | Val | Pro | Ser | Gly |
| 145 | | | | | 150 | | | | | 155 | | | | | 160 |
| Lys | Gly | Ser | Thr | Thr | Pro | Thr | Lys | Ala | Gly | Val | Ile | Leu | Asn | Asn | Ser |
| | | | | 165 | | | | | 170 | | | | | 175 | |
| Glu | Tyr | Lys | Met | Leu | Ile | Asp | Asn | Gly | Tyr | Met | Val | His | Val | Asp | Lys |
| | | | 180 | | | | | 185 | | | | | 190 | | |
| Val | Ser | Lys | Val | Val | Lys | Lys | Gly | Val | Glu | Cys | Leu | Gln | Ile | Glu | Gly |
| | | 195 | | | | | 200 | | | | | 205 | | | |
| Thr | Leu | Lys | Lys | Ser | Leu | Asp | Phe | Lys | Asn | Asp | Ile | Asn | Ala | Glu | Ala |
| | 210 | | | | | 215 | | | | | 220 | | | | |
| His | Ser | Trp | Gly | Met | Lys | Asn | Tyr | Glu | Glu | Trp | Ala | Lys | Asp | Leu | Thr |
| 225 | | | | | 230 | | | | | 235 | | | | | 240 |
| Asp | Ser | Gln | Arg | Glu | Ala | Leu | Asp | Gly | Tyr | Ala | Arg | Gln | Asp | Tyr | Lys |
| | | | | 245 | | | | | 250 | | | | | 255 | |
| Glu | Ile | Asn | Asn | Tyr | Leu | Arg | Asn | Gln | Gly | Gly | Ser | Gly | Asn | Glu | Lys |
| | | | | 260 | | | | | 265 | | | | | 270 | |
| Leu | Asp | Ala | Gln | Ile | Lys | Asn | Ile | Ser | Asp | Ala | Leu | Gly | Lys | Lys | Pro |
| | | | 275 | | | | | 280 | | | | | 285 | | |
| Ile | Pro | Glu | Asn | Ile | Thr | Val | Tyr | Arg | Trp | Cys | Gly | Met | Pro | Glu | Phe |
| | | 290 | | | | | 295 | | | | | 300 | | | |
| Gly | Tyr | Gln | Ile | Ser | Asp | Pro | Leu | Pro | Ser | Leu | Lys | Asp | Phe | Glu | Glu |
| 305 | | | | | 310 | | | | | 315 | | | | | 320 |
| Gln | Phe | Leu | Asn | Thr | Ile | Lys | Glu | Asp | Lys | Gly | Tyr | Met | Ser | Thr | Ser |

|   |   |   |   |   |   |   | 325 |   |   |   |   | 330 |   |   |   |   | 335 |   |
|---|---|---|---|---|---|---|---|---|---|---|---|---|---|---|---|---|---|---|
| Leu | Ser | Ser | Glu | Arg | Leu | Ala | Ala | Phe | Gly | Ser | Arg | Lys | Ile | Ile | Leu |
|   |   |   | 340 |   |   |   |   | 345 |   |   |   |   | 350 |   |   |
| Arg | Leu | Gln | Val | Pro | Lys | Gly | Ser | Thr | Gly | Ala | Tyr | Leu | Ser | Ala | Ile |
|   |   | 355 |   |   |   |   | 360 |   |   |   |   | 365 |   |   |   |
| Gly | Gly | Phe | Ala | Ser | Glu | Lys | Glu | Ile | Leu | Leu | Asp | Lys | Asp | Ser | Lys |
|   | 370 |   |   |   |   | 375 |   |   |   |   | 380 |   |   |   |   |
| Tyr | His | Ile | Asp | Lys | Val | Thr | Glu | Val | Ile | Ile | Lys | Gly | Val | Lys | Arg |
| 385 |   |   |   |   | 390 |   |   |   |   | 395 |   |   |   |   | 400 |
| Tyr | Val | Val | Asp | Ala | Thr | Leu | Leu | Thr | Asn |
|   |   |   |   | 405 |   |   |   |   | 410 |

( 2 ) INFORMATION FOR SEQ ID NO:41:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide encoding
            eukaryotic secretion signal used to construct pCIB5527"

( i i i ) HYPOTHETICAL: NO ( x i ) SEQUENCE DESCRIPTION: SEQ ID NO:41:

GGATCCACCA TGGGCTGGAG CTGGATCTTC CTGTTCCTGC TGAGCGGCGC CGCGGGCGTG    60

CACTGCCTGC AG    72

( 2 ) INFORMATION FOR SEQ ID NO:42:

( i ) SEQUENCE CHARACTERISTICS:
        ( A ) LENGTH: 1241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1238
        ( D ) OTHER INFORMATION: /note= "Maize optimized DNA
            sequence encoding VIP2A(a) with the Bacillus secretion
      &

-continued

|  |  |  | 475 |  |  |  | 480 |  |  |  | 485 |  |  |  |  |
|---|---|---|---|---|---|---|---|---|---|---|---|---|---|---|---|
| AAG | ATG | TTC | GAC | AAG | ACC | AAC | CTG | AGC | AAC | AGC | ATC | ATC | ACC | TAC | AAG | 290 |
| Lys | Met | Phe | Asp | Lys | Thr | Asn | Leu | Ser | Asn | Ser | Ile | Ile | Thr | Tyr | Lys |
|  | 490 |  |  |  | 495 |  |  |  |  | 500 |  |  |  |  |  |
| AAC | GTG | GAG | CCC | ACC | ACC | ATC | GGC | TTC | AAC | AAG | AGC | CTG | ACC | GAG | GGC | 338 |
| Asn | Val | Glu | Pro | Thr | Thr | Ile | Gly | Phe | Asn | Lys | Ser | Leu | Thr | Glu | Gly |
| 505 |  |  |  |  | 510 |  |  |  |  | 515 |  |  |  |  | 520 |
| AAC | ACC | ATC | AAC | AGC | GAC | GCC | ATG | GCC | CAG | TTC | AAG | GAG | CAG | TTC | CTG | 386 |
| Asn | Thr | Ile | Asn | Ser | Asp | Ala | Met | Ala | Gln | Phe | Lys | Glu | Gln | Phe | Leu |
|  |  |  |  | 525 |  |  |  |  | 530 |  |  |  |  | 535 |  |
| GAC | CGC | GAC | ATC | AAG | TTC | GAC | AGC | TAC | CTG | GAC | ACC | CAC | CTG | ACC | GCC | 434 |
| Asp | Arg | Asp | Ile | Lys | Phe | Asp | Ser | Tyr | Leu | Asp | Thr | His | Leu | Thr | Ala |
|  |  |  | 540 |  |  |  |  | 545 |  |  |  |  | 550 |  |  |
| CAG | CAG | GTG | AGC | AGC | AAG | GAG | CGC | GTG | ATC | CTG | AAG | GTG | ACC | GTC | CCC | 482 |
| Gln | Gln | Val | Ser | Ser | Lys | Glu | Arg | Val | Ile | Leu | Lys | Val | Thr | Val | Pro |
|  |  | 555 |  |  |  |  | 560 |  |  |  |  | 565 |  |  |  |
| AGC | GGC | AAG | GGC | AGC | ACC | ACC | CCC | ACC | AAG | GCC | GGC | GTG | ATC | CTG | AAC | 530 |
| Ser | Gly | Lys | Gly | Ser | Thr | Thr | Pro | Thr | Lys | Ala | Gly | Val | Ile | Leu | Asn |
| 570 |  |  |  |  | 575 |  |  |  |  | 580 |  |  |  |  |  |
| AAC | AGC | GAG | TAC | AAG | ATG | CTG | ATC | GAC | AAC | GGC | TAC | ATG | GTG | CAC | GTG | 578 |
| Asn | Ser | Glu | Tyr | Lys | Met | Leu | Ile | Asp | Asn | Gly | Tyr | Met | Val | His | Val |
| 585 |  |  |  |  | 590 |  |  |  |  | 595 |  |  |  |  | 600 |
| GAC | AAG | GTG | AGC | AAG | GTG | GTG | AAG | AAG | GGC | GTG | GAG | TGC | CTC | CAG | ATC | 626 |
| Asp | Lys | Val | Ser | Lys | Val | Val | Lys | Lys | Gly | Val | Glu | Cys | Leu | Gln | Ile |
|  |  |  |  | 605 |  |  |  |  | 610 |  |  |  |  | 615 |  |
| GAG | GGC | ACC | CTG | AAG | AAG | AGT | CTA | GAC | TTC | AAG | AAC | GAC | ATC | AAC | GCC | 674 |
| Glu | Gly | Thr | Leu | Lys | Lys | Ser | Leu | Asp | Phe | Lys | Asn | Asp | Ile | Asn | Ala |
|  |  |  | 620 |  |  |  |  | 625 |  |  |  |  | 630 |  |  |
| GAG | GCC | CAC | AGC | TGG | GGC | ATG | AAG | AAC | TAC | GAG | GAG | TGG | GCC | AAG | GAC | 722 |
| Glu | Ala | His | Ser | Trp | Gly | Met | Lys | Asn | Tyr | Glu | Glu | Trp | Ala | Lys | Asp |
|  |  | 635 |  |  |  |  | 640 |  |  |  |  | 645 |  |  |  |
| CTG | ACC | GAC | AGC | CAG | CGC | GAG | GCC | CTG | GAC | GGC | TAC | GCC | CGC | CAG | GAC | 770 |
| Leu | Thr | Asp | Ser | Gln | Arg | Glu | Ala | Leu | Asp | Gly | Tyr | Ala | Arg | Gln | Asp |
| 650 |  |  |  |  | 655 |  |  |  |  | 660 |  |  |  |  |  |
| TAC | AAG | GAG | ATC | AAC | AAC | TAC | CTG | CGC | AAC | CAG | GGC | GGC | AGC | GGC | AAC | 818 |
| Tyr | Lys | Glu | Ile | Asn | Asn | Tyr | Leu | Arg | Asn | Gln | Gly | Gly | Ser | Gly | Asn |
| 665 |  |  |  |  | 670 |  |  |  |  | 675 |  |  |  |  | 680 |
| GAG | AAG | CTG | GAC | GCC | CAG | ATC | AAG | AAC | ATC | AGC | GAC | GCC | CTG | GGC | AAG | 866 |
| Glu | Lys | Leu | Asp | Ala | Gln | Ile | Lys | Asn | Ile | Ser | Asp | Ala | Leu | Gly | Lys |
|  |  |  |  | 685 |  |  |  |  | 690 |  |  |  |  | 695 |  |
| AAG | CCC | ATC | CCC | GAG | AAC | ATC | ACC | GTG | TAC | CGC | TGG | TGC | GGC | ATG | CCC | 914 |
| Lys | Pro | Ile | Pro | Glu | Asn | Ile | Thr | Val | Tyr | Arg | Trp | Cys | Gly | Met | Pro |
|  |  |  | 700 |  |  |  |  | 705 |  |  |  |  | 710 |  |  |
| GAG | TTC | GGC | TAC | CAG | ATC | AGC | GAC | CCC | CTG | CCC | AGC | CTG | AAG | GAC | TTC | 962 |
| Glu | Phe | Gly | Tyr | Gln | Ile | Ser | Asp | Pro | Leu | Pro | Ser | Leu | Lys | Asp | Phe |
|  |  | 715 |  |  |  |  | 720 |  |  |  |  | 725 |  |  |  |
| GAG | GAG | CAG | TTC | CTG | AAC | ACC | ATC | AAG | GAG | GAC | AAG | GGC | TAC | ATG | AGC | 1010 |
| Glu | Glu | Gln | Phe | Leu | Asn | Thr | Ile | Lys | Glu | Asp | Lys | Gly | Tyr | Met | Ser |
|  | 730 |  |  |  |  | 735 |  |  |  |  | 740 |  |  |  |  |
| ACC | AGC | CTG | AGC | AGC | GAG | CGC | CTG | GCC | GCC | TTC | GGC | AGC | CGC | AAG | ATC | 1058 |
| Thr | Ser | Leu | Ser | Ser | Glu | Arg | Leu | Ala | Ala | Phe | Gly | Ser | Arg | Lys | Ile |
| 745 |  |  |  |  | 750 |  |  |  |  | 755 |  |  |  |  | 760 |
| ATC | CTG | CGC | CTG | CAG | GTG | CCC | AAG | GGC | AGC | ACT | GGT | GCC | TAC | CTG | AGC | 1106 |
| Ile | Leu | Arg | Leu | Gln | Val | Pro | Lys | Gly | Ser | Thr | Gly | Ala | Tyr | Leu | Ser |
|  |  |  |  | 765 |  |  |  |  | 770 |  |  |  |  | 775 |  |
| GCC | ATC | GGC | GGC | TTC | GCC | AGC | GAG | AAG | GAG | ATC | CTG | CTG | GAT | AAG | GAC | 1154 |
| Ala | Ile | Gly | Gly | Phe | Ala | Ser | Glu | Lys | Glu | Ile | Leu | Leu | Asp | Lys | Asp |
|  |  |  | 780 |  |  |  |  | 785 |  |  |  |  | 790 |  |  |
| AGC | AAG | TAC | CAC | ATC | GAC | AAG | GTG | ACC | GAG | GTG | ATC | ATC | AAG | GGC | GTG | 1202 |
| Ser | Lys | Tyr | His | Ile | Asp | Lys | Val | Thr | Glu | Val | Ile | Ile | Lys | Gly | Val |

|     |     |     |     |     | 795 |     |     |     | 800 |     |     |     | 805 |     |      |
| --- | --- | --- | --- | --- | --- | --- | --- | --- | --- | --- | --- | --- | --- | --- | --- |
| AAG | CGC | TAC | GTG | GTG | GAC | GCC | ACC | CTG | CTG | ACC | AAC | TAG |     |     | 1241 |
| Lys | Arg | Tyr | Val | Val | Asp | Ala | Thr | Leu | Leu | Thr | Asn |     |     |     |      |
| 810 |     |     |     |     | 815 |     |     |     | 820 |     |     |     |     |     |      |

( 2 ) INFORMATION FOR SEQ ID NO:43:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

| Met | Leu | Gln | Asn | Leu | Lys | Ile | Thr | Asp | Lys | Val | Glu | Asp | Phe | Lys | Glu |
|---|---|---|---|---|---|---|---|---|---|---|---|---|---|---|---|
| 1 |  |  |  | 5 |  |  |  |  | 10 |  |  |  |  | 15 |  |
| Asp | Lys | Glu | Lys | Ala | Lys | Glu | Trp | Gly | Lys | Glu | Lys | Glu | Lys | Glu | Trp |
|  |  |  | 20 |  |  |  |  | 25 |  |  |  |  | 30 |  |  |
| Lys | Leu | Thr | Ala | Thr | Glu | Lys | Gly | Lys | Met | Asn | Asn | Phe | Leu | Asp | Asn |
|  |  | 35 |  |  |  |  | 40 |  |  |  |  | 45 |  |  |  |
| Lys | Asn | Asp | Ile | Lys | Thr | Asn | Tyr | Lys | Glu | Ile | Thr | Phe | Ser | Ile | Ala |
|  | 50 |  |  |  |  | 55 |  |  |  |  | 60 |  |  |  |  |
| Gly | Ser | Phe | Glu | Asp | Glu | Ile | Lys | Asp | Leu | Lys | Glu | Ile | Asp | Lys | Met |
| 65 |  |  |  |  | 70 |  |  |  |  | 75 |  |  |  |  | 80 |
| Phe | Asp | Lys | Thr | Asn | Leu | Ser | Asn | Ser | Ile | Ile | Thr | Tyr | Lys | Asn | Val |
|  |  |  |  | 85 |  |  |  |  | 90 |  |  |  |  | 95 |  |
| Glu | Pro | Thr | Thr | Ile | Gly | Phe | Asn | Lys | Ser | Leu | Thr | Glu | Gly | Asn | Thr |
|  |  |  | 100 |  |  |  |  | 105 |  |  |  |  | 110 |  |  |
| Ile | Asn | Ser | Asp | Ala | Met | Ala | Gln | Phe | Lys | Glu | Gln | Phe | Leu | Asp | Arg |
|  |  | 115 |  |  |  |  | 120 |  |  |  |  | 125 |  |  |  |
| Asp | Ile | Lys | Phe | Asp | Ser | Tyr | Leu | Asp | Thr | His | Leu | Thr | Ala | Gln | Gln |
|  | 130 |  |  |  |  | 135 |  |  |  |  | 140 |  |  |  |  |
| Val | Ser | Ser | Lys | Glu | Arg | Val | Ile | Leu | Lys | Val | Thr | Val | Pro | Ser | Gly |
| 145 |  |  |  |  | 150 |  |  |  |  | 155 |  |  |  |  | 160 |
| Lys | Gly | Ser | Thr | Thr | Pro | Thr | Lys | Ala | Gly | Val | Ile | Leu | Asn | Asn | Ser |
|  |  |  |  | 165 |  |  |  |  | 170 |  |  |  |  | 175 |  |
| Glu | Tyr | Lys | Met | Leu | Ile | Asp | Asn | Gly | Tyr | Met | Val | His | Val | Asp | Lys |
|  |  |  | 180 |  |  |  |  | 185 |  |  |  |  | 190 |  |  |
| Val | Ser | Lys | Val | Val | Lys | Lys | Gly | Val | Glu | Cys | Leu | Gln | Ile | Glu | Gly |
|  |  | 195 |  |  |  |  | 200 |  |  |  |  | 205 |  |  |  |
| Thr | Leu | Lys | Lys | Ser | Leu | Asp | Phe | Lys | Asn | Asp | Ile | Asn | Ala | Glu | Ala |
|  | 210 |  |  |  |  | 215 |  |  |  |  | 220 |  |  |  |  |
| His | Ser | Trp | Gly | Met | Lys | Asn | Tyr | Glu | Glu | Trp | Ala | Lys | Asp | Leu | Thr |
| 225 |  |  |  |  | 230 |  |  |  |  | 235 |  |  |  |  | 240 |
| Asp | Ser | Gln | Arg | Glu | Ala | Leu | Asp | Gly | Tyr | Ala | Arg | Gln | Asp | Tyr | Lys |
|  |  |  |  | 245 |  |  |  |  | 250 |  |  |  |  | 255 |  |
| Glu | Ile | Asn | Asn | Tyr | Leu | Arg | Asn | Gln | Gly | Gly | Ser | Gly | Asn | Glu | Lys |
|  |  |  | 260 |  |  |  |  | 265 |  |  |  |  | 270 |  |  |
| Leu | Asp | Ala | Gln | Ile | Lys | Asn | Ile | Ser | Asp | Ala | Leu | Gly | Lys | Lys | Pro |
|  |  | 275 |  |  |  |  | 280 |  |  |  |  | 285 |  |  |  |
| Ile | Pro | Glu | Asn | Ile | Thr | Val | Tyr | Arg | Trp | Cys | Gly | Met | Pro | Glu | Phe |
|  | 290 |  |  |  |  | 295 |  |  |  |  | 300 |  |  |  |  |
| Gly | Tyr | Gln | Ile | Ser | Asp | Pro | Leu | Pro | Ser | Leu | Lys | Asp | Phe | Glu | Glu |
| 305 |  |  |  |  | 310 |  |  |  |  | 315 |  |  |  |  | 320 |
| Gln | Phe | Leu | Asn | Thr | Ile | Lys | Glu | Asp | Lys | Gly | Tyr | Met | Ser | Thr | Ser |
|  |  |  |  | 325 |  |  |  |  | 330 |  |  |  |  | 335 |  |

| Leu | Ser | Ser | Glu<br>340 | Arg | Leu | Ala | Ala | Phe<br>345 | Gly | Ser | Arg | Lys | Ile<br>350 | Ile | Leu |

| Arg | Leu | Gln<br>355 | Val | Pro | Lys | Gly | Ser<br>360 | Thr | Gly | Ala | Tyr | Leu<br>365 | Ser | Ala | Ile |

| Gly | Gly<br>370 | Phe | Ala | Ser | Glu | Lys<br>375 | Glu | Ile | Leu | Leu | Asp<br>380 | Lys | Asp | Ser | Lys |

| Tyr<br>385 | His | Ile | Asp | Lys | Val<br>390 | Thr | Glu | Val | Ile | Ile<br>395 | Lys | Gly | Val | Lys | Arg<br>400 |

| Tyr | Val | Val | Asp | Ala<br>405 | Thr | Leu | Leu | Thr | Asn<br>410 | | | | | | |

( 2 ) INFORMATION FOR SEQ ID NO:44:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide encoding
            vacuolar targetting peptide used to construct pCIB5533"

( i i i ) HYPOTHETICAL: NO ( x i ) SEQUENCE DESCRIPTION: SEQ ID NO:44:

```
CCGCGGGCGT  GCACTGCCTC  AGCAGCAGCA  GCTTCGCCGA  CAGCAACCCC  ATCCGCGTGA      60
CCGACCGCGC  CGCCAGCACC  CTGCAG                                              86
```

( 2 ) INFORMATION FOR SEQ ID NO:45:

( i ) SEQUENCE CHARACTERISTICS:
        ( A ) LENGTH: 1358 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: CDS
        ( B ) LOCATION: 9..1355
        ( D ) OTHER INFORMATION: /note= "Maize optimized VIP2A(a)
            with the Bacillus secretion signal removed and the
            vacuolar targetting signal inserted as contained in
            pCIB5533"

( x i ) SEQUENCE DESCRIPTION: SEQ ID NO:45:

| GATCCACC | ATG<br>Met | GGC<br>Gly | TGG<br>Trp | AGC<br>Ser | TGG<br>Trp<br>415 | ATC<br>Ile | TTC<br>Phe | CTG<br>Leu | TTC<br>Phe | CTG<br>Leu | CTG<br>Leu | AGC<br>Ser | GGC<br>Gly | GCC<br>Ala<br>420 | 50 |

| GCG<br>Ala<br>425 | GGC<br>Gly | GTG<br>Val | CAC<br>His | TGC<br>Cys | CTC<br>Leu<br>430 | AGC<br>Ser | AGC<br>Ser | AGC<br>Ser | AGC<br>Ser | TTC<br>Phe<br>435 | GCC<br>Ala | GAC<br>Asp | AGC<br>Ser | AAC<br>Asn | CCC<br>Pro<br>440 | 98 |

| ATC<br>Ile | CGC<br>Arg | GTG<br>Val | ACC<br>Thr | GAC<br>Asp<br>445 | CGC<br>Arg | GCC<br>Ala | GCC<br>Ala | AGC<br>Ser | ACC<br>Thr<br>450 | CTG<br>Leu | CAG<br>Gln | AAC<br>Asn | CTG<br>Leu | AAG<br>Lys<br>455 | ATC<br>Ile | 146 |

| ACC<br>Thr | GAC<br>Asp | AAG<br>Lys | GTG<br>Val<br>460 | GAG<br>Glu | GAC<br>Asp | TTC<br>Phe | AAG<br>Lys<br>465 | GAG<br>Glu | GAC<br>Asp | AAG<br>Lys | GAG<br>Glu | AAG<br>Lys<br>470 | GCC<br>Ala | AAG<br>Lys | GAG<br>Glu | 194 |

| TGG<br>Trp | GGC<br>Gly | AAG<br>Lys<br>475 | GAG<br>Glu | AAG<br>Lys | GAG<br>Glu | AAG<br>Lys<br>480 | GAG<br>Glu | TGG<br>Trp | AAG<br>Lys | CTT<br>Leu | ACC<br>Thr<br>485 | GCC<br>Ala | ACC<br>Thr | GAG<br>Glu | AAG<br>Lys | 242 |

| | | | | | | | | | | | | | | | | |
|---|---|---|---|---|---|---|---|---|---|---|---|---|---|---|---|---|
| GGC | AAG | ATG | AAC | AAC | TTC | CTG | GAC | AAC | AAG | AAC | GAC | ATC | AAG | ACC | AAC | 290 |
| Gly | Lys | Met | Asn | Asn | Phe | Leu | Asp | Asn | Lys | Asn | Asp | Ile | Lys | Thr | Asn | |
| | 490 | | | | 495 | | | | | 500 | | | | | | |
| TAC | AAG | GAG | ATC | ACC | TTC | AGC | ATA | GCC | GGC | AGC | TTC | GAG | GAC | GAG | ATC | 338 |
| Tyr | Lys | Glu | Ile | Thr | Phe | Ser | Ile | Ala | Gly | Ser | Phe | Glu | Asp | Glu | Ile | |
| 505 | | | | | 510 | | | | | 515 | | | | | 520 | |
| AAG | GAC | CTG | AAG | GAG | ATC | GAC | AAG | ATG | TTC | GAC | AAG | ACC | AAC | CTG | AGC | 386 |
| Lys | Asp | Leu | Lys | Glu | Ile | Asp | Lys | Met | Phe | Asp | Lys | Thr | Asn | Leu | Ser | |
| | | | | 525 | | | | | 530 | | | | | 535 | | |
| AAC | AGC | ATC | ATC | ACC | TAC | AAG | AAC | GTG | GAG | CCC | ACC | ACC | ATC | GGC | TTC | 434 |
| Asn | Ser | Ile | Ile | Thr | Tyr | Lys | Asn | Val | Glu | Pro | Thr | Thr | Ile | Gly | Phe | |
| | | | 540 | | | | | 545 | | | | | 550 | | | |
| AAC | AAG | AGC | CTG | ACC | GAG | GGC | AAC | ACC | ATC | AAC | AGC | GAC | GCC | ATG | GCC | 482 |
| Asn | Lys | Ser | Leu | Thr | Glu | Gly | Asn | Thr | Ile | Asn | Ser | Asp | Ala | Met | Ala | |
| | | 555 | | | | | 560 | | | | | 565 | | | | |
| CAG | TTC | AAG | GAG | CAG | TTC | CTG | GAC | CGC | GAC | ATC | AAG | TTC | GAC | AGC | TAC | 530 |
| Gln | Phe | Lys | Glu | Gln | Phe | Leu | Asp | Arg | Asp | Ile | Lys | Phe | Asp | Ser | Tyr | |
| | 570 | | | | | 575 | | | | | 580 | | | | | |
| CTG | GAC | ACC | CAC | CTG | ACC | GCC | CAG | CAG | GTG | AGC | AGC | AAG | GAG | CGC | GTG | 578 |
| Leu | Asp | Thr | His | Leu | Thr | Ala | Gln | Gln | Val | Ser | Ser | Lys | Glu | Arg | Val | |
| 585 | | | | | 590 | | | | | 595 | | | | | 600 | |
| ATC | CTG | AAG | GTG | ACC | GTC | CCC | AGC | GGC | AAG | GGC | AGC | ACC | ACC | CCC | ACC | 626 |
| Ile | Leu | Lys | Val | Thr | Val | Pro | Ser | Gly | Lys | Gly | Ser | Thr | Thr | Pro | Thr | |
| | | | | 605 | | | | | 610 | | | | | 615 | | |
| AAG | GCC | GGC | GTG | ATC | CTG | AAC | AAC | AGC | GAG | TAC | AAG | ATG | CTG | ATC | GAC | 674 |
| Lys | Ala | Gly | Val | Ile | Leu | Asn | Asn | Ser | Glu | Tyr | Lys | Met | Leu | Ile | Asp | |
| | | | 620 | | | | | 625 | | | | | 630 | | | |
| AAC | GGC | TAC | ATG | GTG | CAC | GTG | GAC | AAG | GTG | AGC | AAG | GTG | GTG | AAG | AAG | 722 |
| Asn | Gly | Tyr | Met | Val | His | Val | Asp | Lys | Val | Ser | Lys | Val | Val | Lys | Lys | |
| | | 635 | | | | | 640 | | | | | 645 | | | | |
| GGC | GTG | GAG | TGC | CTC | CAG | ATC | GAG | GGC | ACC | CTG | AAG | AAG | AGT | CTA | GAC | 770 |
| Gly | Val | Glu | Cys | Leu | Gln | Ile | Glu | Gly | Thr | Leu | Lys | Lys | Ser | Leu | Asp | |
| | 650 | | | | | 655 | | | | | 660 | | | | | |
| TTC | AAG | AAC | GAC | ATC | AAC | GCC | GAG | GCC | CAC | AGC | TGG | GGC | ATG | AAG | AAC | 818 |
| Phe | Lys | Asn | Asp | Ile | Asn | Ala | Glu | Ala | His | Ser | Trp | Gly | Met | Lys | Asn | |
| 665 | | | | | 670 | | | | | 675 | | | | | 680 | |
| TAC | GAG | GAG | TGG | GCC | AAG | GAC | CTG | ACC | GAC | AGC | CAG | CGC | GAG | GCC | CTG | 866 |
| Tyr | Glu | Glu | Trp | Ala | Lys | Asp | Leu | Thr | Asp | Ser | Gln | Arg | Glu | Ala | Leu | |
| | | | | 685 | | | | | 690 | | | | | 695 | | |
| GAC | GGC | TAC | GCC | CGC | CAG | GAC | TAC | AAG | GAG | ATC | AAC | AAC | TAC | CTG | CGC | 914 |
| Asp | Gly | Tyr | Ala | Arg | Gln | Asp | Tyr | Lys | Glu | Ile | Asn | Asn | Tyr | Leu | Arg | |
| | | | 700 | | | | | 705 | | | | | 710 | | | |
| AAC | CAG | GGC | GGC | AGC | GGC | AAC | GAG | AAG | CTG | GAC | GCC | CAG | ATC | AAG | AAC | 962 |
| Asn | Gln | Gly | Gly | Ser | Gly | Asn | Glu | Lys | Leu | Asp | Ala | Gln | Ile | Lys | Asn | |
| | | | 715 | | | | | 720 | | | | | 725 | | | |
| ATC | AGC | GAC | GCC | CTG | GGC | AAG | AAG | CCC | ATC | CCC | GAG | AAC | ATC | ACC | GTG | 1010 |
| Ile | Ser | Asp | Ala | Leu | Gly | Lys | Lys | Pro | Ile | Pro | Glu | Asn | Ile | Thr | Val | |
| | 730 | | | | | 735 | | | | | 740 | | | | | |
| TAC | CGC | TGG | TGC | GGC | ATG | CCC | GAG | TTC | GGC | TAC | CAG | ATC | AGC | GAC | CCC | 1058 |
| Tyr | Arg | Trp | Cys | Gly | Met | Pro | Glu | Phe | Gly | Tyr | Gln | Ile | Ser | Asp | Pro | |
| 745 | | | | | 750 | | | | | 755 | | | | | 760 | |
| CTG | CCC | AGC | CTG | AAG | GAC | TTC | GAG | GAG | CAG | TTC | CTG | AAC | ACC | ATC | AAG | 1106 |
| Leu | Pro | Ser | Leu | Lys | Asp | Phe | Glu | Glu | Gln | Phe | Leu | Asn | Thr | Ile | Lys | |
| | | | | 765 | | | | | 770 | | | | | 775 | | |
| GAG | GAC | AAG | GGC | TAC | ATG | AGC | ACC | AGC | CTG | AGC | AGC | GAG | CGC | CTG | GCC | 1154 |
| Glu | Asp | Lys | Gly | Tyr | Met | Ser | Thr | Ser | Leu | Ser | Ser | Glu | Arg | Leu | Ala | |
| | | | 780 | | | | | 785 | | | | | 790 | | | |
| GCC | TTC | GGC | AGC | CGC | AAG | ATC | ATC | CTG | CGC | CTG | CAG | GTG | CCC | AAG | GGC | 1202 |
| Ala | Phe | Gly | Ser | Arg | Lys | Ile | Ile | Leu | Arg | Leu | Gln | Val | Pro | Lys | Gly | |
| | | | 795 | | | | | 800 | | | | | 805 | | | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| AGC | ACT | GGT | GCC | TAC | CTG | AGC | GCC | ATC | GGC | GGC | TTC | GCC | AGC | GAG | AAG | 1250 |
| Ser | Thr | Gly | Ala | Tyr | Leu | Ser | Ala | Ile | Gly | Gly | Phe | Ala | Ser | Glu | Lys |      |
|     | 810 |     |     |     |     | 815 |     |     |     |     | 820 |     |     |     |     |      |
| GAG | ATC | CTG | CTG | GAT | AAG | GAC | AGC | AAG | TAC | CAC | ATC | GAC | AAG | GTG | ACC | 1298 |
| Glu | Ile | Leu | Leu | Asp | Lys | Asp | Ser | Lys | Tyr | His | Ile | Asp | Lys | Val | Thr |      |
| 825 |     |     |     |     | 830 |     |     |     |     | 835 |     |     |     |     | 840 |      |
| GAG | GTG | ATC | ATC | AAG | GGC | GTG | AAG | CGC | TAC | GTG | GTG | GAC | GCC | ACC | CTG | 1346 |
| Glu | Val | Ile | Ile | Lys | Gly | Val | Lys | Arg | Tyr | Val | Val | Asp | Ala | Thr | Leu |      |
|     |     |     |     | 845 |     |     |     |     | 850 |     |     |     |     | 855 |     |      |
| CTG | ACC | AAC | TAG |     |     |     |     |     |     |     |     |     |     |     |     | 1358 |
| Leu | Thr | Asn |     |     |     |     |     |     |     |     |     |     |     |     |     |      |

( 2 ) INFORMATION FOR SEQ ID NO:46:

( i ) SEQUENCE CHARACTERISTICS:
        ( A ) LENGTH: 449 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Gly | Trp | Ser | Trp | Ile | Phe | Leu | Phe | Leu | Leu | Ser | Gly | Ala | Ala | Gly |
| 1   |     |     |     | 5   |     |     |     |     | 10  |     |     |     |     | 15  |     |
| Val | His | Cys | Leu | Ser | Ser | Ser | Ser | Phe | Ala | Asp | Ser | Asn | Pro | Ile | Arg |
|     |     |     | 20  |     |     |     |     | 25  |     |     |     |     | 30  |     |     |
| Val | Thr | Asp | Arg | Ala | Ala | Ser | Thr | Leu | Gln | Asn | Leu | Lys | Ile | Thr | Asp |
|     |     | 35  |     |     |     |     | 40  |     |     |     |     | 45  |     |     |     |
| Lys | Val | Glu | Asp | Phe | Lys | Glu | Asp | Lys | Glu | Lys | Ala | Lys | Glu | Trp | Gly |
|     | 50  |     |     |     |     | 55  |     |     |     |     | 60  |     |     |     |     |
| Lys | Glu | Lys | Glu | Lys | Glu | Trp | Lys | Leu | Thr | Ala | Thr | Glu | Lys | Gly | Lys |
| 65  |     |     |     |     | 70  |     |     |     |     | 75  |     |     |     |     | 80  |
| Met | Asn | Asn | Phe | Leu | Asp | Asn | Lys | Asn | Asp | Ile | Lys | Thr | Asn | Tyr | Lys |
|     |     |     |     | 85  |     |     |     |     | 90  |     |     |     |     | 95  |     |
| Glu | Ile | Thr | Phe | Ser | Ile | Ala | Gly | Ser | Phe | Glu | Asp | Glu | Ile | Lys | Asp |
|     |     |     | 100 |     |     |     |     | 105 |     |     |     |     | 110 |     |     |
| Leu | Lys | Glu | Ile | Asp | Lys | Met | Phe | Asp | Lys | Thr | Asn | Leu | Ser | Asn | Ser |
|     |     | 115 |     |     |     |     | 120 |     |     |     |     | 125 |     |     |     |
| Ile | Ile | Thr | Tyr | Lys | Asn | Val | Glu | Pro | Thr | Thr | Ile | Gly | Phe | Asn | Lys |
|     | 130 |     |     |     |     | 135 |     |     |     |     | 140 |     |     |     |     |
| Ser | Leu | Thr | Glu | Gly | Asn | Thr | Ile | Asn | Ser | Asp | Ala | Met | Ala | Gln | Phe |
| 145 |     |     |     |     | 150 |     |     |     |     | 155 |     |     |     |     | 160 |
| Lys | Glu | Gln | Phe | Leu | Asp | Arg | Asp | Ile | Lys | Phe | Asp | Ser | Tyr | Leu | Asp |
|     |     |     |     | 165 |     |     |     |     | 170 |     |     |     |     | 175 |     |
| Thr | His | Leu | Thr | Ala | Gln | Gln | Val | Ser | Ser | Lys | Glu | Arg | Val | Ile | Leu |
|     |     |     | 180 |     |     |     |     | 185 |     |     |     |     | 190 |     |     |
| Lys | Val | Thr | Val | Pro | Ser | Gly | Lys | Gly | Ser | Thr | Thr | Pro | Thr | Lys | Ala |
|     |     | 195 |     |     |     |     | 200 |     |     |     |     | 205 |     |     |     |
| Gly | Val | Ile | Leu | Asn | Asn | Ser | Glu | Tyr | Lys | Met | Leu | Ile | Asp | Asn | Gly |
|     | 210 |     |     |     |     | 215 |     |     |     |     | 220 |     |     |     |     |
| Tyr | Met | Val | His | Val | Asp | Lys | Val | Ser | Lys | Val | Val | Lys | Lys | Gly | Val |
| 225 |     |     |     |     | 230 |     |     |     |     | 235 |     |     |     |     | 240 |
| Glu | Cys | Leu | Gln | Ile | Glu | Gly | Thr | Leu | Lys | Lys | Ser | Leu | Asp | Phe | Lys |
|     |     |     |     | 245 |     |     |     |     | 250 |     |     |     |     | 255 |     |
| Asn | Asp | Ile | Asn | Ala | Glu | Ala | His | Ser | Trp | Gly | Met | Lys | Asn | Tyr | Glu |
|     |     |     | 260 |     |     |     |     | 265 |     |     |     |     | 270 |     |     |
| Glu | Trp | Ala | Lys | Asp | Leu | Thr | Asp | Ser | Gln | Arg | Glu | Ala | Leu | Asp | Gly |

-continued

```
            275                     280                     285

Tyr Ala Arg Gln Asp Tyr Lys Glu Ile Asn Asn Tyr Leu Arg Asn Gln
    290                     295                     300

Gly Gly Ser Gly Asn Glu Lys Leu Asp Ala Gln Ile Lys Asn Ile Ser
305                 310                     315                 320

Asp Ala Leu Gly Lys Lys Pro Ile Pro Glu Asn Ile Thr Val Tyr Arg
                325                     330                     335

Trp Cys Gly Met Pro Glu Phe Gly Tyr Gln Ile Ser Asp Pro Leu Pro
            340                     345                     350

Ser Leu Lys Asp Phe Glu Glu Gln Phe Leu Asn Thr Ile Lys Glu Asp
        355                     360                     365

Lys Gly Tyr Met Ser Thr Ser Leu Ser Ser Glu Arg Leu Ala Ala Phe
    370                     375                     380

Gly Ser Arg Lys Ile Ile Leu Arg Leu Gln Val Pro Lys Gly Ser Thr
385                 390                     395                 400

Gly Ala Tyr Leu Ser Ala Ile Gly Gly Phe Ala Ser Glu Lys Glu Ile
                405                     410                     415

Leu Leu Asp Lys Asp Ser Lys Tyr His Ile Asp Lys Val Thr Glu Val
            420                     425                     430

Ile Ile Lys Gly Val Lys Arg Tyr Val Val Asp Ala Thr Leu Leu Thr
        435                     440                     445

Asn
```

( 2 ) INFORMATION FOR SEQ ID NO:47:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i x ) FEATURE:
( A ) NAME/KEY: Peptide
( B ) LOCATION: 1..16
( D ) OTHER INFORMATION: /note= "linker peptide for fusion of VIP1A(a) and VIP2A(a) used to construct pCIB5533"

( x i ) SEQUENCE DESCRIPTION: SEQ ID NO:47:

```
Pro Ser Thr Pro Pro Thr Pro Ser Pro Ser Thr Pro Pro Thr Pro Ser
1               5                   10                  15
```

( 2 ) INFORMATION FOR SEQ ID NO:48:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA encoding linker peptide used to construct pCIB5533"

( i i i ) HYPOTHETICAL: NO ( x i ) SEQUENCE DESCRIPTION: SEQ ID NO:48:

```
CCCGGGCCTT CTACTCCCCC AACTCCCTCT CCTAGCACGC CTCCGACACC TAGCGATATC    60

GGATCC                                                               66
```

(2) INFORMATION FOR SEQ ID NO:49:

(i) SEQUENCE CHARACTERISTICS:
    (A) LENGTH: 4031 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic DNA"

(iii) HYPOTHETICAL: NO (ix) FEATURE:
    (A) NAME/KEY: CDS
    (B) LOCATION: 6..4019
    (D) OTHER INFORMATION: /note= "Maize optimized DNA
      sequence encoding a VIP2A(a) - VIP1A(a) fusion protein as
      contained in pCIB5531"

(xi) SEQUENCE DESCRIPTION: SEQ ID NO:49:

```
GATCC ATG AAG CGC ATG GAG GGC AAG CTG TTC ATG GTG AGC AAG AAG          47
      Met Lys Arg Met Glu Gly Lys Leu Phe Met Val Ser Lys Lys
      450             455             460

CTC CAG GTG GTG ACC AAG ACC GTG CTG CTG AGC ACC GTG TTC AGC ATC        95
Leu Gln Val Val Thr Lys Thr Val Leu Leu Ser Thr Val Phe Ser Ile
    465             470             475

AGC CTG CTG AAC AAC GAG GTG ATC AAG GCC GAG CAG CTG AAC ATC AAC       143
Ser Leu Leu Asn Asn Glu Val Ile Lys Ala Glu Gln Leu Asn Ile Asn
480             485             490             495

AGC CAG AGC AAG TAC ACC AAC CTC CAG AAC CTG AAG ATC ACC GAC AAG       191
Ser Gln Ser Lys Tyr Thr Asn Leu Gln Asn Leu Lys Ile Thr Asp Lys
            500             505             510

GTG GAG GAC TTC AAG GAG GAC AAG GAG AAG GCC AAG GAG TGG GGC AAG       239
Val Glu Asp Phe Lys Glu Asp Lys Glu Lys Ala Lys Glu Trp Gly Lys
        515             520             525

GAG AAG GAG AAG GAG TGG AAG CTT ACC GCC ACC GAG AAG GGC AAG ATG       287
Glu Lys Glu Lys Glu Trp Lys Leu Thr Ala Thr Glu Lys Gly Lys Met
    530             535             540

AAC AAC TTC CTG GAC AAC AAG AAC GAC ATC AAG ACC AAC TAC AAG GAG       335
Asn Asn Phe Leu Asp Asn Lys Asn Asp Ile Lys Thr Asn Tyr Lys Glu
545             550             555

ATC ACC TTC AGC ATA GCC GGC AGC TTC GAG GAC GAG ATC AAG GAC CTG       383
Ile Thr Phe Ser Ile Ala Gly Ser Phe Glu Asp Glu Ile Lys Asp Leu
560             565             570             575

AAG GAG ATC GAC AAG ATG TTC GAC AAG ACC AAC CTG AGC AAC AGC ATC       431
Lys Glu Ile Asp Lys Met Phe Asp Lys Thr Asn Leu Ser Asn Ser Ile
            580             585             590

ATC ACC TAC AAG AAC GTG GAG CCC ACC ACC ATC GGC TTC AAC AAG AGC       479
Ile Thr Tyr Lys Asn Val Glu Pro Thr Thr Ile Gly Phe Asn Lys Ser
        595             600             605

CTG ACC GAG GGC AAC ACC ATC AAC AGC GAC GCC ATG GCC CAG TTC AAG       527
Leu Thr Glu Gly Asn Thr Ile Asn Ser Asp Ala Met Ala Gln Phe Lys
    610             615             620

GAG CAG TTC CTG GAC CGC GAC ATC AAG TTC GAC AGC TAC CTG GAC ACC       575
Glu Gln Phe Leu Asp Arg Asp Ile Lys Phe Asp Ser Tyr Leu Asp Thr
625             630             635

CAC CTG ACC GCC CAG CAG GTG AGC AGC AAG GAG CGC GTG ATC CTG AAG       623
His Leu Thr Ala Gln Gln Val Ser Ser Lys Glu Arg Val Ile Leu Lys
640             645             650             655

GTG ACC GTC CCC AGC GGC AAG GGC AGC ACC ACC CCC ACC AAG GCC GGC       671
Val Thr Val Pro Ser Gly Lys Gly Ser Thr Thr Pro Thr Lys Ala Gly
            660             665             670

GTG ATC CTG AAC AAC AGC GAG TAC AAG ATG CTG ATC GAC AAC GGC TAC       719
Val Ile Leu Asn Asn Ser Glu Tyr Lys Met Leu Ile Asp Asn Gly Tyr
```

-continued

|  | 675 |  |  |  | 680 |  |  |  | 685 |  |  |  |  |
|---|---|---|---|---|---|---|---|---|---|---|---|---|---|
| ATG | GTG | CAC | GTG | GAC | AAG | GTG | AGC | AAG | GTG | GTG | AAG | AAG | GGC | GTG | GAG | 767 |
| Met | Val | His | Val | Asp | Lys | Val | Ser | Lys | Val | Val | Lys | Lys | Gly | Val | Glu |  |
|  |  | 690 |  |  |  |  | 695 |  |  |  |  | 700 |  |  |  |  |
| TGC | CTC | CAG | ATC | GAG | GGC | ACC | CTG | AAG | AAG | AGT | CTA | GAC | TTC | AAG | AAC | 815 |
| Cys | Leu | Gln | Ile | Glu | Gly | Thr | Leu | Lys | Lys | Ser | Leu | Asp | Phe | Lys | Asn |  |
| 705 |  |  |  |  |  | 710 |  |  |  |  |  | 715 |  |  |  |  |
| GAC | ATC | AAC | GCC | GAG | GCC | CAC | AGC | TGG | GGC | ATG | AAG | AAC | TAC | GAG | GAG | 863 |
| Asp | Ile | Asn | Ala | Glu | Ala | His | Ser | Trp | Gly | Met | Lys | Asn | Tyr | Glu | Glu |  |
| 720 |  |  |  |  | 725 |  |  |  |  | 730 |  |  |  |  | 735 |  |
| TGG | GCC | AAG | GAC | CTG | ACC | GAC | AGC | CAG | CGC | GAG | GCC | CTG | GAC | GGC | TAC | 911 |
| Trp | Ala | Lys | Asp | Leu | Thr | Asp | Ser | Gln | Arg | Glu | Ala | Leu | Asp | Gly | Tyr |  |
|  |  |  |  | 740 |  |  |  |  | 745 |  |  |  |  | 750 |  |  |
| GCC | CGC | CAG | GAC | TAC | AAG | GAG | ATC | AAC | AAC | TAC | CTG | CGC | AAC | CAG | GGC | 959 |
| Ala | Arg | Gln | Asp | Tyr | Lys | Glu | Ile | Asn | Asn | Tyr | Leu | Arg | Asn | Gln | Gly |  |
|  |  |  | 755 |  |  |  |  | 760 |  |  |  |  | 765 |  |  |  |
| GGC | AGC | GGC | AAC | GAG | AAG | CTG | GAC | GCC | CAG | ATC | AAG | AAC | ATC | AGC | GAC | 1007 |
| Gly | Ser | Gly | Asn | Glu | Lys | Leu | Asp | Ala | Gln | Ile | Lys | Asn | Ile | Ser | Asp |  |
|  |  | 770 |  |  |  |  | 775 |  |  |  |  | 780 |  |  |  |  |
| GCC | CTG | GGC | AAG | AAG | CCC | ATC | CCC | GAG | AAC | ATC | ACC | GTG | TAC | CGC | TGG | 1055 |
| Ala | Leu | Gly | Lys | Lys | Pro | Ile | Pro | Glu | Asn | Ile | Thr | Val | Tyr | Arg | Trp |  |
| 785 |  |  |  |  | 790 |  |  |  |  | 795 |  |  |  |  |  |  |
| TGC | GGC | ATG | CCC | GAG | TTC | GGC | TAC | CAG | ATC | AGC | GAC | CCC | CTG | CCC | AGC | 1103 |
| Cys | Gly | Met | Pro | Glu | Phe | Gly | Tyr | Gln | Ile | Ser | Asp | Pro | Leu | Pro | Ser |  |
| 800 |  |  |  |  | 805 |  |  |  |  | 810 |  |  |  |  | 815 |  |
| CTG | AAG | GAC | TTC | GAG | GAG | CAG | TTC | CTG | AAC | ACC | ATC | AAG | GAG | GAC | AAG | 1151 |
| Leu | Lys | Asp | Phe | Glu | Glu | Gln | Phe | Leu | Asn | Thr | Ile | Lys | Glu | Asp | Lys |  |
|  |  |  |  | 820 |  |  |  |  | 825 |  |  |  |  | 830 |  |  |
| GGC | TAC | ATG | AGC | ACC | AGC | CTG | AGC | AGC | GAG | CGC | CTG | GCC | GCC | TTC | GGC | 1199 |
| Gly | Tyr | Met | Ser | Thr | Ser | Leu | Ser | Ser | Glu | Arg | Leu | Ala | Ala | Phe | Gly |  |
|  |  |  |  | 835 |  |  |  |  | 840 |  |  |  |  | 845 |  |  |
| AGC | CGC | AAG | ATC | ATC | CTG | CGC | CTG | CAG | GTG | CCC | AAG | GGC | AGC | ACT | GGT | 1247 |
| Ser | Arg | Lys | Ile | Ile | Leu | Arg | Leu | Gln | Val | Pro | Lys | Gly | Ser | Thr | Gly |  |
|  |  | 850 |  |  |  |  | 855 |  |  |  |  | 860 |  |  |  |  |
| GCC | TAC | CTG | AGC | GCC | ATC | GGC | GGC | TTC | GCC | AGC | GAG | AAG | GAG | ATC | CTG | 1295 |
| Ala | Tyr | Leu | Ser | Ala | Ile | Gly | Gly | Phe | Ala | Ser | Glu | Lys | Glu | Ile | Leu |  |
| 865 |  |  |  |  | 870 |  |  |  |  | 875 |  |  |  |  |  |  |
| CTG | GAT | AAG | GAC | AGC | AAG | TAC | CAC | ATC | GAC | AAG | GTG | ACC | GAG | GTG | ATC | 1343 |
| Leu | Asp | Lys | Asp | Ser | Lys | Tyr | His | Ile | Asp | Lys | Val | Thr | Glu | Val | Ile |  |
| 880 |  |  |  |  | 885 |  |  |  |  | 890 |  |  |  |  | 895 |  |
| ATC | AAG | GGC | GTG | AAG | CGC | TAC | GTG | GTG | GAC | GCC | ACC | CTG | CTG | ACC | AAC | 1391 |
| Ile | Lys | Gly | Val | Lys | Arg | Tyr | Val | Val | Asp | Ala | Thr | Leu | Leu | Thr | Asn |  |
|  |  |  |  | 900 |  |  |  |  | 905 |  |  |  |  | 910 |  |  |
| TCC | CGG | GGG | CCT | TCT | ACT | CCC | CCA | ACT | CCC | TCT | CCT | AGC | ACG | CCT | CCG | 1439 |
| Ser | Arg | Gly | Pro | Ser | Thr | Pro | Pro | Thr | Pro | Ser | Pro | Ser | Thr | Pro | Pro |  |
|  |  |  | 915 |  |  |  |  | 920 |  |  |  |  | 925 |  |  |  |
| ACA | CCT | AGC | GAT | ATC | GGA | TCC | ACC | ATG | AAG | ACC | AAC | CAG | ATC | AGC | ACC | 1487 |
| Thr | Pro | Ser | Asp | Ile | Gly | Ser | Thr | Met | Lys | Thr | Asn | Gln | Ile | Ser | Thr |  |
|  |  |  | 930 |  |  |  |  | 935 |  |  |  |  | 940 |  |  |  |
| ACC | CAG | AAG | AAC | CAG | CAG | AAG | GAG | ATG | GAC | CGC | AAG | GGC | CTG | CTG | GGC | 1535 |
| Thr | Gln | Lys | Asn | Gln | Gln | Lys | Glu | Met | Asp | Arg | Lys | Gly | Leu | Leu | Gly |  |
|  |  | 945 |  |  |  |  | 950 |  |  |  |  | 955 |  |  |  |  |
| TAC | TAC | TTC | AAG | GGC | AAG | GAC | TTC | AGC | AAC | CTG | ACC | ATG | TTC | GCC | CCC | 1583 |
| Tyr | Tyr | Phe | Lys | Gly | Lys | Asp | Phe | Ser | Asn | Leu | Thr | Met | Phe | Ala | Pro |  |
| 960 |  |  |  |  | 965 |  |  |  |  | 970 |  |  |  |  | 975 |  |
| ACG | CGT | GAC | AGC | ACC | CTG | ATC | TAC | GAC | CAG | CAG | ACC | GCC | AAC | AAG | CTG | 1631 |
| Thr | Arg | Asp | Ser | Thr | Leu | Ile | Tyr | Asp | Gln | Gln | Thr | Ala | Asn | Lys | Leu |  |
|  |  |  |  | 980 |  |  |  |  | 985 |  |  |  |  | 990 |  |  |
| CTG | GAC | AAG | AAG | CAG | CAG | GAG | TAC | CAG | AGC | ATC | CGC | TGG | ATC | GGC | CTG | 1679 |
| Leu | Asp | Lys | Lys | Gln | Gln | Glu | Tyr | Gln | Ser | Ile | Arg | Trp | Ile | Gly | Leu |  |

|  |  |  |  |  |  |  |  |  |  |  |  |  |  |  |  |
|---|---|---|---|---|---|---|---|---|---|---|---|---|---|---|---|
|  |  |  | 995 |  |  |  |  | 1000 |  |  |  |  | 1005 |  |  |
| ATC | CAG | AGC | AAG | GAG | ACC | GGC | GAC | TTC | ACC | TTC | AAC | CTG | AGC | GAG | GAC | 1727 |
| Ile | Gln | Ser | Lys | Glu | Thr | Gly | Asp | Phe | Thr | Phe | Asn | Leu | Ser | Glu | Asp |  |
|  |  |  | 1010 |  |  |  |  | 1015 |  |  |  |  | 1020 |  |  |
| GAG | CAG | GCC | ATC | ATC | GAG | ATC | AAC | GGC | AAG | ATC | ATC | AGC | AAC | AAG | GGC | 1775 |
| Glu | Gln | Ala | Ile | Ile | Glu | Ile | Asn | Gly | Lys | Ile | Ile | Ser | Asn | Lys | Gly |  |
|  |  |  | 1025 |  |  |  |  | 1030 |  |  |  |  | 1035 |  |  |
| AAG | GAG | AAG | CAG | GTG | GTG | CAC | CTG | GAG | AAG | GGC | AAG | CTG | GTG | CCC | ATC | 1823 |
| Lys | Glu | Lys | Gln | Val | Val | His | Leu | Glu | Lys | Gly | Lys | Leu | Val | Pro | Ile |  |
| 1040 |  |  |  |  | 1045 |  |  |  |  | 1050 |  |  |  |  | 1055 |  |
| AAG | ATC | GAG | TAC | CAG | AGC | GAC | ACC | AAG | TTC | AAC | ATC | GAC | AGC | AAG | ACC | 1871 |
| Lys | Ile | Glu | Tyr | Gln | Ser | Asp | Thr | Lys | Phe | Asn | Ile | Asp | Ser | Lys | Thr |  |
|  |  |  |  | 1060 |  |  |  |  | 1065 |  |  |  |  | 1070 |  |  |
| TTC | AAG | GAG | CTG | AAG | CTT | TTC | AAG | ATC | GAC | AGC | CAG | AAC | CAG | CCC | CAG | 1919 |
| Phe | Lys | Glu | Leu | Lys | Leu | Phe | Lys | Ile | Asp | Ser | Gln | Asn | Gln | Pro | Gln |  |
|  |  |  | 1075 |  |  |  |  | 1080 |  |  |  |  | 1085 |  |  |
| CAG | GTG | CAG | CAG | GAC | GAG | CTG | CGC | AAC | CCC | GAG | TTC | AAC | AAG | AAG | GAG | 1967 |
| Gln | Val | Gln | Gln | Asp | Glu | Leu | Arg | Asn | Pro | Glu | Phe | Asn | Lys | Lys | Glu |  |
|  |  |  | 1090 |  |  |  |  | 1095 |  |  |  |  | 1100 |  |  |
| AGC | CAG | GAG | TTC | CTG | GCC | AAG | CCC | AGC | AAG | ATC | AAC | CTG | TTC | ACC | CAG | 2015 |
| Ser | Gln | Glu | Phe | Leu | Ala | Lys | Pro | Ser | Lys | Ile | Asn | Leu | Phe | Thr | Gln |  |
|  |  |  | 1105 |  |  |  |  | 1110 |  |  |  |  | 1115 |  |  |
| CAG | ATG | AAG | CGC | GAG | ATC | GAC | GAG | GAC | ACC | GAC | ACC | GAC | GGC | GAC | AGC | 2063 |
| Gln | Met | Lys | Arg | Glu | Ile | Asp | Glu | Asp | Thr | Asp | Thr | Asp | Gly | Asp | Ser |  |
| 1120 |  |  |  |  | 1125 |  |  |  |  | 1130 |  |  |  |  | 1135 |  |
| ATC | CCC | GAC | CTG | TGG | GAG | GAG | AAC | GGC | TAC | ACC | ATC | CAG | AAC | CGC | ATC | 2111 |
| Ile | Pro | Asp | Leu | Trp | Glu | Glu | Asn | Gly | Tyr | Thr | Ile | Gln | Asn | Arg | Ile |  |
|  |  |  |  | 1140 |  |  |  |  | 1145 |  |  |  |  | 1150 |  |  |
| GCC | GTG | AAG | TGG | GAC | GAC | AGC | CTG | GCT | AGC | AAG | GGC | TAC | ACC | AAG | TTC | 2159 |
| Ala | Val | Lys | Trp | Asp | Asp | Ser | Leu | Ala | Ser | Lys | Gly | Tyr | Thr | Lys | Phe |  |
|  |  |  | 1155 |  |  |  |  | 1160 |  |  |  |  | 1165 |  |  |
| GTG | AGC | AAC | CCC | CTG | GAG | AGC | CAC | ACC | GTG | GGC | GAC | CCC | TAC | ACC | GAC | 2207 |
| Val | Ser | Asn | Pro | Leu | Glu | Ser | His | Thr | Val | Gly | Asp | Pro | Tyr | Thr | Asp |  |
|  |  |  | 1170 |  |  |  |  | 1175 |  |  |  |  | 1180 |  |  |
| TAC | GAG | AAG | GCC | GCC | CGC | GAC | CTG | GAC | CTG | AGC | AAC | GCC | AAG | GAG | ACC | 2255 |
| Tyr | Glu | Lys | Ala | Ala | Arg | Asp | Leu | Asp | Leu | Ser | Asn | Ala | Lys | Glu | Thr |  |
|  |  |  | 1185 |  |  |  |  | 1190 |  |  |  |  | 1195 |  |  |
| TTC | AAC | CCC | CTG | GTG | GCC | GCC | TTC | CCC | AGC | GTG | AAC | GTG | AGC | ATG | GAG | 2303 |
| Phe | Asn | Pro | Leu | Val | Ala | Ala | Phe | Pro | Ser | Val | Asn | Val | Ser | Met | Glu |  |
| 1200 |  |  |  |  | 1205 |  |  |  |  | 1210 |  |  |  |  | 1215 |  |
| AAG | GTG | ATC | CTG | AGC | CCC | AAC | GAG | AAC | CTG | AGC | AAC | AGC | GTG | GAG | AGC | 2351 |
| Lys | Val | Ile | Leu | Ser | Pro | Asn | Glu | Asn | Leu | Ser | Asn | Ser | Val | Glu | Ser |  |
|  |  |  |  | 1220 |  |  |  |  | 1225 |  |  |  |  | 1230 |  |  |
| CAC | TCG | AGC | ACC | AAC | TGG | AGC | TAC | ACC | AAC | ACC | GAG | GGC | GCC | AGC | GTG | 2399 |
| His | Ser | Ser | Thr | Asn | Trp | Ser | Tyr | Thr | Asn | Thr | Glu | Gly | Ala | Ser | Val |  |
|  |  |  | 1235 |  |  |  |  | 1240 |  |  |  |  | 1245 |  |  |
| GAG | GCC | GGC | ATC | GGT | CCC | AAG | GGC | ATC | AGC | TTC | GGC | GTG | AGC | GTG | AAC | 2447 |
| Glu | Ala | Gly | Ile | Gly | Pro | Lys | Gly | Ile | Ser | Phe | Gly | Val | Ser | Val | Asn |  |
|  |  |  | 1250 |  |  |  |  | 1255 |  |  |  |  | 1260 |  |  |
| TAC | CAG | CAC | AGC | GAG | ACC | GTG | GCC | CAG | GAG | TGG | GGC | ACC | AGC | ACC | GGC | 2495 |
| Tyr | Gln | His | Ser | Glu | Thr | Val | Ala | Gln | Glu | Trp | Gly | Thr | Ser | Thr | Gly |  |
|  |  |  | 1265 |  |  |  |  | 1270 |  |  |  |  | 1275 |  |  |
| AAC | ACC | AGC | CAG | TTC | AAC | ACC | GCC | AGC | GCC | GGC | TAC | CTG | AAC | GCC | AAC | 2543 |
| Asn | Thr | Ser | Gln | Phe | Asn | Thr | Ala | Ser | Ala | Gly | Tyr | Leu | Asn | Ala | Asn |  |
| 1280 |  |  |  |  | 1285 |  |  |  |  | 1290 |  |  |  |  | 1295 |  |
| GTG | CGC | TAC | AAC | AAC | GTG | GGC | ACC | GGC | GCC | ATC | TAC | GAC | GTG | AAG | CCC | 2591 |
| Val | Arg | Tyr | Asn | Asn | Val | Gly | Thr | Gly | Ala | Ile | Tyr | Asp | Val | Lys | Pro |  |
|  |  |  | 1300 |  |  |  |  | 1305 |  |  |  |  | 1310 |  |  |
| ACC | ACC | AGC | TTC | GTG | CTG | AAC | AAC | GAC | ACC | ATC | GCC | ACC | ATC | ACC | GCC | 2639 |
| Thr | Thr | Ser | Phe | Val | Leu | Asn | Asn | Asp | Thr | Ile | Ala | Thr | Ile | Thr | Ala |  |

|     |     |     |     |     |     |     |     |     |     |     |     |     |     |     |     |
|---|---|---|---|---|---|---|---|---|---|---|---|---|---|---|---|
| AAG | TCG | AAT | TCC | ACC | GCC | CTG | AAC | ATC | AGC | CCC | GGC | GAG | AGC | TAC | CCC | 2687
| Lys | Ser | Asn | Ser | Thr | Ala | Leu | Asn | Ile | Ser | Pro | Gly | Glu | Ser | Tyr | Pro |
|     |     |     | 1330 |     |     |     |     | 1335 |     |     |     |     | 1340 |     |     |

```
            1315                          1320                          1325

AAG TCG AAT TCC ACC GCC CTG AAC ATC AGC CCC GGC GAG AGC TAC CCC         2687
Lys Ser Asn Ser Thr Ala Leu Asn Ile Ser Pro Gly Glu Ser Tyr Pro
        1330                1335                    1340

AAG AAG GGC CAG AAC GGC ATC GCC ATC ACC AGC ATG GAC GAC TTC AAC         2735
Lys Lys Gly Gln Asn Gly Ile Ala Ile Thr Ser Met Asp Asp Phe Asn
    1345                1350                1355

AGC CAC CCC ATC ACC CTG AAC AAG AAG CAG GTG GAC AAC CTG CTG AAC         2783
Ser His Pro Ile Thr Leu Asn Lys Lys Gln Val Asp Asn Leu Leu Asn
1360                1365                1370                    1375

AAC AAG CCC ATG ATG CTG GAG ACC AAC CAG ACC GAC GGC GTC TAC AAG         2831
Asn Lys Pro Met Met Leu Glu Thr Asn Gln Thr Asp Gly Val Tyr Lys
                1380                1385                1390

ATC AAG GAC ACC CAC GGC AAC ATC GTG ACG GGC GGC GAG TGG AAC GGC         2879
Ile Lys Asp Thr His Gly Asn Ile Val Thr Gly Gly Glu Trp Asn Gly
            1395                1400                1405

GTG ATC CAG CAG ATC AAG GCC AAG ACC GCC AGC ATC ATC GTC GAC GAC         2927
Val Ile Gln Gln Ile Lys Ala Lys Thr Ala Ser Ile Ile Val Asp Asp
        1410                1415                1420

GGC GAG CGC GTG GCC GAG AAG CGC GTG GCC GCC AAG GAC TAC GAG AAC         2975
Gly Glu Arg Val Ala Glu Lys Arg Val Ala Ala Lys Asp Tyr Glu Asn
    1425                1430                1435

CCC GAG GAC AAG ACC CCC AGC CTG ACC CTG AAG GAC GCC CTG AAG CTG         3023
Pro Glu Asp Lys Thr Pro Ser Leu Thr Leu Lys Asp Ala Leu Lys Leu
1440                1445                1450                    1455

AGC TAC CCC GAC GAG ATC AAG GAG ATC GAG GGC TTG CTG TAC TAC AAG         3071
Ser Tyr Pro Asp Glu Ile Lys Glu Ile Glu Gly Leu Leu Tyr Tyr Lys
                1460                1465                1470

AAC AAG CCC ATC TAC GAG AGC AGC GTG ATG ACC TAT CTA GAC GAG AAC         3119
Asn Lys Pro Ile Tyr Glu Ser Ser Val Met Thr Tyr Leu Asp Glu Asn
            1475                1480                1485

ACC GCC AAG GAG GTG ACC AAG CAG CTG AAC GAC ACC ACC GGC AAG TTC         3167
Thr Ala Lys Glu Val Thr Lys Gln Leu Asn Asp Thr Thr Gly Lys Phe
        1490                1495                1500

AAG GAC GTG AGC CAC CTG TAC GAC GTG AAG CTG ACC CCC AAG ATG AAC         3215
Lys Asp Val Ser His Leu Tyr Asp Val Lys Leu Thr Pro Lys Met Asn
    1505                1510                1515

GTG ACC ATC AAG CTG AGC ATC CTG TAC GAC AAC GCC GAG AGC AAC GAC         3263
Val Thr Ile Lys Leu Ser Ile Leu Tyr Asp Asn Ala Glu Ser Asn Asp
1520                1525                1530                    1535

AAC AGC ATC GGC AAG TGG ACC AAC ACC AAC ATC GTG AGC GGC GGC AAC         3311
Asn Ser Ile Gly Lys Trp Thr Asn Thr Asn Ile Val Ser Gly Gly Asn
                1540                1545                1550

AAC GGC AAG AAG CAG TAC AGC AGC AAC AAC CCC GAC GCC AAC CTG ACC         3359
Asn Gly Lys Lys Gln Tyr Ser Ser Asn Asn Pro Asp Ala Asn Leu Thr
            1555                1560                1565

CTG AAC ACC GAC GCC CAG GAG AAG CTG AAC AAG AAC CGC GAC TAC TAC         3407
Leu Asn Thr Asp Ala Gln Glu Lys Leu Asn Lys Asn Arg Asp Tyr Tyr
        1570                1575                1580

ATC AGC CTG TAC ATG AAG AGC GAG AAG AAC ACC CAG TGC GAG ATC ACC         3455
Ile Ser Leu Tyr Met Lys Ser Glu Lys Asn Thr Gln Cys Glu Ile Thr
    1585                1590                1595

ATC GAC GGC GAG ATA TAC CCC ATC ACC ACC AAG ACC GTG AAC GTG AAC         3503
Ile Asp Gly Glu Ile Tyr Pro Ile Thr Thr Lys Thr Val Asn Val Asn
1600                1605                1610                    1615

AAG GAC AAC TAC AAG CGC CTG GAC ATC ATC GCC CAC AAC ATC AAG AGC         3551
Lys Asp Asn Tyr Lys Arg Leu Asp Ile Ile Ala His Asn Ile Lys Ser
                1620                1625                1630

AAC CCC ATC AGC AGC CTG CAC ATC AAG ACC AAC GAC GAG ATC ACC CTG         3599
Asn Pro Ile Ser Ser Leu His Ile Lys Thr Asn Asp Glu Ile Thr Leu
```

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |     |     | 1635 |    |     |     |     | 1640 |    |     |     |     | 1645 |    |
| TTC | TGG | GAC | GAC | ATA | TCG | ATT | ACC | GAC | GTC | GCC | AGC | ATC | AAG | CCC | GAG | 3647 |
| Phe | Trp | Asp | Asp | Ile | Ser | Ile | Thr | Asp | Val | Ala | Ser | Ile | Lys | Pro | Glu |
|     |     | 1650 |   |     |     |     | 1655 |   |     |     |     | 1660 |   |     |     |
| AAC | CTG | ACC | GAC | AGC | GAG | ATC | AAG | CAG | ATA | TAC | AGT | CGC | TAC | GGC | ATC | 3695 |
| Asn | Leu | Thr | Asp | Ser | Glu | Ile | Lys | Gln | Ile | Tyr | Ser | Arg | Tyr | Gly | Ile |
|     |     | 1665 |   |     |     |     | 1670 |   |     |     |     | 1675 |   |     |     |
| AAG | CTG | GAG | GAC | GGC | ATC | CTG | ATC | GAC | AAG | AAA | GGC | GGC | ATC | CAC | TAC | 3743 |
| Lys | Leu | Glu | Asp | Gly | Ile | Leu | Ile | Asp | Lys | Lys | Gly | Gly | Ile | His | Tyr |
| 1680 |   |     |     |     |     | 1685 |   |     |     |     | 1690 |   |     |     | 1695 |
| GGC | GAG | TTC | ATC | AAC | GAG | GCC | AGC | TTC | AAC | ATC | GAG | CCC | CTG | CAG | AAC | 3791 |
| Gly | Glu | Phe | Ile | Asn | Glu | Ala | Ser | Phe | Asn | Ile | Glu | Pro | Leu | Gln | Asn |
|     |     |     |     | 1700 |   |     |     |     | 1705 |   |     |     |     | 1710 |   |
| TAC | GTG | ACC | AAG | TAC | GAG | GTG | ACC | TAC | AGC | AGC | GAG | CTG | GGC | CCC | AAC | 3839 |
| Tyr | Val | Thr | Lys | Tyr | Glu | Val | Thr | Tyr | Ser | Ser | Glu | Leu | Gly | Pro | Asn |
|     |     |     | 1715 |   |     |     |     | 1720 |   |     |     |     | 1725 |   |     |
| GTG | AGC | GAC | ACC | CTG | GAG | AGC | GAC | AAG | ATT | TAC | AAG | GAC | GGC | ACC | ATC | 3887 |
| Val | Ser | Asp | Thr | Leu | Glu | Ser | Asp | Lys | Ile | Tyr | Lys | Asp | Gly | Thr | Ile |
|     |     |     | 1730 |   |     |     |     | 1735 |   |     |     |     | 1740 |   |     |
| AAG | TTC | GAC | TTC | ACC | AAG | TAC | AGC | AAG | AAC | GAG | CAG | GGC | CTG | TTC | TAC | 3935 |
| Lys | Phe | Asp | Phe | Thr | Lys | Tyr | Ser | Lys | Asn | Glu | Gln | Gly | Leu | Phe | Tyr |
|     |     | 1745 |   |     |     |     | 1750 |   |     |     |     | 1755 |   |     |     |
| GAC | AGC | GGC | CTG | AAC | TGG | GAC | TTC | AAG | ATC | AAC | GCC | ATC | ACC | TAC | GAC | 3983 |
| Asp | Ser | Gly | Leu | Asn | Trp | Asp | Phe | Lys | Ile | Asn | Ala | Ile | Thr | Tyr | Asp |
| 1760 |   |     |     |     |     | 1765 |   |     |     |     | 1770 |   |     |     | 1775 |
| GGC | AAG | GAG | ATG | AAC | GTG | TTC | CAC | CGC | TAC | AAC | AAG | TAGATCTGAG |     |     |     | 4029 |
| Gly | Lys | Glu | Met | Asn | Val | Phe | His | Arg | Tyr | Asn | Lys |
|     |     |     |     | 1780 |   |     |     |     | 1785 |   |     |
| CT  |     |     |     |     |     |     |     |     |     |     |     |     |     |     |     | 4031 |

( 2 ) INFORMATION FOR SEQ ID NO:50:

( i ) SEQUENCE CHARACTERISTICS:
        ( A ) LENGTH: 1338 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

| Met | Lys | Arg | Met | Glu | Gly | Lys | Leu | Phe | Met | Val | Ser | Lys | Lys | Leu | Gln |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Val | Val | Thr | Lys | Thr | Val | Leu | Leu | Ser | Thr | Val | Phe | Ser | Ile | Ser | Leu |
|     |     |     | 20  |     |     |     |     | 25  |     |     |     |     | 30  |     |     |
| Leu | Asn | Asn | Glu | Val | Ile | Lys | Ala | Glu | Gln | Leu | Asn | Ile | Asn | Ser | Gln |
|     |     |     | 35  |     |     |     |     | 40  |     |     |     |     | 45  |     |     |
| Ser | Lys | Tyr | Thr | Asn | Leu | Gln | Asn | Leu | Lys | Ile | Thr | Asp | Lys | Val | Glu |
|     |     | 50  |     |     |     |     | 55  |     |     |     |     | 60  |     |     |     |
| Asp | Phe | Lys | Glu | Asp | Lys | Glu | Lys | Ala | Lys | Glu | Trp | Gly | Lys | Glu | Lys |
| 65  |     |     |     |     | 70  |     |     |     |     | 75  |     |     |     |     | 80  |
| Glu | Lys | Glu | Trp | Lys | Leu | Thr | Ala | Thr | Glu | Lys | Gly | Lys | Met | Asn | Asn |
|     |     |     |     | 85  |     |     |     |     | 90  |     |     |     |     | 95  |     |
| Phe | Leu | Asp | Asn | Lys | Asn | Asp | Ile | Lys | Thr | Asn | Tyr | Lys | Glu | Ile | Thr |
|     |     |     | 100 |     |     |     |     | 105 |     |     |     |     | 110 |     |     |
| Phe | Ser | Ile | Ala | Gly | Ser | Phe | Glu | Asp | Glu | Ile | Lys | Asp | Leu | Lys | Glu |
|     |     |     | 115 |     |     |     |     | 120 |     |     |     |     | 125 |     |     |
| Ile | Asp | Lys | Met | Phe | Asp | Lys | Thr | Asn | Leu | Ser | Asn | Ser | Ile | Ile | Thr |
|     |     | 130 |     |     |     |     | 135 |     |     |     |     | 140 |     |     |     |
| Tyr | Lys | Asn | Val | Glu | Pro | Thr | Thr | Ile | Gly | Phe | Asn | Lys | Ser | Leu | Thr |

-continued

```
            145                         150                         155                         160
Glu   Gly   Asn   Thr   Ile   Asn   Ser   Asp   Ala   Met   Ala   Gln   Phe   Lys   Glu   Gln
                         165                         170                         175
Phe   Leu   Asp   Arg   Asp   Ile   Lys   Phe   Asp   Ser   Tyr   Leu   Asp   Thr   His   Leu
                         180                         185                         190
Thr   Ala   Gln   Gln   Val   Ser   Ser   Lys   Glu   Arg   Val   Ile   Leu   Lys   Val   Thr
                         195                         200                         205
Val   Pro   Ser   Gly   Lys   Gly   Ser   Thr   Thr   Pro   Thr   Lys   Ala   Gly   Val   Ile
      210                         215                         220
Leu   Asn   Asn   Ser   Glu   Tyr   Lys   Met   Leu   Ile   Asp   Asn   Gly   Tyr   Met   Val
225                         230                         235                         240
His   Val   Asp   Lys   Val   Ser   Lys   Val   Val   Lys   Lys   Gly   Val   Glu   Cys   Leu
                         245                         250                         255
Gln   Ile   Glu   Gly   Thr   Leu   Lys   Lys   Ser   Leu   Asp   Phe   Lys   Asn   Asp   Ile
                         260                         265                         270
Asn   Ala   Glu   Ala   His   Ser   Trp   Gly   Met   Lys   Asn   Tyr   Glu   Glu   Trp   Ala
                         275                         280                         285
Lys   Asp   Leu   Thr   Asp   Ser   Gln   Arg   Glu   Ala   Leu   Asp   Gly   Tyr   Ala   Arg
      290                         295                         300
Gln   Asp   Tyr   Lys   Glu   Ile   Asn   Asn   Tyr   Leu   Arg   Asn   Gln   Gly   Gly   Ser
305                         310                         315                         320
Gly   Asn   Glu   Lys   Leu   Asp   Ala   Gln   Ile   Lys   Asn   Ile   Ser   Asp   Ala   Leu
                         325                         330                         335
Gly   Lys   Lys   Pro   Ile   Pro   Glu   Asn   Ile   Thr   Val   Tyr   Arg   Trp   Cys   Gly
                  340                         345                         350
Met   Pro   Glu   Phe   Gly   Tyr   Gln   Ile   Ser   Asp   Pro   Leu   Pro   Ser   Leu   Lys
                  355                         360                         365
Asp   Phe   Glu   Glu   Gln   Phe   Leu   Asn   Thr   Ile   Lys   Glu   Asp   Lys   Gly   Tyr
      370                         375                         380
Met   Ser   Thr   Ser   Leu   Ser   Ser   Glu   Arg   Leu   Ala   Ala   Phe   Gly   Ser   Arg
385                         390                         395                         400
Lys   Ile   Ile   Leu   Arg   Leu   Gln   Val   Pro   Lys   Gly   Ser   Thr   Gly   Ala   Tyr
                  405                         410                         415
Leu   Ser   Ala   Ile   Gly   Gly   Phe   Ala   Ser   Glu   Lys   Glu   Ile   Leu   Leu   Asp
                  420                         425                         430
Lys   Asp   Ser   Lys   Tyr   His   Ile   Asp   Lys   Val   Thr   Glu   Val   Ile   Ile   Lys
                  435                         440                         445
Gly   Val   Lys   Arg   Tyr   Val   Val   Asp   Ala   Thr   Leu   Leu   Thr   Asn   Ser   Arg
      450                         455                         460
Gly   Pro   Ser   Thr   Pro   Thr   Pro   Ser   Pro   Ser   Thr   Pro   Pro   Thr   Pro
465                         470                         475                         480
Ser   Asp   Ile   Gly   Ser   Thr   Met   Lys   Thr   Asn   Gln   Ile   Ser   Thr   Thr   Gln
                  485                         490                         495
Lys   Asn   Gln   Gln   Lys   Glu   Met   Asp   Arg   Lys   Gly   Leu   Leu   Gly   Tyr   Tyr
                  500                         505                         510
Phe   Lys   Gly   Lys   Asp   Phe   Ser   Asn   Leu   Thr   Met   Phe   Ala   Pro   Thr   Arg
                  515                         520                         525
Asp   Ser   Thr   Leu   Ile   Tyr   Asp   Gln   Gln   Thr   Ala   Asn   Lys   Leu   Leu   Asp
      530                         535                         540
Lys   Lys   Gln   Gln   Glu   Tyr   Gln   Ser   Ile   Arg   Trp   Ile   Gly   Leu   Ile   Gln
545                         550                         555                         560
Ser   Lys   Glu   Thr   Gly   Asp   Phe   Thr   Phe   Asn   Leu   Ser   Glu   Asp   Glu   Gln
                  565                         570                         575
```

| | | | | | | | | | | | | | | |
|---|---|---|---|---|---|---|---|---|---|---|---|---|---|---|
| Ala | Ile | Ile | Glu 580 | Ile | Asn | Gly | Lys | Ile 585 | Ser | Asn | Lys | Gly 590 | Lys | Glu |
| Lys | Gln | Val 595 | Val | His | Leu | Glu | Lys 600 | Gly | Lys | Leu | Val | Pro 605 | Ile | Lys | Ile |
| Glu | Tyr 610 | Gln | Ser | Asp | Thr | Lys 615 | Phe | Asn | Ile | Asp | Ser 620 | Lys | Thr | Phe | Lys |
| Glu 625 | Leu | Lys | Leu | Phe | Lys 630 | Ile | Asp | Ser | Gln | Asn 635 | Gln | Pro | Gln | Gln | Val 640 |
| Gln | Gln | Asp | Glu | Leu 645 | Arg | Asn | Pro | Glu | Phe 650 | Asn | Lys | Lys | Glu | Ser 655 | Gln |
| Glu | Phe | Leu | Ala 660 | Lys | Pro | Ser | Lys | Ile 665 | Asn | Leu | Phe | Thr | Gln 670 | Gln | Met |
| Lys | Arg | Glu 675 | Ile | Asp | Glu | Asp | Thr 680 | Asp | Thr | Asp | Gly | Asp 685 | Ser | Ile | Pro |
| Asp | Leu 690 | Trp | Glu | Glu | Asn | Gly 695 | Tyr | Thr | Ile | Gln | Asn 700 | Arg | Ile | Ala | Val |
| Lys 705 | Trp | Asp | Asp | Ser | Leu 710 | Ala | Ser | Lys | Gly | Tyr 715 | Thr | Lys | Phe | Val | Ser 720 |
| Asn | Pro | Leu | Glu | Ser 725 | His | Thr | Val | Gly | Asp 730 | Pro | Tyr | Thr | Asp | Tyr 735 | Glu |
| Lys | Ala | Ala | Arg 740 | Asp | Leu | Asp | Leu | Ser 745 | Asn | Ala | Lys | Glu | Thr 750 | Phe | Asn |
| Pro | Leu | Val 755 | Ala | Ala | Phe | Pro | Ser 760 | Val | Asn | Val | Ser | Met 765 | Glu | Lys | Val |
| Ile | Leu 770 | Ser | Pro | Asn | Glu | Asn 775 | Leu | Ser | Asn | Ser | Val 780 | Glu | Ser | His | Ser |
| Ser 785 | Thr | Asn | Trp | Ser | Tyr 790 | Thr | Asn | Thr | Glu | Gly 795 | Ala | Ser | Val | Glu | Ala 800 |
| Gly | Ile | Gly | Pro | Lys 805 | Gly | Ile | Ser | Phe | Gly 810 | Val | Ser | Val | Asn | Tyr 815 | Gln |
| His | Ser | Glu | Thr 820 | Val | Ala | Gln | Glu | Trp 825 | Gly | Thr | Ser | Thr | Gly 830 | Asn | Thr |
| Ser | Gln | Phe 835 | Asn | Thr | Ala | Ser | Ala 840 | Gly | Tyr | Leu | Asn | Ala 845 | Asn | Val | Arg |
| Tyr | Asn 850 | Asn | Val | Gly | Thr | Gly 855 | Ala | Ile | Tyr | Asp | Val 860 | Lys | Pro | Thr | Thr |
| Ser 865 | Phe | Val | Leu | Asn | Asn 870 | Asp | Thr | Ile | Ala | Thr 875 | Ile | Thr | Ala | Lys | Ser 880 |
| Asn | Ser | Thr | Ala | Leu 885 | Asn | Ile | Ser | Pro | Gly 890 | Glu | Ser | Tyr | Pro | Lys 895 | Lys |
| Gly | Gln | Asn | Gly 900 | Ile | Ala | Ile | Thr | Ser 905 | Met | Asp | Asp | Phe | Asn 910 | Ser | His |
| Pro | Ile | Thr 915 | Leu | Asn | Lys | Lys | Gln 920 | Val | Asp | Asn | Leu | Leu 925 | Asn | Asn | Lys |
| Pro | Met 930 | Met | Leu | Glu | Thr | Asn 935 | Gln | Thr | Asp | Gly | Val 940 | Tyr | Lys | Ile | Lys |
| Asp 945 | Thr | His | Gly | Asn | Ile 950 | Val | Thr | Gly | Gly | Glu 955 | Trp | Asn | Gly | Val | Ile 960 |
| Gln | Gln | Ile | Lys | Ala 965 | Lys | Thr | Ala | Ser | Ile 970 | Ile | Val | Asp | Asp | Gly 975 | Glu |
| Arg | Val | Ala | Glu 980 | Lys | Arg | Val | Ala | Ala 985 | Lys | Asp | Tyr | Glu | Asn 990 | Pro | Glu |
| Asp | Lys | Thr 995 | Pro | Ser | Leu | Thr | Leu 1000 | Lys | Asp | Ala | Leu | Lys 1005 | Leu | Ser | Tyr |

-continued

```
Pro Asp Glu Ile Lys Glu Ile Glu Gly Leu Leu Tyr Tyr Lys Asn Lys
    1010                1015                1020

Pro Ile Tyr Glu Ser Ser Val Met Thr Tyr Leu Asp Glu Asn Thr Ala
1025                1030                1035                1040

Lys Glu Val Thr Lys Gln Leu Asn Asp Thr Thr Gly Lys Phe Lys Asp
                1045                1050                1055

Val Ser His Leu Tyr Asp Val Lys Leu Thr Pro Lys Met Asn Val Thr
            1060                1065                1070

Ile Lys Leu Ser Ile Leu Tyr Asp Asn Ala Glu Ser Asn Asp Asn Ser
        1075                1080                1085

Ile Gly Lys Trp Thr Asn Thr Asn Ile Val Ser Gly Gly Asn Asn Gly
    1090                1095                1100

Lys Lys Gln Tyr Ser Ser Asn Asn Pro Asp Ala Asn Leu Thr Leu Asn
1105                1110                1115                1120

Thr Asp Ala Gln Glu Lys Leu Asn Lys Asn Arg Asp Tyr Tyr Ile Ser
                1125                1130                1135

Leu Tyr Met Lys Ser Glu Lys Asn Thr Gln Cys Glu Ile Thr Ile Asp
            1140                1145                1150

Gly Glu Ile Tyr Pro Ile Thr Thr Lys Thr Val Asn Val Asn Lys Asp
        1155                1160                1165

Asn Tyr Lys Arg Leu Asp Ile Ile Ala His Asn Ile Lys Ser Asn Pro
    1170                1175                1180

Ile Ser Ser Leu His Ile Lys Thr Asn Asp Glu Ile Thr Leu Phe Trp
1185                1190                1195                1200

Asp Asp Ile Ser Ile Thr Asp Val Ala Ser Ile Lys Pro Glu Asn Leu
                1205                1210                1215

Thr Asp Ser Glu Ile Lys Gln Ile Tyr Ser Arg Tyr Gly Ile Lys Leu
            1220                1225                1230

Glu Asp Gly Ile Leu Ile Asp Lys Lys Gly Gly Ile His Tyr Gly Glu
        1235                1240                1245

Phe Ile Asn Glu Ala Ser Phe Asn Ile Glu Pro Leu Gln Asn Tyr Val
    1250                1255                1260

Thr Lys Tyr Glu Val Thr Tyr Ser Ser Glu Leu Gly Pro Asn Val Ser
1265                1270                1275                1280

Asp Thr Leu Glu Ser Asp Lys Ile Tyr Lys Asp Gly Thr Ile Lys Phe
                1285                1290                1295

Asp Phe Thr Lys Tyr Ser Lys Asn Glu Gln Gly Leu Phe Tyr Asp Ser
            1300                1305                1310

Gly Leu Asn Trp Asp Phe Lys Ile Asn Ala Ile Thr Tyr Asp Gly Lys
        1315                1320                1325

Glu Met Asn Val Phe His Arg Tyr Asn Lys
    1330                1335
```

What is claimed is:

1. An auxiliary protein isolated from Bacillus which enhances the insecticidal activity of a pesticidal protein, wherein said auxiliary protein is expressed during vegetative growth and has a molecular weight of about 50 kDa.

2. The auxiliary protein of claim 1 wherein said auxiliary protein is from *Bacillus cereus.*

3. The auxiliary protein of claim 2 wherein said auxiliary protein is from strain AB78.

4. The auxiliary protein of claim 3 wherein said protein has the sequence disclosed in SEQ ID NO:2.

5. The auxiliary protein of claim 1 wherein said auxiliary protein is from *Bacillus thuringiensis var. tenebrionis.*

6. The auxiliary protein of claim 5 wherein said protein has the sequence disclosed in SEQ ID NO:20.

* * * * *